United States Patent [19]

Taylor

[11] Patent Number: 5,407,901
[45] Date of Patent: Apr. 18, 1995

[54] HERBICIDAL OXATRICYCLIC ETHERS

[75] Inventor: Eric de G. Taylor, Wilmington, Del.

[73] Assignee: E. I. Du Pont de Nemours, Wilmington, Del.

[21] Appl. No.: 146,007

[22] PCT Filed: May 15, 1992

[86] PCT No.: PCT/US92/03879
§ 371 Date: Nov. 16, 1993
§ 102(e) Date: Nov. 16, 1993

[87] PCT Pub. No.: WO92/20684
PCT Pub. Date: Nov. 26, 1992

Related U.S. Application Data

[63] Continuation-in-part of Ser. No. 702,997, May 20, 1991, abandoned.

[51] Int. Cl.$^6$ ............... A01N 43/14; C07D 311/90
[52] U.S. Cl. .................. 504/292; 504/235; 504/247; 504/231; 504/271; 544/336; 546/141; 546/153; 546/269; 548/247; 548/491; 549/23; 549/52; 549/54; 549/60; 549/386
[58] Field of Search ............. 544/336; 548/247, 491; 549/23, 52, 54, 60, 386; 546/141, 153, 269; 504/235, 247, 251, 271, 292

[56] References Cited

U.S. PATENT DOCUMENTS 4,670,041 6/1987 Payne et al. .................. 549/463
4,782,169 11/1988 Soloway et al. ................ 549/459
4,828,603 5/1989 Patel et al. .................... 544/335

FOREIGN PATENT DOCUMENTS 0081893 6/1983 European Pat. Off. .
WO91/03464 3/1991 WIPO .

Primary Examiner—Bernard Dentz

[57] ABSTRACT

This patent application relates to Certain tricyclic ether herbicidal compounds and their use to control a broad spectrum of undesirable plant growth.

10 Claims, No Drawings

HERBICIDAL OXATRICYCLIC ETHERS

CROSS-REFERENCE TO RELATED APPLICATION

This application is a 371 of PCT/US92/03879 filed May 15, 1992 which application is a continuation-in-part of co-pending application U.S. Ser. No. 07/702,997 filed May 20, 1991, now abandoned.

BACKGROUND OF THE INVENTION

This invention relates to certain herbicidal ethers, agriculturally suitable compositions thereof, and a method for their use as broad spectrum preemergent or postemergent herbicides.

New compounds effective for controlling the growth of undesired vegetation are in constant demand. In the most common situation, such compounds are sought to selectively control the growth of weeds in useful crops such as cotton, rice, corn, wheat and soybeans, to name a few. Unchecked weed growth in such crops can cause significant losses, reducing profit to the farmer and increasing costs to the consumer. In other situations, herbicides are desired which will control all plant growth. Examples of areas in which complete control of all vegetation is desired are areas around railroad tracks, storage tanks and industrial storage areas. There are many products commercially available for these purposes, but the search continues for products which are more effective, less costly and environmentally safe.

U.S. Pat. No. 4,670,041 discloses herbicidal compounds of the formula:

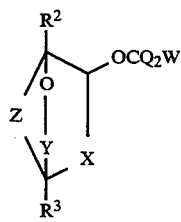

wherein, inter alia:

Y is $(-CR^5R^6-)_n$ in which n is 0, 1 or 2; and $R^5$ and $R^6$ (in part) form an alkylene group containing 4 or 5 carbon atoms.

U.S. Pat. No. 4,828,603 discloses herbicidal compounds of the formula:

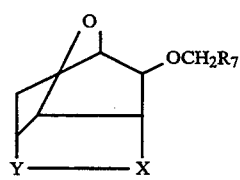

wherein, inter alia:

X is O, S, NR or $CH_2$; and

Y is (in part) $CH_2$.

SUMMARY OF THE INVENTION

This invention pertains to compounds of Formulas I through XV including stereoisomers, suitable compositions containing them and their use as broad spectrum preemergence and postemergence herbicides

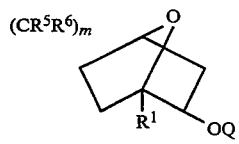

I

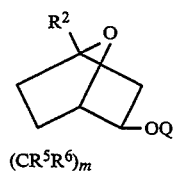

II

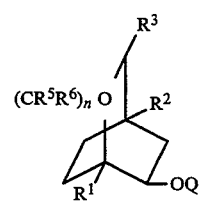

III

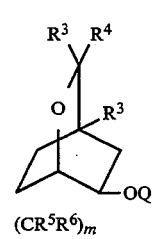

IV

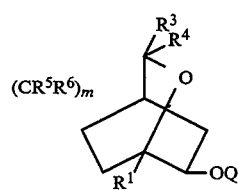

V

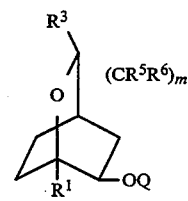

VI

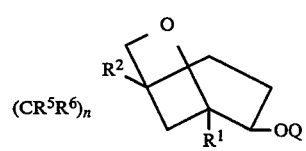

VII

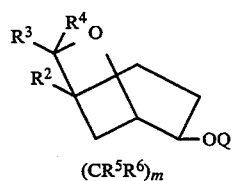

VIII

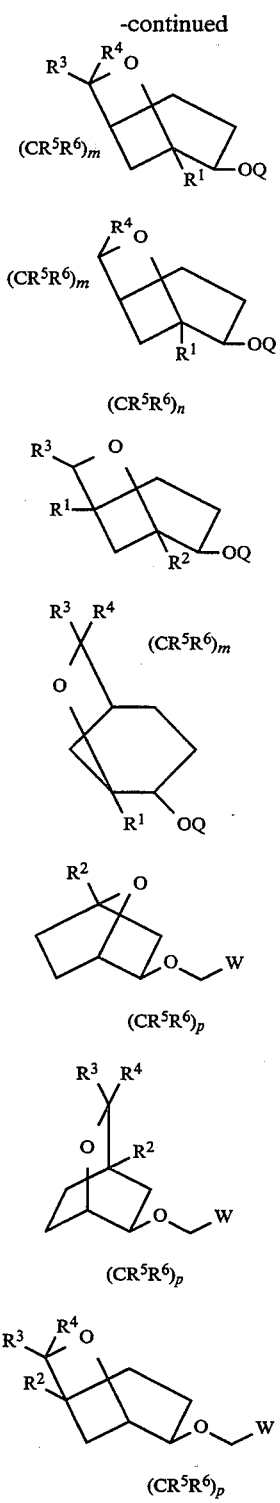

wherein:
n is 2, 3 or 4;
m is 3, 4 or 5;
p is 2 or 3;
$R^1$ is straight chain $C_1$-$C_3$ alkyl;
$R^2$ is H, $C_1$-$C_4$ alkyl, $C_2$-$C_4$ alkenyl or $C_2$-$C_4$ alkynyl;
$R^3$ and $R^4$ are independently H, $C_1$-$C_4$ alkyl, $C_2$-$C_4$ alkenyl, $C_2$-$C_4$ alkynyl or $C_1$-$C_3$ alkyl substituted with $OCH_3$ or $OCH_2CH_3$;

$R^5$ and $R^6$ are independently H, $OCH_3$ or $C_1$-$C_2$ alkyl;
Q is $CH_2W$ or q and r are independently 0–2;
$R^7$ is H, halogen, $C_1$-$C_3$ alkyl, $OR^8$, $SR^8$ or CN;
$R^8$ is $C_1$-$C_3$ alkyl or $C_1$-$C_3$ haloalkyl;
Z is $CH_2$, $NR^9$, O, S or may be CH and taken to form a double bond with an adjacent carbon;
$R^9$ is H or $C_1$-$C_3$ alkyl;
W is phenyl optionally substituted with 1–3 substituents selected from halogen, $C_1$-$C_3$ alkyl, $C_1$-$C_3$ alkoxy, OH, CN, $C_1$-$C_3$ haloalkyl, $C_1$-$C_3$ haloalkoxy, $C_1$-$C_3$ alkylthio, $C_2$-$C_4$ alkenyl and $C_2$-$C_4$ alkynyl; or W is 5-, 6- or 7-membered heterocyclic ring containing 0–2 nitrogens, 0–2 oxygens or 0–2 sulfurs, each ring optionally substituted with 1–2 substituents selected from halogen, $CH_3$ and $OCH_3$;
provided that
1) the sum of q and r is 0–2;
2) if the sum of q and r is 0 then Z is $CH_2$; and
3) if W is a heterocycle then the total number of heteroatoms contained within the heterocyclic rings is 3 or less.

Representative examples of the aforementioned heterocycles included in the definition of W include but are not limited to pyrrole, furan, thiophene, tetrahydropyran, tetrahydrofuran, isoxazole, oxazole, pyrazole, imidazole, thiazole, pyridine and pyrazine.

In the above definitions, the term "alkyl", used either alone or in compound words such as "haloalkyl" or "alkylthio", includes straight chain or branched alkyl, e.g., methyl, ethyl, n-propyl, isopropyl or the different butyl isomers.

"Alkoxy", "alkenyl" and "alkynyl" includes straight chain or branched isomers, e.g., ethoxy, n-propyloxy, isopropyloxy, 1-propenyl, 2-propenyl and 3-propenyl.

"Halogen", either alone or in compound words such as "haloalkyl", means fluorine, chlorine, bromine or iodine. Further, when used in compound words such as "haloalkyl" said alkyl may be partially or fully substituted with halogen atoms which may be the same or different. Examples of haloalkyl include $CH_2CH_2F$, $CF_2CF_3$ and $CH_2CHFCl$.

The compounds of the invention which are preferred for either their biological activity and/or ease of synthesis are:

1. Compounds of Formulas I, II, III, V or VIII wherein:
W is phenyl optionally substituted by 1–2 substituents selected from F, Cl, Br, $CH_3$ and $OCH_3$; or W is tetrahydropyran, tetrahydrofuran, thiophene, isoxazole, pyridine or pyrazine, each ring optionally substituted with 1–2 substituents selected from F, Cl, Br, $CH_3$ and $OCH_3$;
Q is $CH_2W$ or

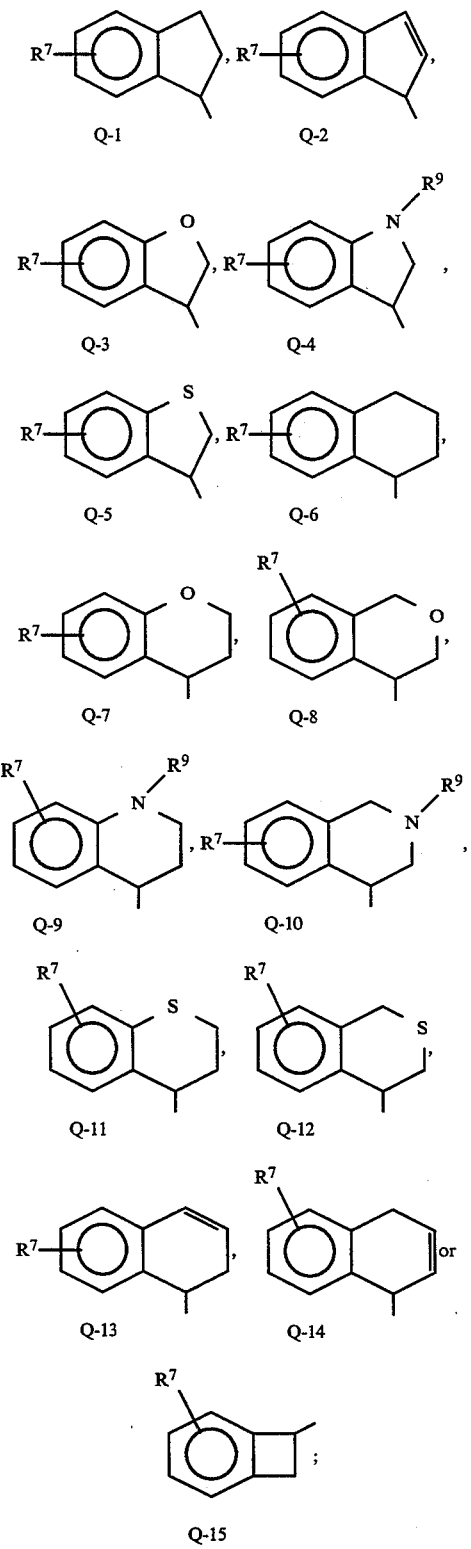

$R^5$ and $R^6$ are independently H or $C_1$–$C_2$ alkyl.

2. Compounds of Preferred 1 wherein:
$R^2$ is H, $C_1$–$C_3$ alkyl, $C_2$–$C_3$ alkenyl or $C_2$–$C_3$ alkynyl.

3. Compounds of Preferred 2 wherein:
$R^3$ is H, $C_1$–$C_3$ alkyl, $C_3$–$C_4$ alkenyl or $C_3$–$C_4$ alkynyl;
$R^4$ is H, $C_1$–$C_3$ alkyl, $C_3$–$C_4$ alkenyl or $C_3$–$C_4$ alkynyl.

4. Compounds of Preferred 3 wherein:

Q is CH$_2$W or Q-1, Q-3, Q-4, Q-6, Q-7, Q-8 or Q-15;
$R^5$ and $R^6$ are independently H;
W is phenyl optionally substituted with 1–2 substituents selected from F, Cl, Br and CH$_3$; tetrahydrofuran; thiophene optionally substituted with Cl or Br; or pyridine.

5. Compounds of Preferred 4 wherein:
$R^1$ is CH$_3$ or CH$_2$CH$_3$;
$R^2$ is H, CH$_3$, CH$_2$CH$_3$ or allyl; and
$R^3$ and $R^4$ are H.

6. Compounds of Preferred 5 wherein the formula is Formula I.

7. Compounds of Preferred 5 wherein the formula is Formula II.

8. Compounds of Preferred 5 wherein the formula is Formula III.

9. Compounds of Preferred 5 wherein the formula is Formula V.

10. Compounds of Preferred 5 wherein the formula is Formula VIII.

Compounds of the invention which are specifically preferred for their biological activity and/or ease of synthesis are the compounds of Preferred 5 which are:

(2α,3β,4aβ,5α,7aβ)-3-[(2-fluorophenyl)methoxy]octahydro-2,4a-dimethyl-2,5-methanocyclopenta-[b]pyran;

(2α,3β,4a,5α,9aβ)-3-[(2,6-difluorophenyl)methoxy]-decahydro-2-methyl-2,5-methanocyclohepta[b]pyran;

(2α,3β,4a,5α,7β)-3-[(2-fluorophenyl)methoxy]octahydro-2-methyl-2,5-methanocyclopenta[b]pyran;

(2α,3β,4aβ,5α,9aβ)-3l-[(2-fluorophenyl)methoxy]-decahydro-2-methyl-2,5-methanocyclohepta[b]pyran;

(2α,3β,4aβ,5α,7aβ)-octahydro-2,4a-dimethyl-3-(phenylmethoxy)-2,5-methanocyclopenta[b]-pyran;

(2α,3β,4aβ,5α,7aβ)-3-[(2-chlorophenyl)methoxy]octahydro-2,4a-dimethyl-2,5-methanocyclopenta-[b]pyran; and (2α,3β,4aβ,5α,7aβ)-octahydro-2,4a-dimethyl-3-[(2-methylphenyl)methoxy]-2,5-methanocyclopenta[b]-pyran.

Compounds of Formula I–XV that have the QO group syn with respect to the oxygen-containing bridge are usually more herbicidally active than the anti form. The present invention contemplates all of the herbicidally active forms resulting from synthesis and from deliberately created mixtures.

Compositions suitable for controlling the growth of undesired vegetation are also contemplated as within the scope of this invention. Such compositions comprise an effective amount of any of the compounds disclosed herein and at least one of the following: surfactant, solid diluent or liquid diluent.

Methods for controlling the growth of undesired vegetation are similarly considered to be within the scope of the invention. These methods comprise applying to the locus to be protected an effective amount of any of the compounds disclosed herein. Of particular importance is the method wherein the locus to be protected is rice, corn, soybeans or cereals.

DETAILED DESCRIPTION OF THE INVENTION

The compounds I–XII of the invention are prepared by treating the appropriately substituted oxatricycloalkanol (Ia–XIIa wherein Q is H) with a compound of the formula QX in which X is a halogen atom or a mesyloxy or a tosyloxy group or the like. This reaction is carried out, as shown in Scheme 1, in the presence of a strong base, such as an alkali metal hydride, in an inert solvent, such as ethers, aromatic hydrocarbons, dimethylformamide and the like. Suitable temperatures for the reaction are preferably from 20° C. to 100° C. The product ethers are recovered and isolated by conventional techniques.

Scheme 1

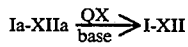

The alkylating agents QX are prepared in the conventional manners known to those skilled in the art from the alcohols QOH.

The alcohols, QOH, are generally known in the art and are most conveniently prepared through metal hydride (e.g., sodium borohydride) reduction of the corresponding carbonyl compounds or the corresponding ketones which can be derived by Friedel-Crafts type cyclization of derivatives of phenylalkylcarboxylic acid, phenoxyalkylcarboxylic acids, benzyloxyalkylcarboxylic acids, phenylthioalkylcarboxylic acids, and benzylthioalkylcarboxylic acids. Details may be found in a) T. Laird in *Comprehensive Organic Chemistry*, D. Barton and W. D. Ollis, ed., Vol. 1, pp. 1165–1168, Pergamon Press, New York (1979); b) M. H. Palmer and N. M. Scollick, *J. Chem. Soc. C.*, (1968), 2833; c) C. E. Dolgliesck and Mann, *J. Chem. Soc.*, (1945), 893; d) C. D. Hurd and S. Hayao, *J. Am. Chem. Soc.*, (1954), 76, 4299 and 5056; and e) R. Lesser, *Chem. Ber.* (1923), 56, 1642.

Alternatively, the compounds of Formulas I–XII may be prepared by the coupling procedure described in Scheme 2, which is used in cases where the standard Williamson ether synthesis proves problematic. This procedure uses a Lewis acidic metal oxide wherein the metal can remove the halide ion by forming an insoluble precipitate. For example, silver (I) oxide can be used and the silver halide is the co-product. Alternative metal oxides that may be used are HgO, CaO, MgO. N,N-Dimethylformamide and ethereal solvents, such as diethyl ether, tetrahydrofuran, dioxane, or 1,2-dimethoxyethane are the preferred solvents. Other solvents likely to provide good yields include dipolar aprotic solvents like dimethyl sulfoxide, acetone, and N,N'-dimethylpropyleneurea.

Scheme 2

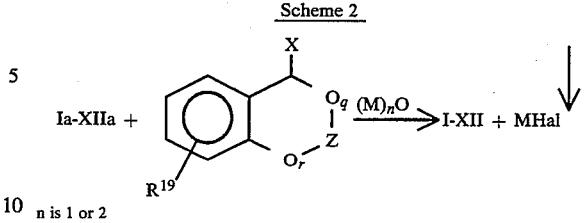

n is 1 or 2

The oxatricycloalkanols Ia–XIIa can be obtained generally by the route shown in Scheme 3. This route comprises epoxidation of unsaturated bicyclic alkanols Ib–XIIb (Scheme 4) by treatment with a peroxyacid or other epoxidizing agent known in the art, with or without isolation of the intermediate epoxyalkanol, and cyclization by treatment with a protic or Lewis acid in an inert solvent.

Scheme 3

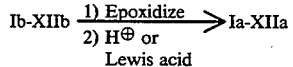

The unsaturated bicyclic alkanols Ib–XIIb are generally known in the art. They can be prepared directly or from appropriate aldehydes, ketones or carboxylic acids or esters or the like by methods known in the art or obvious modifications thereof.

Scheme 4

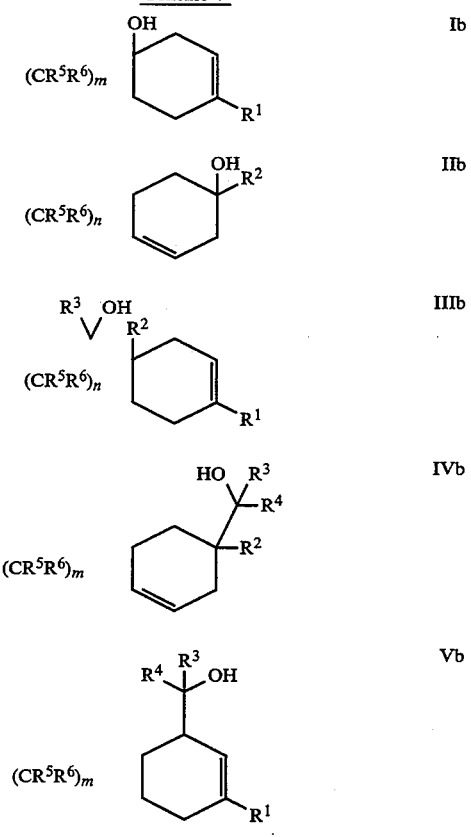

-continued
Scheme 4

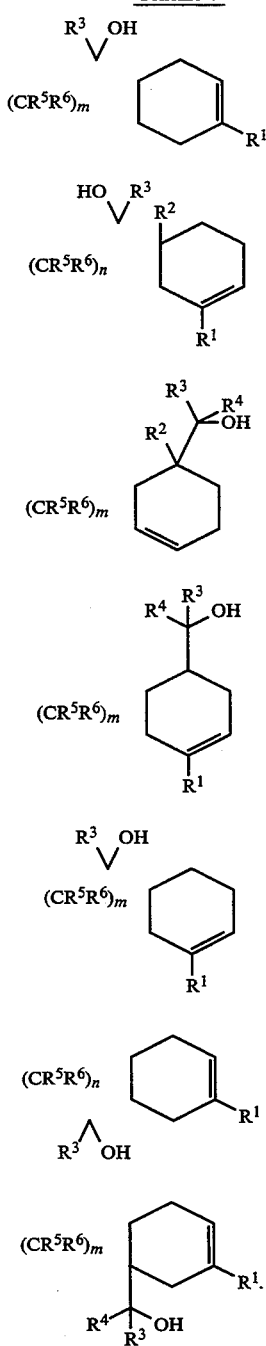

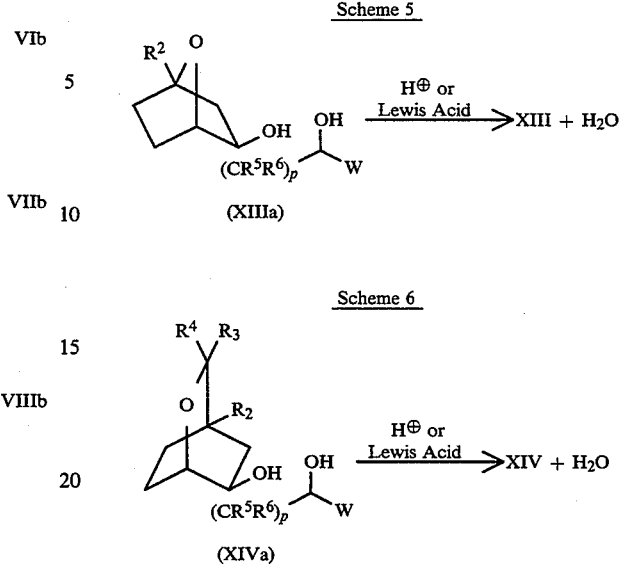

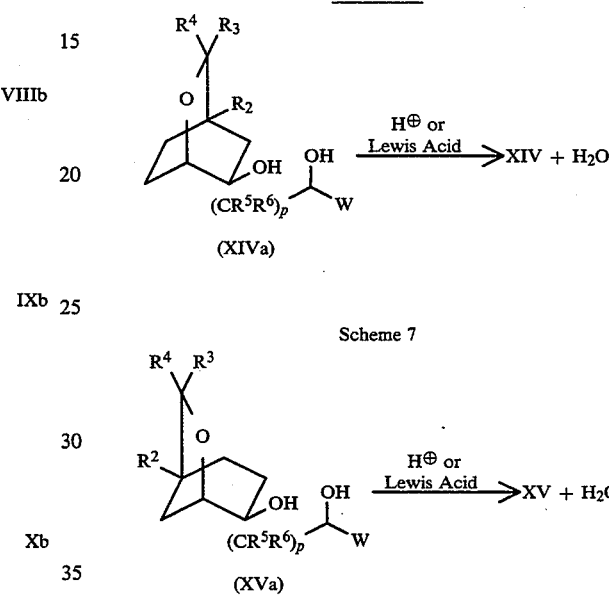

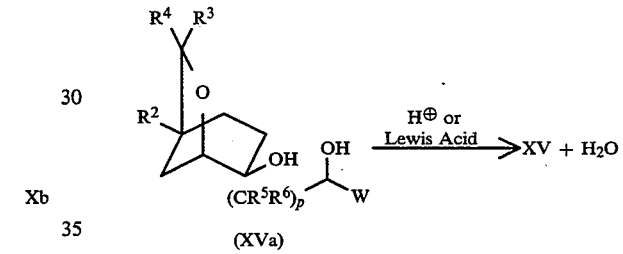

The compounds of XIII–XV of the invention can be prepared by treating the appropriately substituted oxabicycloalkanediols XIIIa–XVa with a protic acid, such as methanesulfonic acid or para-toluenesulfonic acid, or with a Lewis acid, such as aluminum trichloride zinc dichloride, or boron trifluoride, in an inert solvent, such as halogenated hydrocarbons, aromatic hydrocarbons and the like. Suitable temperatures for the reaction are preferably from −78° C. to 100° C. The reaction is carried out as short in Schemes 5–7 and the product ethers are recovered and isolated by conventional techniques.

Alternatively, some of the compounds XIII–XV can be prepared from the appropriately substituted halooxatricyclic ethers (XIIIb–XVb, wherein $R^5$ or $R^6$ is Br or I) as shown in Scheme 8. The halogen atom of XIIIb–XVb is replaced by $OCH_3$ by treatment with methanol in the presence of a silver salt or by treatment with a metal methoxide in a solvent such as methanol or N,N-dimethylformamide, optionally in the presence of a catalyst such as a copper salt or a silver salt, or the halogen atom is replaced by an alkyl group by treatment with a metal alkylcuprate or similar reagent in a solvent such as tetrahydrofuran, or the halogen atom is replaced by H by reduction. This reduction can be accomplished by methods known in the art including treatment with a trialkyltin hydride in an inert solvent such as benzene or toluene in the presence of a radical initiator such as benzoyl peroxide, preferably at temperatures of 20° C. to 110° C., or treatment with lithium aluminum hydride in an ethereal solvent, such as tetrahydrofuran or 1,2-dimethoxyethane, preferably at temperatures of 20° C. to 100° C., or treatment with hydrogen gas in the presence of a metal catalyst, such as platinum or palladium, in an inert solvent.

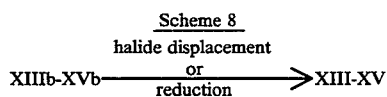

Non-limiting illustrations of the preparation of oxabicycloalkanediols XIIIa–XVa are shown in Schemes 9 and 10.

The compounds of Formula XIIIa are synthesized as shown in Scheme 9. Readily available haloaryl ethers 1 is subjected to metal-halogen exchange (e.g., by treatment with lithium metal or an alkyllithium) followed by treatment with a haloolefin optionally in the presence of a catalyst such as a cuprous salt to produce adduct 2 (Equation 9a).

Adduct 2 is subjected to the conditions of the Birch reduction (Birch, A. J., *Quart Rev.* (London) 1950 4 69; Watt, G. W., *Chem. Rev.* 1950 46 318; Birch, A. J.; Smith, M., *Quart Rev.* (London) 1958 12 17; Caine, D., *Organic Reactions* 1976 23 1) followed by mild acid hydrolysis of the intermediate enol ether to produce dienone 3 (Equation 9b).

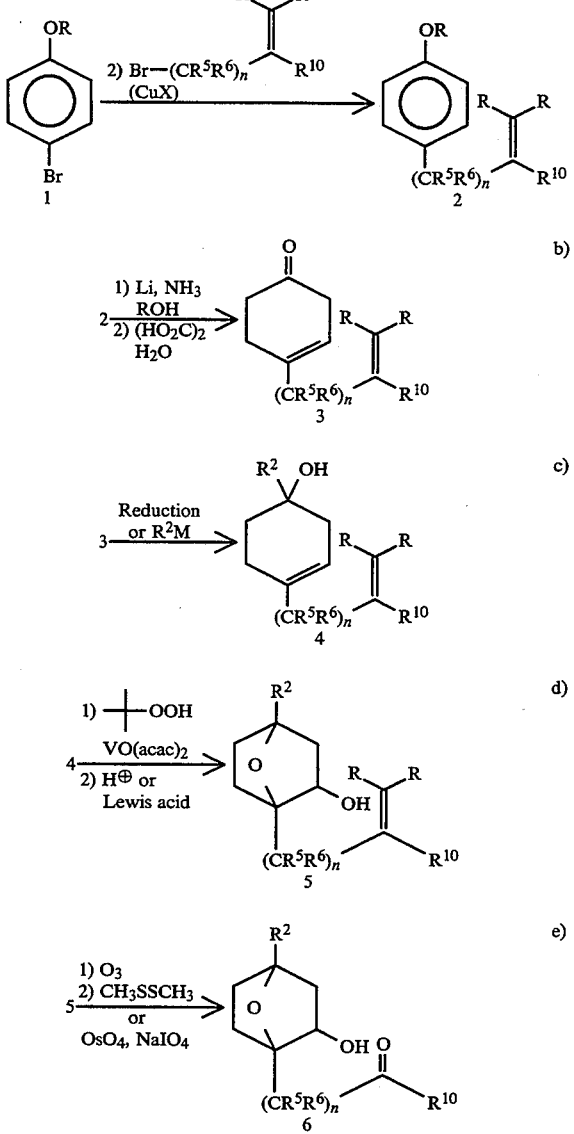

-continued
Scheme 9

Dienone 3 is treated with an appropriate Grignard reagent or organolithium reagent ($R^2M$) or with a reducing agent (e.g., sodium borohydride) to produce dienol 4 (Equation 9c).

Dienol 4 is treated with a metal catalyst epoxidizing reagent known in the art (e.g., tert-butylhydroperoxide catalyzed by vanadyl acetylacetonate) followed by acid-catalyzed cyclization to produce hydroxyoxabicycloalkene 5 (Equation 9d).

Compound 5 is treated with ozone followed by reductive work-up (e.g., with methyl disulfide) or with osmium tetroxide and sodium periodate to produce aldehyde 6 (or the corresponding hemiacetal) (Equation 9e).

Aldehyde 6 is treated with two equivalents of a Grignard reagent (WMgX) or of an organolithium reagent (WLi) to produce oxabicycloalkanediol XIIIa (Equation 9f).

The compounds of Formula IVa are synthesized as shown in Scheme 10.

Dienone 3 is homologated (e.g., with a Wittig reagent) to produce aldehyde 7 (Equation 10a).

Aldehyde 7 is optionally converted to the corresponding ester by methods known in the art and optionally alkylated at the α-position using an alkylating agent ($R^2X$) and general methods known in the art, then treated with organometallic reagents ($R^3M$, $R^4M$) or with a reducing agent (e.g., lithium aluminum hydride) to produce dienol 8 (Equation 10b).

Dienol 8 is treated using the methods (or modifications thereof) described in Equations 9d–9f to produce oxabicycloalkanediol XIVa (Equations 10c–10e).

Scheme 10

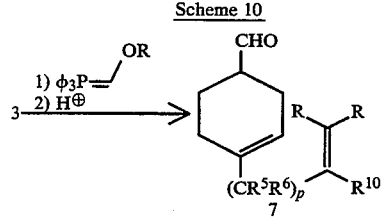

Scheme 10 -continued

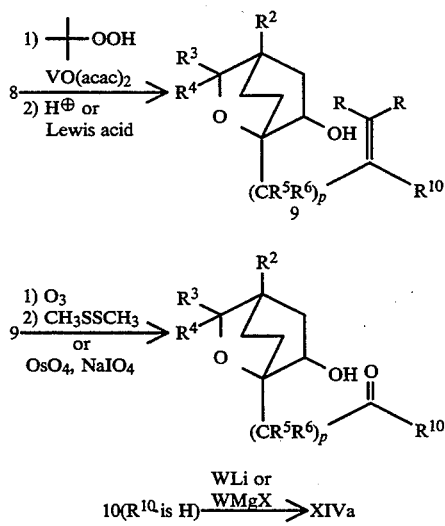

A non-limiting illustration of the preparation of halooxatricyclic ethers XIIIb–XVb is shown in Scheme 11. Carbonyl compound 11 (6, where $R^{10}$ is $R^5$ and p is p-1) is treated with a Witting reagent to produce hydroxyoxabicycloalkene 12 (Equation 11a).

Treatment of intermediate 12 with a source of electrophilic halogen such as bromine or N-halosuccinimide in the presence of an acid catalyst produces halooxatricyclic ether XIIIb (Equation 11b).

Scheme 11

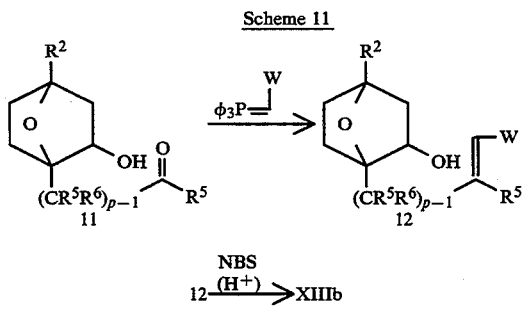

Alternatively, oxatricycloalkanediols XIIIa, where p is 3, can be synthesized as shown in Scheme 12.

Oxatricycloalkenones 13 are available by methods, or modifications thereof, known in the art. (See Keay, B. A., *J. Chem. Soc. Chem Comm.* 1987 419; DeClercq, P. J.; Van Royen, L. A., *Synth. Comm.* 1979, 9, 771.) Treatment of compound 13 with hydrogen gas in the presence of a metal catalyst produces oxatricycloalkanone 14 (Equation 12a).

Treatment of ketone 14 with a peroxyacid under conditions of the Baeyer-Villiger reaction (Hassal, C. W., *Organic Reactions* 1957 9 73; Lee, S. B.; Uff, B.C., *Quart. Rev. Chem. Soc.* 1967 21 429) produces lactone 15 (Equation 12b).

Treatment of lactone 15 with one equivalent of a reducing agent such as di-iso-butylaluminum hydride produces hydroxyaldehyde 16 (Equation 12c).

Treatment of hydroxyaldehyde 16 with at least two equivalents of a Grignard reagent (WMgX) or an organolithium reagent (WLi) produces oxatricycloalkanediol XIIIa (p is 3) (Equation 12d).

Scheme 12

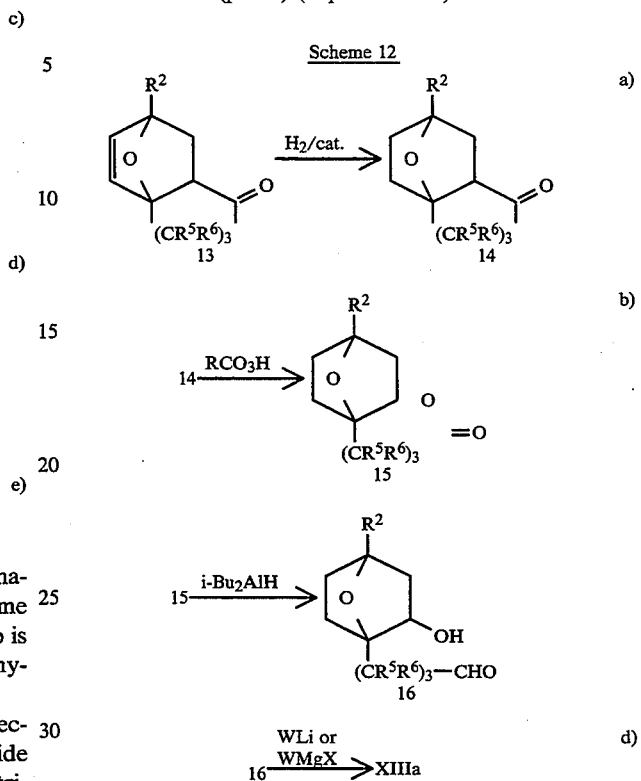

The following examples represent the preparation of typical species of the invention. The examples are for illustration and should not be regarded as limiting the invention in any way.

EXAMPLE 1

(±)-(2α,3β,4aβ,5α,7aβ)-Octahydro-2,4a-dimethyl-3-(phenylmethoxy)-2,5-methanocyclopenta[b]pyran Step A: (±)-(1α,3aβ,7aβ)-2,3,3a4,7,7a-hexahydro-5,7a-dimethyl-1H-inden-1-ol A solution of 0.82 g (5.0 mmol) of cis-2,3,3a,4,7,7a-hexahydro-5,7a-dimethyl-1H-inden-1-one (for a synthesis see Finguelli, F., et al., *J. Org. Chem.* 1982 47 5056–5064) in 5 mL of ethanol was added dropwise to a suspension of 0.38 g ( 10 mmol) of sodium borohydride in 5 mL of ethanol maintained at 0°–5° C. The mixture was stirred for 1 h at 0° C., then it was poured into 50 mL of saturated aqueous ammonium chloride solution and extracted twice with 50 mL of diethyl ether. The combined organic extracts were dried over $MgSO_4$, filtered, and the solvent removed in vacuo to afford the title compound (0.58 g, 70%), which crystallized to form a white solid, m.p. 60°–69° C. $^1$H NMR: δ 0.96 (s, 3H), 1.4–1.8 (m, 6H), 1.64 (s, 3H), 2.0–2.1 (m, 2H), 2.15 (br, 1H), 3.76 (t, 1H), 5.54 (m, 1H). $^{13}$C NMR: δ 22.8, 23.4, 26.4, 26.9, 29.6, 30.2, 40.3, 40.6, 82.0, 118.0, 130.3.

Step B: (±)-(1aα,2aα,3β,5aα,6aα)-octahydro-2a,6a-dimethyl-3H-indeno[5.6-b]oxiran-3-ol A solution of (±)-1α,3aβ,7aβ)-2,3,3a,4,7,7a-hexahydro-5,7a-dimethyl-1H-inden-1-ol (82 mmol) in 160 mL dichloromethane was cooled to 0° C. Vanadyl acetylacetonate (0.43 g, 1.6 mmol) was added, followed by 90% tert-butyl hydroperoxide (13.6 mL, 122 mmol). The cooling bath was removed and the mixture was stirred for 2 h. The mixture was again cooled to 0° C. and 160 mL of a 10% aqueous solution of sodium sulfite was added dropwise at 0°-10° C. This two-phase mixture was stirred for 30 min at 0° C., then the organic layer was separated and the aqueous layer was extracted with 50 mL of dichloromethane. The organic layers were combined, washed with 100 mL of a saturated aqueous solution of sodium bicarbonate, dried over MgSO$_4$, faltered, and the solvent evaporated in vacuo. Flash chromatography yielded a residue, which was triturated with hexanes to afford the title compound (4.36 g, 29%) as a white powder, m.p. 83°-85° C. $^1$NMR: δ 0.96 (s, 3H), 1.32 (s, 3H), 1.5-2.0 (m, 8H), 2.30 (dd, 1H), 3.03 (m, 1H), 3.09 (d, 1H), 3.55 (m, 1H).

Step C: (±)-(2α,3β,4aβ,5α,7aβ)-octahydro-2,4a-dimethyl-2,5-methanocyclopenta[b]pyran-3-ol The product of Step B (4.00 g, 22 mmol) was dissolved in 50 mL of dichloromethane. Camphorsulfonic acid (0.36 g, 1.5 mmol) was added and the mixture was stirred overnight at room temperature. The reaction mixture was then poured into 100 mL of diethyl ether, washed with a saturated aqueous solution of sodium bicarbonate, dried over MgSO$_4$, filtered, and the solvent evaporated in vacuo. The residue was subjected to flash chromatography to afford the title compound (1.56 g, 39%) as a colorless oil. $^1$H NMR: δ 0.77 (s, 3H), 1.10 (s, 3H), 1.4-2.2 (m, 9H), 3.44 (dd, 1H), 3.8 (m, 2H).

Step D: (2α,3β,4aβ,5α,7aβ)-octahydro-2,4a-dimethyl-3-(phenylmethoxy)-2,5-methanocyclopenta[b]pyran 0.12 grams of a sodium hydride 60% dispersion in oil (3.0 mmol), was washed with hexanes, then suspended in 4 mL of dry THF and the mixture was cooled to 0° C. 0.36 g (2.0 mmol) of the product from Step C was dissolved in 4 mL THF and then added dropwise at 0°-5° C. The mixture was stirred at 0° C. for 30 min, then 0.28 mL of benzyl bromide (2.4 mmol) and 0.03 grams of potassium iodide (0.2 mmol) were added and the mixture was refluxed for 4 hours. The mixture was cooled, 0.2 mL of 2-propanol was added, then the mixture was poured into 20 grams of ice and 20 mL of 1.0N hydrochloric acid and extracted into 40 mL of dichloromethane followed by two 20 mL extractions. The combined organic layers were dried over MgSO$_4$, filtered, and the solvent evaporated in vacuo. Flash chromatography afforded the title compound (0.28 g, 52%) as a colorless oil. $^1$H NMR: δ 0.78 (s, 3H), 1.12 (s, 3H), 1.38 (d, 1H), 1.48 (dd, 1H), 1.6-2.1 (m, 7H), 3.19 (dd, 1H), 3.86 (m, 1H), 4.48 (d, 1H), 4.73 (d, 1H), 7.2-7.4 (m, 5H).

EXAMPLE 2

(±)-(5aα,8α,9a,β)-8-Ethyloctahydro-2-(2-methylphenyl)-5a,8-epoxy-6H-1-benzoxepin Step A: (±)-(2α,4aα,8aβ)-2-ethylhexahydro-2H-2,4a-epoxynaphthalen-8(7H)-one To a solution of 10.84 grams of (±)-(2α,4aα,8aβ)-2-ethyl-1,5,6,8a-tetrahydro-2H-2,4a-epoxynaphthalen-8(7H)-one (synthesized by modification of the methods described by Keay in *J. Chem. Soc. Chem. Comm.* 1987 419 and by DeClercq and VanRoyen in *Synth. Comm.* 1979 9 771, starting with 2-ethylfuran) in 225 mL of ethanol was added 3.4 grams of 5% palladium on carbon. The mixture was treated with hydrogen gas overnight at room temperature and atmospheric pressure. The catalyst was then filtered off, rinsed with ethanol, and the solvent was evaporated in vacuo to afford the title compound (10.24 g, 93%) as an oil. $^1$H NMR: δ 0.96 (t, 3H), 1.5-1.9 (m, 7H), 1.9-2.1 (m, 3H), 2.1-2.3 (m, 3H), 2.45 (m 2H).

Step B: (±)-(5aα,8α,9aβ)-8-ethylhexahydro-6H-5a,8-epoxy-1-benzoxepin-2(3H)-one

The product of Step A was dissolved in 350 mL of dichloromethane and 27.5 grams of 50% meta-chloroperoxybenzoic acid (1.5 equivalents) was added. The mixture was stirred for 3 days, then 35 mL of a 10% aqueous solution of sodium hydrogen sulfite was added dropwise with cooling to maintain the temperature of the mixture below 30° C. The mixture was stirred for 30 min, then 900 mL dichloromethane was added and the organic layer was separated, washed with 260 mL of a 1.0N solution of sodium hydroxide, dried over MgSO$_4$ and filtered. The solvent was evaporated in vacuo to afford the title compound (11.08 g, 100%) as a light yellow oil. $^1$H NMR: δ 1.00 (t, 3H), 1.5-2.2 (m, 12H), 2.6-2.9 (m, 2H), 4.50 (dd, 1H).

Step C: (±)-exo-4-ethyl-2-hydroxy-7-oxabicyclo[2.2.1]heptane-1-butanal

A portion of the product of Step B (2.10 g, 10 mmol) was dissolved in 40 mL of toluene. The solution was cooled to −70° C., then 10 mL of a diisobutylaluminum hydride solution (1.5M solution in toluene, 15 mmol) was added dropwise, maintaining the temperature below −60° C. The reaction mixture was stirred for 1 hour at −70° C., then transferred via cannula to a stirred mixture of 50 grams of ice, 40 mL of water and 10 mL of acetic acid. This mixture was stirred for 5 min, then extracted with two 50 mL portions of diethyl ether. The combined ether layers were washed with 50 mL of water, then with 50 mL of saturated aqueous sodium bicarbonate solution. All of the aqueous layers were combined, saturated with sodium chloride, and extracted with three 50 mL portions of dichloromethane. The dichloromethane layers were combined and washed with two 50 mL portions of saturated aqueous sodium bicarbonate solution. All of the organic layers were dried over MgSO$_4$ and filtered, and the solvents were removed in vacuo to afford the title compound (1.30 g, 61%) as an oil. Due to equilibration between aldehyde and diastereomeric lactol forms, complete spectral characterization of the title compound was difficult. $^1$H NMR (inter alia): δ 0.97 (t), 9.77 (s).

Step D: (±)-exo-4-ethyl-2-hydroxy-α-(2-methylphenyl)-7-oxabicyclo[2.2.1]heptane-1-butanol The product of Step C was dissolved in 15 mL of diethyl ether and the solution was cooled to 0° C. Then 8 mL of a solution of ortho-tolylmagnesium bromide (2 M solution, 16 mmol) was added dropwise, maintaining the temperature of the reaction mixture at 0°-5=C. The mixture was stirred for 1 hour at 0° C., then 2 mL of additional ortho-tolylmagnesium bromide (2 M solution, 4 mmol) was added dropwise at 0°-5° C. The mixture was stirred for 40 min at 0° C., then 10 mL of a saturated aqueous solution of ammonium chloride was added dropwise. Water and diethyl ether were added to dissolve solids, the organic layer was separated, and the aqueous layer was extracted with 20 mL of diethyl ether. The combined organic layers were washed with a saturated aqueous solution of sodium bicarbonate, dried over MgSO$_4$ and faltered. The solvent was removed in vacuo and the solid residue was triturated with hexanes to afford the title compound (1.19 g, 64%) as a white solid, m.p. 108°–119° C. $^1$H NMR: δ 0.97 (t, 3H), 1.3–2.2 (m, 15H), 2.33 (s, 3H), 3.88 (m, 1H), 4.97 (m, 1H), 7.1–7.3 (m, 3H), 7.48 (d, 1H).

Step E: (±)-(5aα,8α,9aβ)-8-ethyloctahydro-2-(2-methylphenyl)-5a,8-epoxy-6H-1-benzoxepin A portion of the product of Step D (0.46 g, 1.5 mmol) and 0.21 grams of zinc chloride (1.5 mmol) were combined in 30 mL of dichloromethane and the mixture was refluxed for 5 hours. The mixture was then cooled, diluted with 60 mL of dichloromethane, and washed with 30 mL of water, then with a saturated aqueous solution of 30 mL of sodium bicarbonate. The organic layer was dried over MgSO$_4$ and filtered and the solvent was removed in vacuo. The residue was subjected to flash chromatography on silica gel to afford the less polar diastereomer of the title compound (0.06 g, 14%) as an oil, followed by the more polar diastereomer of the title compound (0.10 g, 23%) as an oil. $^1$H NMR (less polar diastereomer): δ 1.03 (t, 3H), 1.5–1.8 (m, 7H), 1.8–2.0 (m, 5H), 2.12 (m, 2H), 2.31 (s, 3H), 4.12 (m, 1H), 5.07 (d, 1H), 7.10 (m, 2H), 7.18 (t, 1H), 7.42 (d, 1H). $^1$H NMR (more polar diastereomer): δ 0.98 (t, 3H), 1.4–1.6 (m, 5H), 1.7–1.9 (m, 4H), 1.9–2.1 (m, 2H), 2.1–2.2 (m, 2H), 2.24 (m, 1H), 2.31 (s, 3H), 3.89 (m, 1H), 4.52 (d, 1H), 7.1–7.2 (m, 3H), 7.51 (d, 1H).

By the general procedures described in Schemes 1–12 and Examples 1–2, or by obvious modifications thereof, the compounds of Tables 1–15 can be prepared.

GENERAL STRUCTURES FOR TABLES 1–16

General Structure 1:

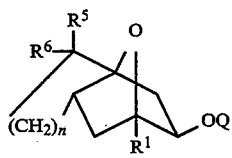

General Structure 2:

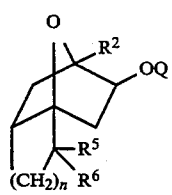

General Structure 3:

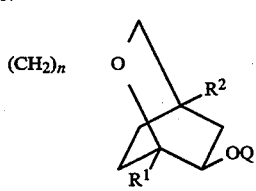

General Structure 4:

-continued
GENERAL STRUCTURES FOR TABLES 1–16

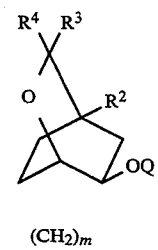

General Structure 5:

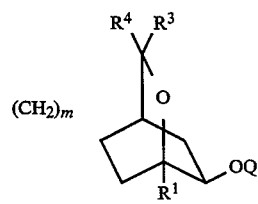

General Structure 6:

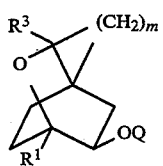

General Structure 7:

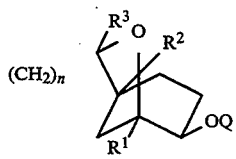

General Structure 8:

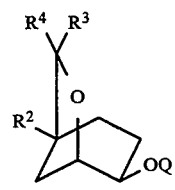

General Structure 9:

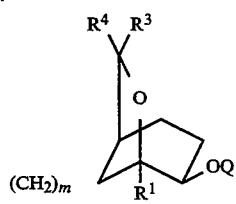

General Structure 10:

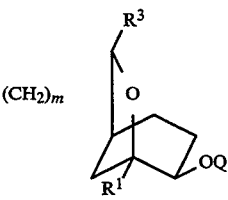

General Structure 11:

-continued
GENERAL STRUCTURES FOR TABLES 1-16

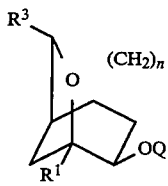

General Structure 12:

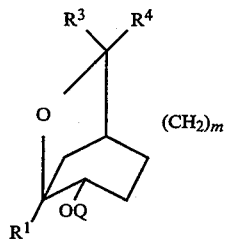

General Structure 13:

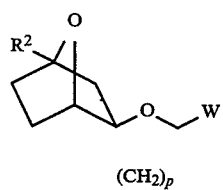

General Structure 14:

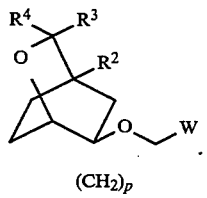

General Structure 15:

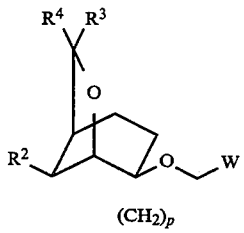

TABLE 1

| Q | n | Q | n |
|---|---|---|---|
| General Structure 1, $R^5 = R^6$ is H, $R^1$ is CH$_3$ | | | |
| CH$_2$(C$_6$H$_5$) | 2 | CH$_2$(2-tetrahydrofuranyl) | 2 |
| CH$_2$(2-FC$_6$H$_4$) | 2 | CH$_2$(2-tetrahydropyranyl) | 2 |
| CH$_2$(3-FC$_6$H$_4$) | 2 | Q-1 | 2 |
| CH$_2$(4-FC$_6$H$_4$) | 2 | Q-3 | 2 |
| CH$_2$(2,3-F$_2$C$_6$H$_3$) | 2 | Q-4 | 2 |
| CH$_2$(2,4-F$_2$C$_6$H$_3$) | 2 | Q-6 | 2 |
| CH$_2$(2,5-F$_2$C$_6$H$_3$) | 2 | Q-7 | 2 |
| CH$_2$(2,6-F$_2$C$_6$H$_3$) | 2 | Q-8 | 2 |
| CH$_2$(2,4,6-F$_3$C$_6$H$_2$) | 2 | Q-15 | 2 |
| CH$_2$(2-ClC$_6$H$_4$) | 2 | CH$_2$(2-BrC$_6$H$_4$) | 2 |
| CH$_2$(3-ClC$_6$H$_4$) | 2 | CH$_2$(2,6-Br$_2$C$_6$H$_3$) | 2 |
| CH$_2$(4-ClC$_6$H$_4$) | 2 | CH$_2$(2-Cl-6-FC$_6$H$_3$) | 2 |
| CH$_2$(2,6-Cl$_2$C$_6$H$_3$) | 2 | CH$_2$(2-(OCH$_3$)C$_6$H$_4$) | 2 |
| CH$_2$(2-(CH$_3$)C$_6$H$_4$) | 2 | CH$_2$(2-(CN)C$_6$H$_4$) | 2 |
| CH$_2$(3-(CH$_3$)C$_6$H$_4$) | 2 | CH$_2$(2-(CF$_3$)C$_6$H$_4$) | 2 |
| CH$_2$(4-(CH$_3$)C$_6$H$_4$) | 2 | CH$_2$(2-(OCF$_3$)C$_6$H$_4$) | 2 |
| CH$_2$(2-pyridyl) | 2 | CH$_2$(2-(SCH$_3$)C$_6$H$_4$) | 2 |
| CH$_2$(2-thienyl) | 2 | CH$_2$(2-(CH=CH$_2$)C$_6$H$_4$) | 2 |

TABLE 1-continued

| Q | n | Q | n |
|---|---|---|---|
| CH$_2$(2-furanyl) | 2 | CH$_2$(2-(C≡CH)C$_6$H$_4$) | 2 |
| CH$_2$(C$_6$H$_5$) | 3 | CH$_2$(2-tetrahydrofuranyl) | 3 |
| CH$_2$(2-FC$_6$H$_4$) | 3 | CH$_2$(2-tetrahydropyranyl) | 3 |
| CH$_2$(3-FC$_6$H$_4$) | 3 | Q-1 | 3 |
| CH$_2$(4-FC$_6$H$_4$) | 3 | Q-3 | 3 |
| CH$_2$(2,3-F$_2$C$_6$H$_3$) | 3 | Q-4 | 3 |
| CH$_2$(2,4-F$_2$C$_6$H$_3$) | 3 | Q-6 | 3 |
| CH$_2$(2,5-F$_2$C$_6$H$_3$) | 3 | Q-7 | 3 |
| CH$_2$(2,6-F$_2$C$_6$H$_3$) | 3 | Q-8 | 3 |
| CH$_2$(2,4,6-F$_3$C$_6$H$_2$) | 3 | Q-15 | 3 |
| CH$_2$(2-ClC$_6$H$_4$) | 3 | CH$_2$(2-BrC$_6$H$_4$) | 3 |
| CH$_2$(3-ClC$_6$H$_4$) | 3 | CH$_2$(2,6-Br$_2$C$_6$H$_3$) | 3 |
| CH$_2$(4-ClC$_6$H$_4$) | 3 | CH$_2$(2-Cl-6-FC$_6$H$_3$) | 3 |
| CH$_2$(2,6-Cl$_2$C$_6$H$_3$) | 3 | CH$_2$(2-(OCH$_3$)C$_6$H$_4$) | 3 |
| CH$_2$(2-(CH$_3$)C$_6$H$_4$) | 3 | CH$_2$(2-(CN)C$_6$H$_4$) | 3 |
| CH$_2$(3-(CH$_3$)C$_6$H$_4$) | 3 | CH$_2$(2-(CF$_3$)C$_6$H$_4$) | 3 |
| CH$_2$(4-(CH$_3$)C$_6$H$_4$) | 3 | CH$_2$(2-(OCF$_3$)C$_6$H$_4$) | 3 |
| CH$_2$(2-pyridyl) | 3 | CH$_2$(2-(SCH$_3$)C$_6$H$_4$) | 3 |
| CH$_2$(2-thienyl) | 3 | CH$_2$(2-(CH=CH$_2$)C$_6$H$_4$) | 3 |
| CH$_2$(2-furanyl) | 3 | CH$_2$(2-(C≡CH)C$_6$H$_4$) | 3 |
| CH$_2$(C$_6$H$_5$) | 4 | CH$_2$(2-tetrahydrofuranyl) | 4 |
| CH$_2$(2-FC$_6$H$_4$) | 4 | CH$_2$(2-tetrahydropyranyl) | 4 |
| CH$_2$(3-FC$_6$H$_4$) | 4 | Q-1 | 4 |
| CH$_2$(4-FC$_6$H$_4$) | 4 | Q-3 | 4 |
| CH$_2$(2,3-F$_2$C$_6$H$_3$) | 4 | Q-4 | 4 |
| CH$_2$(2,4-F$_2$C$_6$H$_3$) | 4 | Q-6 | 4 |
| CH$_2$(2,5-F$_2$C$_6$H$_3$) | 4 | Q-7 | 4 |
| CH$_2$(2,6-F$_2$C$_6$H$_3$) | 4 | Q-8 | 4 |
| CH$_2$(2,4,6-F$_3$C$_6$H$_2$) | 4 | Q-15 | 4 |
| CH$_2$(2-ClC$_6$H$_4$) | 4 | CH$_2$(2-BrC$_6$H$_4$) | 4 |
| CH$_2$(3-ClC$_6$H$_4$) | 4 | CH$_2$(2,6-Br$_2$C$_6$H$_3$) | 4 |
| CH$_2$(4-ClC$_6$H$_4$) | 4 | CH$_2$(2-Cl-6-FC$_6$H$_3$) | 4 |
| CH$_2$(2,6-Cl$_2$C$_6$H$_3$) | 4 | CH$_2$(2-(OCH$_3$)C$_6$H$_4$) | 4 |
| CH$_2$(2-(CH$_3$)C$_6$H$_4$) | 4 | CH$_2$(2-(CN)C$_6$H$_4$) | 4 |
| CH$_2$(3-(CH$_3$)C$_6$H$_4$) | 4 | CH$_2$(2-(CF$_3$)C$_6$H$_4$) | 4 |
| CH$_2$(4-(CH$_3$)C$_6$H$_4$) | 4 | CH$_2$(2-(OCF$_3$)C$_6$H$_4$) | 4 |
| CH$_2$(2-pyridyl) | 4 | CH$_2$(2-(SCH$_3$)C$_6$H$_4$) | 4 |
| CH$_2$(2-thienyl) | 4 | CH$_2$(2-(CH=CH$_2$)C$_6$H$_4$) | 4 |
| CH$_2$(2-furanyl) | 4 | CH$_2$(2-(C≡CH)C$_6$H$_4$) | 4 |
| General Structure 1, $R^5 = R^6$ is H, $R^1$ is CH$_2$CH$_3$ | | | |
| CH$_2$(C$_6$H$_5$) | 3 | CH$_2$(2-tetrahydrofuranyl) | 3 |
| CH$_2$(2-FC$_6$H$_4$) | 3 | CH$_2$(2-tetrahydropyranyl) | 3 |
| CH$_2$(3-FC$_6$H$_4$) | 3 | Q-1 | 3 |
| CH$_2$(4-FC$_6$H$_4$) | 3 | Q-3 | 3 |
| CH$_2$(2,3-F$_2$C$_6$H$_3$) | 3 | Q-4 | 3 |
| CH$_2$(2,4-F$_2$C$_6$H$_3$) | 3 | Q-6 | 3 |
| CH$_2$(2,5-F$_2$C$_6$H$_3$) | 3 | Q-7 | 3 |
| CH$_2$(2,6-F$_2$C$_6$H$_3$) | 3 | Q-8 | 3 |
| CH$_2$(2,4,6-F$_3$C$_6$H$_2$) | 3 | Q-15 | 3 |
| CH$_2$(2-ClC$_6$H$_4$) | 3 | CH$_2$(2-BrC$_6$H$_4$) | 3 |
| CH$_2$(3-ClC$_6$H$_4$) | 3 | CH$_2$(2,6-Br$_2$C$_6$H$_3$) | 3 |
| CH$_2$(4-ClC$_6$H$_4$) | 3 | CH$_2$(2-Cl-6-FC$_6$H$_3$) | 3 |
| CH$_2$(2,6-Cl$_2$C$_6$H$_3$) | 3 | CH$_2$(2-(OCH$_3$)C$_6$H$_4$) | 3 |
| CH$_2$(2-(CH$_3$)C$_6$H$_4$) | 3 | CH$_2$(2-(CN)C$_6$H$_4$) | 3 |
| CH$_2$(3-(CH$_3$)C$_6$H$_4$) | 3 | CH$_2$(2-(CF$_3$)C$_6$H$_4$) | 3 |
| CH$_2$(4-(CH$_3$)C$_6$H$_4$) | 3 | CH$_2$(2-(OCF$_3$)C$_6$H$_4$) | 3 |
| CH$_2$(2-pyridyl) | 3 | CH$_2$(2-(SCH$_3$)C$_6$H$_4$) | 3 |
| CH$_2$(2-thienyl) | 3 | CH$_2$(2-(CH=CH$_2$)C$_6$H$_4$) | 3 |
| CH$_2$(2-furanyl) | 3 | CH$_2$(2-(C≡CH)C$_6$H$_4$) | 3 |
| General Structure 1, $R^5$ is OCH$_3$, $R^6$ is H, $R^1$ is CH$_3$ | | | |
| CH$_2$(C$_6$H$_5$) | 3 | CH$_2$(2-tetrahydrofuranyl) | 3 |
| CH$_2$(2-FC$_6$H$_4$) | 3 | CH$_2$(2-tetrahydropyranyl) | 3 |
| CH$_2$(3-FC$_6$H$_4$) | 3 | Q-1 | 3 |
| CH$_2$(4-FC$_6$H$_4$) | 3 | Q-3 | 3 |
| CH$_2$(2,3-F$_2$C$_6$H$_3$) | 3 | Q-4 | 3 |
| CH$_2$(2,4-F$_2$C$_6$H$_3$) | 3 | Q-6 | 3 |
| CH$_2$(2,5-F$_2$C$_6$H$_3$) | 3 | Q-7 | 3 |
| CH$_2$(2,6-F$_2$C$_6$H$_3$) | 3 | Q-8 | 3 |
| CH$_2$(2,4,6-F$_3$C$_6$H$_2$) | 3 | Q-15 | 3 |
| CH$_2$(2-ClC$_6$H$_4$) | 3 | CH$_2$(2-BrC$_6$H$_4$) | 3 |
| CH$_2$(3-ClC$_6$H$_4$) | 3 | CH$_2$(2,6-Br$_2$C$_6$H$_3$) | 3 |
| CH$_2$(4-ClC$_6$H$_4$) | 3 | CH$_2$(2-Cl-6-FC$_6$H$_3$) | 3 |
| CH$_2$(2,6-Cl$_2$C$_6$H$_3$) | 3 | CH$_2$(2-(OCH$_3$)C$_6$H$_4$) | 3 |
| CH$_2$(2-(CH$_3$)C$_6$H$_4$) | 3 | CH$_2$(2-(CN)C$_6$H$_4$) | 3 |
| CH$_2$(3-(CH$_3$)C$_6$H$_4$) | 3 | CH$_2$(2-(CF$_3$)C$_6$H$_4$) | 3 |
| CH$_2$(4-(CH$_3$)C$_6$H$_4$) | 3 | CH$_2$(2-(OCF$_3$)C$_6$H$_4$) | 3 |
| CH$_2$(2-pyridyl) | 3 | CH$_2$(2-(SCH$_3$)C$_6$H$_4$) | 3 |
| CH$_2$(2-thienyl) | 3 | CH$_2$(2-(CH=CH$_2$)C$_6$H$_4$) | 3 |
| CH$_2$(2-furanyl) | 3 | CH$_2$(2-(C≡CH)C$_6$H$_4$) | 3 |

TABLE 2

| Q | n | Q | n |
|---|---|---|---|
| General Structure 2, $R^5 = R^6$ is H, $R^2$ is $CH_3$ | | | |
| $CH_2(C_6H_5)$ | 2 | $CH_2$(2-tetrahydrofuranyl) | 2 |
| $CH_2$(2-$FC_6H_4$) | 2 | $CH_2$(2-tetrahydropyranyl) | 2 |
| $CH_2$(3-$FC_6H_4$) | 2 | Q-1 | 2 |
| $CH_2$(4-$FC_6H_4$) | 2 | Q-3 | 2 |
| $CH_2$(2,3-$F_2C_6H_3$) | 2 | Q-4 | 2 |
| $CH_2$(2,4-$F_2C_6H_3$) | 2 | Q-6 | 2 |
| $CH_2$(2,5-$F_2C_6H_3$) | 2 | Q-7 | 2 |
| $CH_2$(2,6-$F_2C_6H_3$) | 2 | Q-8 | 2 |
| $CH_2$(2,4,6-$F_3C_6H_2$) | 2 | Q-15 | 2 |
| $CH_2$(2-$ClC_6H_4$) | 2 | $CH_2$(2-$BrC_6H_4$) | 2 |
| $CH_2$(3-$ClC_6H_4$) | 2 | $CH_2$(2,6-$Br_2C_6H_3$) | 2 |
| $CH_2$(4-$ClC_6H_4$) | 2 | $CH_2$(2-Cl-6-$FC_6H_3$) | 2 |
| $CH_2$(2,6-$Cl_2C_6H_3$) | 2 | $CH_2$(2-($OCH_3$)$C_6H_4$) | 2 |
| $CH_2$(2-($CH_3$)$C_6H_4$) | 2 | $CH_2$(2-(CN)$C_6H_4$) | 2 |
| $CH_2$(3-($CH_3$)$C_6H_4$) | 2 | $CH_2$(2-$CF_3$)$C_6H_4$) | 2 |
| $CH_2$(4-($CH_3$)$C_6H_4$) | 2 | $CH_2$(2-($OCF_3$)$C_6H_4$) | 2 |
| $CH_2$(2-pyridyl) | 2 | $CH_2$(2-($SCH_3$)$C_6H_4$) | 2 |
| $CH_2$(2-thienyl) | 2 | $CH_2$(2-(CH=$CH_2$)$C_6H_4$) | 2 |
| $CH_2$(2-furanyl) | 2 | $CH_2$(2-(C≡CH)$C_6H_4$) | 2 |
| $CH_2(C_6H_5)$ | 3 | $CH_2$(2-tetrahydrofuranyl) | 3 |
| $CH_2$(2-$FC_6H_4$) | 3 | $CH_2$(2-tetrahydropyranyl) | 3 |
| $CH_2$(3-$FC_6H_4$) | 3 | Q-1 | 3 |
| $CH_2$(4-$FC_6H_4$) | 3 | Q-3 | 3 |
| $CH_2$(2,3-$F_2C_6H_3$) | 3 | Q-4 | 3 |
| $CH_2$(2,4-$F_2C_6H_3$) | 3 | Q-6 | 3 |
| $CH_2$(2,5-$F_2C_6H_3$) | 3 | Q-7 | 3 |
| $CH_2$(2,6-$F_2C_6H_3$) | 3 | Q-8 | 3 |
| $CH_2$(2,4,6-$F_3C_6H_2$) | 3 | Q-15 | 3 |
| $CH_2$(2-$ClC_6H_4$) | 3 | $CH_2$(2-$BrC_6H_4$) | 3 |
| $CH_2$(3-$ClC_6H_4$) | 3 | $CH_2$(2,6-$Br_2C_6H_3$) | 3 |
| $CH_2$(4-$ClC_6H_4$) | 3 | $CH_2$(2-Cl-6-$FC_6H_3$) | 3 |
| $CH_2$(2,6-$Cl_2C_6H_3$) | 3 | $CH_2$(2-($OCH_3$)$C_6H_4$) | 3 |
| $CH_2$(2-($CH_3$)$C_6H_4$) | 3 | $CH_2$(2-(CN)$C_6H_4$) | 3 |
| $CH_2$(3-($CH_3$)$C_6H_4$) | 3 | $CH_2$(2-$CF_3$)$C_6H_4$) | 3 |
| $CH_2$(4-($CH_3$)$C_6H_4$) | 3 | $CH_2$(2-($OCF_3$)$C_6H_4$) | 3 |
| $CH_2$(2-pyridyl) | 3 | $CH_2$(2-($SCH_3$)$C_6H_4$) | 3 |
| $CH_2$(2-thienyl) | 3 | $CH_2$(2-(CH=$CH_2$)$C_6H_4$) | 3 |
| $CH_2$(2-furanyl) | 3 | $CH_2$(2-(C≡CH)$C_6H_4$) | 3 |
| General Structure 2, $R^5 = R^6$ is H, $R^2$ is $CH_2CH_3$ | | | |
| $CH_2(C_6H_5)$ | 3 | $CH_2$(2-tetrahydrofuranyl) | 3 |
| $CH_2$(2-$FC_6H_4$) | 3 | $CH_2$(2-tetrahydropyranyl) | 3 |
| $CH_2$(3-$FC_6H_4$) | 3 | Q-1 | 3 |
| $CH_2$(4-$FC_6H_4$) | 3 | Q-3 | 3 |
| $CH_2$(2,3-$F_2C_6H_3$) | 3 | Q-4 | 3 |
| $CH_2$(2,4-$F_2C_6H_3$) | 3 | Q-6 | 3 |
| $CH_2$(2,5-$F_2C_6H_3$) | 3 | Q-7 | 3 |
| $CH_2$(2,6-$F_2C_6H_3$) | 3 | Q-8 | 3 |
| $CH_2$(2,4,6-$F_3C_6H_2$) | 3 | Q-15 | 3 |
| $CH_2$(2-$ClC_6H_4$) | 3 | $CH_2$(2-$BrC_6H_4$) | 3 |
| $CH_2$(3-$ClC_6H_4$) | 3 | $CH_2$(2,6-$Br_2C_6H_3$) | 3 |
| $CH_2$(4-$ClC_6H_4$) | 3 | $CH_2$(2-Cl-6-$FC_6H_3$) | 3 |
| $CH_2$(2,6-$Cl_2C_6H_3$) | 3 | $CH_2$(2-($OCH_3$)$C_6H_4$) | 3 |
| $CH_2$(2-($CH_3$)$C_6H_4$) | 3 | $CH_2$(2-(CN)$C_6H_4$) | 3 |
| $CH_2$(3-($CH_3$)$C_6H_4$) | 3 | $CH_2$(2-$CF_3$)$C_6H_4$) | 3 |
| $CH_2$(4-($CH_3$)$C_6H_4$) | 3 | $CH_2$(2-($OCF_3$)$C_6H_4$) | 3 |
| $CH_2$(2-pyridyl) | 3 | $CH_2$(2-($SCH_3$)$C_6H_4$) | 3 |
| $CH_2$(2-thienyl) | 3 | $CH_2$(2-(CH=$CH_2$)$C_6H_4$) | 3 |
| $CH_2$(2-furanyl) | 3 | $CH_2$(2-(C≡CH)$C_6H_4$) | 3 |
| General Structure 2, $R^5$ is $OCH_3$, $R^6$ is H, $R^2$ is $CH_3$ | | | |
| $CH_2(C_6H_5)$ | 3 | $CH_2$(2-tetrahydrofuranyl) | 3 |
| $CH_2$(2-$FC_6H_4$) | 3 | $CH_2$(2-tetrahydropyranyl) | 3 |
| $CH_2$(3-$FC_6H_4$) | 3 | Q-1 | 3 |
| $CH_2$(4-$FC_6H_4$) | 3 | Q-3 | 3 |
| $CH_2$(2,3-$F_2C_6H_3$) | 3 | Q-4 | 3 |
| $CH_2$(2,4-$F_2C_6H_3$) | 3 | Q-6 | 3 |
| $CH_2$(2,5-$F_2C_6H_3$) | 3 | Q-7 | 3 |
| $CH_2$(2,6-$F_2C_6H_3$) | 3 | Q-8 | 3 |
| $CH_2$(2,4,6-$F_3C_6H_2$) | 3 | Q-15 | 3 |
| $CH_2$(2-$ClC_6H_4$) | 3 | $CH_2$(2-$BrC_6H_4$) | 3 |
| $CH_2$(3-$ClC_6H_4$) | 3 | $CH_2$(2,6-$Br_2C_6H_3$) | 3 |
| $CH_2$(4-$ClC_6H_4$) | 3 | $CH_2$(2-Cl-6-$FC_6H_3$) | 3 |
| $CH_2$(2,6-$Cl_2C_6H_3$) | 3 | $CH_2$(2-($OCH_3$)$C_6H_4$) | 3 |
| $CH_2$(2-($CH_3$)$C_6H_4$) | 3 | $CH_2$(2-(CN)$C_6H_4$) | 3 |
| $CH_2$(3-($CH_3$)$C_6H_4$) | 3 | $CH_2$(2-$CF_3$)$C_6H_4$) | 3 |
| $CH_2$(4-($CH_3$)$C_6H_4$) | 3 | $CH_2$(2-($OCF_3$)$C_6H_4$) | 3 |
| $CH_2$(2-pyridyl) | 3 | $CH_2$(2-($SCH_3$)$C_6H_4$) | 3 |
| $CH_2$(2-thienyl) | 3 | $CH_2$(2-(CH=$CH_2$)$C_6H_4$) | 3 |
| $CH_2$(2-furanyl) | 3 | $CH_2$(2-(C≡CH)$C_6H_4$) | 3 |

TABLE 3

| Q | $R^3$ | Q | $R^3$ |
|---|---|---|---|
| General Structure 3, n is 2, $R^1$ is $CH_3$, $R^2$ is H | | | |
| $CH_2(C_6H_5)$ | H | $CH_2$(2-tetrahydrofuranyl) | H |
| $CH_2$(2-$FC_6H_4$) | H | $CH_2$(2-tetrahydropyranyl) | H |
| $CH_2$(3-$FC_6H_4$) | H | Q-1 | H |
| $CH_2$(4-$FC_6H_4$) | H | Q-3 | H |
| $CH_2$(2,3-$F_2C_6H_3$) | H | Q-4 | H |
| $CH_2$(2,4-$F_2C_6H_3$) | H | Q-6 | H |
| $CH_2$(2,5-$F_2C_6H_3$) | H | Q-7 | H |
| $CH_2$(2,6-$F_2C_6H_3$) | H | Q-8 | H |
| $CH_2$(2,4,6-$F_3C_6H_2$) | H | Q-15 | H |
| $CH_2$(2-$ClC_6H_4$) | H | $CH_2$(2-$BrC_6H_4$) | H |
| $CH_2$(3-$ClC_6H_4$) | H | $CH_2$(2,6-$Br_2C_6H_3$) | H |
| $CH_2$(4-$ClC_6H_4$) | H | $CH_2$(2-Cl-6-$FC_6H_3$) | H |
| $CH_2$(2,6-$Cl_2C_6H_3$) | H | $CH_2$(2-($OCH_3$)$C_6H_4$) | H |
| $CH_2$(2-($CH_3$)$C_6H_4$) | H | $CH_2$(2-(CN)$C_6H_4$) | H |
| $CH_2$(3-($CH_3$)$C_6H_4$) | H | $CH_2$(2-$CF_3$)$C_6H_4$) | H |
| $CH_2$(4-($CH_3$)$C_6H_4$) | H | $CH_2$(2-$OCF_3$)$C_6H_4$) | H |
| $CH_2$(2-pyridyl) | H | $CH_2$(2-($SCH_3$)$C_6H_4$) | H |
| $CH_2$(2-thienyl) | H | $CH_2$(2-(CH=$CH_2$)$C_6H_4$) | H |
| $CH_2$(2-furanyl) | H | $CH_2$(2-(C≡CH)$C_6H_4$) | H |
| $CH_2(C_6H_5)$ | $CH_3$ | $CH_2$(2-tetrahydrofuranyl) | $CH_3$ |
| $CH_2$(2-$FC_6H_4$) | $CH_3$ | $CH_2$(2-tetrahydropyranyl) | $CH_3$ |
| $CH_2$(3-$FC_6H_4$) | $CH_3$ | Q-1 | $CH_3$ |
| $CH_2$(4-$FC_6H_4$) | $CH_3$ | Q-3 | $CH_3$ |
| $CH_2$(2,3-$F_2C_6H_3$) | $CH_3$ | Q-4 | $CH_3$ |
| $CH_2$(2,4-$F_2C_6H_3$) | $CH_3$ | Q-6 | $CH_3$ |
| $CH_2$(2,5-$F_2C_6H_3$) | $CH_3$ | Q-7 | $CH_3$ |
| $CH_2$(2,6-$F_2C_6H_3$) | $CH_3$ | Q-8 | $CH_3$ |
| $CH_2$(2,4,6-$F_3C_6H_2$) | $CH_3$ | Q-15 | $CH_3$ |
| $CH_2$(2-$ClC_6H_4$) | $CH_3$ | $CH_2$(2-$BrC_6H_4$) | $CH_3$ |
| $CH_2$(3-$ClC_6H_4$) | $CH_3$ | $CH_2$(2,6-$Br_2C_6H_3$) | $CH_3$ |
| $CH_2$(4-$ClC_6H_4$) | $CH_3$ | $CH_2$(2-Cl-6-$FC_6H_3$) | $CH_3$ |
| $CH_2$(2,6-$Cl_2C_6H_3$) | $CH_3$ | $CH_2$(2-($OCH_3$)$C_6H_4$) | $CH_3$ |
| $CH_2$(2-($CH_3$)$C_6H_4$) | $CH_3$ | $CH_2$(2-(CN)$C_6H_4$) | $CH_3$ |
| $CH_2$(3-($CH_3$)$C_6H_4$) | $CH_3$ | $CH_2$(2-$CF_3$)$C_6H_4$) | $CH_3$ |
| $CH_2$(4-($CH_3$)$C_6H_4$) | $CH_3$ | $CH_2$(2-($OCF_3$)$C_6H_4$) | $CH_3$ |

TABLE 3-continued

| Q | R³ | Q | R³ |
|---|---|---|---|
| CH₂(2-pyridyl) | CH₃ | CH₂(2-(SCH₃)C₆H₄) | CH₃ |
| CH₂(2-thienyl) | CH₃ | CH₂(2-(CH=CH₂)C₆H₄) | CH₃ |
| CH₂(2-furanyl) | CH₃ | CH₂(2-(C≡CH)C₆H₄) | CH₃ |
| CH₂(C₆H₅) | CH₂CH₃ | CH₂(C₆H₅) | CH₂C≡CH |
| CH₂(2-FC₆H₄) | CH₂CH₃ | CH₂(2-FC₆H₄) | CH₂C≡CH |
| CH₂(2,6-F₂C₆H₃) | CH₂CH₃ | CH₂(2,6-F₂C₆H₃) | CH₂C≡CH |
| CH₂(2-ClC₆H₄) | CH₂CH₃ | CH₂(2-ClC₆H₄) | CH₂C≡CH |
| CH₂(2-Cl-6-FC₆H₃) | CH₂CH₃ | CH₂(2-Cl-6-FC₆H₃) | CH₂C≡CH |
| CH₂(2-(CH₃)C₆H₄) | CH₂CH₃ | CH₂(2-(CH₃)C₆H₄) | CH₂C≡CH |
| CH₂(2-pyridyl) | CH₂CH₃ | CH₂(2-pyridyl) | CH₂C≡CH |
| Q-1 | CH₂CH₃ | Q-1 | CH₂C≡CH |
| CH₂(C₆H₅) | CH₂CH=CH₂ | CH₂(C₆H₅) | CH₂CH₂OCH₃ |
| CH₂(2-FC₆H₄) | CH₂CH=CH₂ | CH₂(2-FC₆H₄) | CH₂CH₂OCH₃ |
| CH₂(2,6-F₂C₆H₃) | CH₂CH=CH₂ | CH₂(2,6-F₂C₆H₃) | CH₂CH₂OCH₃ |
| CH₂(2-ClC₆H₄) | CH₂CH=CH₂ | CH₂(2-ClC₆H₄) | CH₂CH₂OCH₃ |
| CH₂(2-Cl-6-FC₆H₃) | CH₂CH=CH₂ | CH₂(2-Cl-6-FC₆H₃) | CH₂CH₂OCH₃ |
| CH₂(2-(CH₃)C₆H₄) | CH₂CH=CH₂ | CH₂(2-(CH₃)C₆H₄) | CH₂CH₂OCH₃ |
| CH₂(2-pyridyl) | CH₂CH=CH₂ | CH₂(2-pyridyl) | CH₂CH₂OCH₃ |
| Q-1 | CH₂CH=CH₂ | Q-1 | CH₂CH₂OCH₃ |
| General Structure 3, n is 2, R¹ is CH₃, R² is CH₃ ||||
| CH₂(C₆H₅) | H | CH₂(2-tetrahydrofuranyl) | H |
| CH₂(2-FC₆H₄) | H | CH₂(2-tetrahydropyranyl) | H |
| CH₂(3-FC₆H₄) | H | Q-1 | H |
| CH₂(4-FC₆H₄) | H | Q-3 | H |
| CH₂(2,3-F₂C₆H₃) | H | Q-4 | H |
| CH₂(2,4-F₂C₆H₃) | H | Q-6 | H |
| CH₂(2,5-F₂C₆H₃) | H | Q-7 | H |
| CH₂(2,6-F₂C₆H₃) | H | Q-8 | H |
| CH₂(2,4,6-F₃C₆H₂) | H | Q-15 | H |
| CH₂(2-ClC₆H₄) | H | CH₂(2-BrC₆H₄) | H |
| CH₂(3-ClC₆H₄) | H | CH₂(2,6-Br₂C₆H₃) | H |
| CH₂(4-ClC₆H₄) | H | CH₂(2-Cl-6-FC₆H₃) | H |
| CH₂(2,6-Cl₂C₆H₃) | H | CH₂(2-(OCH₃)C₆H₄) | H |
| CH₂(2-(CH₃)C₆H₄) | H | CH₂(2-(CN)C₆H₄) | H |
| CH₂(3-(CH₃)C₆H₄) | H | CH₂(2-(CF₃)C₆H₄) | H |
| CH₂(4-(CH₃)C₆H₄) | H | CH₂(2-(OCF₃)C₆H₄) | H |
| CH₂(2-pyridyl) | H | CH₂(2-(SCH₃)C₆H₄) | H |
| CH₂(2-thienyl) | H | CH₂(2-(CH=CH₂)C₆H₄) | H |
| CH₂(2-furanyl) | H | CH₂(2-(C≡CH)C₆H₄) | H |
| CH₂(C₆H₅) | CH₃ | CH₂(2-tetrahydrofuranyl) | CH₃ |
| CH₂(2-FC₆H₄) | CH₃ | CH₂(2-tetrahydropyranyl) | CH₃ |
| CH₂(3-FC₆H₄) | CH₃ | Q-1 | CH₃ |
| CH₂(4-FC₆H₄) | CH₃ | Q-3 | CH₃ |
| CH₂(2,3-F₂C₆H₃) | CH₃ | Q-4 | CH₃ |
| CH₂(2,4-F₂C₆H₃) | CH₃ | Q-6 | CH₃ |
| CH₂(2,5-F₂C₆H₃) | CH₃ | Q-7 | CH₃ |
| CH₂(2,6-F₂C₆H₃) | CH₃ | Q-8 | CH₃ |
| CH₂(2,4,6-F₃C₆H₂) | CH₃ | Q-15 | CH₃ |
| CH₂(2-ClC₆H₄) | CH₃ | CH₂(2-BrC₆H₄) | CH₃ |
| CH₂(3-ClC₆H₄) | CH₃ | CH₂(2,6-Br₂C₆H₃) | CH₃ |
| CH₂(4-ClC₆H₄) | CH₃ | CH₂(2-Cl-6-FC₆H₃) | CH₃ |
| CH₂(2,6-Cl₂C₆H₃) | CH₃ | CH₂(2-(OCH₃)C₆H₄) | CH₃ |
| CH₂(2-(CH₃)C₆H₄) | CH₃ | CH₂(2-(CN)C₆H₄) | CH₃ |
| CH₂(3-(CH₃)C₆H₄) | CH₃ | CH₂(2-(CF₃)C₆H₄) | CH₃ |
| CH₂(4-(CH₃)C₆H₄) | CH₃ | CH₂(2-(OCF₃)C₆H₄) | CH₃ |
| CH₂(2-pyridyl) | CH₃ | CH₂(2-(SCH₃)C₆H₄) | CH₃ |
| CH₂(2-thienyl) | CH₃ | CH₂(2-(CH=CH₂)C₆H₄) | CH₃ |
| CH₂(2-furanyl) | CH₃ | CH₂(2-(C≡CH)C₆H₄) | CH₃ |
| CH₂(C₆H₅) | CH₂CH₃ | CH₂(C₆H₅) | CH₂C≡CH |
| CH₂(2-FC₆H₄) | CH₂CH₃ | CH₂(2-FC₆H₄) | CH₂C≡CH |
| CH₂(2,6-F₂C₆H₃) | CH₂CH₃ | CH₂(2,6-F₂C₆H₃) | CH₂C≡CH |
| CH₂(2-ClC₆H₄) | CH₂CH₃ | CH₂(2-ClC₆H₄) | CH₂C≡CH |
| CH₂(2-Cl-6-FC₆H₃) | CH₂CH₃ | CH₂(2-Cl-6-FC₆H₃) | CH₂C≡CH |
| CH₂(2-(CH₃)C₆H₄) | CH₂CH₃ | CH₂(2-(CH₃)C₆H₄) | CH₂C≡CH |
| CH₂(2-pyridyl) | CH₂CH₃ | CH₂(2-pyridyl) | CH₂C≡CH |
| Q-1 | CH₂CH₃ | Q-1 | CH₂C≡CH |
| CH₂(C₆H₅) | CH₂CH=CH₂ | CH₂(C₆H₅) | CH₂CH₂OCH₃ |
| CH₂(2-FC₆H₄) | CH₂CH=CH₂ | CH₂(2-FC₆H₄) | CH₂CH₂OCH₃ |
| CH₂(2,6-F₂C₆H₃) | CH₂CH=CH₂ | CH₂(2,6-F₂C₆H₃) | CH₂CH₂OCH₃ |
| CH₂(2-ClC₆H₄) | CH₂CH=CH₂ | CH₂(2-ClC₆H₄) | CH₂CH₂OCH₃ |
| CH₂(2-Cl-6-FC₆H₃) | CH₂CH=CH₂ | CH₂(2-Cl-6-FC₆H₃) | CH₂CH₂OCH₃ |
| CH₂(2-(CH₃)C₆H₄) | CH₂CH=CH₂ | CH₂(2-(CH₃)C₆H₄) | CH₂CH₂OCH₃ |
| CH₂(2-pyridyl) | CH₂CH=CH₂ | CH₂(2-pyridyl) | CH₂CH₂OCH₃ |
| Q-1 | CH₂CH=CH₂ | Q-1 | CH₂CH₂OCH₃ |
| General Structure 3, n is 3, R¹ is CH₃, R² is H ||||
| CH₂(C₆H₅) | H | CH₂(2-tetrahydrofuranyl) | H |
| CH₂(2-FC₆H₄) | H | CH₂(2-tetrahydropyranyl) | H |
| CH₂(3-FC₆H₄) | H | Q-1 | H |
| CH₂(4-FC₆H₄) | H | Q-3 | H |
| CH₂(2,3-F₂C₆H₃) | H | Q-4 | H |

TABLE 3-continued

| Q | R³ | Q | R³ |
|---|---|---|---|
| CH₂(2,4-F₂C₆H₃) | H | Q-6 | H |
| CH₂(2,5-F₂C₆H₃) | H | Q-7 | H |
| CH₂(2,6-F₂C₆H₃) | H | Q-8 | H |
| CH₂(2,4,6-F₃C₆H₂) | H | Q-15 | H |
| CH₂(2-ClC₆H₄) | H | CH₂(2-BrC₆H₄) | H |
| CH₂(3-ClC₆H₄) | H | CH₂(2,6-Br₂C₆H₃) | H |
| CH₂(4-ClC₆H₄) | H | CH₂(2-Cl-6-FC₆H₃) | H |
| CH₂(2,6-Cl₂C₆H₃) | H | CH₂(2-(OCH₃)C₆H₄) | H |
| CH₂(2-(CH₃)C₆H₄) | H | CH₂(2-(CN)C₆H₄) | H |
| CH₂(3-(CH₃)C₆H₄) | H | CH₂(2-(CF₃)C₆H₄) | H |
| CH₂(4-(CH₃)C₆H₄) | H | CH₂(2-(OCF₃)C₆H₄) | H |
| CH₂(2-pyridyl) | H | CH₂(2-(SCH₃)C₆H₄) | H |
| CH₂(2-thienyl) | H | CH₂(2-(CH=CH₂)C₆H₄) | H |
| CH₂(2-furanyl) | H | CH₂(2-(C≡CH)C₆H₄) | H |
| CH₂(C₆H₅) | CH₃ | CH₂(2-tetrahydrofuranyl) | CH₃ |
| CH₂(2-FC₆H₄) | CH₃ | CH₂(2-tetrahydropyranyl) | CH₃ |
| CH₂(3-FC₆H₄) | CH₃ | Q-1 | CH₃ |
| CH₂(4-FC₆H₄) | CH₃ | Q-3 | CH₃ |
| CH₂(2,3-F₂C₆H₃) | CH₃ | Q-4 | CH₃ |
| CH₂(2,4-F₂C₆H₃) | CH₃ | Q-6 | CH₃ |
| CH₂(2,5-F₂C₆H₃) | CH₃ | Q-7 | CH₃ |
| CH₂(2,6-F₂C₆H₃) | CH₃ | Q-8 | CH₃ |
| CH₂(2,4,6-F₃C₆H₂) | CH₃ | Q-15 | CH₃ |
| CH₂(2-ClC₆H₄) | CH₃ | CH₂(2-BrC₆H₄) | CH₃ |
| CH₂(3-ClC₆H₄) | CH₃ | CH₂(2,6-Br₂C₆H₃) | CH₃ |
| CH₂(4-ClC₆H₄) | CH₃ | CH₂(2-Cl-6-FC₆H₃) | CH₃ |
| CH₂(2,6-Cl₂C₆H₃) | CH₃ | CH₂(2-(OCH₃)C₆H₄) | CH₃ |
| CH₂(2-(CH₃)C₆H₄) | CH₃ | CH₂(2-(CN)CH₆H₄) | CH₃ |
| CH₂(3-(CH₃)C₆H₄) | CH₃ | CH₂(2-(CF₃)C₆H₄) | CH₃ |
| CH₂(4-(CH₃)C₆H₄) | CH₃ | CH₂(2-(OCF₃)C₆H₄) | CH₃ |
| CH₂(2-pyridyl) | CH₃ | CH₂(2-(SCH₃)C₆H₄) | CH₃ |
| CH₂(2-thienyl) | CH₃ | CH₂(2-(CH=CH₂)C₆H₄) | CH₃ |
| CH₂(2-furanyl) | CH₃ | CH₂(2-(C≡CH)C₆H₄) | CH₃ |
| CH₂(C₆H₅) | CH₂CH₃ | CH₂(C₆H₅) | CH₂C≡CH |
| CH₂(2-FC₆H₄) | CH₂CH₃ | CH₂(2-FC₆H₄) | CH₂C≡CH |
| CH₂(2,6-F₂C₆H₃) | CH₂CH₃ | CH₂(2,6-F₂C₆H₃) | CH₂C≡CH |
| CH₂(2-ClC₆H₄) | CH₂CH₃ | CH₂(2-ClC₆H₄) | CH₂C≡CH |
| CH₂(2-Cl-6-FC₆H₃) | CH₂CH₃ | CH₂(2-Cl-6-FC₆H₃) | CH₂C≡CH |
| CH₂(2-(CH₃)C₆H₄) | CH₂CH₃ | CH₂(2-(CH₃)C₆H₄) | CH₂C≡CH |
| CH₂(2-pyridyl) | CH₂CH₃ | CH₂(2-pyridyl) | CH₂C≡CH |
| Q-1 | CH₂CH₃ | Q-1 | CH₂C≡CH |
| CH₂(C₆H₅) | CH₂CH=CH₂ | CH₂(C₆H₅) | CH₂CH₂OCH₃ |
| CH₂(2-FC₆H₄) | CH₂CH=CH₂ | CH₂(2-FC₆H₄) | CH₂CH₂OCH₃ |
| CH₂(2,6-F₂C₆H₃) | CH₂CH=CH₂ | CH₂(2,6-F₂C₆H₃) | CH₂CH₂OCH₃ |
| CH₂(2-ClC₆H₄) | CH₂CH=CH₂ | CH₂(2-ClC₆H₄) | CH₂CH₂OCH₃ |
| CH₂(2-Cl-6-FC₆H₃) | CH₂CH=CH₂ | CH₂(2-Cl-6-FC₆H₃) | CH₂CH₂OCH₃ |
| CH₂(2-(CH₃)C₆H₄) | CH₂CH=CH₂ | CH₂(2-(CH₃)C₆H₄) | CH₂CH₂OCH₃ |
| CH₂(2-pyridyl) | CH₂CH=CH₂ | CH₂(2-pyridyl) | CH₂CH₂OCH₃ |
| Q-1 | CH₂CH=CH₂ | Q-1 | CH₂CH₂OCH₃ |
| General Structure 3, n is 3, R¹ is CH₃, R² is CH₃ | | | |
| CH₂(C₆H₅) | H | CH₂(2-tetrahydrofuranyl) | H |
| CH₂(2-FC₆H₄) | H | CH₂(2-tetrahydropyranyl) | H |
| CH₂(3-FC₆H₄) | H | Q-1 | H |
| CH₂(4-FC₆H₄) | H | Q-3 | H |
| CH₂(2,3-F₂C₆H₃) | H | Q-4 | H |
| CH₂(2,4-F₂C₆H₃) | H | Q-6 | H |
| CH₂(2,5-F₂C₆H₃) | H | Q-7 | H |
| CH₂(2,6-F₂C₆H₃) | H | Q-8 | H |
| CH₂(2,4,6-F₃C₆H₂) | H | Q-15 | H |
| CH₂(2-ClC₆H₄) | H | CH₂(2-BrC₆H₄) | H |
| CH₂(3-ClC₆H₄) | H | CH₂(2,6-Br₂C₆H₃) | H |
| CH₂(4-ClC₆H₄) | H | CH₂(2-Cl-6-FC₆H₃) | H |
| CH₂(2,6-Cl₂C₆H₃) | H | CH₂(2-(OCH₃)C₆H₄) | H |
| CH₂(2-(CH₃)C₆H₄) | H | CH₂(2-(CN)C₆H₄) | H |
| CH₂(3-(CH₃)C₆H₄) | H | CH₂(2-(CF₃)C₆H₄) | H |
| CH₂(4-(CH₃)C₆H₄) | H | CH₂(2-(OCF₃)C₆H₄) | H |
| CH₂(2-pyridyl) | H | CH₂(2-(SCH₃)C₆H₄) | H |
| CH₂(2-thienyl) | H | CH₂(2-(CH=CH₂)C₆H₄) | H |
| CH₂(2-furanyl) | H | CH₂(2-(C≡CH)C₆H₄) | H |
| CH₂(C₆H₅) | CH₃ | CH₂(2-tetrahydrofuranyl) | CH₃ |
| CH₂(2-FC₆H₄) | CH₃ | CH₂(2-tetrahydropyranyl) | CH₃ |
| CH₂(3-FC₆H₄) | CH₃ | Q-1 | CH₃ |
| CH₂(4-FC₆H₄) | CH₃ | Q-3 | CH₃ |
| CH₂(2,3-F₂C₆H₃) | CH₃ | Q-4 | CH₃ |
| CH₂(2,4-F₂C₆H₃) | CH₃ | Q-6 | CH₃ |
| CH₂(2,6-F₂C₆H₃) | CH₃ | Q-7 | CH₃ |
| CH₂(2,6-F₂C₆H₃) | CH₃ | Q-8 | CH₃ |
| CH₂(2,4,6-F₃C₆H₂) | CH₃ | Q-15 | CH₃ |
| CH₂(2-ClC₆H₄) | CH₃ | CH₂(2-BrC₆H₄) | CH₃ |
| CH₂(3-ClC₆H₄) | CH₃ | CH₂(2,6-Br₂C₆H₃) | CH₃ |
| CH₂(4-ClC₆H₄) | CH₃ | CH₂(2-Cl-6-FC₆H₃) | CH₃ |

TABLE 3-continued

| Q | R³ | Q | R³ |
|---|---|---|---|
| CH₂(2,6-Cl₂C₆H₃) | CH₃ | CH₂(2-(OCH₃)C₆H₄) | CH₃ |
| CH₂(2-(CH₃)C₆H₄) | CH₃ | CH₂(2-(CN)C₆H₄) | CH₃ |
| CH₂(3-(CH₃)C₆H₄) | CH₃ | CH₂(2-(CF₃)C₆H₄) | CH₃ |
| CH₂(4-(CH₃)C₆H₄) | CH₃ | CH₂(2-(OCF₃)C₆H₄) | CH₃ |
| CH₂(2-pyridyl) | CH₃ | CH₂(2-(SCH₃)C₆H₄) | CH₃ |
| CH₂(2-thienyl) | CH₃ | CH₂(2-(CH=CH₂)C₆H₄) | CH₃ |
| CH₂(2-furanyl) | CH₃ | CH₂(2-(C≡CH)C₆H₄) | CH₃ |
| CH₂(C₆H₅) | CH₂CH₃ | CH₂(C₆H₅) | CH₂C≡CH |
| CH₂(2-FC₆H₄) | CH₂CH₃ | CH₂(2-FC₆H₄) | CH₂C≡CH |
| CH₂(2,6-F₂C₆H₃) | CH₂CH₃ | CH₂(2,6-F₂C₆H₃) | CH₂C≡CH |
| CH₂(2-ClC₆H₄) | CH₂CH₃ | CH₂(2-ClC₆H₄) | CH₂C≡CH |
| CH₂(2-Cl-6-FC₆H₃) | CH₂CH₃ | CH₂(2-Cl-6-FC₆H₃) | CH₂C≡CH |
| CH₂(2-(CH₃)C₆H₄) | CH₂CH₃ | CH₂(2-(CH₃)C₆H₄) | CH₂C≡CH |
| CH₂(2-pyridyl) | CH₂CH₃ | CH₂(2-pyridyl) | CH₂C≡CH |
| Q-1 | CH₂CH₃ | Q-1 | CH₂C≡CH |
| CH₂(C₆H₅) | CH₂CH=CH₂ | CH₂(C₆H₅) | CH₂CH₂OCH₃ |
| CH₂(2-FC₆H₄) | CH₂CH=CH₂ | CH₂(2-FC₆H₄) | CH₂CH₂OCH₃ |
| CH₂(2,6-F₂C₆H₃) | CH₂CH=CH₂ | CH₂(2,6-F₂C₆H₃) | CH₂CH₂OCH₃ |
| CH₂(2-ClC₆H₄) | CH₂CH=CH₂ | CH₂(2-ClC₆H₄) | CH₂CH₂OCH₃ |
| CH₂(2-Cl-6-FC₆H₃) | CH₂CH=CH₂ | CH₂(2-Cl-6-FC₆H₃) | CH₂CH₂OCH₃ |
| CH₂(2-(CH₃)C₆H₄) | CH₂CH=CH₂ | CH₂(2-(CH₃)C₆H₄) | CH₂CH₂OCH₃ |
| CH₂(2-pyridyl) | CH₂CH=CH₂ | CH₂(2-pyridyl) | CH₂CH₂OCH₃ |
| Q-1 | CH₂CH=CH₂ | Q-1 | CH₂CH₂OCH₃ |
| General Structure 3, n is 4, R¹ is CH₃, R² is H | | | |
| CH₂(C₆H₅) | H | CH₂(2-tetrahydrofuranyl) | H |
| CH₂(2-FC₆H₄) | H | CH₂(2-tetrahydropyranyl) | H |
| CH₂(3-FC₆H₄) | H | Q-1 | H |
| CH₂(4-FC₆H₄) | H | Q-3 | H |
| CH₂(2,3-F₂C₆H₃) | H | Q-4 | H |
| CH₂(2,4-F₂C₆H₃) | H | Q-6 | H |
| CH₂(2,5-F₂C₆H₃) | H | Q-7 | H |
| CH₂(2,6-F₂C₆H₃) | H | Q-8 | H |
| CH₂(2,4,6-F₃C₆H₂) | H | Q-15 | H |
| CH₂(2-ClC₆H₄) | H | CH₂(2-BrC₆H₄) | H |
| CH₂(3-ClC₆H₄) | H | CH₂(2,6-Br₂C₆H₃) | H |
| CH₂(4-ClC₆H₄) | H | CH₂(2-Cl-6-FC₆H₃) | H |
| CH₂(2,6-Cl₂C₆H₃) | H | CH₂(2-(OCH₃)C₆H₄) | H |
| CH₂(2-(CH₃)C₆H₄) | H | CH₂(2-(CN)C₆H₄) | H |
| CH₂(3-(CH₃)C₆H₄) | H | CH₂(2-(CF₃)C₆H₄) | H |
| CH₂(4-(CH₃)C₆H₄) | H | CH₂(2-(OCF₃)C₆H₄) | H |
| CH₂(2-pyridyl) | H | CH₂(2-(SCH₃)C₆H₄) | H |
| CH₂(2-thienyl) | H | CH₂(2-(CH=CH₂)C₆H₄) | H |
| CH₂(2-furanyl) | H | CH₂(2-(C≡CH)C₆H₄) | H |
| CH₂(C₆H₅) | CH₃ | CH₂(2-tetrahydrofuranyl) | CH₃ |
| CH₂(2-FC₆H₄) | CH₃ | CH₂(2-tetrahydropyranyl) | CH₃ |
| CH₂(3-FC₆H₄) | CH₃ | Q-1 | CH₃ |
| CH₂(4-FC₆H₄) | CH₃ | Q-3 | CH₃ |
| CH₂(2,3-F₂C₆H₃) | CH₃ | Q-4 | CH₃ |
| CH₂(2,4-F₂C₆H₃) | CH₃ | Q-6 | CH₃ |
| CH₂(2,5-F₂C₆H₃) | CH₃ | Q-7 | CH₃ |
| CH₂(2,6-F₂C₆H₃) | CH₃ | Q-8 | CH₃ |
| CH₂(2,4,6-F₃C₆H₂) | CH₃ | Q-15 | CH₃ |
| CH₂(2-ClC₆H₄) | CH₃ | CH₂(2-BrC₆H₄) | CH₃ |
| CH₂(3-ClC₆H₄) | CH₃ | CH₂(2,6-Br₂C₆H₃) | CH₃ |
| CH₂(4-ClC₆H₄) | CH₃ | CH₂(2-Cl-6-FC₆H₃) | CH₃ |
| CH₂(2,6-Cl₂C₆H₃) | CH₃ | CH₂(2-(OCH₃)C₆H₄) | CH₃ |
| CH₂(2-(CH₃)C₆H₄) | CH₃ | CH₂(2-(CN)C₆H₄) | CH₃ |
| CH₂(3-(CH₃)C₆H₄) | CH₃ | CH₂(2-(CF₃)C₆H₄) | CH₃ |
| CH₂(4-(CH₃)C₆H₄) | CH₃ | CH₂(2-(OCF₃)C₆H₄) | CH₃ |
| CH₂(2-pyridyl) | CH₃ | CH₂(2-(SCH₃)C₆H₄) | CH₃ |
| CH₂(2-thienyl) | CH₃ | CH₂(2-(CH=CH₂)C₆H₄) | CH₃ |
| CH₂(2-furanyl) | CH₃ | CH₂(2-(C≡CH)C₆H₄) | CH₃ |
| CH₂(C₆H₅) | CH₂CH₃ | CH₂(C₆H₅) | CH₂C≡CH |
| CH₂(2-FC₆H₄) | CH₂CH₃ | CH₂(2-FC₆H₄) | CH₂C≡CH |
| CH₂(2-6-F₂C₆H₃) | CH₂CH₃ | CH₂(2,6-F₂C₆H₃) | CH₂C≡CH |
| CH₂(2-ClC₆H₄) | CH₂CH₃ | CH₂(2-ClC₆H₄) | CH₂C≡CH |
| CH₂(2-Cl-6-FC₆H₃) | CH₂CH₃ | CH₂(2-Cl-6-FC₆H₃) | CH₂C≡CH |
| CH₂(2-(CH₃)C₆H₄) | CH₂CH₃ | CH₂(2-(CH₃)C₆H₄) | CH₂C≡CH |
| CH₂(2-pyridyl) | CH₂CH₃ | CH₂(2-pyridyl) | CH₂C≡CH |
| Q-1 | CH₂CH₃ | Q-1 | CH₂C≡CH |
| CH₂(C₆H₅) | CH₂CH=CH₂ | CH₂(C₆H₅) | CH₂CH₂OCH₃ |
| CH₂(2-FC₆H₄) | CH₂CH=CH₂ | CH₂(2-FC₆H₄) | CH₂CH₂OCH₃ |
| CH₂(2,6-F₂C₆H₃) | CH₂CH=CH₂ | CH₂(2,6-F₂C₆H₃) | CH₂CH₂OCH₃ |
| CH₂(2-ClC₆H₄) | CH₂CH=CH₂ | CH₂(2-ClC₆H₄) | CH₂CH₂OCH₃ |
| CH₂(2-Cl-6-FC₆H₃) | CH₂CH=CH₂ | CH₂(2-Cl-6-FC₆H₃) | CH₂CH₂OCH₃ |
| CH₂(2-(CH₃)C₆H₄) | CH₂CH=CH₂ | CH₂(2-(CH₃)C₆H₄) | CH₂CH₂OCH₃ |
| CH₂(2-pyridyl) | CH₂CH=CH₂ | CH₂(2-pyridyl) | CH₂CH₂OCH₃ |
| Q-1 | CH₂CH=CH₂ | Q-1 | CH₂CH₂OCH₃ |
| General Structure 3, n is 4, R¹ is CH₃, R² is CH₃ | | | |
| CH₂(C₆H₅) | H | CH₂(2-tetrahydrofuranyl) | H |

TABLE 3-continued

| Q | R³ | Q | R³ |
|---|---|---|---|
| CH₂(2-FC₆H₄) | H | CH₂(2-tetrahydropyranyl) | H |
| CH₂(3-FC₆H₄) | H | Q-1 | H |
| CH₂(4-FC₆H₄) | H | Q-3 | H |
| CH₂(2,3-F₂C₆H₃) | H | Q-4 | H |
| CH₂(2,4-F₂C₆H₃) | H | Q-6 | H |
| CH₂(2,5-F₂C₆H₃) | H | Q-7 | H |
| CH₂(2,6-F₂C₆H₃) | H | Q-8 | H |
| CH₂(2,4,6-F₃C₆H₂) | H | Q-15 | H |
| CH₂(2-ClC₆H₄) | H | CH₂(2-BrC₆H₄) | H |
| CH₂(3-ClC₆H₄) | H | CH₂(2,6-Br₂C₆H₃) | H |
| CH₂(4-ClC₆H₄) | H | CH₂(2-Cl-6-FC₆H₃) | H |
| CH₂(2,6-Cl₂C₆H₃) | H | CH₂(2-(OCH₃)C₆H₄) | H |
| CH₂(2-(CH₃)C₆H₄) | H | CH₂(2-(CN)C₆H₄) | H |
| CH₂(3-(CH₃)C₆H₄) | H | CH₂(2-(CF₃)C₆H₄) | H |
| CH₂(4-(CH₃)C₆H₄) | H | CH₂(2-(OCF₃)C₆H₄) | H |
| CH₂(2-pyridyl) | H | CH₂(2-(SCH₃)C₆H₄) | H |
| CH₂(2-thienyl) | H | CH₂(2-(CH=CH₂)C₆H₄) | H |
| CH₂(2-furanyl) | H | CH₂(2-(C≡CH)C₆H₄) | H |
| CH₂(C₆H₅) | CH₃ | CH₂(2-tetrahydrofuranyl) | CH₃ |
| CH₂(2-FC₆H₄) | CH₃ | CH₂(2-tetrahydropyranyl) | CH₃ |
| CH₂(3-FC₆H₄) | CH₃ | Q-1 | CH₃ |
| CH₂(4-FC₆H₄) | CH₃ | Q-3 | CH₃ |
| CH₂(2,3-F₂C₆H₃) | CH₃ | Q-4 | CH₃ |
| CH₂(2,4-F₂C₆H₃) | CH₃ | Q-6 | CH₃ |
| CH₂(2,5-F₂C₆H₃) | CH₃ | Q-7 | CH₃ |
| CH₂(2,6-F₂C₆H₃) | CH₃ | Q-8 | CH₃ |
| CH₂(2,4,6-F₃C₆H₂) | CH₃ | Q-15 | CH₃ |
| CH₂(2-ClC₆H₄) | CH₃ | CH₂(2-BrC₆H₄) | CH₃ |
| CH₂(3-ClC₆H₄) | CH₃ | CH₂(2,6-Br₂C₆H₃) | CH₃ |
| CH₂(4-ClC₆H₄) | CH₃ | CH₂(2-Cl-6-FC₆H₃) | CH₃ |
| CH₂(2,6-Cl₂C₆H₃) | CH₃ | CH₂(2-(OCH₃)C₆H₄) | CH₃ |
| CH₂(2-(CH₃)C₆H₄) | CH₃ | CH₂(2-(CN)C₆H₄) | CH₃ |
| CH₂(3-(CH₃)C₆H₄) | CH₃ | CH₂(2-(CF₃)C₆H₄) | CH₃ |
| CH₂(4-(CH₃)C₆H₄) | CH₃ | CH₂(2-(OCF₃)C₆H₄) | CH₃ |
| CH₂(2-pyridyl) | CH₃ | CH₂(2-(SCH₃)C₆H₄) | CH₃ |
| CH₂(2-thienyl) | CH₃ | CH₂(2-(CH=CH₂)C₆H₄) | CH₃ |
| CH₂(2-furanyl) | CH₃ | CH₂(2-(C≡CH)C₆H₄) | CH₃ |
| CH₂(C₆H₅) | CH₂CH₃ | CH₂(C₆H₅) | CH₂C≡CH |
| CH₂(2-FC₆H₄) | CH₂CH₃ | CH₂(2-FC₆H₄) | CH₂C≡CH |
| CH₂(2,6-F₂C₆H₃) | CH₂CH₃ | CH₂(2,6-F₂C₆H₃) | CH₂C≡CH |
| CH₂(2-ClC₆H₄) | CH₂CH₃ | CH₂(2-ClC₆H₄) | CH₂C≡CH |
| CH₂(2-Cl-6-FC₆H₃) | CH₂CH₃ | CH₂(2-Cl-6-FC₆H₃) | CH₂C≡CH |
| CH₂(2-(CH₃)C₆H₄) | CH₂CH₃ | CH₂(2-(CH₃)C₆H₄) | CH₂C≡CH |
| CH₂(2-pyridyl) | CH₂CH₃ | CH₂(2-pyridyl) | CH₂C≡CH |
| Q-1 | CH₂CH₃ | Q-1 | CH₂C≡CH |
| CH₂(C₆H₅) | CH₂CH=CH₂ | CH₂(C₆H₅) | CH₂CH₂OCH₃ |
| CH₂(2-FC₆H₄) | CH₂CH=CH₂ | CH₂(2-FC₆H₄) | CH₂CH₂OCH₃ |
| CH₂(2,6-F₂C₆H₃) | CH₂CH=CH₂ | CH₂(2,6-F₂C₆H₃) | CH₂CH₂OCH₃ |
| CH₂(2-ClC₆H₄) | CH₂CH=CH₂ | CH₂(2-ClC₆H₄) | CH₂CH₂OCH₃ |
| CH₂(2-Cl-6-FC₆H₃) | CH₂CH=CH₂ | CH₂(2-Cl-6-FC₆H₃) | CH₂CH₂OCH₃ |
| CH₂(2-(CH₃)C₆H₄) | CH₂CH=CH₂ | CH₂(2-(CH₃)C₆H₄) | CH₂CH₂OCH₃ |
| CH₂(2-pyridyl) | CH₂CH=CH₂ | CH₂(2-pyridyl) | CH₂CH₂OCH₃ |
| Q-1 | CH₂CH=CH₂ | Q-1 | CH₂CH₂OCH₃ |

TABLE 4

| Q | R² | Q | R² |
|---|---|---|---|
| General Structure 4, m is 3, R³=R⁴ is H | | | |
| CH₂(C₆H₅) | H | CH₂(2-tetrahydropyranyl) | H |
| CH₂(2-FC₆H₄) | H | Q-1 | H |
| CH₂(3-FC₆H₄) | H | Q-3 | H |
| CH₂(4-FC₆H₄) | H | Q-4 | H |
| CH₂(2,3-F₂C₆H₃) | H | Q-6 | H |
| CH₂(2,4-F₂C₆H₃) | H | Q-7 | H |
| CH₂(2,5-F₂C₆H₃) | H | Q-8 | H |
| CH₂(2,6-F₂C₆H₃) | H | Q-15 | H |
| CH₂(2,4,6-F₃C₆H₂) | H | CH₂(2-BrC₆H₄) | H |
| CH₂(2-ClC₆H₄) | H | CH₂(2,6-Br₂C₆H₃) | H |
| CH₂(3-ClC₆H₄) | H | CH₂(2-Cl-6-FC₆H₃) | H |
| CH₂(4-ClC₆H₄) | H | CH₂(2-(OCH₃)C₆H₄) | H |
| CH₂(2,6-Cl₂C₆H₃) | H | CH₂(2-(CN)C₆H₄) | H |
| CH₂(2-(CH₃)C₆H₄) | H | CH₂(2-(CF₃)C₆H₄) | H |
| CH₂(3-(CH₃)C₆H₄) | H | CH₂(2-(OCF₃)C₆H₄) | H |
| CH₂(2-pyridyl) | H | CH₂(2-(SCH₃)C₆H₄) | H |
| CH₂(2-thienyl) | H | CH₂(2-(CH=CH₂)C₆H₄) | H |
| CH₂(2-furanyl) | H | CH₂(2-(C≡CH)C₆H₄) | H |
| CH₂(2-tetrahydrofuranyl) | H | | |
| CH₂(C₆H₅) | CH₃ | CH₂(2-tetrahydropyranyl) | CH₃ |
| CH₂(2-FC₆H₄) | CH₃ | Q-1 | CH₃ |

TABLE 4-continued

| Q | R² | Q | R² |
|---|---|---|---|
| CH₂(3-FC₆H₄) | CH₃ | Q-3 | CH₃ |
| CH₂(4-FC₆H₄) | CH₃ | Q-4 | CH₃ |
| CH₂(2,3-F₂C₆H₃) | CH₃ | Q-6 | CH₃ |
| CH₂(2,4-F₂C₆H₃) | CH₃ | Q-7 | CH₃ |
| CH₂(2,5-F₂C₆H₃) | CH₃ | Q-8 | CH₃ |
| CH₂(2,6-F₂C₆H₃) | CH₃ | Q-15 | CH₃ |
| CH₂(2,4,6-F₃C₆H₂) | CH₃ | CH₂(2-BrC₆H₄) | CH₃ |
| CH₂(2-ClC₆H₄) | CH₃ | CH₂(2,6-Br₂C₆H₃) | CH₃ |
| CH₂(3-ClC₆H₄) | CH₃ | CH₂(2-Cl-6-FC₆H₃) | CH₃ |
| CH₂(4-ClC₆H₄) | CH₃ | CH₂(2-(OCH₃)C₆H₄) | CH₃ |
| CH₂(2,6-Cl₂C₆H₃) | CH₃ | CH₂(2-(CN)C₆H₄) | CH₃ |
| CH₂(2-(CH₃)C₆H₄) | CH₃ | CH₂(2-(CF₃)C₆H₄) | CH₃ |
| CH₂(3-(CH₃)C₆H₄) | CH₃ | CH₂(2-(OCF₃)C₆H₄) | CH₃ |
| CH₂(2-pyridyl) | CH₃ | CH₂(2-(SCH₃)C₆H₄) | CH₃ |
| CH₂(2-thienyl) | CH₃ | CH₂(2-(CH=CH₂)C₆H₄) | CH₃ |
| CH₂(2-furanyl) | CH₃ | CH₂(2-(C≡CH)C₆H₄) | CH₃ |
| CH₂(2-tetrahydrofuranyl) | CH₃ | | |
| General Structure 4, m is 3, R³=R⁴ is CH³ | | | |
| CH₂(C₆H₅) | H | CH₂(2-tetrahydropyranyl) | H |
| CH₂(2-FC₆H₄) | H | Q-1 | H |
| CH₂(3-FC₆H₄) | H | Q-3 | H |
| CH₂(4-FC₆H₄) | H | Q-4 | H |
| CH₂(2,3-F₂C₆H₃) | H | Q-6 | H |
| CH₂(2,4-F₂C₆H₃) | H | Q-7 | H |
| CH₂(2,5-F₂C₆H₃) | H | Q-8 | H |
| CH₂(2,6-F₂C₆H₃) | H | Q-15 | H |
| CH₂(2,4,6-F₃C₆H₂) | H | CH₂(2-BrC₆H₄) | H |
| CH₂(2-ClC₆H₄) | H | CH₂(2,6-Br₂C₆H₃) | H |
| CH₂(3-ClC₆H₄) | H | CH₂(2-Cl-6-FC₆H₃) | H |
| CH₂(4-ClC₆H₄) | H | CH₂(2-(OCH₃)C₆H₄) | H |
| CH₂(2,6-Cl₂C₆H₃) | H | CH₂(2-(CN)C₆H₄) | H |
| CH₂(2-(CH₃)C₆H₄) | H | CH₂(2-(CF₃)C₆H₄) | H |
| CH₂(3-(CH₃)C₆H₄) | H | CH₂(2-(OCF₃)C₆H₄) | H |
| CH₂(2-pyridyl) | H | CH₂(2-(SCH₃)C₆H₄) | H |
| CH₂(2-thienyl) | H | CH₂(2-(CH=CH₂)C₆H₄) | H |
| CH₂(2-furanyl) | H | CH₂(2-(C≡CH)C₆H₄) | H |
| CH₂(2-tetrahydrofuranyl) | H | | |
| CH₂(C₆H₅) | CH₃ | CH₂(2-tetrahydropyranyl) | CH₃ |
| CH₂(2-FC₆H₄) | CH₃ | Q-1 | CH₃ |
| CH₂(3-FC₆H₄) | CH₃ | Q-3 | CH₃ |
| CH₂(4-FC₆H₄) | CH₃ | Q-4 | CH₃ |
| CH₂(2,3-F₂C₆H₃) | CH₃ | Q-6 | CH₃ |
| CH₂(2,4-F₂C₆H₃) | CH₃ | Q-7 | CH₃ |
| CH₂(2,5-F₂C₆H₃) | CH₃ | Q-8 | CH₃ |
| CH₂(2,6-F₂C₆H₃) | CH₃ | Q-15 | CH₃ |
| CH₂(2,4,6-F₃C₆H₂) | CH₃ | CH₂(2-BrC₆H₄) | CH₃ |
| CH₂(2-ClC₆H₄) | CH₃ | CH₂(2,6-Br₂C₆H₃) | CH₃ |
| CH₂(3-ClC₆H₄) | CH₃ | CH₂(2-Cl-6-FC₆H₃) | CH₃ |
| CH₂(4-ClC₆H₄) | CH₃ | CH₂(2-(OCH₃)C₆H₄) | CH₃ |
| CH₂(2,6-Cl₂C₆H₃) | CH₃ | CH₂(2-(CN)C₆H₄) | CH₃ |
| CH₂(2-(CH₃)C₆H₄) | CH₃ | CH₂(2-(CF₃)C₆H₄) | CH₃ |
| CH₂(3-(CH₃)C₆H₄) | CH₃ | CH₂(2-(OCF₃)C₆H₄) | CH₃ |
| CH₂(2-pyridyl) | CH₃ | CH₂(2-(SCH₃)C₆H₄) | CH₃ |
| CH₂(2-thienyl) | CH₃ | CH₂(2-(CH=CH₂)C₆H₄) | CH₃ |
| CH₂(2-furanyl) | CH₃ | CH₂(2-(C≡CH)C₆H₄) | CH₃ |
| CH₂(2-tetrahydrofuranyl) | CH₃ | | |
| General Structure 4, m is 4, R³=R⁴ is H | | | |
| CH₂(C₆H₅) | H | CH₂(2-tetrahydropyranyl) | H |
| CH₂(2-FC₆H₄) | H | Q-1 | H |
| CH₂(3-FC₆H₄) | H | Q-3 | H |
| CH₂(4-FC₆H₄) | H | Q-4 | H |
| CH₂(2,3-F₂C₆H₃) | H | Q-6 | H |
| CH₂(2,4-F₂C₆H₃) | H | Q-7 | H |
| CH₂(2,5-F₂C₆H₃) | H | Q-8 | H |
| CH₂(2,6-F₂C₆H₃) | H | Q-15 | H |
| CH₂(2,4,6-F₃C₆H₂) | H | CH₂(2-BrC₆H₄) | H |
| CH₂(2-ClC₆H₄) | H | CH₂(2,6-Br₂C₆H₃) | H |
| CH₂(3-ClC₆H₄) | H | CH₂(2-Cl-6-FC₆H₃) | H |
| CH₂(4-ClC₆H₄) | H | CH₂(2-(OCH₃)C₆H₄) | H |
| CH₂(2,6-Cl₂C₆H₃) | H | CH₂(2-(CN)C₆H₄) | H |
| CH₂(2-(CH₃)C₆H₄) | H | CH₂(2-(CF₃)C₆H₄) | H |
| CH₂(3-(CH₃)C₆H₄) | H | CH₂(2-(OCF₃)C₆H₄) | H |
| CH₂(2-pyridyl) | H | CH₂(2-(SCH₃)C₆H₄) | H |
| CH₂(2-thienyl) | H | CH₂(2-(CH=CH₂)C₆H₄) | H |
| CH₂(2-furanyl) | H | CH₂(2-(C≡CH)C₆H₄) | H |
| CH₂(2-tetrahydrofuranyl) | H | | |
| CH₂(C₆H₅) | CH₃ | CH₂(2-tetrahydropyranyl) | CH₃ |
| CH₂(2-FC₆H₄) | CH₃ | Q-1 | CH₃ |
| CH₂(3-FC₆H₄) | CH₃ | Q-3 | CH₃ |
| CH₂(4-FC₆H₄) | CH₃ | Q-4 | CH₃ |

TABLE 4-continued

| Q | R² | Q | R² |
|---|---|---|---|
| CH₂(2,3-F₂C₆H₃) | CH₃ | Q-6 | CH₃ |
| CH₂(2,4-F₂C₆H₃) | CH₃ | Q-7 | CH₃ |
| CH₂(2,5-F₂C₆H₃) | CH₃ | Q-8 | CH₃ |
| CH₂(2,6-F₂C₆H₃) | CH₃ | Q-15 | CH₃ |
| CH₂(2,4,6-F₃C₆H₂) | CH₃ | CH₂(2-BrC₆H₄) | CH₃ |
| CH₂(2-ClC₆H₄) | CH₃ | CH₂(2,6-Br₂C₆H₃) | CH₃ |
| CH₂(3-ClC₆H₄) | CH₃ | CH₂(2-Cl-6-FC₆H₃) | CH₃ |
| CH₂(4-ClC₆H₄) | CH₃ | CH₂(2-(OCH₃)C₆H₄) | CH₃ |
| CH₂(2,6-Cl₂C₆H₃) | CH₃ | CH₂(2-(CN)C₆H₄) | CH₃ |
| CH₂(2-(CH₃)C₆H₄) | CH₃ | CH₂(2-(CF₃)C₆H₄) | CH₃ |
| CH₂(3-(CH₃)C₆H₄) | CH₃ | CH₂(2-(OCF₃)C₆H₄) | CH₃ |
| CH₂(2-pyridyl) | CH₃ | CH₂(2-(SCH₃)C₆H₄) | CH₃ |
| CH₂(2-thienyl) | CH₃ | CH₂(2-(CH=CH₂)C₆H₄) | CH₃ |
| CH₂(2-furanyl) | CH₃ | CH₂(2-(C≡CH)C₆H₄) | CH₃ |
| CH₂(2-tetrahydrofuranyl) | CH₃ | | |
| General Structure 4, m is 4, R³=R⁴ is CH₃ | | | |
| CH₂(C₆H₅) | H | CH₂(2-tetrahydropyranyl) | H |
| CH₂(2-FC₆H₄) | H | Q-1 | H |
| CH₂(3-FC₆H₄) | H | Q-3 | H |
| CH₂(4-FC₆H₄) | H | Q-4 | H |
| CH₂(2,3-F₂C₆H₃) | H | Q-6 | H |
| CH₂(2,4-F₂C₆H₃) | H | Q-7 | H |
| CH₂(2,5-F₂C₆H₃) | H | Q-8 | H |
| CH₂(2,6-F₂C₆H₃) | H | Q-15 | H |
| CH₂(2,4,6-F₃C₆H₂) | H | CH₂(2-BrC₆H₄) | H |
| CH₂(2-ClC₆H₄) | H | CH₂(2,6-Br₂C₆H₃) | H |
| CH₂(3-ClC₆H₄) | H | CH₂(2-Cl-6-FC₆H₃) | H |
| CH₂(4-ClC₆H₄) | H | CH₂(2-(OCH₃)C₆H₄) | H |
| CH₂(2,6-Cl₂C₆H₃) | H | CH₂(2-(CN)C₆H₄) | H |
| CH₂(2-(CH₃)C₆H₄) | H | CH₂(2-(CF₃)C₆H₄) | H |
| CH₂(3-(CH₃)C₆H₄) | H | CH₂(2-(OCF₃)C₆H₄) | H |
| CH₂(2-pyridyl) | H | CH₂(2-(SCH₃)C₆H₄) | H |
| CH₂(2-thienyl) | H | CH₂(2-(CH=CH₂)C₆H₄) | H |
| CH₂(2-furanyl) | H | CH₂(2-(C≡CH)C₆H₄) | H |
| CH₂(2-tetrahydrofuranyl) | H | | |
| CH₂(C₆H₅) | CH₃ | CH₂(2-tetrahydropyranyl) | CH₃ |
| CH₂(2-FC₆H₄) | CH₃ | Q-1 | CH₃ |
| CH₂(3-FC₆H₄) | CH₃ | Q-3 | CH₃ |
| CH₂(4-FC₆H₄) | CH₃ | Q-4 | CH₃ |
| CH₂(2,3-F₂C₆H₃) | CH₃ | Q-6 | CH₃ |
| CH₂(2,4-F₂C₆H₃) | CH₃ | Q-7 | CH₃ |
| CH₂(2,5-F₂C₆H₃) | CH₃ | Q-8 | CH₃ |
| CH₂(2,6-F₂C₆H₃) | CH₃ | Q-15 | CH₃ |
| CH₂(2,4,6-F₃C₆H₂) | CH₃ | CH₂(2-BrC₆H₄) | CH₃ |
| CH₂(2-ClC₆H₄) | CH₃ | CH₂(2,6-Br₂C₆H₃) | CH₃ |
| CH₂(3-ClC₆H₄) | CH₃ | CH₂(2-Cl-6-FC₆H₃) | CH₃ |
| CH₂(4-ClC₆H₄) | CH₃ | CH₂(2-(OCH₃)C₆H₄) | CH₃ |
| CH₂(2,6-Cl₂C₆H₃) | CH₃ | CH₂(2-(CN)C₆H₄) | CH₃ |
| CH₂(2-(CH₃)C₆H₄) | CH₃ | CH₂(2-(CF₃)C₆H₄) | CH₃ |
| CH₂(3-(CH₃)C₆H₄) | CH₃ | CH₂(2-(OCF₃)C₆H₄) | CH₃ |
| CH₂(2-pyridyl) | CH₃ | CH₂(2-(SCH₃)C₆H₄) | CH₃ |
| CH₂(2-thienyl) | CH₃ | CH₂(2-(CH=CH₂)C₆H₄) | CH₃ |
| CH₂(2-furanyl) | CH₃ | CH₂(2-(C≡CH)C₆H₄) | CH₃ |
| CH₂(2-tetrahydrofuranyl) | CH₃ | | |
| General Structure 4, m is 5, R³=R⁴ is H | | | |
| CH₂(C₆H₅) | H | CH₂(2-tetrahydropyranyl) | H |
| CH₂(2-FC₆H₄) | H | Q-1 | H |
| CH₂(3-FC₆H₄) | H | Q-3 | H |
| CH₂(4-FC₆H₄) | H | Q-4 | H |
| CH₂(2,3-F₂C₆H₃) | H | Q-6 | H |
| CH₂(2,4-F₂C₆H₃) | H | Q-7 | H |
| CH₂(2,5-F₂C₆H₃) | H | Q-8 | H |
| CH₂(2,6-F₂C₆H₃) | H | Q-15 | H |
| CH₂(2,4,6-F₃C₆H₂) | H | CH₂(2-BrC₆H₄) | H |
| CH₂(2-ClC₆H₄) | H | CH₂(2,6-Br₂C₆H₃) | H |
| CH₂(3-ClC₆H₄) | H | CH₂(2-Cl-6-FC₆H₃) | H |
| CH₂(4-ClC₆H₄) | H | CH₂(2-(OCH₃)C₆H₄) | H |
| CH₂(2,6-Cl₂C₆H₃) | H | CH₂(2-(CN)C₆H₄) | H |
| CH₂(2-(CH₃)C₆H₄) | H | CH₂(2-(CF₃)C₆H₄) | H |
| CH₂(3-(CH₃)C₆H₄) | H | CH₂(2-(OCF₃)C₆H₄) | H |
| CH₂(2-pyridyl) | H | CH₂(2-(SCH₃)C₆H₄) | H |
| CH₂(2-thienyl) | H | CH₂(2-(CH=CH₂)C₆H₄) | H |
| CH₂(2-furanyl) | H | CH₂(2-(C≡CH)C₆H₄) | H |
| CH₂(2-tetrahydrofuranyl) | H | | |

TABLE 5

| Q | R¹ | Q | R¹ |
|---|---|---|---|
| General Structure 5, m is 3, R³=R⁴ is H | | | |

TABLE 5-continued

| Q | R¹ | Q | R¹ |
|---|---|---|---|
| CH₂(C₆H₅) | CH₃ | CH₂(2-tetrahydropyranyl) | CH₃ |
| CH₂(2-FC₆H₄) | CH₃ | Q-1 | CH₃ |
| CH₂(3-FC₆H₄) | CH₃ | Q-3 | CH₃ |
| CH₂(4-FC₆H₄) | CH₃ | Q-4 | CH₃ |
| CH₂(2,3-F₂C₆H₃) | CH₃ | Q-6 | CH₃ |
| CH₂(2,4-F₂C₆H₃) | CH₃ | Q-7 | CH₃ |
| CH₂(2,5-F₂C₆H₃) | CH₃ | Q-8 | CH₃ |
| CH₂(2,6-F₂C₆H₃) | CH₃ | Q-15 | CH₃ |
| CH₂(2,4,6-F₃C₆H₂) | CH₃ | CH₂(2-BrC₆H₄) | CH₃ |
| CH₂(2-ClC₆H₄) | CH₃ | CH₂(2,6-Br₂C₆H₃) | CH₃ |
| CH₂(3-ClC₆H₄) | CH₃ | CH₂(2-Cl-6-FC₆H₃) | CH₃ |
| CH₂(4-ClC₆H₄) | CH₃ | CH₂(2-(OCH₃)C₆H₄) | CH₃ |
| CH₂(2,6-Cl₂C₆H₃) | CH₃ | CH₂(2-(CN)C₆H₄) | CH₃ |
| CH₂(2-(CH₃)C₆H₄) | CH₃ | CH₂(2-(CF₃)C₆H₄) | CH₃ |
| CH₂(3-(CH₃)C₆H₄) | CH₃ | CH₂(2-(OCF₃)C₆H₄) | CH₃ |
| CH₂(2-pyridyl) | CH₃ | CH₂(2-(SCH₃)C₆H₄) | CH₃ |
| CH₂(2-thienyl) | CH₃ | CH₂(2-(CH=CH₂)C₆H₄) | CH₃ |
| CH₂(2-furanyl) | CH₃ | CH₂(2-(C≡CH)C₆H₄) | CH₃ |
| CH₂(2-tetrahydrofuranyl) | CH₃ | | |
| CH₂(C₆H₅) | CH₂CH₃ | CH₂(2-tetrahydropyranyl) | CH₂CH₃ |
| CH₂(2-FC₆H₄) | CH₂CH₃ | Q-1 | CH₂CH₃ |
| CH₂(3-FC₆H₄) | CH₂CH₃ | Q-3 | CH₂CH₃ |
| CH₂(4-FC₆H₄) | CH₂CH₃ | Q-4 | CH₂CH₃ |
| CH₂(2,3-F₂C₆H₃) | CH₂CH₃ | Q-6 | CH₂CH₃ |
| CH₂(2,4-F₂C₆H₃) | CH₂CH₃ | Q-7 | CH₂CH₃ |
| CH₂(2,5-F₂C₆H₃) | CH₂CH₃ | Q-8 | CH₂CH₃ |
| CH₂(2,6-F₂C₆H₃) | CH₂CH₃ | Q-15 | CH₂CH₃ |
| CH₂(2,4,6-F₃C₆H₂) | CH₂CH₃ | CH₂(2-BrC₆H₄) | CH₂CH₃ |
| CH₂(2-ClC₆H₄) | CH₂CH₃ | CH₂(2,6-Br₂C₆H₃) | CH₂CH₃ |
| CH₂(3-ClC₆H₄) | CH₂CH₃ | CH₂(2-Cl-6-FC₆H₃) | CH₂CH₃ |
| CH₂(4-ClC₆H₄) | CH₂CH₃ | CH₂(2-(OCH₃)C₆H₄) | CH₂CH₃ |
| CH₂(2,6-Cl₂C₆H₃) | CH₂CH₃ | CH₂(2-(CN)C₆H₄) | CH₂CH₃ |
| CH₂(2-(CH₃)C₆H₄) | CH₂CH₃ | CH₂(2-(CF₃)C₆H₄) | CH₂CH₃ |
| CH₂(3-(CH₃)C₆H₄) | CH₂CH₃ | CH₂(2-(OCF₃)C₆H₄) | CH₂CH₃ |
| CH₂(2-pyridyl) | CH₂CH₃ | CH₂(2-(SCH₃)C₆H₄) | CH₂CH₃ |
| CH₂(2-thienyl) | CH₂CH₃ | CH₂(2-(CH=CH₂)C₆H₄) | CH₂CH₃ |
| CH₂(2-furanyl) | CH₂CH₃ | CH₂(2-(C≡CH)C₆H₄) | CH₂CH₃ |
| CH₂(2-tetrahydrofuranyl) | CH₂CH₃ | | |
| General Structure 5, m is 3, R³=R⁴ is CH³ ||||
| CH₂(C₆H₅) | CH₃ | CH₂(2-tetrahydropyranyl) | CH₃ |
| CH₂(2-FC₆H₄) | CH₃ | Q-1 | CH₃ |
| CH₂(3-FC₆H₄) | CH₃ | Q-3 | CH₃ |
| CH₂(4-FC₆H₄) | CH₃ | Q-4 | CH₃ |
| CH₂(2,3-F₂C₆H₃) | CH₃ | Q-6 | CH₃ |
| CH₂(2,4-F₂C₆H₃) | CH₃ | Q-7 | CH₃ |
| CH₂(2,5-F₂C₆H₃) | CH₃ | Q-8 | CH₃ |
| CH₂(2,6-F₂C₆H₃) | CH₃ | Q-15 | CH₃ |
| CH₂(2,4,6-F₃C₆H₂) | CH₃ | CH₂(2-BrC₆H₄) | CH₃ |
| CH₂(2-ClC₆H₄) | CH₃ | CH₂(2,6-Br₂C₆H₃) | CH₃ |
| CH₂(3-ClC₆H₄) | CH₃ | CH₂(2-Cl-6-FC₆H₃) | CH₃ |
| CH₂(4-ClC₆H₄) | CH₃ | CH₂(2-(OCH₃)C₆H₄) | CH₃ |
| CH₂(2,6-Cl₂C₆H₃) | CH₃ | CH₂(2-(CN)C₆H₄) | CH₃ |
| CH₂(2-(CH₃)C₆H₄) | CH₃ | CH₂(2-(CF₃)C₆H₄) | CH₃ |
| CH₂(3-(CH₃)C₆H₄) | CH₃ | CH₂(2-(OCF₃)C₆H₄) | CH₃ |
| CH₂(2-pyridyl) | CH₃ | CH₂(2-(SCH₃)C₆H₄) | CH₃ |
| CH₂(2-thienyl) | CH₃ | CH₂(2-(CH=CH₂)C₆H₄) | CH₃ |
| CH₂(2-furanyl) | CH₃ | CH₂(2-(C≡CH)C₆H₄) | CH₃ |
| CH₂(2-tetrahydrofuranyl) | CH₃ | | |
| CH₂(C₆H₅) | CH₂CH₃ | CH₂(2-tetrahydropyranyl) | CH₂CH₃ |
| CH₂(2-FC₆H₄) | CH₂CH₃ | Q-1 | CH₂CH₃ |
| CH₂(3-FC₆H₄) | CH₂CH₃ | Q-3 | CH₂CH₃ |
| CH₂(4-FC₆H₄) | CH₂CH₃ | Q-4 | CH₂CH₃ |
| CH₂(2,3-F₂C₆H₃) | CH₂CH₃ | Q-6 | CH₂CH₃ |
| CH₂(2,4-F₂C₆H₃) | CH₂CH₃ | Q-7 | CH₂CH₃ |
| CH₂(2,5-F₂C₆H₃) | CH₂CH₃ | Q-8 | CH₂CH₃ |
| CH₂(2,6-F₂C₆H₃) | CH₂CH₃ | Q-15 | CH₂CH₃ |
| CH₂(2,4,6-F₃C₆H₂) | CH₂CH₃ | CH₂(2-BrC₆H₄) | CH₂CH₃ |
| CH₂(2-ClC₆H₄) | CH₂CH₃ | CH₂(2,6-Br₂C₆H₃) | CH₂CH₃ |
| CH₂(3-ClC₆H₄) | CH₂CH₃ | CH₂(2-Cl-6-FC₆H₃) | CH₂CH₃ |
| CH₂(4-ClC₆H₄) | CH₂CH₃ | CH₂(2-(OCH₃)C₆H₄) | CH₂CH₃ |
| CH₂(2,6-Cl₂C₆H₃) | CH₂CH₃ | CH₂(2-(CN)C₆H₄) | CH₂CH₃ |
| CH₂(2-(CH₃)C₆H₄) | CH₂CH₃ | CH₂(2-(CF₃)C₆H₄) | CH₂CH₃ |
| CH₂(3-(CH₃)C₆H₄) | CH₂CH₃ | CH₂(2-(OCF₃)C₆H₄) | CH₂CH₃ |
| CH₂(2-pyridyl) | CH₂CH₃ | CH₂(2-(SCH₃)C₆H₄) | CH₂CH₃ |
| CH₂(2-thienyl) | CH₂CH₃ | CH₂(2-(CH=CH₂)C₆H₄) | CH₂CH₃ |
| CH₂(2-furanyl) | CH₂CH₃ | CH₂(2-(C≡CH)C₆H₄) | CH₂CH₃ |
| CH₂(2-tetrahydrofuranyl) | CH₂CH₃ | | |
| General Structure 5, m is 4, R³=R⁴ is CH₃ ||||
| CH₂(C₆H₅) | CH₃ | CH₂(2-tetrahydropyranyl) | CH₃ |
| CH₂(2-FC₆H₄) | CH₃ | Q-1 | CH₃ |

TABLE 5-continued

| Q | R¹ | Q | R¹ |
|---|---|---|---|
| $CH_2(3\text{-}FC_6H_4)$ | $CH_3$ | Q-3 | $CH_3$ |
| $CH_2(4\text{-}FC_6H_4)$ | $CH_3$ | Q-4 | $CH_3$ |
| $CH_2(2,3\text{-}F_2C_6H_3)$ | $CH_3$ | Q-6 | $CH_3$ |
| $CH_2(2,4\text{-}F_2C_6H_3)$ | $CH_3$ | Q-7 | $CH_3$ |
| $CH_2(2,5\text{-}F_2C_6H_3)$ | $CH_3$ | Q-8 | $CH_3$ |
| $CH_2(2,6\text{-}F_2C_6H_3)$ | $CH_3$ | Q-15 | $CH_3$ |
| $CH_2(2,4,6\text{-}F_3C_6H_2)$ | $CH_3$ | $CH_2(2\text{-}BrC_6H_4)$ | $CH_3$ |
| $CH_2(2\text{-}ClC_6H_4)$ | $CH_3$ | $CH_2(2,6\text{-}Br_2C_6H_3)$ | $CH_3$ |
| $CH_2(3\text{-}ClC_6H_4)$ | $CH_3$ | $CH_2(2\text{-}Cl\text{-}6\text{-}FC_6H_3)$ | $CH_3$ |
| $CH_2(4\text{-}ClC_6H_4)$ | $CH_3$ | $CH_2(2\text{-}(OCH_3)C_6H_4)$ | $CH_3$ |
| $CH_2(2,6\text{-}Cl_2C_6H_3)$ | $CH_3$ | $CH_2(2\text{-}(CN)C_6H_4)$ | $CH_3$ |
| $CH_2(2\text{-}(CH_3)C_6H_4)$ | $CH_3$ | $CH_2(2\text{-}(CF_3)C_6H_4)$ | $CH_3$ |
| $CH_2(3\text{-}(CH_3)C_6H_4)$ | $CH_3$ | $CH_2(2\text{-}(OCF_3)C_6H_4)$ | $CH_3$ |
| $CH_2(2\text{-pyridyl})$ | $CH_3$ | $CH_2(2\text{-}(SCH_3)C_6H_4)$ | $CH_3$ |
| $CH_2(2\text{-thienyl})$ | $CH_3$ | $CH_2(2\text{-}(CH=CH_2)C_6H_4)$ | $CH_3$ |
| $CH_2(2\text{-furanyl})$ | $CH_3$ | $CH_2(2\text{-}(C\equiv CH)C_6H_4)$ | $CH_3$ |
| $CH_2(2\text{-tetrahydrofuranyl})$ | $CH_3$ | | |
| $CH_2(C_6H_5)$ | $CH_2CH_3$ | $CH_2(2\text{-tetrahydropyranyl})$ | $CH_2CH_3$ |
| $CH_2(2\text{-}FC_6H_4)$ | $CH_2CH_3$ | Q-1 | $CH_2CH_3$ |
| $CH_2(3\text{-}FC_6H_4)$ | $CH_2CH_3$ | Q-3 | $CH_2CH_3$ |
| $CH_2(4\text{-}FC_6H_4)$ | $CH_2CH_3$ | Q-4 | $CH_2CH_3$ |
| $CH_2(2,3\text{-}F_2C_6H_3)$ | $CH_2CH_3$ | Q-6 | $CH_2CH_3$ |
| $CH_2(2,4\text{-}F_2C_6H_3)$ | $CH_2CH_3$ | Q-7 | $CH_2CH_3$ |
| $CH_2(2,5\text{-}F_2C_6H_3)$ | $CH_2CH_3$ | Q-8 | $CH_2CH_3$ |
| $CH_2(2,6\text{-}F_2C_6H_3)$ | $CH_2CH_3$ | Q-15 | $CH_2CH_3$ |
| $CH_2(2,4,6\text{-}F_3C_6H_2)$ | $CH_2CH_3$ | $CH_2(2\text{-}BrC_6H_4)$ | $CH_2CH_3$ |
| $CH_2(2\text{-}ClC_6H_4)$ | $CH_2CH_3$ | $CH_2(2,6\text{-}Br_2C_6H_3)$ | $CH_2CH_3$ |
| $CH_2(3\text{-}ClC_6H_4)$ | $CH_2CH_3$ | $CH_2(2\text{-}Cl\text{-}6\text{-}FC_6H_3)$ | $CH_2CH_3$ |
| $CH_2(4\text{-}ClC_6H_4)$ | $CH_2CH_3$ | $CH_2(2\text{-}(OCH_3)C_6H_4)$ | $CH_2CH_3$ |
| $CH_2(2,6\text{-}Cl_2C_6H_3)$ | $CH_2CH_3$ | $CH_2(2\text{-}(CN)C_6H_4)$ | $CH_2CH_3$ |
| $CH_2(2\text{-}(CH_3)C_6H_4)$ | $CH_2CH_3$ | $CH_2(2\text{-}(CF_3)C_6H_4)$ | $CH_2CH_3$ |
| $CH_2(3\text{-}(CH_3)C_6H_4)$ | $CH_2CH_3$ | $CH_2(2\text{-}(OCF_3)C_6H_4)$ | $CH_2CH_3$ |
| $CH_2(2\text{-pyridyl})$ | $CH_2CH_3$ | $CH_2(2\text{-}(SCH_3)C_6H_4)$ | $CH_2CH_3$ |
| $CH_2(2\text{-thienyl})$ | $CH_2CH_3$ | $CH_2(2\text{-}(CH=CH_2)C_6H_4)$ | $CH_2CH_3$ |
| $CH_2(2\text{-furanyl})$ | $CH_2CH_3$ | $CH_2(2\text{-}(C\equiv CH)C_6H_4)$ | $CH_2CH_3$ |
| $CH_2(2\text{-tetrahydrofuranyl})$ | $CH_2CH_3$ | | |
| General Structure 5, m is 4, $R^3=R^4$ is $CH_3$ | | | |
| $CH_2(C_6H_5)$ | $CH_3$ | $CH_2(2\text{-tetrahydropyranyl})$ | $CH_3$ |
| $CH_2(2\text{-}FC_6H_4)$ | $CH_3$ | Q-1 | $CH_3$ |
| $CH_2(3\text{-}FC_6H_4)$ | $CH_3$ | Q-3 | $CH_3$ |
| $CH_2(4\text{-}FC_6H_4)$ | $CH_3$ | Q-4 | $CH_3$ |
| $CH_2(2,3\text{-}F_2C_6H_3)$ | $CH_3$ | Q-6 | $CH_3$ |
| $CH_2(2,4\text{-}F_2C_6H_3)$ | $CH_3$ | Q-7 | $CH_3$ |
| $CH_2(2,5\text{-}F_2C_6H_3)$ | $CH_3$ | Q-8 | $CH_3$ |
| $CH_2(2,6\text{-}F_2C_6H_3)$ | $CH_3$ | Q-15 | $CH_3$ |
| $CH_2(2,4,6\text{-}F_3C_6H_2)$ | $CH_3$ | $CH_2(2\text{-}BrC_6H_4)$ | $CH_3$ |
| $CH_2(2\text{-}ClC_6H_4)$ | $CH_3$ | $CH_2(2,6\text{-}Br_2C_6H_3)$ | $CH_3$ |
| $CH_2(3\text{-}ClC_6H_4)$ | $CH_3$ | $CH_2(2\text{-}Cl\text{-}6\text{-}FC_6H_3)$ | $CH_3$ |
| $CH_2(4\text{-}ClC_6H_4)$ | $CH_3$ | $CH_2(2\text{-}(OCH_3)C_6H_4)$ | $CH_3$ |
| $CH_2(2,6\text{-}Cl_2C_6H_3)$ | $CH_3$ | $CH_2(2\text{-}(CN)C_6H_4)$ | $CH_3$ |
| $CH_2(2\text{-}(CH_3)C_6H_4)$ | $CH_3$ | $CH_2(2\text{-}(CF_3)C_6H_4)$ | $CH_3$ |
| $CH_2(3\text{-}(CH_3)C_6H_4)$ | $CH_3$ | $CH_2(2\text{-}(OCF_3)C_6H_4)$ | $CH_3$ |
| $CH_2(2\text{-pyridyl})$ | $CH_3$ | $CH_2(2\text{-}(SCH_3)C_6H_4)$ | $CH_3$ |
| $CH_2(2\text{-thienyl})$ | $CH_3$ | $CH_2(2\text{-}(CH=CH_2)C_6H_4)$ | $CH_3$ |
| $CH_2(2\text{-furanyl})$ | $CH_3$ | $CH_2(2\text{-}(C\equiv CH)C_6H_4)$ | $CH_3$ |
| $CH_2(2\text{-tetrahydrofuranyl})$ | $CH_3$ | | |
| $CH_2(C_6H_5)$ | $CH_2CH_3$ | $CH_2(2\text{-tetrahydropyranyl})$ | $CH_2CH_3$ |
| $CH_2(2\text{-}FC_6H_4)$ | $CH_2CH_3$ | Q-1 | $CH_2CH_3$ |
| $CH_2(3\text{-}FC_6H_4)$ | $CH_2CH_3$ | Q-3 | $CH_2CH_3$ |
| $CH_2(4\text{-}FC_6H_4)$ | $CH_2CH_3$ | Q-4 | $CH_2CH_3$ |
| $CH_2(2,3\text{-}F_2C_6H_3)$ | $CH_2CH_3$ | Q-6 | $CH_2CH_3$ |
| $CH_2(2,4\text{-}F_2C_6H_3)$ | $CH_2CH_3$ | Q-7 | $CH_2CH_3$ |
| $CH_2(2,5\text{-}F_2C_6H_3)$ | $CH_2CH_3$ | Q-8 | $CH_2CH_3$ |
| $CH_2(2,6\text{-}F_2C_6H_3)$ | $CH_2CH_3$ | Q-15 | $CH_2CH_3$ |
| $CH_2(2,4,6\text{-}F_3C_6H_2)$ | $CH_2CH_3$ | $CH_2(2\text{-}BrC_6H_4)$ | $CH_2CH_3$ |
| $CH_2(2\text{-}ClC_6H_4)$ | $CH_2CH_3$ | $CH_2(2,6\text{-}Br_2C_6H_3)$ | $CH_2CH_3$ |
| $CH_2(3\text{-}ClC_6H_4)$ | $CH_2CH_3$ | $CH_2(2\text{-}Cl\text{-}6\text{-}FC_6H_3)$ | $CH_2CH_3$ |
| $CH_2(4\text{-}ClC_6H_4)$ | $CH_2CH_3$ | $CH_2(2\text{-}(OCH_3)C_6H_4)$ | $CH_2CH_3$ |
| $CH_2(2,6\text{-}Cl_2C_6H_3)$ | $CH_2CH_3$ | $CH_2(2\text{-}(CN)C_6H_4)$ | $CH_2CH_3$ |
| $CH_2(2\text{-}(CH_3)C_6H_4)$ | $CH_2CH_3$ | $CH_2(2\text{-}(CF_3)C_6H_4)$ | $CH_2CH_3$ |
| $CH_2(3\text{-}(CH_3)C_6H_4)$ | $CH_2CH_3$ | $CH_2(2\text{-}(OCF_3)C_6H_4)$ | $CH_2CH_3$ |
| $CH_2(2\text{-pyridyl})$ | $CH_2CH_3$ | $CH_2(2\text{-}(SCH_3)C_6H_4)$ | $CH_2CH_3$ |
| $CH_2(2\text{-thienyl})$ | $CH_2CH_3$ | $CH_2(2\text{-}(CH=CH_2)C_6H_4)$ | $CH_2CH_3$ |
| $CH_2(2\text{-furanyl})$ | $CH_2CH_3$ | $CH_2(2\text{-}(C\equiv CH)C_6H_4)$ | $CH_2CH_3$ |
| $CH_2(2\text{-tetrahydrofuranyl})$ | $CH_2CH_3$ | | |
| General Structure 5, m is 5, $R^3=R^4$ is $CH_3$ | | | |
| $CH_2(C_6H_5)$ | $CH_3$ | $CH_2(2\text{-tetrahydropyranyl})$ | $CH_3$ |
| $CH_2(2\text{-}FC_6H_4)$ | $CH_3$ | Q-1 | $CH_3$ |
| $CH_2(3\text{-}FC_6H_4)$ | $CH_3$ | Q-3 | $CH_3$ |
| $CH_2(4\text{-}FC_6H_4)$ | $CH_3$ | Q-4 | $CH_3$ |

TABLE 5-continued

| Q | R$^1$ | Q | R$^1$ |
|---|---|---|---|
| CH$_2$(2,3-F$_2$C$_6$H$_3$) | CH$_3$ | Q-6 | CH$_3$ |
| CH$_2$(2,4-F$_2$C$_6$H$_3$) | CH$_3$ | Q-7 | CH$_3$ |
| CH$_2$(2,5-F$_2$C$_6$H$_3$) | CH$_3$ | Q-8 | CH$_3$ |
| CH$_2$(2,6-F$_2$C$_6$H$_3$) | CH$_3$ | Q-15 | CH$_3$ |
| CH$_2$(2,4,6-F$_3$C$_6$H$_2$) | CH$_3$ | CH$_2$(2-BrC$_6$H$_4$) | CH$_3$ |
| CH$_2$(2-ClC$_6$H$_4$) | CH$_3$ | CH$_2$(2,6-Br$_2$C$_6$H$_3$) | CH$_3$ |
| CH$_2$(3-ClC$_6$H$_4$) | CH$_3$ | CH$_2$(2-Cl-6-FC$_6$H$_3$) | CH$_3$ |
| CH$_2$(4-ClC$_6$H$_4$) | CH$_3$ | CH$_2$(2-(OCH$_3$)C$_6$H$_4$) | CH$_3$ |
| CH$_2$(2,6-Cl$_2$C$_6$H$_3$) | CH$_3$ | CH$_2$(2-(CN)C$_6$H$_4$) | CH$_3$ |
| CH$_2$(2-(CH$_3$)C$_6$H$_4$) | CH$_3$ | CH$_2$(2-(CF$_3$)C$_6$H$_4$) | CH$_3$ |
| CH$_2$(3-(CH$_3$)C$_6$H$_4$) | CH$_3$ | CH$_2$(2-(OCF$_3$)C$_6$H$_4$) | CH$_3$ |
| CH$_2$(2-pyridyl) | CH$_3$ | CH$_2$(2-(SCH$_3$)C$_6$H$_4$) | CH$_3$ |
| CH$_2$(2-thienyl) | CH$_3$ | CH$_2$(2-(CH=CH$_2$)C$_6$H$_4$) | CH$_3$ |
| CH$_2$(2-furanyl) | CH$_3$ | CH$_2$(2-(C≡CH)C$_6$H$_4$) | CH$_3$ |
| CH$_2$(2-tetrahydrofuranyl) | CH$_3$ | | |

TABLE 6

| Q | R$^2$ | Q | R$^2$ |
|---|---|---|---|
| \multicolumn{4}{c}{General Structure 6, m is 3, R$^1$ is CH$_3$} | | | |
| CH$_2$(C$_6$H$_5$) | H | CH$_2$(2-tetrahydropyranyl) | H |
| CH$_2$(2-FC$_6$H$_4$) | H | Q-1 | H |
| CH$_2$(3-FC$_6$H$_4$) | H | Q-3 | H |
| CH$_2$(4-FC$_6$H$_4$) | H | Q-4 | H |
| CH$_2$(2,3-F$_2$C$_6$H$_3$) | H | Q-6 | H |
| CH$_2$(2,4-F$_2$C$_6$H$_3$) | H | Q-7 | H |
| CH$_2$(2,5-F$_2$C$_6$H$_3$) | H | Q-8 | H |
| CH$_2$(2,6-F$_2$C$_6$H$_3$) | H | Q-15 | H |
| CH$_2$(2,4,6-F$_3$C$_6$H$_2$) | H | CH$_2$(2-BrC$_6$H$_4$) | H |
| CH$_2$(2-ClC$_6$H$_4$) | H | CH$_2$(2,6-Br$_2$C$_6$H$_3$) | H |
| CH$_2$(3-ClC$_6$H$_4$) | H | CH$_2$(2-Cl-6-FC$_6$H$_3$) | H |
| CH$_2$(4-ClC$_6$H$_4$) | H | CH$_2$(2-(OCH$_3$)C$_6$H$_4$) | H |
| CH$_2$(2,6-Cl$_2$C$_6$H$_3$) | H | CH$_2$(2-(CN)C$_6$H$_4$) | H |
| CH$_2$(2-(CH$_3$)C$_6$H$_4$) | H | CH$_2$(2-(CF$_3$)C$_6$H$_4$) | H |
| CH$_2$(3-(CH$_3$)C$_6$H$_4$) | H | CH$_2$(2-(OCF$_3$)C$_6$H$_4$) | H |
| CH$_2$(2-pyridyl) | H | CH$_2$(2-(SCH$_3$)C$_6$H$_4$) | H |
| CH$_2$(2-thienyl) | H | CH$_2$(2-(CH=CH$_2$)C$_6$H$_4$) | H |
| CH$_2$(2-furanyl) | H | CH$_2$(2-(C≡CH)C$_6$H$_4$) | H |
| CH$_2$(2-tetrahydrofuranyl) | H | | |
| CH$_2$(C$_6$H$_5$) | CH$_3$ | CH$_2$(2-tetrahydropyranyl) | CH$_3$ |
| CH$_2$(2-FC$_6$H$_4$) | CH$_3$ | Q-1 | CH$_3$ |
| CH$_2$(3-FC$_6$H$_4$) | CH$_3$ | Q-3 | CH$_3$ |
| CH$_2$(4-FC$_6$H$_4$) | CH$_3$ | Q-4 | CH$_3$ |
| CH$_2$(2,3-F$_2$C$_6$H$_3$) | CH$_3$ | Q-6 | CH$_3$ |
| CH$_2$(2,4-F$_2$C$_6$H$_3$) | CH$_3$ | Q-7 | CH$_3$ |
| CH$_2$(2,5-F$_2$C$_6$H$_3$) | CH$_3$ | Q-8 | CH$_3$ |
| CH$_2$(2,6-F$_2$C$_6$H$_3$) | CH$_3$ | Q-15 | CH$_3$ |
| CH$_2$(2,4,6-F$_3$C$_6$H$_2$) | CH$_3$ | CH$_2$(2-BrC$_6$H$_4$) | CH$_3$ |
| CH$_2$(2-ClC$_6$H$_4$) | CH$_3$ | CH$_2$(2,6-Br$_2$C$_6$H$_3$) | CH$_3$ |
| CH$_2$(3-ClC$_6$H$_4$) | CH$_3$ | CH$_2$(2-Cl-6-FC$_6$H$_3$) | CH$_3$ |
| CH$_2$(4-ClC$_6$H$_4$) | CH$_3$ | CH$_2$(2-(OCH$_3$)C$_6$H$_4$) | CH$_3$ |
| CH$_2$(2,6-Cl$_2$C$_6$H$_3$) | CH$_3$ | CH$_2$(2-(CN)C$_6$H$_4$) | CH$_3$ |
| CH$_2$(2-(CH$_3$)C$_6$H$_4$) | CH$_3$ | CH$_2$(2-(CF$_3$)C$_6$H$_4$) | CH$_3$ |
| CH$_2$(3-(CH$_3$)C$_6$H$_4$) | CH$_3$ | CH$_2$(2-(OCF$_3$)C$_6$H$_4$) | CH$_3$ |
| CH$_2$(2-pyridyl) | CH$_3$ | CH$_2$(2-(SCH$_3$)C$_6$H$_4$) | CH$_3$ |
| CH$_2$(2-thienyl) | CH$_3$ | CH$_2$(2-(CH=CH$_2$)C$_6$H$_4$) | CH$_3$ |
| CH$_2$(2-furanyl) | CH$_3$ | CH$_2$(2-(C≡CH)C$_6$H$_4$) | CH$_3$ |
| CH$_2$(2-tetrahydrofuranyl) | CH$_3$ | | |
| \multicolumn{4}{c}{General Structure 6, m is 3, R$^1$ is CH$_2$CH$^3$} | | | |
| CH$_2$(C$_6$H$_5$) | H | CH$_2$(2-tetrahydropyranyl) | H |
| CH$_2$(2-FC$_6$H$_4$) | H | Q-1 | H |
| CH$_2$(3-FC$_6$H$_4$) | H | Q-3 | H |
| CH$_2$(4-FC$_6$H$_4$) | H | Q-4 | H |
| CH$_2$(2,3-F$_2$C$_6$H$_3$) | H | Q-6 | H |
| CH$_2$(2,4-F$_2$C$_6$H$_3$) | H | Q-7 | H |
| CH$_2$(2,5-F$_2$C$_6$H$_3$) | H | Q-8 | H |
| CH$_2$(2,6-F$_2$C$_6$H$_3$) | H | Q-15 | H |
| CH$_2$(2,4,6-F$_3$C$_6$H$_2$) | H | CH$_2$(2-BrC$_6$H$_4$) | H |
| CH$_2$(2-ClC$_6$H$_4$) | H | CH$_2$(2,6-Br$_2$C$_6$H$_3$) | H |
| CH$_2$(3-ClC$_6$H$_4$) | H | CH$_2$(2-Cl-6-FC$_6$H$_3$) | H |
| CH$_2$(4-ClC$_6$H$_4$) | H | CH$_2$(2-(OCH$_3$)C$_6$H$_4$) | H |
| CH$_2$(2,6-Cl$_2$C$_6$H$_3$) | H | CH$_2$(2-(CN)C$_6$H$_4$) | H |
| CH$_2$(2-(CH$_3$)C$_6$H$_4$) | H | CH$_2$(2-(CF$_3$)C$_6$H$_4$) | H |
| CH$_2$(3-(CH$_3$)C$_6$H$_4$) | H | CH$_2$(2-(OCF$_3$)C$_6$H$_4$) | H |
| CH$_2$(2-pyridyl) | H | CH$_2$(2-(SCH$_3$)C$_6$H$_4$) | H |
| CH$_2$(2-thienyl) | H | CH$_2$(2-(CH=CH$_2$)C$_6$H$_4$) | H |
| CH$_2$(2-furanyl) | H | CH$_2$(2-(C≡CH)C$_6$H$_4$) | H |
| CH$_2$(2-tetrahydrofuranyl) | H | | |
| CH$_2$(C$_6$H$_5$) | CH$_3$ | CH$_2$(2-tetrahydropyranyl) | CH$_3$ |

TABLE 6-continued

| Q | R² | Q | R² |
|---|---|---|---|
| CH₂(2-FC₆H₄) | CH₃ | Q-1 | CH₃ |
| CH₂(3-FC₆H₄) | CH₃ | Q-3 | CH₃ |
| CH₂(4-FC₆H₄) | CH₃ | Q-4 | CH₃ |
| CH₂(2,3-F₂C₆H₃) | CH₃ | Q-6 | CH₃ |
| CH₂(2,4-F₂C₆H₃) | CH₃ | Q-7 | CH₃ |
| CH₂(2,5-F₂C₆H₃) | CH₃ | Q-8 | CH₃ |
| CH₂(2,6-F₂C₆H₃) | CH₃ | Q-15 | CH₃ |
| CH₂(2,4,6-F₃C₆H₂) | CH₃ | CH₂(2-BrC₆H₄) | CH₃ |
| CH₂(2-ClC₆H₄) | CH₃ | CH₂(2,6-Br₂C₆H₃) | CH₃ |
| CH₂(3-ClC₆H₄) | CH₃ | CH₂(2-Cl-6-FC₆H₃) | CH₃ |
| CH₂(4-ClC₆H₄) | CH₃ | CH₂(2-(OCH₃)C₆H₄) | CH₃ |
| CH₂(2,6-Cl₂C₆H₃) | CH₃ | CH₂(2-(CN)C₆H₄) | CH₃ |
| CH₂(2-(CH₃)C₆H₄) | CH₃ | CH₂(2-(CF₃)C₆H₄) | CH₃ |
| CH₂(3-(CH₃)C₆H₄) | CH₃ | CH₂(2-(OCF₃)C₆H₄) | CH₃ |
| CH₂(2-pyridyl) | CH₃ | CH₂(2-(SCH₃)C₆H₄) | CH₃ |
| CH₂(2-thienyl) | CH₃ | CH₂(2-(CH=CH₂)C₆H₄) | CH₃ |
| CH₂(2-furanyl) | CH₃ | CH₂(2-(C≡CH)C₆H₄) | CH₃ |
| CH₂(2-tetrahydrofuranyl) | CH₃ | | |
| General Structure 6, m is 4, R¹ is CH₃ | | | |
| CH₂(C₆H₅) | H | CH₂(2-tetrahydropyranyl) | H |
| CH₂(2-FC₆H₄) | H | Q-1 | H |
| CH₂(3-FC₆H₄) | H | Q-3 | H |
| CH₂(4-FC₆H₄) | H | Q-4 | H |
| CH₂(2,3-F₂C₆H₃) | H | Q-6 | H |
| CH₂(2,4-F₂C₆H₃) | H | Q-7 | H |
| CH₂(2,5-F₂C₆H₃) | H | Q-8 | H |
| CH₂(2,6-F₂C₆H₃) | H | Q-15 | H |
| CH₂(2,4,6-F₃C₆H₂) | H | CH₂(2-BrC₆H₄) | H |
| CH₂(2-ClC₆H₄) | H | CH₂(2,6-Br₂C₆H₃) | H |
| CH₂(3-ClC₆H₄) | H | CH₂(2-Cl-6-FC₆H₃) | H |
| CH₂(4-ClC₆H₄) | H | CH₂(2-(OCH₃)C₆H₄) | H |
| CH₂(2,6-Cl₂C₆H₃) | H | CH₂(2-(CN)C₆H₄) | H |
| CH₂(2-(CH₃)C₆H₄) | H | CH₂(2-(CF₃)C₆H₄) | H |
| CH₂(3-(CH₃)C₆H₄) | H | CH₂(2-(OCF₃)C₆H₄) | H |
| CH₂(2-pyridyl) | H | CH₂(2-(SCH₃)C₆H₄) | H |
| CH₂(2-thienyl) | H | CH₂(2-(CH=CH₂)C₆H₄) | H |
| CH₂(2-furanyl) | H | CH₂(2-(C≡CH)C₆H₄) | H |
| CH₂(2-tetrahydrofuranyl) | H | | |
| CH₂(C₆H₅) | CH₃ | CH₂(2-tetrahydropyranyl) | CH₃ |
| CH₂(2-FC₆H₄) | CH₃ | Q-1 | CH₃ |
| CH₂(3-FC₆H₄) | CH₃ | Q-3 | CH₃ |
| CH₂(4-FC₆H₄) | CH₃ | Q-4 | CH₃ |
| CH₂(2,3-F₂C₆H₃) | CH₃ | Q-6 | CH₃ |
| CH₂(2,4-F₂C₆H₃) | CH₃ | Q-7 | CH₃ |
| CH₂(2,5-F₂C₆H₃) | CH₃ | Q-8 | CH₃ |
| CH₂(2,6-F₂C₆H₃) | CH₃ | Q-15 | CH₃ |
| CH₂(2,4,6-F₃C₆H₂) | CH₃ | CH₂(2-BrC₆H₄) | CH₃ |
| CH₂(2-ClC₆H₄) | CH₃ | CH₂(2,6-Br₂C₆H₃) | CH₃ |
| CH₂(3-ClC₆H₄) | CH₃ | CH₂(2-Cl-6-FC₆H₃) | CH₃ |
| CH₂(4-ClC₆H₄) | CH₃ | CH₂(2-(OCH₃)C₆H₄) | CH₃ |
| CH₂(2,6-Cl₂C₆H₃) | CH₃ | CH₂(2-(CN)C₆H₄) | CH₃ |
| CH₂(2-(CH₃)C₆H₄) | CH₃ | CH₂(2-(CF₃)C₆H₄) | CH₃ |
| CH₂(3-(CH₃)C₆H₄) | CH₃ | CH₂(2-(OCF₃)C₆H₄) | CH₃ |
| CH₂(2-pyridyl) | CH₃ | CH₂(2-(SCH₃)C₆H₄) | CH₃ |
| CH₂(2-thienyl) | CH₃ | CH₂(2-(CH=CH₂)C₆H₄) | CH₃ |
| CH₂(2-furanyl) | CH₃ | CH₂(2-(C≡CH)C₆H₄) | CH₃ |
| CH₂(2-tetrahydrofuranyl) | CH₃ | | |
| General Structure 6, m is 4, R¹ is CH₂CH₃ | | | |
| CH₂(C₆H₅) | H | CH₂(2-tetrahydropyranyl) | H |
| CH₂(2-FC₆H₄) | H | Q-1 | H |
| CH₂(3-FC₆H₄) | H | Q-3 | H |
| CH₂(4-FC₆H₄) | H | Q-4 | H |
| CH₂(2,3-F₂C₆H₃) | H | Q-6 | H |
| CH₂(2,4-F₂C₆H₃) | H | Q-7 | H |
| CH₂(2,5-F₂C₆H₃) | H | Q-8 | H |
| CH₂(2,6-F₂C₆H₃) | H | Q-15 | H |
| CH₂(2,4,6-F₃C₆H₂) | H | CH₂(2-BrC₆H₄) | H |
| CH₂(2-ClC₆H₄) | H | CH₂(2,6-Br₂C₆H₃) | H |
| CH₂(3-ClC₆H₄) | H | CH₂(2-Cl-6-FC₆H₃) | H |
| CH₂(4-ClC₆H₄) | H | CH₂(2-(OCH₃)C₆H₄) | H |
| CH₂(2,6-Cl₂C₆H₃) | H | CH₂(2-(CN)C₆H₄) | H |
| CH₂(2-(CH₃)C₆H₄) | H | CH₂(2-(CF₃)C₆H₄) | H |
| CH₂(3-(CH₃)C₆H₄) | H | CH₂(2-(OCF₃)C₆H₄) | H |
| CH₂(2-pyridyl) | H | CH₂(2-(SCH₃)C₆H₄) | H |
| CH₂(2-thienyl) | H | CH₂(2-(CH=CH₂)C₆H₄) | H |
| CH₂(2-furanyl) | H | CH₂(2-(C≡CH)C₆H₄) | H |
| CH₂(2-tetrahydrofuranyl) | H | | |
| CH₂(C₆H₅) | CH₃ | CH₂(2-tetrahydropyranyl) | CH₃ |
| CH₂(2-FC₆H₄) | CH₃ | Q-1 | CH₃ |
| CH₂(3-FC₆H₄) | CH₃ | Q-3 | CH₃ |

TABLE 6-continued

| Q | R² | Q | R² |
|---|---|---|---|
| CH₂(4-FC₆H₄) | CH₃ | Q-4 | CH₃ |
| CH₂(2,3-F₂C₆H₃) | CH₃ | Q-6 | CH₃ |
| CH₂(2,4-F₂C₆H₃) | CH₃ | Q-7 | CH₃ |
| CH₂(2,5-F₂C₆H₃) | CH₃ | Q-8 | CH₃ |
| CH₂(2,6-F₂C₆H₃) | CH₃ | Q-15 | CH₃ |
| CH₂(2,4,6-F₃C₆H₂) | CH₃ | CH₂(2-BrC₆H₄) | CH₃ |
| CH₂(2-ClC₆H₄) | CH₃ | CH₂(2,6-Br₂C₆H₃) | CH₃ |
| CH₂(3-ClC₆H₄) | CH₃ | CH₂(2-Cl-6-FC₆H₃) | CH₃ |
| CH₂(4-ClC₆H₄) | CH₃ | CH₂(2-(OCH₃)C₆H₄) | CH₃ |
| CH₂(2,6-Cl₂C₆H₃) | CH₃ | CH₂(2-(CN)C₆H₄) | CH₃ |
| CH₂(2-(CH₃)C₆H₄) | CH₃ | CH₂(2-(CF₃)C₆H₄) | CH₃ |
| CH₂(3-(CH₃)C₆H₄) | CH₃ | CH₂(2-(OCF₃)C₆H₄) | CH₃ |
| CH₂(2-pyridyl) | CH₃ | CH₂(2-(SCH₃)C₆H₄) | CH₃ |
| CH₂(2-thienyl) | CH₃ | CH₂(2-(CH=CH₂)C₆H₄) | CH₃ |
| CH₂(2-furanyl) | CH₃ | CH₂(2-(C≡CH)C₆H₄) | CH₃ |
| CH₂(2-tetrahydrofuranyl) | CH₃ | | |
| General Structure 6, m is 5, R¹ is CH₃ | | | |
| CH₂(C₆H₅) | H | CH₂(2-tetrahydropyranyl) | H |
| CH₂(2-FC₆H₄) | H | Q-1 | H |
| CH₂(3-FC₆H₄) | H | Q-3 | H |
| CH₂(4-FC₆H₄) | H | Q-4 | H |
| CH₂(2,3-F₂C₆H₃) | H | Q-6 | H |
| CH₂(2,4-F₂C₆H₃) | H | Q-7 | H |
| CH₂(2,5-F₂C₆H₃) | H | Q-8 | H |
| CH₂(2,6-F₂C₆H₃) | H | Q-15 | H |
| CH₂(2,4,6-F₃C₆H₂) | H | CH₂(2-BrC₆H₄) | H |
| CH₂(2-ClC₆H₄) | H | CH₂(2,6-Br₂C₆H₃) | H |
| CH₂(3-ClC₆H₄) | H | CH₂(2-Cl-6-FC₆H₃) | H |
| CH₂(4-ClC₆H₄) | H | CH₂(2-(OCH₃)C₆H₄) | H |
| CH₂(2,6-Cl₂C₆H₃) | H | CH₂(2-(CN)C₆H₄) | H |
| CH₂(2-(CH₃)C₆H₄) | H | CH₂(2-(CF₃)C₆H₄) | H |
| CH₂(3-(CH₃)C₆H₄) | H | CH₂(2-(OCF₃)C₆H₄) | H |
| CH₂(2-pyridyl) | H | CH₂(2-(SCH₃)C₆H₄) | H |
| CH₂(2-thienyl) | H | CH₂(2-(CH=CH₂)C₆H₄) | H |
| CH₂(2-furanyl) | H | CH₂(2-(C≡CH)C₆H₄) | H |
| CH₂(2-tetrahydrofuranyl) | H | | |

TABLE 7

| Q | R³ | Q | R³ |
|---|---|---|---|
| General Structure 7, n in 2, R¹ is CH₃, R² is H | | | |
| CH₂(C₆H₅) | H | CH₂(2-tetrahydrofuranyl) | H |
| CH₂(2-FC₆H₄) | H | CH₂(2-tetrahydropyranyl) | H |
| CH₂(3-FC₆H₄) | H | Q-1 | H |
| CH₂(4-FC₆H₄) | H | Q-3 | H |
| CH₂(2,3-F₂C₆H₃) | H | Q-4 | H |
| CH₂(2,4-F₂C₆H₃) | H | Q-6 | H |
| CH₂(2,5-F₂C₆H₃) | H | Q-7 | H |
| CH₂(2,6-F₂C₆H₃) | H | Q-8 | H |
| CH₂(2,4,6-F₃C₆H₂) | H | Q-15 | H |
| CH₂(2-ClC₆H₄) | H | CH₂(2-BrC₆H₄) | H |
| CH₂(3-ClC₆H₄) | H | CH₂(2,6-Br₂C₆H₃) | H |
| CH₂(4-ClC₆H₄) | H | CH₂(2-Cl-6-FC₆H₃) | H |
| CH₂(2,6-Cl₂C₆H₃) | H | CH₂(2-(OCH₃)C₆H₄) | H |
| CH₂(2-(CH₃)C₆H₄) | H | CH₂(2-(CN)C₆H₄) | H |
| CH₂(3-(CH₃)C₆H₄) | H | CH₂(2-(CF₃)C₆H₄) | H |
| CH₂(4-(CH₃)C₆H₄) | H | CH₂(2-(OCF₃)C₆H₄) | H |
| CH₂(2-pyridyl) | H | CH₂(2-(SCH₃)C₆H₄) | H |
| CH₂(2-thienyl) | H | CH₂(2-(CH=CH₂)C₆H₄) | H |
| CH₂(2-furanyl) | H | CH₂(2-(C≡CH)C₆H₄) | H |
| CH₂(C₆H₅) | CH₃ | CH₂(2-tetrahydrofuranyl) | CH₃ |
| CH₂(2-FC₆H₄) | CH₃ | CH₂(2-tetrhydropyranyl) | CH₃ |
| CH₂(3-FC₆H₄) | CH₃ | Q-1 | CH₃ |
| CH₂(4-FC₆H₄) | CH₃ | Q-3 | CH₃ |
| CH₂(2,3-F₂C₆H₃) | CH₃ | Q-4 | CH₃ |
| CH₂(2,4-F₂C₆H₃) | CH₃ | Q-6 | CH₃ |
| CH₂(2,5-F₂C₆H₃) | CH₃ | Q-7 | CH₃ |
| CH₂(2,6-F₂C₆H₃) | CH₃ | Q-8 | CH₃ |
| CH₂(2,4,6-F₃C₆H₂) | CH₃ | Q-15 | CH₃ |
| CH₂(2-ClC₆H₄) | CH₃ | CH₂(2-BrC₆H₄) | CH₃ |
| CH₂(3-ClC₆H₄) | CH₃ | CH₂(2,6-Br₂C₆H₃) | CH₃ |
| CH₂(4-ClC₆H₄) | CH₃ | CH₂(2-Cl-6-FC₆H₃) | CH₃ |
| CH₂(2,6-Cl₂C₆H₃) | CH₃ | CH₂(2-(OCH₃)C₆H₄) | CH₃ |
| CH₂(2-(CH₃)C₆H₄) | CH₃ | CH₂(2-(CN)C₆H₄) | CH₃ |
| CH₂(3-(CH₃)C₆H₄) | CH₃ | CH₂(2-(CF₃)C₆H₄) | CH₃ |
| CH₂(4-(CH₃)C₆H₄) | CH₃ | CH₂(2-(OCF₃)C₆H₄) | CH₃ |
| CH₂(2-pyridyl) | CH₃ | CH₂(2-(SCH₃)C₆H₄) | CH₃ |
| CH₂(2-thienyl) | CH₃ | CH₂(2-CH=CH₂)C₆H₄) | CH₃ |
| CH₂(2-furanyl) | CH₃ | CH₂(2-(C≡CH)C₆H₄) | CH₃ |

TABLE 7-continued

| Q | R³ | Q | R³ |
|---|---|---|---|
| CH₂(C₆H₅) | CH₂CH₃ | CH₂(C₆H₅) | CH₂C≡CH |
| CH₂(2-FC₆H₄) | CH₂CH₃ | CH₂(2-FC₆H₄) | CH₂C≡CH |
| CH₂(2,6-F₂C₆H₃) | CH₂CH₃ | CH₂(2,6-F₂C₆H₃) | CH₂C≡CH |
| CH₂(2-ClC₆H₄) | CH₂CH₃ | CH₂(2-ClC₆H₄) | CH₂C≡CH |
| CH₂(2,Cl-6-FC₆H₃) | CH₂CH₃ | CH₂(2-Cl-6-FC₆H₃) | CH₂C≡CH |
| CH₂(2-(CH₃)C₆H₄) | CH₂CH₃ | CH₂(2-(CH₃)C₆H₄) | CH₂C≡CH |
| CH₂(2-pyridyl) | CH₂CH₃ | CH₂(2-pyridyl) | CH₂C≡CH |
| Q-1 | CH₂CH₃ | Q-1 | CH₂C≡CH |
| CH₂(C₆H₅) | CH₂CH=CH₂ | CH₂(C₆H₅) | CH₂CH₂OCH₃ |
| CH₂(2-FC₆H₄) | CH₂CH=CH₂ | CH₂(2-FC₆H₄) | CH₂CH₂OCH₃ |
| CH₂(2,6-F₂C₆H₃) | CH₂CH=CH₂ | CH₂(2,6-F₂C₆H₃) | CH₂CH₂OCH₃ |
| CH₂(2-ClC₆H₄) | CH₂CH=CH₂ | CH₂(2-ClC₆H₄) | CH₂CH₂OCH₃ |
| CH₂(2,Cl-6-FC₆H₃) | CH₂CH=CH₂ | CH₂(2-Cl-6-FC₆H₃) | CH₂CH₂OCH₃ |
| CH₂(2-(CH₃)C₆H₄) | CH₂CH=CH₂ | CH₂(2-(CH₃)C₆H₄) | CH₂CH₂OCH₃ |
| CH₂(2-pyridyl) | CH₂CH=CH₂ | CH₂(2-pyridyl) | CH₂CH₂OCH₃ |
| Q-1 | CH₂CH=CH₂ | Q-1 | CH₂CH₂OCH₃ |
| CH₂(C₆H₅) | H | CH₂(2-tetrahydrofuranyl) | H |
| CH₂(2-FC₆H₄) | H | CH₂(2-tetrahydropyranyl) | H |
| CH₂(3-FC₆H₄) | H | Q-1 | H |
| CH₂(4-FC₆H₄) | H | Q-3 | H |
| CH₂(2,3-F₂C₆H₃) | H | Q-4 | H |
| CH₂(2,4-F₂C₆H₃) | H | Q-6 | H |
| CH₂(2,5-F₂C₆H₃) | H | Q-7 | H |
| CH₂(2,6-F₂C₆H₃) | H | Q-8 | H |
| CH₂(2,4,6-F₃C₆H₂) | H | Q-15 | H |
| CH₂(2-ClC₆H₄) | H | CH₂(2-BrC₆H₄) | H |
| CH₂(3-ClC₆H₄) | H | CH₂(2,6-Br₂C₆H₃) | H |
| CH₂(4-ClC₆H₄) | H | CH₂(2-Cl-6-FC₆H₃) | H |
| CH₂(2,6-Cl₂C₆H₃) | H | CH₂(2-(OCH₃)C₆H₄) | H |
| CH₂(2-(CH₃)C₆H₄) | H | CH₂(2-(CN)C₆H₄) | H |
| CH₂(3-(CH₃)C₆H₄) | H | CH₂(2-(CF₃)C₆H₄) | H |
| CH₂(4-(CH₃)C₆H₄) | H | CH₂(2-(OCF₃)C₆H₄) | H |
| CH₂(2-pyridyl) | H | CH₂(2-(SCH₃)C₆H₄) | H |
| CH₂(2-thienyl) | H | CH₂(2-(CH=CH₂)C₆H₄) | H |
| CH₂(2-furanyl) | H | CH₂(2-(C≡CH)C₆H₄) | H |
| CH₂(C₆H₅) | CH₃ | CH₂(2-tetrahydrofuranyl) | CH₃ |
| CH₂(2-FC₆H₄) | CH₃ | CH₂(2-tetrahydropyranyl) | CH₃ |
| CH₂(3-FC₆H₄) | CH₃ | Q-1 | CH₃ |
| CH₂(4-FC₆H₄) | CH₃ | Q-3 | CH₃ |
| CH₂(2,3-F₂C₆H₃) | CH₃ | Q-4 | CH₃ |
| CH₂(2,4-F₂C₆H₃) | CH₃ | Q-6 | CH₃ |
| CH₂(2,5-F₂C₆H₃) | CH₃ | Q-7 | CH₃ |
| CH₂(2,6-F₂C₆H₃) | CH₃ | Q-8 | CH₃ |
| CH₂(2,4,6-F₃C₆H₂) | CH₃ | Q-15 | CH₃ |
| CH₂(2-ClC₆H₄) | CH₃ | CH₂(2-BrC₆H₄) | CH₃ |
| CH₂(3-ClC₆H₄) | CH₃ | CH₂(2,6-Br₂C₆H₃) | CH₃ |
| CH₂(4-ClC₆H₄) | CH₃ | CH₂(2-Cl-6-FC₆H₃) | CH₃ |
| CH₂(2,6-Cl₂C₆H₃) | CH₃ | CH₂(2-(OCH₃)C₆H₄) | CH₃ |
| CH₂(2-(CH₃)C₆H₄) | CH₃ | CH₂(2-(CN)C₆H₄) | CH₃ |
| CH₂(3-(CH₃)C₆H₄) | CH₃ | CH₂(2-(CF₃)C₆H₄) | CH₃ |
| CH₂(4-(CH₃)C₆H₄) | CH₃ | CH₂(2-(OCF₃)C₆H₄) | CH₃ |
| CH₂(2-pyridyl) | CH₃ | CH₂(2-(SCH₃)C₆H₄) | CH₃ |
| CH₂(2-thienyl) | CH₃ | CH₂(2-(CH=CH₂)C₆H₄) | CH₃ |
| CH₂(2-furanyl) | CH₃ | CH₂(2-(C≡CH)C₆H₄) | CH₃ |
| General Structure 7, n is 2, R¹ is CH₃, R² is CH₃ | | | |
| CH₂(C₆H₅) | CH₂CH₃ | CH₂(C₆H₅) | CH₂C≡CH |
| CH₂(2-FC₆H₄) | CH₂CH₃ | CH₂(2-FC₆H₄) | CH₂C≡CH |
| CH₂(2,6-F₂C₆H₃) | CH₂CH₃ | CH₂(2,6-F₂C₆H₃) | CH₂C≡CH |
| CH₂(2-ClC₆H₄) | CH₂CH₃ | CH₂(2-ClC₆H₄) | CH₂C≡CH |
| CH₂(2-Cl-6-FC₆H₃) | CH₂CH₃ | CH₂(2-Cl-6-FC₆H₃) | CH₂C≡CH |
| CH₂(2-(CH₃)C₆H₄) | CH₂CH₃ | CH₂(2-(CH₃)C₆H₄) | CH₂C≡CH |
| CH₂(2-pyridyl) | CH₂CH₃ | CH₂(2-pyridyl) | CH₂C≡CH |
| Q-1 | CH₂CH₃ | Q-1 | CH₂C≡CH |
| CH₂(C₆H₅) | CH₂CH=CH₂ | CH₂(C₆H₅) | CH₂CH₂OCH₃ |
| CH₂(2-FC₆H₄) | CH₂CH=CH₂ | CH₂(2-FC₆H₄) | CH₂CH₂OCH₃ |
| CH₂(2,6-F₂C₆H₃) | CH₂CH=CH₂ | CH₂(2,6-F₂C₆H₃) | CH₂CH₂OCH₃ |
| CH₂(2-ClC₆H₄) | CH₂CH=CH₂ | CH₂(2-ClC₆H₄) | CH₂CH₂OCH₃ |
| CH₂(2-Cl-6-FC₆H₃) | CH₂CH=CH₂ | CH₂(2-Cl-6-FC₆H₃) | CH₂CH₂OCH₃ |
| CH₂(2-(CH₃)C₆H₄) | CH₂CH=CH₂ | CH₂(2-(CH₃)C₆H₄) | CH₂CH₂OCH₃ |
| CH₂(2-pyridyl) | CH₂CH=CH₂ | CH₂(2-pyridyl) | CH₂CH₂OCH₃ |
| Q-1 | CH₂CH=CH₂ | Q-1 | CH₂CH₂OCH₃ |
| General Structure 7, n is 3, R¹ is CH₃, R² is H | | | |
| CH₂(C₆H₅) | H | CH₂(2-tetrahydrofuranyl) | H |
| CH₂(2-FC₆H₄) | H | CH₂(2-tetrahydropyranyl) | H |
| CH₂(3-FC₆H₄) | H | Q-1 | H |
| CH₂(4-FC₆H₄) | H | Q-3 | H |
| CH₂(2,3-F₂C₆H₃) | H | Q-4 | H |
| CH₂(2,4-F₂C₆H₃) | H | Q-6 | H |
| CH₂(2,5-F₂C₆H₃) | H | Q-7 | H |
| CH₂(2,6-F₂C₆H₃) | H | Q-8 | H |

TABLE 7-continued

| Q | R³ | Q | R³ |
|---|---|---|---|
| CH₂(2,4,6-F₃C₆H₂) | H | Q-15 | H |
| CH₂(2-ClC₆H₄) | H | CH₂(2-BrC₆H₄) | H |
| CH₂(3-ClC₆H₄) | H | CH₂(2,6-Br₂C₆H₃) | H |
| CH₂(4-ClC₆H₄) | H | CH₂(2-Cl-6-FC₆H₃) | H |
| CH₂(2,6-Cl₂C₆H₃) | H | CH₂(2-(OCH₃)C₆H₄) | H |
| CH₂(2-(CH₃)C₆H₄) | H | CH₂(2-(CN)C₆H₄) | H |
| CH₂(3-(CH₃)C₆H₄) | H | CH₂(2-(CF₃)C₆H₄) | H |
| CH₂(4-(CH₃)C₆H₄) | H | CH₂(2-(OCF₃)C₆H₄) | H |
| CH₂(2-pyridyl) | H | CH₂(2-(SCH₃)C₆H₄) | H |
| CH₂(2-thienyl) | H | CH₂(2-(CH=CH₂)C₆H₄) | H |
| CH₂(2-furanyl) | H | CH₂(2-(C≡CH)C₆H₄) | H |
| CH₂(C₆H₅) | CH₃ | CH₂(2-tetrahydrofuranyl) | CH₃ |
| CH₂(2-FC₆H₄) | CH₃ | CH₂(2-tetrahydropyranyl) | CH₃ |
| CH₂(3-FC₆H₄) | CH₃ | Q-1 | CH₃ |
| CH₂(4-FC₆H₄) | CH₃ | Q-3 | CH₃ |
| CH₂(2,3-F₂C₆H₃) | CH₃ | Q-4 | CH₃ |
| CH₂(2,4-F₂C₆H₃) | CH₃ | Q-6 | CH₃ |
| CH₂(2,5-F₂C₆H₃) | CH₃ | Q-7 | CH₃ |
| CH₂(2,6-F₂C₆H₃) | CH₃ | Q-8 | CH₃ |
| CH₂(2,4,6-F₃C₆H₂) | CH₃ | Q-15 | CH₃ |
| CH₂(2-ClC₆H₄) | CH₃ | CH₂(2-BrC₆H₄) | CH₃ |
| CH₂(3-ClC₆H₄) | CH₃ | CH₂(2,6-Br₂C₆H₃) | CH₃ |
| CH₂(4-ClC₆H₄) | CH₃ | CH₂(2-Cl-6-FC₆H₃) | CH₃ |
| CH₂(2,6-Cl₂C₆H₃) | CH₃ | CH₂(2-(OCH₃)C₆H₄) | CH₃ |
| CH₂(2-(CH₃)C₆H₄) | CH₃ | CH₂(2-(CN)C₆H₄) | CH₃ |
| CH₂(3-(CH₃)C₆H₄) | CH₃ | CH₂(2-(CF₃)C=CH | CH₃ |
| CH₂(4-(CH₃)C₆H₄) | CH₃ | CH₂(2-(OCF₃)C₆H₄) | CH₃ |
| CH₂(2-pyridyl) | CH₃ | CH₂(2-(SCH₃)C₆H₄) | CH₃ |
| CH₂(2-thienyl) | CH₃ | CH₂(2-(CH=CH₂)C₆H₄) | CH₃ |
| CH₂(2-furanyl) | CH₃ | CH₂(2-(C≡CH)C₆H₄) | CH₃ |
| CH₂(C₆H₅) | CH₂CH₃ | CH₂(C₆H₅) | CH₂C≡CH |
| CH₂(2-FC₆H₄) | CH₂CH₃ | CH₂(2-FC₆H₄) | CH₂C≡CH |
| CH₂(2,6-F₂C₆H₃) | CH₂CH₃ | CH₂(2,6-F₂C₆H₃) | CH₂C≡CH |
| CH₂(2-ClC₆H₄) | CH₂CH₃ | CH₂(2-ClC₆H₄) | CH₂C≡CH |
| CH₂(2-Cl-6-FC₆H₃) | CH₂CH₃ | CH₂(2-Cl-6-FC₆H₃) | CH₂C≡CH |
| CH₂(2-(CH₃)C₆H₄) | CH₂CH₃ | CH₂(2-(CH₃)C₆H₄) | CH₂C≡CH |
| CH₂(2-pyridyl) | CH₂CH₃ | CH₂(2-pyridyl) | CH₂C≡CH |
| Q-1 | CH₂CH₃ | Q-1 | CH₂C≡CH |
| CH₂(C₆H₅) | CH₂CH=CH₂ | CH₂(C₆H₅) | CH₂CH₂OCH₃ |
| CH₂(2-FC₆H₄) | CH₂CH=CH₂ | CH₂(2-FC₆H₄) | CH₂CH₂OCH₃ |
| CH₂(2,6-F₂C₆H₃) | CH₂CH=CH₂ | CH₂(2,6-F₂C₆H₃) | CH₂CH₂OCH₃ |
| CH₂(2-ClC₆H₄) | CH₂CH=CH₂ | CH₂(2-ClC₆H₄) | CH₂CH₂OCH₃ |
| CH₂(2-Cl-6-FC₆H₃) | CH₂CH=CH₂ | CH₂(2-Cl-6-FC₆H₃) | CH₂CH₂OCH₃ |
| CH₂(2-(CH₃)C₆H₄) | CH₂CH=CH₂ | CH₂(2-(CH₃)C₆H₄) | CH₂CH₂OCH₃ |
| CH₂(2-pyridyl) | CH₂CH=CH₂ | CH₂(2-pyridyl) | CH₂CH₂OCH₃ |
| Q-1 | CH₂CH=CH₂ | Q-1 | CH₂CH₂OCH₃ |
| General Structure 7, n is 3, R¹ is CH₃, R² is CH₃ | | | |
| CH₂(C₆H₅) | H | CH₂(2-tetrahydrofuranyl) | H |
| CH₂(2-FC₆H₄) | H | CH₂(2-tetrahydropyranyl) | H |
| CH₂(3-FC₆H₄) | H | Q-1 | H |
| CH₂(4-FC₆H₄) | H | Q-3 | H |
| CH₂(2,3-F₂C₆H₃) | H | Q-4 | H |
| CH₂(2,4-F₂C₆H₃) | H | Q-6 | H |
| CH₂(2,5-F₂C₆H₃) | H | Q-7 | H |
| CH₂(2,6-F₂C₆H₃) | H | Q-8 | H |
| CH₂(2,4,6-F₃C₆H₂) | H | Q-15 | H |
| CH₂(2-ClC₆H₄) | H | CH₂(2-BrC₆H₄) | H |
| CH₂(3-ClC₆H₄) | H | CH₂(2,6-Br₂C₆H₃) | H |
| CH₂(4-ClC₆H₄) | H | CH₂(2-Cl-6-FC₆H₃) | H |
| CH₂(2,6-Cl₂C₆H₃) | H | CH₂(2-(OCH₃)C₆H₄) | H |
| CH₂(2-CH₃)C₆H₄) | H | CH₂(2-(CN)C₆H₄) | H |
| CH₂(3-(CH₃)C₆H₄) | H | CH₂(2-(CF₃)C₆H₄) | H |
| CH₂(4-(CH₃)C₆H₄) | H | CH₂(2-(OCF₃)C₆H₄) | H |
| CH₂(2-pyridyl) | H | CH₂(2-(SCH₃)C₆H₄) | H |
| CH₂(2-thienyl) | H | CH₂(2-(CH=CH₂)C₆H₄) | H |
| CH₂(2-furanyl) | H | CH₂(2-(C≡CH)C₆H₄) | H |
| CH₂(C₆H₅) | CH₃ | CH₂(2-tetrahydrofuranyl) | CH₃ |
| CH₂(2-FC₆H₄) | CH₃ | CH₂(2-tetrahydropyranyl) | CH₃ |
| CH₂(3-FC₆H₄) | CH₃ | Q-1 | CH₃ |
| CH₂(4-FC₆H₄) | CH₃ | Q-3 | CH₃ |
| CH₂(2,3-F₂C₆H₃) | CH₃ | Q-4 | CH₃ |
| CH₂(2,4-F₂C₆H₃) | CH₃ | Q-6 | CH₃ |
| CH₂(2,5-F₂C₆H₃) | CH₃ | Q-7 | CH₃ |
| CH₂(2,6-F₂C₆H₃) | CH₃ | Q-8 | CH₃ |
| CH₂(2,4,6-F₃C₆H₂) | CH₃ | Q-15 | CH₃ |
| CH₂(2-ClC₆H₄) | CH₃ | CH₂(2-BrC₆H₄) | CH₃ |
| CH₂(3-ClC₆H₄) | CH₃ | CH₂(2,6-Br₂C₆H₃) | CH₃ |
| CH₂(4-ClC₆H₄) | CH₃ | CH₂(2-Cl-6-FC₆H₃) | CH₃ |
| CH₂(2,6-Cl₂C₆H₃) | CH₃ | CH₂(2-(OCH₃)C₆H₄) | CH₃ |
| CH₂(2-(CH₃)C₆H₄) | CH₃ | CH₂(2-(CN)C₆H₄) | CH₃ |
| CH₂(3-(CH₃)C₆H₄) | CH₃ | CH₂(2-(CF₃)C₆H₄) | CH₃ |

TABLE 7-continued

| Q | R³ | Q | R³ |
|---|---|---|---|
| CH₂(4-(CH₃)C₆H₄) | CH₃ | CH₂(2-(OCF₃)C₆H₄) | CH₃ |
| CH₂(2-pyridyl) | CH₃ | CH₂(2-(SCH₃)C₆H₄) | CH₃ |
| CH₂(2-thienyl) | CH₃ | CH₂(2-(CH=CH₂)C₆H₄) | CH₃ |
| CH₂(2-furanyl) | CH₃ | CH₂(2-(C≡CH)C₆H₄) | CH₃ |
| CH₂(C₆H₅) | CH₂CH₃ | CH₂(C₆H₅) | CH₂C≡CH |
| CH₂(2-FC₆H₄) | CH₂CH₃ | CH₂(2-FC₆H₄) | CH₂C≡CH |
| CH₂(2,6-F₂C₆H₃) | CH₂CH₃ | CH₂(2,6-F₂C₆H₃) | CH₂C≡CH |
| CH₂(2-ClC₆H₄) | CH₂CH₃ | CH₂(2-ClC₆H₄) | CH₂C≡CH |
| CH₂(2-Cl-6-FC₆H₃) | CH₂CH₃ | CH₂(2-Cl-6-FC₆H₃) | CH₂C≡CH |
| CH₂(2-(CH₃)C₆H₄) | CH₂CH₃ | CH₂(2-(CH₃)C₆H₄) | CH₂C≡CH |
| CH₂(2-pyridyl) | CH₂CH₃ | CH₂(2-pyridyl) | CH₂C≡CH |
| Q-1 | CH₂CH₃ | Q-1 | CH₂C≡CH |
| CH₂(C₆H₅) | CH₂CH=CH₂ | CH₂(C₆H₅) | CH₂CH₂OCH₃ |
| CH₂(2-FC₆H₄) | CH₂CH=CH₂ | CH₂(2-FC₆H₄) | CH₂CH₂OCH₃ |
| CH₂(2,6-F₂C₆H₃) | CH₂CH=CH₂ | CH₂(2,6-F₂C₆H₃) | CH₂CH₂OCH₃ |
| CH₂(2-ClC₆H₄) | CH₂CH=CH₂ | CH₂(2-ClC₆H₄) | CH₂CH₂OCH₃ |
| CH₂(2-Cl-6-FC₆H₃) | CH₂CH=CH₂ | CH₂(2-Cl-6-FC₆H₃) | CH₂CH₂OCH₃ |
| CH₂(2-(CH₃)C₆H₄) | CH₂CH=CH₂ | CH₂(2-(CH₃)C₆H₄) | CH₂CH₂OCH₃ |
| CH₂(2-pyridyl) | CH₂CH=CH₂ | CH₂(2-pyridyl) | CH₂CH₂OCH₃ |
| Q-1 | CH₂CH=CH₂ | Q-1 | CH₂CH₂OCH₃ |
| General Structure 7, n is 4, R¹ is CH₃, R² is H | | | |
| CH₂(C₆H₅) | H | CH₂(2-tetrahydrofuranyl) | H |
| CH₂(2-FC₆H₄) | H | CH₂(2-tetrahydropyranyl) | H |
| CH₂(3-FC₆H₄) | H | Q-1 | H |
| CH₂(4-FC₆H₄) | H | Q-3 | H |
| CH₂(2,3-F₂C₆H₃) | H | Q-4 | H |
| CH₂(2,4-F₂C₆H₃) | H | Q-6 | H |
| CH₂(2,5-F₂C₆H₃) | H | Q-7 | H |
| CH₂(2,6-F₂C₆H₃) | H | Q-8 | H |
| CH₂(2,4,6-F₃C₆H₂) | H | Q-15 | H |
| CH₂(2-ClC₆H₄) | H | CH₂(2-BrC₆H₄) | H |
| CH₂(3-ClC₆H₄) | H | CH₂(2,6-Br₂C₆H₃) | H |
| CH₂(4-ClC₆H₄) | H | CH₂(2-Cl-6-FC₆H₃) | H |
| CH₂(2,6-Cl₂C₆H₃) | H | CH₂(2-(OCH₃)C₆H₄) | H |
| CH₂(2-(CH₃)C₆H₄) | H | CH₂(2-(CN)C₆H₄) | H |
| CH₂(3-(CH₃)C₆H₄) | H | CH₂(2-(CF₃)C₆H₄) | H |
| CH₂(4-(CH₃)C₆H₄) | H | CH₂(2-(OCF₃)C₆H₄ | H |
| CH₂(2-pyridyl) | H | CH₂(2-(SCH₃)C₆H₄) | H |
| CH₂(2-thienyl) | H | CH₂(2-(CH=CH₂)C₆H₄) | H |
| CH₂(2-furanyl) | H | CH₂(2-(C≡CH)C₆H₄) | H |
| CH₂(C₆H₅) | CH₃ | CH₂(2-tetrahydrofuranyl) | CH₃ |
| CH₂(2-FC₆H₄) | CH₃ | CH₂(2-tetrahydropyranyl) | CH₃ |
| CH₂(3-FC₆H₄) | CH₃ | Q-1 | CH₃ |
| CH₂(4-FC₆H₄) | CH₃ | Q-3 | CH₃ |
| CH₂(2,3-F₂C₆H₃) | CH₃ | Q-4 | CH₃ |
| CH₂(2,4-F₂C₆H₃) | CH₃ | Q-6 | CH₃ |
| CH₂(2,5-F₂C₆H₃) | CH₃ | Q-7 | CH₃ |
| CH₂(2,6-F₂C₆H₃) | CH₃ | Q-8 | CH₃ |
| CH₂(2,4,6-F₃C₆H₂) | CH₃ | Q-15 | CH₃ |
| CH₂(2-ClC₆H₄) | CH₃ | CH₂(2-BrC₆H₄) | CH₃ |
| CH₂(3-ClC₆H₄) | CH₃ | CH₂(2-BrC₆H₃) | CH₃ |
| CH₂(4-ClC₆H₄) | CH₃ | CH₂(2-Cl-6-FC₆H₃) | CH₃ |
| CH₂(2,6-Cl₂C₆H₃) | CH₃ | CH₂(2-(OCH₃)C₆H₄) | CH₃ |
| CH₂(2-(CH₃)C₆H₄) | CH₃ | CH₂(2-(CN)C₆H₄) | CH₃ |
| CH₂(3-(CH₃)C₆H₄) | CH₃ | CH₂(2-(CF₃)C₆H₄) | CH₃ |
| CH₂(4-(CH₃)C₆H₄) | CH₃ | CH₂(2-(OCF₃)C₆H₄) | CH₃ |
| CH₂(2-pyridyl) | CH₃ | CH₂(2-(SCH₃)C₆H₄) | CH₃ |
| CH₂(2-thienyl) | CH₃ | CH₂(2-(CH=CH₂)C₆H₄) | CH₃ |
| CH₂(2-furanyl) | CH₃ | CH₂(2-(C≡CH)C₆H₄) | CH₃ |
| CH₂(C₆H₅) | CH₂CH₃ | CH₂(C₆H₅) | CH₂C≡CH |
| CH₂(2-FC₆H₄) | CH₂CH₃ | CH₂(2-FC₆H₄) | CH₂C≡CH |
| CH₂(2,6-F₂C₆H₃) | CH₂CH₃ | CH₂(2,6-F₂C₆H₃) | CH₂C≡CH |
| CH₂(2-ClC₆H₄) | CH₂CH₃ | CH₂(2-ClC₆H₄) | CH₂C≡CH |
| CH₂(2-Cl-6-FC₆H₃) | CH₂CH₃ | CH₂(2-Cl-6-FC₆H₃) | CH₂C≡CH |
| CH₂(2-(CH₃)C₆H₄) | CH₂CH₃ | CH₂(2-(CH₃)C₆H₄) | CH₂C≡CH |
| CH₂(2-pyridyl) | CH₂CH₃ | CH₂(2-pyridyl) | CH₂C≡CH |
| Q-1 | CH₂CH₃ | Q-1 | CH₂C≡CH |
| CH₂(C₆H₅) | CH₂CH=CH₂ | CH₂(C₆H₅) | CH₂CH₂OCH₃ |
| CH₂(2-FC₆H₄) | CH₂CH=CH₂ | CH₂(2-FC₆H₄) | CH₂CH₂OCH₃ |
| CH₂(2,6-F₂C₆H₃) | CH₂CH=CH₂ | CH₂(2,6-F₂C₆H₃) | CH₂CH₂OCH₃ |
| CH₂(2-ClC₆H₄) | CH₂CH=CH₂ | CH₂(2-ClC₆H₄) | CH₂CH₂OCH₃ |
| CH₂(2,Cl-6-FC₆H₃) | CH₂CH=CH₂ | CH₂(2-Cl-6-FC₆H₃) | CH₂CH₂OCH₃ |
| CH₂(2-(CH₃)C₆H₄) | CH₂CH=CH₂ | CH₂(2-(CH₃)C₆H₄) | CH₂CH₂OCH₃ |
| CH₂(2-pyridyl) | CH₂CH=CH₂ | CH₂(2-pyridyl) | CH₂CH₂OCH₃ |
| Q-1 | CH₂CH=CH₂ | Q-1 | CH₂CH₂OCH₃ |
| General Structure 7, n is 4, R¹ is CH₃, R² is CH₃ | | | |
| CH₂(C₆H₅) | H | CH₂(2-tetrahydrofuranyl) | H |
| CH₂(2-FC₆H₄) | H | CH₂(2-tetrahydropyranyl) | H |
| CH₂(3-FC₆H₄) | H | Q-1 | H |
| CH₂(4-FC₆H₄) | H | Q-3 | H |

TABLE 7-continued

| Q | $R^3$ | Q | $R^3$ |
|---|---|---|---|
| $CH_2(2,3-F_2C_6H_3)$ | H | Q-4 | H |
| $CH_2(2,4-F_2C_6H_3)$ | H | Q-6 | H |
| $CH_2(2,5-F_2C_6H_3)$ | H | Q-7 | H |
| $CH_2(2,6-F_2C_6H_3)$ | H | Q-8 | H |
| $CH_2(2,4,6-F_3C_6H_2)$ | H | Q-15 | H |
| $CH_2(2-ClC_6H_4)$ | H | $CH_2(2-BrC_6H_4)$ | H |
| $CH_2(3-ClC_6H_4)$ | H | $CH_2(2,6-Br_2C_6H_3)$ | H |
| $CH_2(4-ClC_6H_4)$ | H | $CH_2(2-Cl-6-FC_6H_3)$ | H |
| $CH_2(2,6-Cl_2C_6H_3)$ | H | $CH_2(2-(OCH_3)C_6H_4)$ | H |
| $CH_2(2-(CH_3)C_6H_4)$ | H | $CH_2(2-(CN)C_6H_4)$ | H |
| $CH_2(3-(CH_3)C_6H_4)$ | H | $CH_2(2-(CF_3)C_6H_4)$ | H |
| $CH_2(4-(CH_3)C_6H_4)$ | H | $CH_2(2-(OCF_3)C_6H_4)$ | H |
| $CH_2(2\text{-pyridyl})$ | H | $CH_2(2-(SCH_3)C_6H_4)$ | H |
| $CH_2(2\text{-thienyl})$ | H | $CH_2(2-(CH=CH_2)C_6H_4)$ | H |
| $CH_2(2\text{-furanyl})$ | H | $CH_2(2-(C\equiv CH)C_6H_4)$ | H |
| $CH_2(C_6H_5)$ | $CH_3$ | $CH_2(2\text{-tetrahydrofuranyl})$ | $CH_3$ |
| $CH_2(2-FC_6H_4)$ | $CH_3$ | $CH_2(2\text{-tetrahydropyranyl})$ | $CH_3$ |
| $CH_2(3-FC_6H_4)$ | $CH_3$ | Q-1 | $CH_3$ |
| $CH_2(4-FC_6H_4)$ | $CH_3$ | Q-3 | $CH_3$ |
| $CH_2(2,3-F_2C_6H_3)$ | $CH_3$ | Q-4 | $CH_3$ |
| $CH_2(2,4-F_2C_6H_3)$ | $CH_3$ | Q-6 | $CH_3$ |
| $CH_2(2,5-F_2C_6H_3)$ | $CH_3$ | Q-7 | $CH_3$ |
| $CH_2(2,6-F_2C_6H_3)$ | $CH_3$ | Q-8 | $CH_3$ |
| $CH_2(2,4,6-F_3C_6H_2)$ | $CH_3$ | Q-15 | $CH_3$ |
| $CH_2(2-ClC_6H_4)$ | $CH_3$ | $CH_2(2-BrC_6H_4)$ | $CH_3$ |
| $CH_2(3-ClC_6H_4)$ | $CH_3$ | $CH_2(2,6-Br_2C_6H_3)$ | $CH_3$ |
| $CH_2(4-ClC_6H_4)$ | $CH_3$ | $CH_2(2-Cl-6-FC_6H_3)$ | $CH_3$ |
| $CH_2(2,6-Cl_2C_6H_3)$ | $CH_3$ | $CH_2(2-(OCH_3)C_6H_4)$ | $CH_3$ |
| $CH_2(2-(CH_3)C_6H_4)$ | $CH_3$ | $CH_2(2-(CN)C_6H_4)$ | $CH_3$ |
| $CH_2(3-(CH_3)C_6H_4)$ | $CH_3$ | $CH_2(2-(CF_3)C_6H_4)$ | $CH_3$ |
| $CH_2(4-(CH_3)C_6H_4)$ | $CH_3$ | $CH_2(2-(OCF_3)C_6H_4)$ | $CH_3$ |
| $CH_2(2\text{-pyridyl})$ | $CH_3$ | $CH_2(2-(SCH_3)C_6H_4)$ | $CH_3$ |
| $CH_2(2\text{-thienyl})$ | $CH_3$ | $CH_2(2-(CH=CH_2)C_6H_4)$ | $CH_3$ |
| $CH_2(2\text{-furanyl})$ | $CH_3$ | $CH_2(2-(C\equiv CH)C_6H_4)$ | $CH_3$ |
| $CH_2(C_6H_5)$ | $CH_2CH_3$ | $CH_2(C_6H_5)$ | $CH_2C\equiv CH$ |
| $CH_2(2-FC_6H_4)$ | $CH_2CH_3$ | $CH_2(2-FC_6H_4)$ | $CH_2C\equiv CH$ |
| $CH_2(2,6-F_2C_6H_3)$ | $CH_2CH_3$ | $CH_2(2,6-F_2C_6H_3)$ | $CH_2C\equiv CH$ |
| $CH_2(2-ClC_6H_4)$ | $CH_2CH_3$ | $CH_2(2-ClC_6H_4)$ | $CH_2C\equiv CH$ |
| $CH_2(2-Cl-6-FC_6H_3)$ | $CH_2(2,Cl-6-FC_6H_3)$ | $CH_2\equiv CH$ | |
| $CH_2(2-(CH_3)C_6H_4)$ | $CH_2CH_3$ | $CH_2(2-(CH_3)C_6H_4)$ | $CH_2C\equiv CH$ |
| $CH_2(2\text{-pyridyl})$ | $CH_2CH_3$ | $CH_2(2\text{-pyridyl})$ | $CH_2C\equiv CH$ |
| Q-1 | $CH_2CH_3$ | Q-1 | $CH_2C\equiv CH$ |
| $CH_2(C_6H_5)$ | $CH_2CH=CH_2$ | $CH_2(C_6H_5)$ | $CH_2CH_2OCH_3$ |
| $CH_2(2-FC_6H_4)$ | $CH_2CH=CH_2$ | $CH_2(2-FC_6H_4)$ | $CH_2CH_2OCH_3$ |
| $CH_2(2,6-F_2C_6H_3)$ | $CH_2CH=CH_2$ | $CH_2(2,6-F_2C_6H_3)$ | $CH_2CH_2OCH_3$ |
| $CH_2(2-ClC_6H_4)$ | $CH_2CH=CH_2$ | $CH_2(2-ClC_6H_4)$ | $CH_2CH_2OCH_3$ |
| $CH_2(2-Cl-6-FC_6H_3)$ | $CH_2CH=CH_2$ | $CH_2(2-Cl-6-FC_6H_3)$ | $CH_2CH_2OCH_3$ |
| $CH_2(2-(CH_3)C_6H_4)$ | $CH_2CH=CH_2$ | $CH_2(2-(CH_3)C_6H_4)$ | $CH_2CH_2OCH_3$ |
| $CH_2(2\text{-pyridyl})$ | $CH_2CH=CH_2$ | $CH_2(2\text{-pyridyl})$ | $CH_2CH_2OCH_3$ |
| Q-1 | $CH_2CH=CH_2$ | Q-1 | $CH_2CH_2OCH_3$ |

TABLE 8

| Q | $R^2$ | Q | $R^2$ |
|---|---|---|---|
| General Structure 8, m is 3, $R^3 = R^4$ is H ||||
| $CH_2(C_6H_5)$ | H | $CH_2(2\text{-tetrahydropyranyl})$ | H |
| $CH_2(2-FC_6H_4)$ | H | Q-1 | H |
| $CH_2(3-FC_6H_4)$ | H | Q-3 | H |
| $CH_2(4-FC_6H_4)$ | H | Q-4 | H |
| $CH_2(2,3-F_2C_6H_3)$ | H | Q-6 | H |
| $CH_2(2,4-F_2C_6H_3)$ | H | Q-7 | H |
| $CH_2(2,5-F_2C_6H_3)$ | H | Q-8 | H |
| $CH_2(2,6-F_2C_6H_3)$ | H | Q-15 | H |
| $CH_2(2,4,6-F_3C_6H_2)$ | H | $CH_2(2-BrC_6H_4)$ | H |
| $CH_2(2-ClC_6H_4)$ | H | $CH_2(2,6-Br_2C_6H_3)$ | H |
| $CH_2(3-ClC_6H_4)$ | H | $CH_2(2-Cl-6-FC_6H_3)$ | H |
| $CH_2(4-ClC_6H_4)$ | H | $CH_2(2-(OCH_3)C_6H_4)$ | H |
| $CH_2(2,6-Cl_2C_6H_3)$ | H | $CH_2(2-(CN)C_6H_4)$ | H |
| $CH_2(2-(CH_3)C_6H_4)$ | H | $CH_2(2-(CF_3)C_6H_4)$ | H |
| $CH_2(3-(CH_3)C_6H_4)$ | H | $CH_2(2-(OCF_3)C_6H_4)$ | H |
| $CH_2(2\text{-pyridyl})$ | H | $CH_2(2-(SCH_3)C_6H_4)$ | H |
| $CH_2(2\text{-thienyl})$ | H | $CH_2(2-(CH=CH_2)C_6H_4)$ | H |
| $CH_2(2\text{-furanyl})$ | H | $CH_2(2-(C\equiv CH)C_6H_4)$ | H |
| $CH_2(2\text{-tetrahydrofuranyl})$ | H | | |
| $CH_2(C_6H_5)$ | $CH_3$ | $CH_2(2\text{-tetrahydropyranyl})$ | $CH_3$ |
| $CH_2(2-FC_6H_4)$ | $CH_3$ | Q-1 | $CH_3$ |
| $CH_2(3-FC_6H_4)$ | $CH_3$ | Q-3 | $CH_3$ |
| $CH_2(4-FC_6H_4)$ | $CH_3$ | Q-4 | $CH_3$ |

TABLE 8-continued

| Q | R² | Q | R² |
|---|---|---|---|
| CH₂(2,3-F₂C₆H₃) | CH₃ | Q-6 | CH₃ |
| CH₂(2,4-F₂C₆H₃) | CH₃ | Q-7 | CH₃ |
| CH₂(2,5-F₂C₆H₃) | CH₃ | Q-8 | CH₃ |
| CH₂(2,6-F₂C₆H₃) | CH₃ | Q-15 | CH₃ |
| CH₂(2,4,6-F₃C₆H₂) | CH₃ | CH₂(2-BrC₆H₄) | CH₃ |
| CH₂(2-ClC₆H₄) | CH₃ | CH₂(2,6-Br₂C₆H₃) | CH₃ |
| CH₂(3-ClC₆H₄) | CH₃ | CH₂(2-Cl-6-FC₆H₃) | CH₃ |
| CH₂(4-ClC₆H₄) | CH₃ | CH₂(2-(OCH₃)C₆H₄) | CH₃ |
| CH₂(2,6-Cl₂C₆H₃) | CH₃ | CH₂(2-(CN)C₆H₄) | CH₃ |
| CH₂(2-(CH₃)C₆H₄) | CH₃ | CH₂(2-(CF₃)C₆H₄) | CH₃ |
| CH₂(3-(CH₃)C₆H₄) | CH₃ | CH₂(2-(OCF₃)C₆H₄) | CH₃ |
| CH₂(2-pyridyl) | CH₃ | CH₂(2-(SCH₃)C₆H₄) | CH₃ |
| CH₂(2-thienyl) | CH₃ | CH₂(2-(CH=CH₂)C₆H₄) | CH₃ |
| CH₂(2-furanyl) | CH₃ | CH₂(2-(C≡CH)C₆H₄) | CH₃ |
| CH₂(2-tetrahydrofuranyl) | CH₃ | | |
| General Structure 8, m is 3, R³ = R⁴ is CH₃ | | | |
| CH₂(C₆H₅) | H | CH₂(2-tetrahydropyranyl) | H |
| CH₂(2-FC₆H₄) | H | Q-1 | H |
| CH₂(3-FC₆H₄) | H | Q-3 | H |
| CH₂(4-FC₆H₄) | H | Q-4 | H |
| CH₂(2,3-F₂C₆H₃) | H | Q-6 | H |
| CH₂(2,4-F₂C₆H₃) | H | Q-7 | H |
| CH₂(2,5-F₂C₆H₃) | H | Q-8 | H |
| CH₂(2,6-F₂C₆H₃) | H | Q-15 | H |
| CH₂(2,4,6-F₃C₆H₂) | H | CH₂(2-BrC₆H₄) | H |
| CH₂(2-ClC₆H₄) | H | CH₂(2,6-Br₂C₆H₃) | H |
| CH₂(3-ClC₆H₄) | H | CH₂(2,Cl-6-FC₆H₃) | H |
| CH₂(4-ClC₆H₄) | H | CH₂(2-(OCH₃)C₆H₄) | H |
| CH₂(2,6-Cl₂C₆H₃) | H | CH₂(2-(CN)C₆H₄) | H |
| CH₂(2-(CH₃)C₆H₄) | H | CH₂(2-(CF₃)C₆H₄) | H |
| CH₂(3-(CH₃)C₆H₄) | H | CH₂(2-(OCF₃)C₆H₄) | H |
| CH₂(2-pyridyl) | H | CH₂(2-(SCH₃)C₆H₄) | H |
| CH₂(2-thienyl) | H | CH₂(2-(CH=CH₂)C₆H₄) | H |
| CH₂(2-furanyl) | H | CH₂(2-(C≡CH)C₆H₄) | H |
| CH₂(2-tetrahydrofuranyl) | H | | |
| CH₂(C₆H₅) | CH₃ | CH₂(2-tetrahydropyranyl) | CH₃ |
| CH₂(2-FC₆H₄) | CH₃ | Q-1 | CH₃ |
| CH₂(3-FC₆H₄) | CH₃ | Q-3 | CH₃ |
| CH₂(4-FC₆H₄) | CH₃ | Q-4 | CH₃ |
| CH₂(2,3-F₂C₆H₃) | CH₃ | Q-6 | CH₃ |
| CH₂(2,4-F₂C₆H₃) | CH₃ | Q-7 | CH₃ |
| CH₂(2,5-F₂C₆H₃) | CH₃ | Q-8 | CH₃ |
| CH₂(2,6-F₂C₆H₃) | CH₃ | Q-15 | CH₃ |
| CH₂(2,4,6-F₃C₆H₂) | CH₃ | CH₂(2-BrC₆H₄) | CH₃ |
| CH₂(2-ClC₆H₄) | CH₃ | CH₂(2,6-Br₂C₆H₃) | CH₃ |
| CH₂(3-ClC₆H₄) | CH₃ | CH₂(2-Cl-6-FC₆H₃) | CH₃ |
| CH₂(4-ClC₆H₄) | CH₃ | CH₂(2-(OCH₃)C₆H₄) | CH₃ |
| CH₂(2,6-Cl₂C₆H₃) | CH₃ | CH₂(2-(CN)C₆H₄) | CH₃ |
| CH₂(2-(CH₃)C₆H₄) | CH₃ | CH₂(2-(CF₃)C₆H₄) | CH₃ |
| CH₂(3-(CH₃)C₆H₄) | CH₃ | CH₂(2-(OCF₃)C₆H₄) | CH₃ |
| CH₂(2-pyridyl) | CH₃ | CH₂(2-(SCH₃)C₆H₄) | CH₃ |
| CH₂(2-thienyl) | CH₃ | CH₂(2-(CH=CH₂)C₆H₄) | CH₃ |
| CH₂(2-furanyl) | CH₃ | CH₂(C≡CH)C₆H₄) | CH₃ |
| CH₂(2-tetrahydrofuranyl) | CH₃ | | |
| General Structure 8, m is 4, R³ = R⁴ is H | | | |
| CH₂(C₆H₅) | H | CH₂(2-tetrahydropyranyl) | H |
| CH₂(2-FC₆H₄) | H | Q-1 | H |
| CH₂(3-FC₆H₄) | H | Q-3 | H |
| CH₂(4-FC₆H₄) | H | Q-4 | H |
| CH₂(2,3-F₂C₆H₃) | H | Q-6 | H |
| CH₂(2,4-F₂C₆H₃) | H | Q-7 | H |
| CH₂(2,6-F₂C₆H₃) | H | Q-8 | H |
| CH₂(2,6-F₂C₆H₃) | H | Q-15 | H |
| CH₂(2,4,6-F₃C₆H₂) | H | CH₂(2-BrC₆H₄) | H |
| CH₂(2-ClC₆H₄) | H | CH₂(2,6-Br₂C₆H₃) | H |
| CH₂(3-ClC₆H₄) | H | CH₂(2-Cl-6-FC₆H₃) | H |
| CH₂(4-ClC₆H₄) | H | CH₂(2-(OCH₃)C₆H₄) | H |
| CH₂(2,6-Cl₂C₆H₃) | H | CH₂(2-(CN)C₆H₄) | H |
| CH₂(2-(CH₃)C₆H₄) | H | CH₂(2-(CF₃)C₆H₄) | H |
| CH₂(3-(CH₃)C₆H₄) | H | CH₂(2-(OCF₃)C₆H₄) | H |
| CH₂(2-pyridyl) | H | CH₂(2-(SCH₃)C₆H₄) | H |
| CH₂(2-thienyl) | H | CH₂(2-(CH=CH₂)C₆H₄) | H |
| CH₂(2-furanyl) | H | CH₂(2-(C≡CH)C₆H₄) | H |
| CH₂(2-tetrahydrofuranyl) | H | | |
| CH₂(C₆H₅) | CH₃ | CH₂(2-tetrahydropyranyl) | CH₃ |
| CH₂(2-FC₆H₄) | CH₃ | Q-1 | CH₃ |
| CH₂(3-FC₆H₄) | CH₃ | Q-3 | CH₃ |
| CH₂(4-FC₆H₄) | CH₃ | Q-4 | CH₃ |
| CH₂(2,3-F₂C₆H₃) | CH₃ | Q-6 | CH₃ |
| CH₂(2,4-F₂C₆H₃) | CH₃ | Q-7 | CH₃ |

TABLE 8-continued

| Q | R² | Q | R² |
|---|---|---|---|
| CH₂(2,5-F₂C₆H₃) | CH₃ | Q-8 | CH₃ |
| CH₂(2,6-F₂C₆H₃) | CH₃ | Q-15 | CH₃ |
| CH₂(2,4,6-F₃C₆H₂) | CH₃ | CH₂(2-BrC₆H₄) | CH₃ |
| CH₂(2-ClC₆H₄) | CH₃ | CH₂(2,6-Br₂C₆H₃) | CH₃ |
| CH₂(3-ClC₆H₄) | CH₃ | CH₂(2-Cl-6-FC₆H₃) | CH₃ |
| CH₂(4-ClC₆H₄) | CH₃ | CH₂(2-(OCH₃)C₆H₄) | CH₃ |
| CH₂(2,6-Cl₂C₆H₃) | CH₃ | CH₂(2-(CN)C₆H₄) | CH₃ |
| CH₂(2-(CH₃)C₆H₄) | CH₃ | CH₂(2-(CF₃)C₆H₄) | CH₃ |
| CH₂(3-(CH₃)C₆H₄) | CH₃ | CH₂(2-(OCF₃)C₆H₄) | CH₃ |
| CH₂(2-pyridyl) | CH₃ | CH₂(2-(SCH₃)C₆H₄) | CH₃ |
| CH₂(2-thienyl) | CH₃ | CH₂(2-(CH=CH₂)C₆H₄) | CH₃ |
| CH₂(2-furanyl) | CH₃ | CH₂(2-(C≡CH)C₆H₄) | CH₃ |
| CH₂(2-tetrahydrofuranyl) | CH₃ | | |
| General Structure 8, m is 4, R³ = R⁴ is CH₃ | | | |
| CH₂(C₆H₅) | H | CH₂(2-tetrahydropyranyl) | H |
| CH₂(2-FC₆H₄) | H | Q-1 | H |
| CH₂(3-FC₆H₄) | H | Q-3 | H |
| CH₂(4-FC₆H₄) | H | Q-4 | H |
| CH₂(2,3-F₂C₆H₃) | H | Q-6 | H |
| CH₂(2,4-F₂C₆H₃) | H | Q-7 | H |
| CH₂(2,5-F₂C₆H₃) | H | Q-8 | H |
| CH₂(2,6-F₂C₆H₃) | H | Q-15 | H |
| CH₂(2,4,6-F₃C₆H₂) | H | CH₂(2-BrC₆H₄) | H |
| CH₂(2-ClC₆H₄) | H | CH₂(2,6-Br₂C₆H₃) | H |
| CH₂(3-ClC₆H₄) | H | CH₂(2-Cl-6-FC₆H₃) | H |
| CH₂(4-ClC₆H₄) | H | CH₂(2-(OCH₃)C₆H₄) | H |
| CH₂(2,6-Cl₂C₆H₃) | H | CH₂(2-(CN)C₆H₄) | H |
| CH₂(2-(CH₃)C₆H₄) | H | CH₂(2-(CF₃)C₆H₄) | H |
| CH₂(3-(CH₃)C₆H₄) | H | CH₂(2-(OCF₃)C₆H₄) | H |
| CH₂(2-pyridyl) | H | CH₂(2-(SCH₃)C₆H₄) | H |
| CH₂(2-thienyl) | H | CH₂(2-(CH=CH₂)C₆H₄) | H |
| CH₂(2-furanyl) | H | CH₂(2-(C≡CH)C₆H₄) | H |
| CH₂(2-tetrahydrofuranyl) | H | | |
| CH₂(C₆H₅) | CH₃ | CH₂(2-tetrahydropyranyl) | CH₃ |
| CH₂(2-FC₆H₄) | CH₃ | Q-1 | CH₃ |
| CH₂(3-FC₆H₄) | CH₃ | Q-3 | CH₃ |
| CH₂(4-FC₆H₄) | CH₃ | Q-4 | CH₃ |
| CH₂(2,3-F₂C₆H₃) | CH₃ | Q-6 | CH₃ |
| CH₂(2,4-F₂C₆H₃) | CH₃ | Q-7 | CH₃ |
| CH₂(2,5-F₂C₆H₃) | CH₃ | Q-8 | CH₃ |
| CH₂(2,6-F₂C₆H₃) | CH₃ | Q-15 | CH₃ |
| CH₂(2,4,6-F₃C₆H₂) | CH₃ | CH₂(2-BrC₆H₄) | CH₃ |
| CH₂(2-ClC₆H₄) | CH₃ | CH₂(2,6-Br₂C₆H₃) | CH₃ |
| CH₂(3-ClC₆H₄) | CH₃ | CH₂(2-Cl-6-FC₆H₃) | CH₃ |
| CH₂(4-ClC₆H₄) | CH₃ | CH₂(2-(OCH₃)C₆H₄) | CH₃ |
| CH₂(2,6-Cl₂C₆H₃) | CH₃ | CH₂(2-(CN)C₆H₄) | CH₃ |
| CH₂(2-(CH₃)C₆H₄) | CH₃ | CH₂(2-(CF₃)C₆H₄) | CH₃ |
| CH₂(3-(CH₃)C₆H₄) | CH₃ | CH₂(2-(OCF₃)C₆H₄) | CH₃ |
| CH₂(2-pyridyl) | CH₃ | CH₂(2-(SCH₃)C₆H₄) | CH₃ |
| CH₂(2-thienyl) | CH₃ | CH₂(2-(CH=CH₂)C₆H₄) | CH₃ |
| CH₂(2-furanyl) | CH₃ | CH₂(2-(C≡CH)C₆H₄) | CH₃ |
| CH₂(2-tetrahydrofuranyl) | CH₃ | | |
| General Structure 8, m is 5, R³ = R⁴ is H | | | |
| CH₂(C₆H₅) | H | CH₂(2-tetrahydropyranyl) | H |
| CH₂(2-FC₆H₄) | H | Q-1 | H |
| CH₂(3-FC₆H₄) | H | Q-3 | H |
| CH₂(4-FC₆H₄) | H | Q-4 | H |
| CH₂(2,3-F₂C₆H₃) | H | Q-6 | H |
| CH₂(2,4-F₂C₆H₃) | H | Q-7 | H |
| CH₂(2,5-F₂C₆H₃) | H | Q-8 | H |
| CH₂(2,6-F₂C₆H₃) | H | Q-15 | H |
| CH₂(2,4,6-F₃C₆H₂) | H | CH₂(2-BrC₆H₄) | H |
| CH₂(2-ClC₆H₄) | H | CH₂(2,6-Br₂C₆H₃) | H |
| CH₂(3-ClC₆H₄) | H | CH₂(2-Cl-6-FC₆H₃) | H |
| CH₂(4-ClC₆H₄) | H | CH₂(2-(OCH₃)C₆H₄) | H |
| CH₂(2,6-Cl₂C₆H₃) | H | CH₂(2-(CN)C₆H₄) | H |
| CH₂(2-(CH₃)C₆H₄) | H | CH₂(2-(CF₃)C₆H₄) | H |
| CH₂(3-(CH₃)C₆H₄) | H | CH₂(2-(OCF₃)C₆H₄) | H |
| CH₂(2-pyridyl) | H | CH₂(2-(SCH₃)C₆H₄) | H |
| CH₂(2-thienyl) | H | CH₂(2-CH=CH₂)C₆H₄) | H |
| CH₂(2-furanyl) | H | CH₂(2-(C≡CH)C₆H₄) | H |
| CH₂(2-tetrahydrofuranyl) | H | | |

TABLE 9

| Q | R¹ | Q | R¹ |
|---|---|---|---|
| General Structure 9, m is 3, R³ = R⁴ is H | | | |
| CH₂(C₆H₅) | CH₃ | CH₂(2-tetrahydropyranyl) | CH₃ |
| CH₂(2-FC₆H₄) | CH₃ | Q-1 | CH₃ |

TABLE 9-continued

| Q | R[1] | Q | R[1] |
|---|---|---|---|
| CH$_2$(3-FC$_6$H$_4$) | CH$_3$ | Q-3 | CH$_3$ |
| CH$_2$(4-FC$_6$H$_4$) | CH$_3$ | Q-4 | CH$_3$ |
| CH$_2$(2,3-F$_2$C$_6$H$_3$) | CH$_3$ | Q-6 | CH$_3$ |
| CH$_2$(2,4-F$_2$C$_6$H$_3$) | CH$_3$ | Q-7 | CH$_3$ |
| CH$_2$(2,5-F$_2$C$_6$H$_3$) | CH$_3$ | Q-8 | CH$_3$ |
| CH$_2$(2,6-F$_2$C$_6$H$_3$) | CH$_3$ | Q-15 | CH$_3$ |
| CH$_2$(2,4,6-F$_3$C$_6$H$_2$) | CH$_3$ | CH$_2$(2-BrC$_6$H$_4$) | CH$_3$ |
| CH$_2$(2-ClC$_6$H$_4$) | CH$_3$ | CH$_2$(2,6-Br$_2$C$_6$H$_3$) | CH$_3$ |
| CH$_2$(3-ClC$_6$H$_4$) | CH$_3$ | CH$_2$(2-Cl-6-FC$_6$H$_3$) | CH$_3$ |
| CH$_2$(4-ClC$_6$H$_4$) | CH$_3$ | CH$_2$(2-(OCH$_3$)C$_6$H$_4$) | CH$_3$ |
| CH$_2$(2,6-Cl$_2$C$_6$H$_3$) | CH$_3$ | CH$_2$(2-(CN)C$_6$H$_4$) | CH$_3$ |
| CH$_2$(CH$_3$)C$_6$H$_4$) | CH$_3$ | CH$_2$(2-(CF$_3$)C$_6$H$_4$) | CH$_3$ |
| CH$_2$(3-(CH$_3$)C$_6$H$_4$) | CH$_3$ | CH$_2$(2-(OCF$_3$)C$_6$H$_4$) | CH$_3$ |
| CH$_2$(2-pyridyl) | CH$_3$ | CH$_2$(2-(SCH$_3$)C$_6$H$_4$) | CH$_3$ |
| CH$_2$(2-thienyl) | CH$_3$ | CH$_2$(2-(CH=CH$_2$)C$_6$H$_4$) | CH$_3$ |
| CH$_2$(2-furanyl) | CH$_3$ | CH$_2$(2-(C≡CH)C$_6$H$_4$) | CH$_3$ |
| CH$_2$(2-tetrahydrofuranyl) | CH$_3$ | | |
| CH$_2$(C$_6$H$_5$) | CH$_2$CH$_3$ | CH$_2$(2-tetrahydropyranyl) | CH$_2$CH$_3$ |
| CH$_2$(2-FC$_6$H$_4$) | CH$_2$CH$_3$ | Q-1 | CH$_2$CH$_3$ |
| CH$_2$(3-FC$_6$H$_4$) | CH$_2$CH$_3$ | Q-3 | CH$_2$CH$_3$ |
| CH$_2$(4-FC$_6$H$_4$) | CH$_2$CH$_3$ | Q-4 | CH$_2$CH$_3$ |
| CH$_2$(2,3-F$_2$C$_6$H$_3$) | CH$_2$CH$_3$ | Q-6 | CH$_2$CH$_3$ |
| CH$_2$(2,4-F$_2$C$_6$H$_3$) | CH$_2$CH$_3$ | Q-7 | CH$_2$CH$_3$ |
| CH$_2$(2,5-F$_2$C$_6$H$_3$) | CH$_2$CH$_3$ | Q-8 | CH$_2$CH$_3$ |
| CH$_2$(2,6-F$_2$C$_6$H$_3$) | CH$_2$CH$_3$ | Q-15 | CH$_2$CH$_3$ |
| CH$_2$(2,4,6-F$_3$C$_6$H$_2$) | CH$_2$CH$_3$ | CH$_2$(2-BrC$_6$H$_4$) | CH$_2$CH$_3$ |
| CH$_2$(2-ClC$_6$H$_4$) | CH$_2$CH$_3$ | CH$_2$(2,6-Br$_2$C$_6$H$_3$) | CH$_2$CH$_3$ |
| CH$_2$(3-ClC$_6$H$_4$) | CH$_2$CH$_3$ | CH$_2$(2-Cl-6-FC$_6$H$_3$) | CH$_2$CH$_3$ |
| CH$_2$(4-ClC$_6$H$_4$) | CH$_2$CH$_3$ | CH$_2$(2-(OCH$_3$)C$_6$H$_4$) | CH$_2$CH$_3$ |
| CH$_2$(2,6-Cl$_2$C$_6$H$_3$) | CH$_2$CH$_3$ | CH$_2$(2-(CN)C$_6$H$_4$) | CH$_2$CH$_3$ |
| CH$_2$(2-(CH$_3$)C$_6$H$_4$) | CH$_2$CH$_3$ | CH$_2$(2-(CF$_3$)C$_6$H$_4$) | CH$_2$CH$_3$ |
| CH$_2$(3-(CH$_3$)C$_6$H$_4$) | CH$_2$CH$_3$ | CH$_2$(2-(OCF$_3$)C$_6$H$_4$) | CH$_2$CH$_3$ |
| CH$_2$(2-pyridyl) | CH$_2$CH$_3$ | CH$_2$(2-(SCH$_3$)C$_6$H$_4$) | CH$_2$CH$_3$ |
| CH$_2$(2-thienyl) | CH$_2$CH$_3$ | CH$_2$(2-(CH=CH$_2$)C$_6$H$_4$) | CH$_2$CH$_3$ |
| CH$_2$(2-furanyl) | CH$_2$CH$_3$ | CH$_2$(2-(C≡CH)C$_6$H$_4$) | CH$_2$CH$_3$ |
| CH$_2$(2-tetrahydrofuranyl) | CH$_2$CH$_3$ | | |
| General Structure 9, m is 3, R$^3$ = R$^4$ is CH$_3$ | | | |
| CH$_2$(C$_6$H$_5$) | CH$_3$ | CH$_2$(2-tetrahydropyranyl) | CH$_3$ |
| CH$_2$(2-FC$_6$H$_4$) | CH$_3$ | Q-1 | CH$_3$ |
| CH$_2$(3-FC$_6$H$_4$) | CH$_3$ | Q-3 | CH$_3$ |
| CH$_2$(4-FC$_6$H$_4$) | CH$_3$ | Q-4 | CH$_3$ |
| CH$_2$(2,3-F$_2$C$_6$H$_3$) | CH$_3$ | Q-6 | CH$_3$ |
| CH$_2$(2,4-F$_2$C$_6$H$_3$) | CH$_3$ | Q-7 | CH$_3$ |
| CH$_2$(2,5-F$_2$C$_6$H$_3$) | CH$_3$ | Q-8 | CH$_3$ |
| CH$_2$(2,6-F$_2$C$_6$H$_3$) | CH$_3$ | Q-15 | CH$_3$ |
| CH$_2$(2,4,6-F$_3$C$_6$H$_2$) | CH$_3$ | CH$_2$(2-BrC$_6$H$_4$) | CH$_3$ |
| CH$_2$(2-ClC$_6$H$_4$) | CH$_3$ | CH$_2$(2,6-Br$_2$C$_6$H$_3$) | CH$_3$ |
| CH$_2$(3-ClC$_6$H$_4$) | CH$_3$ | CH$_2$(2-Cl-6-FC$_6$H$_3$) | CH$_3$ |
| CH$_2$(4-ClC$_6$H$_4$) | CH$_3$ | CH$_2$(2-(OCH$_3$)C$_6$H$_4$) | CH$_3$ |
| CH$_2$(2,6-Cl$_2$C$_6$H$_3$) | CH$_3$ | CH$_2$(2-(CN)C$_6$H$_4$) | CH$_3$ |
| CH$_2$(2-(CH$_3$)C$_6$H$_4$) | CH$_3$ | CH$_2$(2-(CF$_3$)C$_6$H$_4$) | CH$_3$ |
| CH$_2$(3-(CH$_3$)C$_6$H$_4$) | CH$_3$ | CH$_2$(2-(OCF$_3$)C$_6$H$_4$) | CH$_3$ |
| CH$_2$(2-pyridyl) | CH$_3$ | CH$_2$(2-(SCH$_3$)C$_6$H$_4$) | CH$_3$ |
| CH$_2$(2-thienyl) | CH$_3$ | CH$_2$(2-(CH=CH$_2$)C$_6$H$_4$) | CH$_3$ |
| CH$_2$(2-furanyl) | CH$_3$ | CH$_2$(2-(C≡CH)C$_6$H$_4$) | CH$_3$ |
| CH$_2$(2-tetrahydrofuranyl) | CH$_3$ | | |
| CH$_2$(C$_6$H$_5$) | CH$_2$CH$_3$ | CH$_2$(2-tetrahydropyranyl) | CH$_2$CH$_3$ |
| CH$_2$(2-FC$_6$H$_4$) | CH$_2$CH$_3$ | Q-1 | CH$_2$CH$_3$ |
| CH$_2$(3-FC$_6$H$_4$) | CH$_2$CH$_3$ | Q-3 | CH$_2$CH$_3$ |
| CH$_2$(4-FC$_6$H$_4$) | CH$_2$CH$_3$ | Q-4 | CH$_2$CH$_3$ |
| CH$_2$(2,3-F$_2$C$_6$H$_3$) | CH$_2$CH$_3$ | Q-6 | CH$_2$CH$_3$ |
| CH$_2$(2,4-F$_2$C$_6$H$_3$) | CH$_2$CH$_3$ | Q-7 | CH$_2$CH$_3$ |
| CH$_2$(2,5-F$_2$C$_6$H$_3$) | CH$_2$CH$_3$ | Q-8 | CH$_2$CH$_3$ |
| CH$_2$(2,6-F$_2$C$_6$H$_3$) | CH$_2$CH$_3$ | Q-15 | CH$_2$CH$_3$ |
| CH$_2$(2,4,6-F$_3$C$_6$H$_2$) | CH$_2$CH$_3$ | CH$_2$(2-BrC$_6$H$_4$) | CH$_2$CH$_3$ |
| CH$_2$(2-ClC$_6$H$_4$) | CH$_2$CH$_3$ | CH$_2$(2,6-Br$_2$C$_6$H$_3$) | CH$_2$CH$_3$ |
| CH$_2$(3-ClC$_6$H$_4$) | CH$_2$CH$_3$ | CH$_2$(2-Cl-6-C$_6$H$_3$) | CH$_2$CH$_3$ |
| CH$_2$(4-ClC$_6$H$_4$) | CH$_2$CH$_3$ | CH$_2$(2-(OCH$_3$)C$_6$H$_4$) | CH$_2$CH$_3$ |
| CH$_2$(2,6-Cl$_2$C$_6$H$_3$) | CH$_2$CH$_3$ | CH$_2$(2-(CN)C$_6$H$_4$) | CH$_2$CH$_3$ |
| CH$_2$(2-(CH$_3$)C$_6$H$_4$) | CH$_2$CH$_3$ | CH$_2$(2-(CF$_3$)C$_6$H$_4$) | CH$_2$CH$_3$ |
| CH$_2$(3-(CH$_3$)C$_6$H$_4$) | CH$_2$CH$_3$ | CH$_2$(2-(OCF$_3$)C$_6$H$_4$) | CH$_2$CH$_3$ |
| CH$_2$(2-pyridyl) | CH$_2$CH$_3$ | CH$_2$(2-(SCH$_3$)C$_6$H$_4$) | CH$_2$CH$_3$ |
| CH$_2$(2-thienyl) | CH$_2$CH$_3$ | CH$_2$(2-(CH=CH$_2$)C$_6$H$_4$) | CH$_2$CH$_3$ |
| CH$_2$(2-furanyl) | CH$_2$CH$_3$ | CH$_2$(2-(C≡CH)C$_6$H$_4$) | CH$_2$CH$_3$ |
| CH$_2$(2-tetrahydroduranyl) | CH$_2$CH$_3$ | | |
| General Structure 9, m is 4, R$^3$ = R$^4$ is H | | | |

TABLE 9-continued

| Q | R¹ | Q | R¹ |
|---|---|---|---|
| CH$_2$(C$_6$H$_5$) | CH$_3$ | CH$_2$(2-tetrahydropyranyl) | CH$_3$ |
| CH$_2$(2-FC$_6$H$_4$) | CH$_3$ | Q-1 | CH$_3$ |
| CH$_2$(3-FC$_6$H$_4$) | CH$_3$ | Q-3 | CH$_3$ |
| CH$_2$(4-FC$_6$H$_4$) | CH$_3$ | Q-4 | CH$_3$ |
| CH$_2$(2,3-F$_2$C$_6$H$_3$) | CH$_3$ | Q-6 | CH$_3$ |
| CH$_2$(2,4-F$_2$C$_6$H$_3$) | CH$_3$ | Q-7 | CH$_3$ |
| CH$_2$(2,5-F$_2$C$_6$H$_3$) | CH$_3$ | Q-8 | CH$_3$ |
| CH$_2$(2,6-F$_2$C$_6$H$_3$) | CH$_3$ | Q-15 | CH$_3$ |
| CH$_2$(2,4,6-F$_3$C$_6$H$_2$) | CH$_3$ | CH$_2$(2-BrC$_6$H$_4$) | CH$_3$ |
| CH$_2$(2-ClC$_6$H$_4$) | CH$_3$ | CH$_2$(2,6-Br$_2$C$_6$H$_3$) | CH$_3$ |
| CH$_2$(3-ClC$_6$H$_4$) | CH$_3$ | CH$_2$(2-Cl-6-FC$_6$H$_3$) | CH$_3$ |
| CH$_2$(4-ClC$_6$H$_4$) | CH$_3$ | CH$_2$(2-(OCH$_3$)C$_6$H$_4$) | CH$_3$ |
| CH$_2$(2,6-Cl$_2$C$_6$H$_3$) | CH$_3$ | CH$_2$(2-(CN)C$_6$H$_4$) | CH$_3$ |
| CH$_2$(2-(CH$_3$)C$_6$H$_4$) | CH$_3$ | CH$_2$(2-(CF$_3$)C$_6$H$_4$) | CH$_3$ |
| CH$_2$(3-(CH$_3$)C$_6$H$_4$) | CH$_3$ | CH$_2$(2-(OCF$_3$)C$_6$H$_4$) | CH$_3$ |
| CH$_2$(2-pyridyl) | CH$_3$ | CH$_2$(2-(SCH$_3$)C$_6$H$_4$) | CH$_3$ |
| CH$_2$(2-thienyl) | CH$_3$ | CH$_2$(2-(CH=CH$_2$)C$_6$H$_4$) | CH$_3$ |
| CH$_2$(2-furanyl) | CH$_3$ | CH$_2$(2-(C≡CH)C$_6$H$_4$) | CH$_3$ |
| CH$_2$(2-tetrahydrofuranyl) | CH$_3$ | | |
| CH$_2$(C$_6$H$_5$) | CH$_2$CH$_3$ | CH$_2$(2-tetrahydropyranyl) | CH$_2$CH$_3$ |
| CH$_2$(2-FC$_6$H$_4$) | CH$_2$CH$_3$ | Q-1 | CH$_2$CH$_3$ |
| CH$_2$(3-FC$_6$H$_4$) | CH$_2$CH$_3$ | Q-3 | CH$_2$CH$_3$ |
| CH$_2$(4-FC$_6$H$_4$) | CH$_2$CH$_3$ | Q-4 | CH$_2$CH$_3$ |
| CH$_2$(2,3-F$_2$C$_6$H$_3$) | CH$_2$CH$_3$ | Q-6 | CH$_2$CH$_3$ |
| CH$_2$(2,4-F$_2$C$_6$H$_3$) | CH$_2$CH$_3$ | Q-7 | CH$_2$CH$_3$ |
| CH$_2$(2,5-F$_2$C$_6$H$_3$) | CH$_2$CH$_3$ | Q-8 | CH$_2$CH$_3$ |
| CH$_2$(2,6-F$_2$C$_6$H$_3$) | CH$_2$CH$_3$ | Q-15 | CH$_2$CH$_3$ |
| CH$_2$(2,4,6-F$_3$C$_6$H$_2$) | CH$_2$CH$_3$ | CH$_2$(2-BrC$_6$H$_4$) | CH$_2$CH$_3$ |
| CH$_2$(2-ClC$_6$H$_4$) | CH$_2$CH$_3$ | CH$_2$(2,6-Br$_2$C$_6$H$_3$) | CH$_2$CH$_3$ |
| CH$_2$(3-ClC$_6$H$_4$) | CH$_2$CH$_3$ | CH$_2$(2-Cl-6-FC$_6$H$_3$) | CH$_2$CH$_3$ |
| CH$_2$(4-ClC$_6$H$_4$) | CH$_2$CH$_3$ | CH$_2$(2-(OCH$_3$)C$_6$H$_4$) | CH$_2$CH$_3$ |
| CH$_2$(2,6-Cl$_2$C$_6$H$_3$) | CH$_2$CH$_3$ | CH$_2$(2-(CN)C$_6$H$_4$) | CH$_2$CH$_3$ |
| CH$_2$(2-(CH$_3$)C$_6$H$_4$) | CH$_2$CH$_3$ | CH$_2$(2-(CF$_3$)C$_6$H$_4$) | CH$_2$CH$_3$ |
| CH$_2$(3-(CH$_3$)C$_6$H$_4$) | CH$_2$CH$_3$ | CH$_2$(2-(OCF$_3$)C$_6$H$_4$) | CH$_2$CH$_3$ |
| CH$_2$(2-pyridyl) | CH$_2$CH$_3$ | CH$_2$(2-(SCH$_3$)C$_6$H$_4$) | CH$_2$CH$_3$ |
| CH$_2$(2-thienyl) | CH$_2$CH$_3$ | CH$_2$(2-(CH=CH$_2$)C$_6$H$_4$) | CH$_2$CH$_3$ |
| CH$_2$(2-furanyl) | CH$_2$CH$_3$ | CH$_2$(2-(C≡CH)C$_6$H$_4$) | CH$_2$CH$_3$ |
| CH$_2$(2-tetrahydrofuranyl) | CH$_2$CH$_3$ | | |
| General Structure 9, m is 4, R$^3$ = R$^4$ is CH$_3$ | | | |
| CH$_2$(C$_6$H$_5$) | CH$_3$ | CH$_2$(2-tetrahydropyranyl) | CH$_3$ |
| CH$_2$(2-FC$_6$H$_4$) | CH$_3$ | Q-1 | CH$_3$ |
| CH$_2$(3-FC$_6$H$_4$) | CH$_3$ | Q-3 | CH$_3$ |
| CH$_2$(4-FC$_6$H$_4$) | CH$_3$ | Q-4 | CH$_3$ |
| CH$_2$(2,3-F$_2$C$_6$H$_3$) | CH$_3$ | Q-6 | CH$_3$ |
| CH$_2$(2,4-F$_2$C$_6$H$_3$) | CH$_3$ | Q-7 | CH$_3$ |
| CH$_2$(2,5-F$_2$C$_6$H$_3$) | CH$_3$ | Q-8 | CH$_3$ |
| CH$_2$(2,6-F$_2$C$_6$H$_3$) | CH$_3$ | Q-15 | CH$_3$ |
| CH$_2$(2,4,6-F$_3$C$_6$H$_2$) | CH$_3$ | CH$_2$(2-BrC$_6$H$_4$) | CH$_3$ |
| CH$_2$(2-ClC$_6$H$_4$) | CH$_3$ | CH$_2$(2,6-Br$_2$C$_6$H$_3$) | CH$_3$ |
| CH$_2$(3-ClC$_6$H$_4$) | CH$_3$ | CH$_2$(2-Cl-6-FC$_6$H$_3$) | CH$_3$ |
| CH$_2$(4-ClC$_6$H$_4$) | CH$_3$ | CH$_2$(2-(OCH$_3$)C$_6$H$_4$) | CH$_3$ |
| CH$_2$(2,6-Cl$_2$C$_6$H$_3$) | CH$_3$ | CH$_2$(2-(CN)C$_6$H$_4$) | CH$_3$ |
| CH$_2$(2-(CH$_3$)C$_6$H$_4$) | CH$_3$ | CH$_2$(2-(CF$_3$)C$_6$H$_4$) | CH$_3$ |
| CH$_2$(3-(CH$_3$)C$_6$H$_4$) | CH$_3$ | CH$_2$(2-(OCF$_3$)C$_6$H$_4$) | CH$_3$ |
| CH$_2$(2-pyridyl) | CH$_3$ | CH$_2$(2-(SCH$_3$)C$_6$H$_4$) | CH$_3$ |
| CH$_2$(2-thienyl) | CH$_3$ | CH$_2$(2-(CH=CH$_2$)C$_6$H$_4$) | CH$_3$ |
| CH$_2$(2-furanyl) | CH$_3$ | CH$_2$(2-(C≡CH)C$_6$H$_4$) | CH$_3$ |
| CH$_2$(2-tetrahydrofuranyl) | CH$_3$ | | |
| CH$_2$(C$_6$H$_5$) | CH$_2$CH$_3$ | CH$_2$(2-tetrahydropyranyl) | CH$_2$CH$_3$ |
| CH$_2$(2-FC$_6$H$_4$) | CH$_2$CH$_3$ | Q-1 | CH$_2$CH$_3$ |
| CH$_2$(3-FC$_6$H$_4$) | CH$_2$CH$_3$ | Q-3 | CH$_2$CH$_3$ |
| CH$_2$(4-FC$_6$H$_4$) | CH$_2$CH$_3$ | Q-4 | CH$_2$CH$_3$ |
| CH$_2$(2,3-F$_2$C$_6$H$_3$) | CH$_2$CH$_3$ | Q-6 | CH$_2$CH$_3$ |
| CH$_2$(2,4-F$_2$C$_6$H$_3$) | CH$_2$CH$_3$ | Q-7 | CH$_2$CH$_3$ |
| CH$_2$(2,5-F$_2$C$_6$H$_3$) | CH$_2$CH$_3$ | Q-8 | CH$_2$CH$_3$ |
| CH$_2$(2,6-F$_2$C$_6$H$_3$) | CH$_2$CH$_3$ | Q-15 | CH$_2$CH$_3$ |
| CH$_2$(2,4,6-F$_3$C$_6$H$_2$) | CH$_2$CH$_3$ | CH$_2$(2-BrC$_6$H$_4$) | CH$_2$CH$_3$ |
| CH$_2$(2-ClC$_6$H$_4$) | CH$_2$CH$_3$ | CH$_2$(2,6-Br$_2$C$_6$H$_3$) | CH$_2$CH$_3$ |
| CH$_2$(3-ClC$_6$H$_4$) | CH$_2$CH$_3$ | CH$_2$(2-Cl-6-FC$_6$H$_3$) | CH$_2$CH$_3$ |
| CH$_2$(4-ClC$_6$H$_4$) | CH$_2$CH$_3$ | CH$_2$(2-(OCH$_3$)C$_6$H$_4$) | CH$_2$CH$_3$ |
| CH$_2$(2,6-Cl$_2$C$_6$H$_3$) | CH$_2$CH$_3$ | CH$_2$(2-(CN)C$_6$H$_4$) | CH$_2$CH$_3$ |
| CH$_2$(2-(CH$_3$)C$_6$H$_4$) | CH$_2$CH$_3$ | CH$_2$(2-(CF$_3$)C$_6$H$_4$) | CH$_2$CH$_3$ |
| CH$_2$(3-(CH$_3$)C$_6$H$_4$) | CH$_2$CH$_3$ | CH$_2$(2-(OCF$_3$)C$_6$H$_4$) | CH$_2$CH$_3$ |
| CH$_2$(2-pyridyl) | CH$_2$CH$_3$ | CH$_2$(2-(SCH$_3$)C$_6$H$_4$) | CH$_2$CH$_3$ |
| CH$_2$(2-thienyl) | CH$_2$CH$_3$ | CH$_2$(2-(CH=CH$_2$)C$_6$H$_4$) | CH$_2$CH$_3$ |
| CH$_2$(2-furanyl) | CH$_2$CH$_3$ | CH$_2$(2-(C≡CH)C$_6$H$_4$) | CH$_2$CH$_3$ |
| CH$_2$(2-tetrahydrofuranyl) | CH$_2$CH$_3$ | | |

TABLE 9-continued

General Structure 9, m is 5, $R^3 = R^4$ is H

| Q | $R^1$ | Q | $R^1$ |
|---|---|---|---|
| $CH_2(C_6H_5)$ | $CH_3$ | $CH_2$(2-tetrahydropyranyl) | $CH_3$ |
| $CH_2$(2-$FC_6H_4$) | $CH_3$ | Q-1 | $CH_3$ |
| $CH_2$(3-$FC_6H_4$) | $CH_3$ | Q-3 | $CH_3$ |
| $CH_2$(4-$FC_6H_4$) | $CH_3$ | Q-4 | $CH_3$ |
| $CH_2$(2,3-$F_2C_6H_3$) | $CH_3$ | Q-6 | $CH_3$ |
| $CH_2$(2,4-$F_2C_6H_3$) | $CH_3$ | Q-7 | $CH_3$ |
| $CH_2$(2,5-$F_2C_6H_3$) | $CH_3$ | Q-8 | $CH_3$ |
| $CH_2$(2,6-$F_2C_6H_3$) | $CH_3$ | Q-15 | $CH_3$ |
| $CH_2$(2,4,6-$F_3C_6H_2$) | $CH_3$ | $CH_2$(2-$BrC_6H_4$) | $CH_3$ |
| $CH_2$(2-$ClC_6H_4$) | $CH_3$ | $CH_2$(2,6-$Br_2C_6H_3$) | $CH_3$ |
| $CH_2$(3-$ClC_6H_4$) | $CH_3$ | $CH_2$(2-Cl-6-$FC_6H_3$) | $CH_3$ |
| $CH_2$(4-$ClC_6H_4$) | $CH_3$ | $CH_2$(2-($OCH_3$)$C_6H_4$) | $CH_3$ |
| $CH_2$(2,6-$Cl_2C_6H_3$) | $CH_3$ | $CH_2$(2-(CN)$C_6H_4$) | $CH_3$ |
| $CH_2$(2-($CH_3$)$C_6H_4$) | $CH_3$ | $CH_2$(2-($CF_3$)$C_6H_4$) | $CH_3$ |
| $CH_2$(3-($CH_3$)$C_6H_4$) | $CH_3$ | $CH_2$(2-($OCF_3$)$C_6H_4$) | $CH_3$ |
| $CH_2$(2-pyridyl) | $CH_3$ | $CH_2$(2-($SCH_3$)$C_6H_4$) | $CH_3$ |
| $CH_2$(2-thienyl) | $CH_3$ | $CH_2$(2-(CH=$CH_2$)$C_6H_4$) | $CH_3$ |
| $CH_2$(2-furanyl) | $CH_3$ | $CH_2$(2-(C≡CH)$C_6H_4$) | $CH_3$ |
| $CH_2$(2-tetrahydrofuranyl) | $CH_3$ | | |

TABLE 10

General Structure 10, m is 3, $R^1$ is $CH_3$

| Q | $R^3$ |
|---|---|
| $CH_2(C_6H_5)$ | H |
| $CH_2$(2-$FC_6H_4$) | H |
| $CH_2$(3-$FC_6H_4$) | H |
| $CH_2$(4-$FC_6H_4$) | H |
| $CH_2$(2,3-$F_2C_6H_3$) | H |
| $CH_2$(2,4-$F_2C_6H_3$) | H |
| $CH_2$(2,5-$F_2C_6H_3$) | H |
| $CH_2$(2,6-$F_2C_6H_3$) | H |
| $CH_2$(2,4,6-$F_3C_6H_2$) | H |
| $CH_2$(2-$ClC_6H_4$) | H |
| $CH_2$(3-$ClC_6H_4$) | H |
| $CH_2$(4-$ClC_6H_4$) | H |
| $CH_2$(2,6-$Cl_2C_6H_3$) | H |
| $CH_2$(2-($CH_3$)$C_6H_4$) | H |
| $CH_2$(3-($CH_3$)$C_6H_4$) | H |
| $CH_2$(4-($CH_3$)$C_6H_4$) | H |
| $CH_2$(2-pyridyl) | H |
| $CH_2$(2-thienyl) | H |
| $CH_2$(2-tetrahydrofuranyl) | H |
| $CH_2$(2-tetrahydropyranyl) | H |
| Q-1 | H |
| Q-3 | H |
| Q-4 | H |
| Q-6 | H |
| Q-7 | H |
| Q-8 | H |
| Q-15 | H |
| $CH_2$(2-$BrC_6H_4$) | H |
| $CH_2$(2,6-$Br_2C_6H_3$) | H |
| $CH_2$(2-Cl-6-$FC_6H_3$) | H |
| $CH_2$(2-($OCH_3$)$C_6H_4$) | H |
| $CH_2$(2-(CN)$C_6H_4$) | H |
| $CH_2$(2-($CF_3$)$C_6H_4$) | H |
| $CH_2$(2-($OCF_3$)$C_6H_4$) | H |
| $CH_2$(2-($SCH_3$)$C_6H_4$) | H |
| $CH_2$(2-(CH=$CH_2$)$C_6H_4$) | H |
| $CH_2$(2-(C≡CH)$C_6H_4$) | H |
| $CH_2(C_6H_5)$ | $CH_3$ |
| $CH_2$(2-$FC_6H_4$) | $CH_3$ |
| $CH_2$(3-$FC_6H_4$) | $CH_3$ |
| $CH_2$(4-$FC_6H_4$) | $CH_3$ |
| $CH_2$(2,3-$F_2C_6H_3$) | $CH_3$ |
| $CH_2$(2,4-$F_2C_6H_3$) | $CH_3$ |
| $CH_2$(2,5-$F_2C_6H_3$) | $CH_3$ |
| $CH_2$(2,6-$F_2C_6H_3$) | $CH_3$ |
| $CH_2$(2,4,6-$F_3C_6H_2$) | $CH_3$ |
| $CH_2$(2-$ClC_6H_4$) | $CH_3$ |
| $CH_2$(3-$ClC_6H_4$) | $CH_3$ |
| $CH_2$(4-$ClC_6H_4$) | $CH_3$ |
| $CH_2$(2,6-$Cl_2C_6H_3$) | $CH_3$ |
| $CH_2$(2-($CH_3$)$C_6H_4$) | $CH_3$ |
| $CH_2$(3-($CH_3$)$C_6H_4$) | $CH_3$ |
| $CH_2$(4-($CH_3$)$C_6H_4$) | $CH_3$ |
| $CH_2$(2-pyridyl) | $CH_3$ |
| $CH_2$(2-thienyl) | $CH_3$ |
| $CH_2$(2-tetrahydrofuranyl) | $CH_3$ |
| $CH_2$(2-tetrahydropyranyl) | $CH_3$ |
| Q-1 | $CH_3$ |
| Q-3 | $CH_3$ |
| Q-4 | $CH_3$ |
| Q-6 | $CH_3$ |
| Q-7 | $CH_3$ |
| Q-8 | $CH_3$ |
| Q-15 | $CH_3$ |
| $CH_2$(2-$BrC_6H_4$) | $CH_3$ |
| $CH_2$(2,6-$Br_2C_6H_3$) | $CH_3$ |
| $CH_2$(2-Cl-6-$FC_6H_3$) | $CH_3$ |
| $CH_2$(2-($OCH_3$)$C_6H_4$) | $CH_3$ |
| $CH_2$(2-(CN)$C_6H_4$) | $CH_3$ |
| $CH_2$(2-($CF_3$)$C_6H_4$) | $CH_3$ |
| $CH_2$(2-($OCF_3$)$C_6H_4$) | $CH_3$ |
| $CH_2$(2-($SCH_3$)$C_6H_4$) | $CH_3$ |
| $CH_2$(2-(CH=$CH_2$)$C_6H_4$) | $CH_3$ |
| $CH_2$(2-(C≡CH)$C_6H_4$) | $CH_3$ |

General Structure 10, m is 3, $R^1$ is $CH_2CH_3$

| Q | $R^3$ |
|---|---|
| $CH_2(C_6H_5)$ | H |
| $CH_2$(2-$FC_6H_4$) | H |
| $CH_2$(3-$FC_6H_4$) | H |
| $CH_2$(4-$FC_6H_4$) | H |
| $CH_2$(2,3-$F_2C_6H_3$) | H |
| $CH_2$(2,4-$F_2C_6H_3$) | H |
| $CH_2$(2,5-$F_2C_6H_3$) | H |
| $CH_2$(2,6-$F_2C_6H_3$) | H |
| $CH_2$(2,4,6-$F_3C_6H_2$) | H |
| $CH_2$(2-$ClC_6H_4$) | H |
| $CH_2$(3-$ClC_6H_4$) | H |
| $CH_2$(4-$ClC_6H_4$) | H |
| $CH_2$(2,6-$Cl_2C_6H_3$) | H |
| $CH_2$(2-($CH_3$)$C_6H_4$) | H |
| $CH_2$(3-($CH_3$)$C_6H_4$) | H |
| $CH_2$(4-($CH_3$)$C_6H_4$) | H |
| $CH_2$(2-pyridyl) | H |
| $CH_2$(2-thienyl) | H |
| $CH_2$(2-tetrahydrofuranyl) | H |
| $CH_2$(2-tetrahydropyranyl) | H |
| Q-1 | H |
| Q-3 | H |
| Q-4 | H |
| Q-6 | H |
| Q-7 | H |
| Q-8 | H |
| Q-15 | H |
| $CH_2$(2-$BrC_6H_4$) | H |
| $CH_2$(2,6-$Br_2C_6H_3$) | H |
| $CH_2$(2-Cl-6-$FC_6H_3$) | H |
| $CH_2$(2-($OCH_3$)$C_6H_4$) | H |
| $CH_2$(2-(CN)$C_6H_4$) | H |

TABLE 10-continued

| Q | R³ |
|---|---|
| CH₂(2-(CF₃)C₆H₄) | H |
| CH₂(2-(OCF₃)C₆H₄) | H |
| CH₂(2-(SCH₃)C₆H₄) | H |
| CH₂(2-(CH=CH₂)C₆H₄) | H |
| CH₂(2-(C≡CH)C₆H₄) | H |
| CH₂(C₆H₅) | CH₃ |
| CH₂(2-FC₆H₄) | CH₃ |
| CH₂(3-FC₆H₄) | CH₃ |
| CH₂(4-FC₆H₄) | CH₃ |
| CH₂(2,3-F₂C₆H₃) | CH₃ |
| CH₂(2,4-F₂C₆H₃) | CH₃ |
| CH₂(2,5-F₂C₆H₃) | CH₃ |
| CH₂(2,6-F₂C₆H₃) | CH₃ |
| CH₂(2,4,6-F₃C₆H₂) | CH₃ |
| CH₂(2-ClC₆H₄) | CH₃ |
| CH₂(3-ClC₆H₄) | CH₃ |
| CH₂(4-ClC₆H₄) | CH₃ |
| CH₂(2,6-Cl₂C₆H₃) | CH₃ |
| CH₂(2-(CH₃)C₆H₄) | CH₃ |
| CH₂(3-(CH₃)C₆H₄) | CH₃ |
| CH₂(4-(CH₃)C₆H₄) | CH₃ |
| CH₂(2-pyridyl) | CH₃ |
| CH₂(2-thienyl) | CH₃ |
| CH₂(2-tetrahydrofuranyl) | CH₃ |
| CH₂(2-tetrahydropyranyl) | CH₃ |
| Q-1 | CH₃ |
| Q-3 | CH₃ |
| Q-4 | CH₃ |
| Q-6 | CH₃ |
| Q-7 | CH₃ |
| Q-8 | CH₃ |
| Q-15 | CH₃ |
| CH₂(2-BrC₆H₄) | CH₃ |
| CH₂(2,6-Br₂C₆H₃) | CH₃ |
| CH₂(2-Cl-6-FC₆H₃) | CH₃ |
| CH₂(2-(OCH₃)C₆H₄) | CH₃ |
| CH₂(2-(CN)C₆H₄) | CH₃ |
| CH₂(2-(CF₃)C₆H₄) | CH₃ |
| CH₂(2-(OCF₃)C₆H₄) | CH₃ |
| CH₂(2-(SCH₃)C₆H₄) | CH₃ |
| CH₂(2-(CH=CH₂)C₆H₄) | CH₃ |
| CH₂(2-(C≡CH)C₆H₄) | CH₃ |
| General Structure 10, m is 4, R¹ is CH₃ | |
| CH₂(C₆H₅) | H |
| CH₂(2-FC₆H₄) | H |
| CH₂(3-FC₆H₄) | H |
| CH₂(4-FC₆H₄) | H |
| CH₂(2,3-F₂C₆H₃) | H |
| CH₂(2,4-F₂C₆H₃) | H |
| CH₂(2,5-F₂C₆H₃) | H |
| CH₂(2,6-F₂C₆H₃) | H |
| CH₂(2,4,6-F₃C₆H₂) | H |
| CH₂(2-ClC₆H₄) | H |
| CH₂(3-ClC₆H₄) | H |
| CH₂(4-ClC₆H₄) | H |
| CH₂(2,6-Cl₂C₆H₃) | H |
| CH₂(2-(CH₃)C₆H₄) | H |
| CH₂(3-(CH₃)C₆H₄) | H |
| CH₂(4-(CH₃)C₆H₄) | H |
| CH₂(2-pyridyl) | H |
| CH₂(2-thienyl) | H |
| CH₂(2-tetrahydrofuranyl) | H |
| CH₂(2-tetrahydropyranyl) | H |
| Q-1 | H |
| Q-3 | H |
| Q-4 | H |
| Q-6 | H |
| Q-7 | H |
| Q-8 | H |
| Q-15 | H |
| CH₂(2-BrC₆H₄) | H |
| CH₂(2,6-Br₂C₆H₃) | H |
| CH₂(2-Cl-6-FC₆H₃) | H |
| CH₂(2-(OCH₃)C₆H₄) | H |
| CH₂(2-(CN)C₆H₄) | H |
| CH₂(2-(CF₃)C₆H₄) | H |
| CH₂(2-(OCF₃)C₆H₄) | H |
| CH₂(2-(SCH₃)C₆H₄) | H |
| CH₂(2-(CH=CH₂)C₆H₄) | H |
| CH₂(2-(C≡CH)C₆H₄) | H |
| CH₂(C₆H₅) | CH₃ |
| CH₂(2-FC₆H₄) | CH₃ |
| CH₂(3-FC₆H₄) | CH₃ |
| CH₂(4-FC₆H₄) | CH₃ |
| CH₂(2,3-F₂C₆H₃) | CH₃ |
| CH₂(2,4-F₂C₆H₃) | CH₃ |
| CH₂(2,5-F₂C₆H₃) | CH₃ |
| CH₂(2,6-F₂C₆H₃) | CH₃ |
| CH₂(2,4,6-F₃C₆H₂) | CH₃ |
| CH₂(2-ClC₆H₄) | CH₃ |
| CH₂(3-ClC₆H₄) | CH₃ |
| CH₂(4-ClC₆H₄) | CH₃ |
| CH₂(2,6-Cl₂C₆H₃) | CH₃ |
| CH₂(2-(CH₃)C₆H₄) | CH₃ |
| CH₂(3-(CH₃)C₆H₄) | CH₃ |
| CH₂(4-(CH₃)C₆H₄) | CH₃ |
| CH₂(2-pyridyl) | CH₃ |
| CH₂(2-thienyl) | CH₃ |
| CH₂(2-tetrahydrofuranyl) | CH₃ |
| CH₂(2-tetrahydropyranyl) | CH₃ |
| Q-1 | CH₃ |
| Q-3 | CH₃ |
| Q-4 | CH₃ |
| Q-6 | CH₃ |
| Q-7 | CH₃ |
| Q-8 | CH₃ |
| Q-15 | CH₃ |
| CH₂(2-BrC₆H₄) | CH₃ |
| CH₂(2,6-Br₂C₆H₃) | CH₃ |
| CH₂(2-Cl-6-FC₆H₃) | CH₃ |
| CH₂(2-(OCH₃)C₆H₄) | CH₃ |
| CH₂(2-(CN)C₆H₄) | CH₃ |
| CH₂(2-(CF₃)C₆H₄) | CH₃ |
| CH₂(2-(OCF₃)C₆H₄) | CH₃ |
| CH₂(2-(SCH₃)C₆H₄) | CH₃ |
| CH₂(2-(CH=CH₂)C₆H₄) | CH₃ |
| CH₂(2-(C≡CH)C₆H₄) | CH₃ |
| General Structure 10, m is 4, R¹ is CH₂CH₃ | |
| CH₂(C₆H₅) | H |
| CH₂(2-FC₆H₄) | H |
| CH₂(3-FC₆H₄) | H |
| CH₂(4-FC₆H₄) | H |
| CH₂(2,3-F₂C₆H₃) | H |
| CH₂(2,4-F₂C₆H₃) | H |
| CH₂(2,5-F₂C₆H₃) | H |
| CH₂(2,6-F₂C₆H₃) | H |
| CH₂(2,4,6-F₃C₆H₂) | H |
| CH₂(2-ClC₆H₄) | H |
| CH₂(3-ClC₆H₄) | H |
| CH₂(4-ClC₆H₄) | H |
| CH₂(2,6-Cl₂C₆H₃) | H |
| CH₂(2-(CH₃)C₆H₄) | H |
| CH₂(3-(CH₃)C₆H₄) | H |
| CH₂(4-(CH₃)C₆H₄) | H |
| CH₂(2-pyridyl) | H |
| CH₂(2-thienyl) | H |
| CH₂(2-tetrahydrofuranyl) | H |
| CH₂(2-tetrahydropyranyl) | H |
| Q-1 | H |
| Q-3 | H |
| Q-4 | H |
| Q-6 | H |
| Q-7 | H |
| Q-8 | H |
| Q-15 | H |
| CH₂(2-BrC₆H₄) | H |
| CH₂(2,6-Br₂C₆H₃) | H |
| CH₂(2-Cl-6-FC₆H₃) | H |
| CH₂(2-(OCH₃)C₆H₄) | H |
| CH₂(2-(CN)C₆H₄) | H |
| CH₂(2-(CF₃)C₆H₄) | H |
| CH₂(2-(OCF₃)C₆H₄) | H |
| CH₂(2-(SCH₃)C₆H₄) | H |
| CH₂(2-(CH=CH₂)C₆H₄) | H |
| CH₂(2-(C≡CH)C₆H₄) | H |
| CH₂(C₆H₅) | CH₃ |
| CH₂(2-FC₆H₄) | CH₃ |
| CH₂(3-FC₆H₄) | CH₃ |
| CH₂(4-FC₆H₄) | CH₃ |
| CH₂(2,3-F₂C₆H₃) | CH₃ |

TABLE 10-continued

| Q | R³ |
|---|---|
| CH₂(2,4-F₂C₆H₃) | CH₃ |
| CH₂(2,5-F₂C₆H₃) | CH₃ |
| CH₂(2,6-F₂C₆H₃) | CH₃ |
| CH₂(2,4,6-F₃C₆H₂) | CH₃ |
| CH₂(2-ClC₆H₄) | CH₃ |
| CH₂(3-ClC₆H₄) | CH₃ |
| CH₂(4-ClC₆H₄) | CH₃ |
| CH₂(2,6-Cl₂C₆H₃) | CH₃ |
| CH₂(2-(CH₃)C₆H₄) | CH₃ |
| CH₂(3-(CH₃)C₆H₄) | CH₃ |
| CH₂(4-(CH₃)C₆H₄) | CH₃ |
| CH₂(2-pyridyl) | CH₃ |
| CH₂(2-thienyl) | CH₃ |
| CH₂(2-tetrahydrofuranyl) | CH₃ |
| CH₂(2-tetrahydropyranyl) | CH₃ |
| Q-1 | CH₃ |
| Q-3 | CH₃ |
| Q-4 | CH₃ |
| Q-6 | CH₃ |
| Q-7 | CH₃ |
| Q-8 | CH₃ |
| Q-15 | CH₃ |
| CH₂(2-BrC₆H₄) | CH₃ |
| CH₂(2,6-Br₂C₆H₃) | CH₃ |
| CH₂(2-Cl-6-FC₆H₃) | CH₃ |
| CH₂(2-(OCH₃)C₆H₄) | CH₃ |
| CH₂(2-(CN)C₆H₄) | CH₃ |
| CH₂(2-(CF₃)C₆H₄) | CH₃ |
| CH₂(2-(OCF₃)C₆H₄) | CH₃ |
| CH₂(2-(SCH₃)C₆H₄) | CH₃ |
| CH₂(2-(CH=CH₂)C₆H₄) | CH₃ |
| CH₂(2-(C≡CH)C₆H₄) | CH₃ |
| General Structure 10, m is 5, R¹ is CH₃ | |
| CH₂(C₆H₅) | H |
| CH₂(2-FC₆H₄) | H |
| CH₂(3-FC₆H₄) | H |
| CH₂(4-FC₆H₄) | H |
| CH₂(2,3-F₂C₆H₃) | H |
| CH₂(2,4-F₂C₆H₃) | H |
| CH₂(2,5-F₂C₆H₃) | H |
| CH₂(2,6-F₂C₆H₃) | H |
| CH₂(2,4,6-F₃C₆H₂) | H |
| CH₂(2-ClC₆H₄) | H |
| CH₂(3-ClC₆H₄) | H |
| CH₂(4-ClC₆H₄) | H |
| CH₂(2,6-Cl₂C₆H₃) | H |
| CH₂(2-(CH₃)C₆H₄) | H |
| CH₂(3-(CH₃)C₆H₄) | H |
| CH₂(4-(CH₃)C₆H₄) | H |
| CH₂(2-pyridyl) | H |
| CH₂(2-thienyl) | H |
| CH₂(2-tetrahydrofuranyl) | H |
| CH₂(2-tetrahydropyranyl) | H |
| Q-1 | H |
| Q-3 | H |
| Q-4 | H |
| Q-6 | H |
| Q-7 | H |
| Q-8 | H |
| Q-15 | H |
| CH₂(2-BrC₆H₄) | H |
| CH₂(2,6-Br₂C₆H₃) | H |
| CH₂(2-Cl-6-FC₆H₃) | H |
| CH₂(2-(OCH₃)C₆H₄) | H |
| CH₂(2-(CN)C₆H₄) | H |
| CH₂(2-(CF₃)C₆H₄) | H |
| CH₂(2-(OCF₃)C₆H₄) | H |
| CH₂(2-(SCH₃)C₆H₄) | H |
| CH₂(2-(CH=CH₂)C₆H₄) | H |
| CH₂(2-(C≡CH)C₆H₄) | H |

TABLE 11

| Q | R³ |
|---|---|
| General Structure 11, n is 2, R¹ is CH₃ | |
| CH₂(C₆H₅) | H |
| CH₂(2-FC₆H₄) | H |
| CH₂(3-FC₆H₄) | H |
| CH₂(4-FC₆H₄) | H |

TABLE 11-continued

| Q | R³ |
|---|---|
| CH₂(2,3-F₂C₆H₃) | H |
| CH₂(2,4-F₂C₆H₃) | H |
| CH₂(2,5-F₂C₆H₃) | H |
| CH₂(2,6-F₂C₆H₃) | H |
| CH₂(2,4,6-F₃C₆H₂) | H |
| CH₂(2-ClC₆H₄) | H |
| CH₂(3-ClC₆H₄) | H |
| CH₂(4-ClC₆H₄) | H |
| CH₂(2,6-Cl₂C₆H₃) | H |
| CH₂(2-(CH₃)C₆H₄) | H |
| CH₂(3-(CH₃)C₆H₄) | H |
| CH₂(4-(CH₃)C₆H₄) | H |
| CH₂(2-pyridyl) | H |
| CH₂(2-thienyl) | H |
| CH₂(2-tetrahydrofuranyl) | H |
| CH₂(2-tetrahydropyranyl) | H |
| Q-1 | H |
| Q-3 | H |
| Q-4 | H |
| Q-6 | H |
| Q-7 | H |
| Q-8 | H |
| Q-15 | H |
| CH₂(2-BrC₆H₄) | H |
| CH₂(2,6-Br₂C₆H₃) | H |
| CH₂(2-Cl-6-FC₆H₃) | H |
| CH₂(2-(OCH₃)C₆H₄) | H |
| CH₂(2-(CN)C₆H₄) | H |
| CH₂(2-(CF₃)C₆H₄) | H |
| CH₂(2-(OCF₃)C₆H₄) | H |
| CH₂(2-(SCH₃)C₆H₄) | H |
| CH₂(2-(CH=CH₂)C₆H₄) | H |
| CH₂(2-(C≡CH)C₆H₄) | H |
| CH₂(C₆H₅) | CH₃ |
| CH₂(2-FC₆H₄) | CH₃ |
| CH₂(3-FC₆H₄) | CH₃ |
| CH₂(4-FC₆H₄) | CH₃ |
| CH₂(2,3-F₂C₆H₃) | CH₃ |
| CH₂(2,4-F₂C₆H₃) | CH₃ |
| CH₂(2,5-F₂C₆H₃) | CH₃ |
| CH₂(2,6-F₂C₆H₃) | CH₃ |
| CH₂(2,4,6-F₃C₆H₂) | CH₃ |
| CH₂(2-ClC₆H₄) | CH₃ |
| CH₂(3-ClC₆H₄) | CH₃ |
| CH₂(4-ClC₆H₄) | CH₃ |
| CH₂(2,6-Cl₂C₆H₃) | CH₃ |
| CH₂(2-(CH₃)C₆H₄) | CH₃ |
| CH₂(3-(CH₃)C₆H₄) | CH₃ |
| CH₂(4-(CH₃)C₆H₄) | CH₃ |
| CH₂(2-pyridyl) | CH₃ |
| CH₂(2-thienyl) | CH₃ |
| CH₂(2-tetrahydrofuranyl) | CH₃ |
| CH₂(2-tetrahydropyranyl) | CH₃ |
| Q-1 | CH₃ |
| Q-3 | CH₃ |
| Q-4 | CH₃ |
| Q-6 | CH₃ |
| Q-7 | CH₃ |
| Q-8 | CH₃ |
| Q-15 | CH₃ |
| CH₂(2-BrC₆H₄) | CH₃ |
| CH₂(2,6-Br₂C₆H₃) | CH₃ |
| CH₂(2-Cl-6-FC₆H₃) | CH₃ |
| CH₂(2-(OCH₃)C₆H₄) | CH₃ |
| CH₂(2-(CN)C₆H₄) | CH₃ |
| CH₂(2-(CF₃)C₆H₄) | CH₃ |
| CH₂(2-(OCF₃)C₆H₄) | CH₃ |
| CH₂(2-(SCH₃)C₆H₄) | CH₃ |
| CH₂(2-(CH=CH₂)C₆H₄) | CH₃ |
| CH₂(2-(C≡CH)C₆H₄) | CH₃ |
| General Structure 11, n is 2, R¹ is CH₂CH₃ | |
| CH₂(C₆H₅) | H |
| CH₂(2-FC₆H₄) | H |
| CH₂(3-FC₆H₄) | H |
| CH₂(4-FC₆H₄) | H |
| CH₂(2,3-F₂C₆H₃) | H |
| CH₂(2,4-F₂C₆H₃) | H |
| CH₂(2,5-F₂C₆H₃) | H |
| CH₂(2,6-F₂C₆H₃) | H |
| CH₂(2,4,6-F₃C₆H₂) | H |

TABLE 11-continued

| Q | R³ |
|---|---|
| CH₂(2-ClC₆H₄) | H |
| CH₂(3-ClC₆H₄) | H |
| CH₂(4-ClC₆H₄) | H |
| CH₂(2,6-Cl₂C₆H₃) | H |
| CH₂(2-(CH₃)C₆H₄) | H |
| CH₂(3-(CH₃)C₆H₄) | H |
| CH₂(4-(CH₃)C₆H₄) | H |
| CH₂(2-pyridyl) | H |
| CH₂(2-thienyl) | H |
| CH₂(2-tetrahydrofuranyl) | H |
| CH₂(2-tetrahydropyranyl) | H |
| Q-1 | H |
| Q-3 | H |
| Q-4 | H |
| Q-6 | H |
| Q-7 | H |
| Q-8 | H |
| Q-15 | H |
| CH₂(2-BrC₆H₄) | H |
| CH₂(2,6-Br₂C₆H₃) | H |
| CH₂(2-Cl-6-FC₆H₃) | H |
| CH₂(2-(OCH₃)C₆H₄) | H |
| CH₂(2-(CN)C₆H₄) | H |
| CH₂(2-(CF₃)C₆H₄) | H |
| CH₂(2-(OCF₃)C₆H₄) | H |
| CH₂(2-(SCH₃)C₆H₄) | H |
| CH₂(2-(CH=CH₂)C₆H₄) | H |
| CH₂(2-(C≡CH)C₆H₄) | H |
| CH₂(C₆H₅) | CH₃ |
| CH₂(2-FC₆H₄) | CH₃ |
| CH₂(3-FC₆H₄) | CH₃ |
| CH₂(4-FC₆H₄) | CH₃ |
| CH₂(2,3-F₂C₆H₃) | CH₃ |
| CH₂(2,4-F₂C₆H₃) | CH₃ |
| CH₂(2,5-F₂C₆H₃) | CH₃ |
| CH₂(2,6-F₂C₆H₃) | CH₃ |
| CH₂(2,4,6-F₃C₆H₂) | CH₃ |
| CH₂(2-ClC₆H₄) | CH₃ |
| CH₂(3-ClC₆H₄) | CH₃ |
| CH₂(4-ClC₆H₄) | CH₃ |
| CH₂(2,6-Cl₂C₆H₃) | CH₃ |
| CH₂(2-(CH₃)C₆H₄) | CH₃ |
| CH₂(3-(CH₃)C₆H₄) | CH₃ |
| CH₂(4-(CH₃)C₆H₄) | CH₃ |
| CH₂(2-pyridyl) | CH₃ |
| CH₂(2-thienyl) | CH₃ |
| CH₂(2-tetrahydrofuranyl) | CH₃ |
| CH₂(2-tetrahydropyranyl) | CH₃ |
| Q-1 | CH₃ |
| Q-3 | CH₃ |
| Q-4 | CH₃ |
| Q-6 | CH₃ |
| Q-7 | CH₃ |
| Q-8 | CH₃ |
| Q-15 | CH₃ |
| CH₂(2-BrC₆H₄) | CH₃ |
| CH₂(2,6-Br₂C₆H₃) | CH₃ |
| CH₂(2-Cl-6-FC₆H₃) | CH₃ |
| CH₂(2-(OCH₃)C₆H₄) | CH₃ |
| CH₂(2-(CN)C₆H₄) | CH₃ |
| CH₂(2-(CF₃)C₆H₄) | CH₃ |
| CH₂(2-(OCF₃)C₆H₄) | CH₃ |
| CH₂(2-(SCH₃)C₆H₄) | CH₃ |
| CH₂(2-(CH=CH₂)C₆H₄) | CH₃ |
| CH₂(2-(C≡CH)C₆H₄) | CH₃ |
| General Structure 11, n is 3, R¹ is CH₃ | |
| CH₂(C₆H₅) | H |
| CH₂(2-FC₆H₄) | H |
| CH₂(3-FC₆H₄) | H |
| CH₂(4-FC₆H₄) | H |
| CH₂(2,3-F₂C₆H₃) | H |
| CH₂(2,4-F₂C₆H₃) | H |
| CH₂(2,5-F₂C₆H₃) | H |
| CH₂(2,6-F₂C₆H₃) | H |
| CH₂(2,4,6-F₃C₆H₂) | H |
| CH₂(2-ClC₆H₄) | H |
| CH₂(3-ClC₆H₄) | H |
| CH₂(4-ClC₆H₄) | H |
| CH₂(2,6-Cl₂C₆H₃) | H |
| CH₂(2-(CH₃)C₆H₄) | H |
| CH₂(3-(CH₃)C₆H₄) | H |
| CH₂(4-(CH₃)C₆H₄) | H |
| CH₂(2-pyridyl) | H |
| CH₂(2-thienyl) | H |
| CH₂(2-tetrahydrofuranyl) | H |
| CH₂(2-tetrahydropyranyl) | H |
| Q-1 | H |
| Q-3 | H |
| Q-4 | H |
| Q-6 | H |
| Q-7 | H |
| Q-8 | H |
| Q-15 | H |
| CH₂(2-BrC₆H₄) | H |
| CH₂(2,6-Br₂C₆H₃) | H |
| CH₂(2-Cl-6-FC₆H₃) | H |
| CH₂(2-(OCH₃)C₆H₄) | H |
| CH₂(2-(CN)C₆H₄) | H |
| CH₂(2-(CF₃)C₆H₄) | H |
| CH₂(2-(OCF₃)C₆H₄) | H |
| CH₂(2-(SCH₃)C₆H₄) | H |
| CH₂(2-(CH=CH₂)C₆H₄) | H |
| CH₂(2-(C≡CH)C₆H₄) | H |
| CH₂(C₆H₅) | CH₃ |
| CH₂(2-FC₆H₄) | CH₃ |
| CH₂(3-FC₆H₄) | CH₃ |
| CH₂(4-FC₆H₄) | CH₃ |
| CH₂(2,3-F₂C₆H₃) | CH₃ |
| CH₂(2,4-F₂C₆H₃) | CH₃ |
| CH₂(2,5-F₂C₆H₃) | CH₃ |
| CH₂(2,6-F₂C₆H₃) | CH₃ |
| CH₂(2,4,6-F₃C₆H₂) | CH₃ |
| CH₂(2-ClC₆H₄) | CH₃ |
| CH₂(3-ClC₆H₄) | CH₃ |
| CH₂(4-ClC₆H₄) | CH₃ |
| CH₂(2,6-Cl₂C₆H₃) | CH₃ |
| CH₂(2-(CH₃)C₆H₄) | CH₃ |
| CH₂(3-(CH₃)C₆H₄) | CH₃ |
| CH₂(4-(CH₃)C₆H₄) | CH₃ |
| CH₂(2-pyridyl) | CH₃ |
| CH₂(2-thienyl) | CH₃ |
| CH₂(2-tetrahydrofuranyl) | CH₃ |
| CH₂(2-tetrahydropyranyl) | CH₃ |
| Q-1 | CH₃ |
| Q-3 | CH₃ |
| Q-4 | CH₃ |
| Q-6 | CH₃ |
| Q-7 | CH₃ |
| Q-8 | CH₃ |
| Q-15 | CH₃ |
| CH₂(2-BrC₆H₄) | CH₃ |
| CH₂(2,6-Br₂C₆H₃) | CH₃ |
| CH₂(2-Cl-6-FC₆H₃) | CH₃ |
| CH₂(2-(OCH₃)C₆H₄) | CH₃ |
| CH₂(2-(CN)C₆H₄) | CH₃ |
| CH₂(2-(CF₃)C₆H₄) | CH₃ |
| CH₂(2-(OCF₃)C₆H₄) | CH₃ |
| CH₂(2-(SCH₃)C₆H₄) | CH₃ |
| CH₂(2-(CH=CH₂)C₆H₄) | CH₃ |
| CH₂(2-(C≡CH)C₆H₄) | CH₃ |
| General Structure 11, n is 3, R¹ is CH₂CH₃ | |
| CH₂(C₆H₅) | H |
| CH₂(2-FC₆H₄) | H |
| CH₂(3-FC₆H₄) | H |
| CH₂(4-FC₆H₄) | H |
| CH₂(2,3-F₂C₆H₃) | H |
| CH₂(2,4-F₂C₆H₃) | H |
| CH₂(2,5-F₂C₆H₃) | H |
| CH₂(2,6-F₂C₆H₃) | H |
| CH₂(2,4,6-F₃C₆H₂) | H |
| CH₂(2-ClC₆H₄) | H |
| CH₂(3-ClC₆H₄) | H |
| CH₂(4-ClC₆H₄) | H |
| CH₂(2,6-Cl₂C₆H₃) | H |
| CH₂(2-(CH₃)C₆H₄) | H |
| CH₂(3-(CH₃)C₆H₄) | H |
| CH₂(4-(CH₃)C₆H₄) | H |
| CH₂(2-pyridyl) | H |
| CH₂(2-thienyl) | H |
| CH₂(2-tetrahydrofuranyl) | H |

TABLE 11-continued

| Q | R³ |
|---|---|
| CH₂(2-tetrahydropyranyl) | H |
| Q-1 | H |
| Q-3 | H |
| Q-4 | H |
| Q-6 | H |
| Q-7 | H |
| Q-8 | H |
| Q-15 | H |
| CH₂(2-BrC₆H₄) | H |
| CH₂(2,6-Br₂C₆H₃) | H |
| CH₂(2-Cl-6-FC₆H₃) | H |
| CH₂(2-(OCH₃)C₆H₄) | H |
| CH₂(2-(CN)C₆H₄) | H |
| CH₂(2-(CF₃)C₆H₄) | H |
| CH₂(2-(OCF₃)C₆H₄) | H |
| CH₂(2-(SCH₃)C₆H₄) | H |
| CH₂(2-(CH=CH₂)C₆H₄) | H |
| CH₂(2-(C≡CH)C₆H₄) | H |
| CH₂(C₆H₅) | CH₃ |
| CH₂(2-FC₆H₄) | CH₃ |
| CH₂(3-FC₆H₄) | CH₃ |
| CH₂(4-FC₆H₄) | CH₃ |
| CH₂(2,3-F₂C₆H₃) | CH₃ |
| CH₂(2,4-F₂C₆H₃) | CH₃ |
| CH₂(2,5-F₂C₆H₃) | CH₃ |
| CH₂(2,6-F₂C₆H₃) | CH₃ |
| CH₂(2,4,6-F₃C₆H₂) | CH₃ |
| CH₂(2-ClC₆H₄) | CH₃ |
| CH₂(3-ClC₆H₄) | CH₃ |
| CH₂(4-ClC₆H₄) | CH₃ |
| CH₂(2,6-Cl₂C₆H₃) | CH₃ |
| CH₂(2-(CH₃)C₆H₄) | CH₃ |
| CH₂(3-(CH₃)C₆H₄) | CH₃ |
| CH₂(4-(CH₃)C₆H₄) | CH₃ |
| CH₂(2-pyridyl) | CH₃ |
| CH₂(2-thienyl) | CH₃ |
| CH₂(2-tetrahydrofuranyl) | CH₃ |
| CH₂(2-tetrahydropyranyl) | CH₃ |
| Q-1 | CH₃ |
| Q-3 | CH₃ |
| Q-4 | CH₃ |
| Q-6 | CH₃ |
| Q-7 | CH₃ |
| Q-8 | CH₃ |
| Q-15 | CH₃ |
| CH₂(2-BrC₆H₄) | CH₃ |
| CH₂(2,6-Br₂C₆H₃) | CH₃ |
| CH₂(2-Cl-6-FC₆H₃) | CH₃ |
| CH₂(2-(OCH₃)C₆H₄) | CH₃ |
| CH₂(2-(CN)C₆H₄) | CH₃ |
| CH₂(2-(CF₃)C₆H₄) | CH₃ |
| CH₂(2-(OCF₃)C₆H₄) | CH₃ |
| CH₂(2-(SCH₃)C₆H₄) | CH₃ |
| CH₂(2-(CH=CH₂)C₆H₄) | CH₃ |
| CH₂(2-(C≡CH)C₆H₄) | CH₃ |
| General Structure 11, n is 4, R¹ is CH₃ | |
| CH₂(C₆H₅) | H |
| CH₂(2-FC₆H₄) | H |
| CH₂(3-FC₆H₄) | H |
| CH₂(4-FC₆H₄) | H |
| CH₂(2,3-F₂C₆H₃) | H |
| CH₂(2,4-F₂C₆H₃) | H |
| CH₂(2,5-F₂C₆H₃) | H |
| CH₂(2,6-F₂C₆H₃) | H |
| CH₂(2,4,6-F₃C₆H₂) | H |
| CH₂(2-ClC₆H₄) | H |
| CH₂(3-ClC₆H₄) | H |
| CH₂(4-ClC₆H₄) | H |
| CH₂(2,6-Cl₂C₆H₃) | H |
| CH₂(2-(CH₃)C₆H₄) | H |
| CH₂(3-(CH₃)C₆H₄) | H |
| CH₂(4-(CH₃)C₆H₄) | H |
| CH₂(2-pyridyl) | H |
| CH₂(2-thienyl) | H |
| CH₂(2-tetrahydrofuranyl) | H |
| CH₂(2-tetrahydropyranyl) | H |
| Q-1 | H |
| Q-3 | H |
| Q-4 | H |
| Q-6 | H |
| Q-7 | H |
| Q-8 | H |
| Q-15 | H |
| CH₂(2-BrC₆H₄) | H |
| CH₂(2,6-Br₂C₆H₃) | H |
| CH₂(2-Cl-6-FC₆H₃) | H |
| CH₂(2-(OCH₃)C₆H₄) | H |
| CH₂(2-(CN)C₆H₄) | H |
| CH₂(2-(CF₃)C₆H₄) | H |
| CH₂(2-(OCF₃)C₆H₄) | H |
| CH₂(2-(SCH₃)C₆H₄) | H |
| CH₂(2-(CH=CH₂)C₆H₄) | H |
| CH₂(2-(C≡CH)C₆H₄) | H |

TABLE 12

| Q | R¹ |
|---|---|
| General Structure 12, m is 3, R³=R⁴ is H | |
| CH₂(C₆H₅) | CH₃ |
| CH₂(2-FC₆H₄) | CH₃ |
| CH₂(3-FC₆H₄) | CH₃ |
| CH₂(4-FC₆H₄) | CH₃ |
| CH₂(2,3-F₂C₆H₃) | CH₃ |
| CH₂(2,4-F₂C₆H₃) | CH₃ |
| CH₂(2,5-F₂C₆H₃) | CH₃ |
| CH₂(2,6-F₂C₆H₃) | CH₃ |
| CH₂(2,4,6-F₃C₆H₂) | CH₃ |
| CH₂(2-ClC₆H₄) | CH₃ |
| CH₂(3-ClC₆H₄) | CH₃ |
| CH₂(4-ClC₆H₄) | CH₃ |
| CH₂(2,6-Cl₂C₆H₃) | CH₃ |
| CH₂(2-(CH₃)C₆H₄) | CH₃ |
| CH₂(3-(CH₃)C₆H₄) | CH₃ |
| CH₂(4-(CH₃)C₆H₄) | CH₃ |
| CH₂(2-pyridyl) | CH₃ |
| CH₂(2-thienyl) | CH₃ |
| CH₂(2-tetrahydrofuranyl) | CH₃ |
| CH₂(2-tetrahydropyranyl) | CH₃ |
| Q-1 | CH₃ |
| Q-3 | CH₃ |
| Q-4 | CH₃ |
| Q-6 | CH₃ |
| Q-7 | CH₃ |
| Q-8 | CH₃ |
| Q-15 | CH₃ |
| CH₂(2-BrC₆H₄) | CH₃ |
| CH₂(2,6-Br₂C₆H₃) | CH₃ |
| CH₂(2-Cl-6-FC₆H₃) | CH₃ |
| CH₂(2-(OCH₃)C₆H₄) | CH₃ |
| CH₂(2-(CN)C₆H₄) | CH₃ |
| CH₂(2-(CF₃)C₆H₄) | CH₃ |
| CH₂(2-(OCF₃)C₆H₄) | CH₃ |
| CH₂(2-(SCH₃)C₆H₄) | CH₃ |
| CH₂(2-(CH=CH₂)C₆H₄) | CH₃ |
| CH₂(2-(C≡CH)C₆H₄) | CH₃ |
| CH₂(C₆H₅) | CH₂CH₃ |
| CH₂(2-FC₆H₄) | CH₂CH₃ |
| CH₂(3-FC₆H₄) | CH₂CH₃ |
| CH₂(4-FC₆H₄) | CH₂CH₃ |
| CH₂(2,3-F₂C₆H₃) | CH₂CH₃ |
| CH₂(2,4-F₂C₆H₃) | CH₂CH₃ |
| CH₂(2,5-F₂C₆H₃) | CH₂CH₃ |
| CH₂(2,6-F₂C₆H₃) | CH₂CH₃ |
| CH₂(2,4,6-F₃C₆H₂) | CH₂CH₃ |
| CH₂(2-ClC₆H₄) | CH₂CH₃ |
| CH₂(3-ClC₆H₄) | CH₂CH₃ |
| CH₂(4-ClC₆H₄) | CH₂CH₃ |
| CH₂(2,6-Cl₂C₆H₃) | CH₂CH₃ |
| CH₂(2-(CH₃)C₆H₄) | CH₂CH₃ |
| CH₂(3-(CH₃)C₆H₄) | CH₂CH₃ |
| CH₂(4-(CH₃)C₆H₄) | CH₂CH₃ |
| CH₂(2-pyridyl) | CH₂CH₃ |
| CH₂(2-thienyl) | CH₂CH₃ |
| CH₂(2-tetrahydrofuranyl) | CH₂CH₃ |
| CH₂(2-tetrahydropyranyl) | CH₂CH₃ |
| Q-1 | CH₂CH₃ |
| Q-3 | CH₂CH₃ |
| Q-4 | CH₂CH₃ |
| Q-6 | CH₂CH₃ |

TABLE 12-continued

| Q | R¹ |
|---|---|
| Q-7 | $CH_2CH_3$ |
| Q-8 | $CH_2CH_3$ |
| Q-15 | $CH_2CH_3$ |
| $CH_2(2-BrC_6H_4)$ | $CH_2CH_3$ |
| $CH_2(2,6-Br_2C_6H_3)$ | $CH_2CH_3$ |
| $CH_2(2-Cl-6-FC_6H_3)$ | $CH_2CH_3$ |
| $CH_2(2-(OCH_3)C_6H_4)$ | $CH_2CH_3$ |
| $CH_2(2-(CN)C_6H_4)$ | $CH_2CH_3$ |
| $CH_2(2-(CF_3)C_6H_4)$ | $CH_2CH_3$ |
| $CH_2(2-(OCF_3)C_6H_4)$ | $CH_2CH_3$ |
| $CH_2(2-(SCH_3)C_6H_4)$ | $CH_2CH_3$ |
| $CH_2(2-(CH=CH_2)C_6H_4)$ | $CH_2CH_3$ |
| $CH_2(2-(C\equiv CH)C_6H_4)$ | $CH_2CH_3$ |
| General Structure 12, m is 3, $R^3=R^4$ is $CH_3$ | |
| $CH_2(C_6H_5)$ | $CH_3$ |
| $CH_2(2-FC_6H_4)$ | $CH_3$ |
| $CH_2(3-FC_6H_4)$ | $CH_3$ |
| $CH_2(4-FC_6H_4)$ | $CH_3$ |
| $CH_2(2,3-F_2C_6H_3)$ | $CH_3$ |
| $CH_2(2,4-F_2C_6H_3)$ | $CH_3$ |
| $CH_2(2,5-F_2C_6H_3)$ | $CH_3$ |
| $CH_2(2,6-F_2C_6H_3)$ | $CH_3$ |
| $CH_2(2,4,6-F_3C_6H_2)$ | $CH_3$ |
| $CH_2(2-ClC_6H_4)$ | $CH_3$ |
| $CH_2(3-ClC_6H_4)$ | $CH_3$ |
| $CH_2(4-ClC_6H_4)$ | $CH_3$ |
| $CH_2(2,6-Cl_2C_6H_3)$ | $CH_3$ |
| $CH_2(2-(CH_3)C_6H_4)$ | $CH_3$ |
| $CH_2(3-(CH_3)C_6H_4)$ | $CH_3$ |
| $CH_2(4-(CH_3)C_6H_4)$ | $CH_3$ |
| $CH_2(2-pyridyl)$ | $CH_3$ |
| $CH_2(2-thienyl)$ | $CH_3$ |
| $CH_2(2-tetrahydrofuranyl)$ | $CH_3$ |
| $CH_2(2-tetrahydropyranyl)$ | $CH_3$ |
| Q-1 | $CH_3$ |
| Q-3 | $CH_3$ |
| Q-4 | $CH_3$ |
| Q-6 | $CH_3$ |
| Q-7 | $CH_3$ |
| Q-8 | $CH_3$ |
| Q-15 | $CH_3$ |
| $CH_2(2-BrC_6H_4)$ | $CH_3$ |
| $CH_2(2,6-Br_2C_6H_3)$ | $CH_3$ |
| $CH_2(2-Cl-6-FC_6H_3)$ | $CH_3$ |
| $CH_2(2-(OCH_3)C_6H_4)$ | $CH_3$ |
| $CH_2(2-(CN)C_6H_4)$ | $CH_3$ |
| $CH_2(2-(CF_3)C_6H_4)$ | $CH_3$ |
| $CH_2(2-(OCF_3)C_6H_4)$ | $CH_3$ |
| $CH_2(2-(SCH_3)C_6H_4)$ | $CH_3$ |
| $CH_2(2-(CH=CH_2)C_6H_4)$ | $CH_3$ |
| $CH_2(2-(C\equiv CH)C_6H_4)$ | $CH_3$ |
| $CH_2(C_6H_5)$ | $CH_2CH_3$ |
| $CH_2(2-FC_6H_4)$ | $CH_2CH_3$ |
| $CH_2(3-FC_6H_4)$ | $CH_2CH_3$ |
| $CH_2(4-FC_6H_4)$ | $CH_2CH_3$ |
| $CH_2(2,3-F_2C_6H_3)$ | $CH_2CH_3$ |
| $CH_2(2,4-F_2C_6H_3)$ | $CH_2CH_3$ |
| $CH_2(2,5-F_2C_6H_3)$ | $CH_2CH_3$ |
| $CH_2(2,6-F_2C_6H_3)$ | $CH_2CH_3$ |
| $CH_2(2,4,6-F_3C_6H_2)$ | $CH_2CH_3$ |
| $CH_2(2-ClC_6H_4)$ | $CH_2CH_3$ |
| $CH_2(3-ClC_6H_4)$ | $CH_2CH_3$ |
| $CH_2(4-ClC_6H_4)$ | $CH_2CH_3$ |
| $CH_2(2,6-Cl_2C_6H_3)$ | $CH_2CH_3$ |
| $CH_2(2-(CH_3)C_6H_4)$ | $CH_2CH_3$ |
| $CH_2(3-(CH_3)C_6H_4)$ | $CH_2CH_3$ |
| $CH_2(4-(CH_3)C_6H_4)$ | $CH_2CH_3$ |
| $CH_2(2-pyridyl)$ | $CH_2CH_3$ |
| $CH_2(2-thienyl)$ | $CH_2CH_3$ |
| $CH_2(2-tetrahydrofuranyl)$ | $CH_2CH_3$ |
| $CH_2(2-tetrahydropyranyl)$ | $CH_2CH_3$ |
| Q-1 | $CH_2CH_3$ |
| Q-3 | $CH_2CH_3$ |
| Q-4 | $CH_2CH_3$ |
| Q-6 | $CH_2CH_3$ |
| Q-7 | $CH_2CH_3$ |
| Q-8 | $CH_2CH_3$ |
| Q-15 | $CH_2CH_3$ |
| $CH_2(2-BrC_6H_4)$ | $CH_2CH_3$ |
| $CH_2(2,6-Br_2C_6H_3)$ | $CH_2CH_3$ |
| $CH_2(2-Cl-6-FC_6H_3)$ | $CH_2CH_3$ |
| $CH_2(2-(OCH_3)C_6H_4)$ | $CH_2CH_3$ |
| $CH_2(2-(CN)C_6H_4)$ | $CH_2CH_3$ |
| $CH_2(2-(CF_3)C_6H_4)$ | $CH_2CH_3$ |
| $CH_2(2-(OCF_3)C_6H_4)$ | $CH_2CH_3$ |
| $CH_2(2-(SCH_3)C_6H_4)$ | $CH_2CH_3$ |
| $CH_2(2-(CH=CH_2)C_6H_4)$ | $CH_2CH_3$ |
| $CH_2(2-(C\equiv CH)C_6H_4)$ | $CH_2CH_3$ |
| General Structure 12, m is 4, $R^3=R^4$ is H | |
| $CH_2(C_6H_5)$ | $CH_3$ |
| $CH_2(2-FC_6H_4)$ | $CH_3$ |
| $CH_2(3-FC_6H_4)$ | $CH_3$ |
| $CH_2(4-FC_6H_4)$ | $CH_3$ |
| $CH_2(2,3-F_2C_6H_3)$ | $CH_3$ |
| $CH_2(2,4-F_2C_6H_3)$ | $CH_3$ |
| $CH_2(2,5-F_2C_6H_3)$ | $CH_3$ |
| $CH_2(2,6-F_2C_6H_3)$ | $CH_3$ |
| $CH_2(2,4,6-F_3C_6H_2)$ | $CH_3$ |
| $CH_2(2-ClC_6H_4)$ | $CH_3$ |
| $CH_2(3-ClC_6H_4)$ | $CH_3$ |
| $CH_2(4-ClC_6H_4)$ | $CH_3$ |
| $CH_2(2,6-Cl_2C_6H_3)$ | $CH_3$ |
| $CH_2(2-(CH_3)C_6H_4)$ | $CH_3$ |
| $CH_2(3-(CH_3)C_6H_4)$ | $CH_3$ |
| $CH_2(4-(CH_3)C_6H_4)$ | $CH_3$ |
| $CH_2(2-pyridyl)$ | $CH_3$ |
| $CH_2(2-thienyl)$ | $CH_3$ |
| $CH_2(2-tetrahydrofuranyl)$ | $CH_3$ |
| $CH_2(2-tetrahydropyranyl)$ | $CH_3$ |
| Q-1 | $CH_3$ |
| Q-3 | $CH_3$ |
| Q-4 | $CH_3$ |
| Q-6 | $CH_3$ |
| Q-7 | $CH_3$ |
| Q-8 | $CH_3$ |
| Q-15 | $CH_3$ |
| $CH_2(2-BrC_6H_4)$ | $CH_3$ |
| $CH_2(2,6-Br_2C_6H_3)$ | $CH_3$ |
| $CH_2(2-Cl-6-FC_6H_3)$ | $CH_3$ |
| $CH_2(2-(OCH_3)C_6H_4)$ | $CH_3$ |
| $CH_2(2-(CN)C_6H_4)$ | $CH_3$ |
| $CH_2(2-(CF_3)C_6H_4)$ | $CH_3$ |
| $CH_2(2-(OCF_3)C_6H_4)$ | $CH_3$ |
| $CH_2(2-(SCH_3)C_6H_4)$ | $CH_3$ |
| $CH_2(2-(CH=CH_2)C_6H_4)$ | $CH_3$ |
| $CH_2(2-(C\equiv CH)C_6H_4)$ | $CH_3$ |
| $CH_2(C_6H_5)$ | $CH_2CH_3$ |
| $CH_2(2-FC_6H_4)$ | $CH_2CH_3$ |
| $CH_2(3-FC_6H_4)$ | $CH_2CH_3$ |
| $CH_2(4-FC_6H_4)$ | $CH_2CH_3$ |
| $CH_2(2,3-F_2C_6H_3)$ | $CH_2CH_3$ |
| $CH_2(2,4-F_2C_6H_3)$ | $CH_2CH_3$ |
| $CH_2(2,5-F_2C_6H_3)$ | $CH_2CH_3$ |
| $CH_2(2,6-F_2C_6H_3)$ | $CH_2CH_3$ |
| $CH_2(2,4,6-F_3C_6H_2)$ | $CH_2CH_3$ |
| $CH_2(2-ClC_6H_4)$ | $CH_2CH_3$ |
| $CH_2(3-ClC_6H_4)$ | $CH_2CH_3$ |
| $CH_2(4-ClC_6H_4)$ | $CH_2CH_3$ |
| $CH_2(2,6-Cl_2C_6H_3)$ | $CH_2CH_3$ |
| $CH_2(2-(CH_3)C_6H_4)$ | $CH_2CH_3$ |
| $CH_2(3-(CH_3)C_6H_4)$ | $CH_2CH_3$ |
| $CH_2(4-(CH_3)C_6H_4)$ | $CH_2CH_3$ |
| $CH_2(2-pyridyl)$ | $CH_2CH_3$ |
| $CH_2(2-thienyl)$ | $CH_2CH_3$ |
| $CH_2(2-tetrahydrofuranyl)$ | $CH_2CH_3$ |
| $CH_2(2-tetrahydropyranyl)$ | $CH_2CH_3$ |
| Q-1 | $CH_2CH_3$ |
| Q-3 | $CH_2CH_3$ |
| Q-4 | $CH_2CH_3$ |
| Q-6 | $CH_2CH_3$ |
| Q-7 | $CH_2CH_3$ |
| Q-8 | $CH_2CH_3$ |
| Q-15 | $CH_2CH_3$ |
| $CH_2(2-BrC_6H_4)$ | $CH_2CH_3$ |
| $CH_2(2,6-Br_2C_6H_3)$ | $CH_2CH_3$ |
| $CH_2(2-Cl-6-FC_6H_3)$ | $CH_2CH_3$ |
| $CH_2(2-(OCH_3)C_6H_4)$ | $CH_2CH_3$ |
| $CH_2(2-(CN)C_6H_4)$ | $CH_2CH_3$ |
| $CH_2(2-(CF_3)C_6H_4)$ | $CH_2CH_3$ |
| $CH_2(2-(OCF_3)C_6H_4)$ | $CH_2CH_3$ |

TABLE 12-continued

| Q | $R^1$ |
|---|---|
| $CH_2(2\text{-}(SCH_3)C_6H_4)$ | $CH_2CH_3$ |
| $CH_2(2\text{-}(CH=CH_2)C_6H_4)$ | $CH_2CH_3$ |
| $CH_2(2\text{-}(C\equiv CH)C_6H_4)$ | $CH_2CH_3$ |
| General Structure 12, m is 4, $R^3=R^4$ is $CH_3$ | |
| $CH_2(C_6H_5)$ | $CH_3$ |
| $CH_2(2\text{-}FC_6H_4)$ | $CH_3$ |
| $CH_2(3\text{-}FC_6H_4)$ | $CH_3$ |
| $CH_2(4\text{-}FC_6H_4)$ | $CH_3$ |
| $CH_2(2,3\text{-}F_2C_6H_3)$ | $CH_3$ |
| $CH_2(2,4\text{-}F_2C_6H_3)$ | $CH_3$ |
| $CH_2(2,5\text{-}F_2C_6H_3)$ | $CH_3$ |
| $CH_2(2,6\text{-}F_2C_6H_3)$ | $CH_3$ |
| $CH_2(2,4,6\text{-}F_3C_6H_2)$ | $CH_3$ |
| $CH_2(2\text{-}ClC_6H_4)$ | $CH_3$ |
| $CH_2(3\text{-}ClC_6H_4)$ | $CH_3$ |
| $CH_2(4\text{-}ClC_6H_4)$ | $CH_3$ |
| $CH_2(2,6\text{-}Cl_2C_6H_3)$ | $CH_3$ |
| $CH_2(2\text{-}(CH_3)C_6H_4)$ | $CH_3$ |
| $CH_2(3\text{-}(CH_3)C_6H_4)$ | $CH_3$ |
| $CH_2(4\text{-}(CH_3)C_6H_4)$ | $CH_3$ |
| $CH_2(2\text{-pyridyl})$ | $CH_3$ |
| $CH_2(2\text{-thienyl})$ | $CH_3$ |
| $CH_2(2\text{-tetrahydrofuranyl})$ | $CH_3$ |
| $CH_2(2\text{-tetrahydropyranyl})$ | $CH_3$ |
| Q-1 | $CH_3$ |
| Q-3 | $CH_3$ |
| Q-4 | $CH_3$ |
| Q-6 | $CH_3$ |
| Q-7 | $CH_3$ |
| Q-8 | $CH_3$ |
| Q-15 | $CH_3$ |
| $CH_2(2\text{-}BrC_6H_4)$ | $CH_3$ |
| $CH_2(2,6\text{-}Br_2C_6H_3)$ | $CH_3$ |
| $CH_2(2\text{-}Cl\text{-}6\text{-}FC_6H_3)$ | $CH_3$ |
| $CH_2(2\text{-}(OCH_3)C_6H_4)$ | $CH_3$ |
| $CH_2(2\text{-}(CN)C_6H_4)$ | $CH_3$ |
| $CH_2(2\text{-}(CF_3)C_6H_4)$ | $CH_3$ |
| $CH_2(2\text{-}(OCF_3)C_6H_4)$ | $CH_3$ |
| $CH_2(2\text{-}(SCH_3)C_6H_4)$ | $CH_3$ |
| $CH_2(2\text{-}(CH=CH_2)C_6H_4)$ | $CH_3$ |
| $CH_2(2\text{-}(C\equiv CH)C_6H_4)$ | $CH_3$ |
| $CH_2(C_6H_5)$ | $CH_2CH_3$ |
| $CH_2(2\text{-}FC_6H_4)$ | $CH_2CH_3$ |
| $CH_2(3\text{-}FC_6H_4)$ | $CH_2CH_3$ |
| $CH_2(4\text{-}FC_6H_4)$ | $CH_2CH_3$ |
| $CH_2(2,3\text{-}F_2C_6H_3)$ | $CH_2CH_3$ |
| $CH_2(2,4\text{-}F_2C_6H_3)$ | $CH_2CH_3$ |
| $CH_2(2,5\text{-}F_2C_6H_3)$ | $CH_2CH_3$ |
| $CH_2(2,6\text{-}F_2C_6H_3)$ | $CH_2CH_3$ |
| $CH_2(2,4,6\text{-}F_3C_6H_2)$ | $CH_2CH_3$ |
| $CH_2(2\text{-}ClC_6H_4)$ | $CH_2CH_3$ |
| $CH_2(3\text{-}ClC_6H_4)$ | $CH_2CH_3$ |
| $CH_2(4\text{-}ClC_6H_4)$ | $CH_2CH_3$ |
| $CH_2(2,6\text{-}Cl_2C_6H_3)$ | $CH_2CH_3$ |
| $CH_2(2\text{-}(CH_3)C_6H_4)$ | $CH_2CH_3$ |
| $CH_2(3\text{-}(CH_3)C_6H_4)$ | $CH_2CH_3$ |
| $CH_2(4\text{-}(CH_3)C_6H_4)$ | $CH_2CH_3$ |
| $CH_2(2\text{-pyridyl})$ | $CH_2CH_3$ |
| $CH_2(2\text{-thienyl})$ | $CH_2CH_3$ |
| $CH_2(2\text{-tetrahydrofuranyl})$ | $CH_2CH_3$ |
| $CH_2(2\text{-tetrahydropyranyl})$ | $CH_2CH_3$ |
| Q-1 | $CH_2CH_3$ |
| Q-3 | $CH_2CH_3$ |
| Q-4 | $CH_2CH_3$ |
| Q-6 | $CH_2CH_3$ |
| Q-7 | $CH_2CH_3$ |
| Q-8 | $CH_2CH_3$ |
| Q-15 | $CH_2CH_3$ |
| $CH_2(2\text{-}BrC_6H_4)$ | $CH_2CH_3$ |
| $CH_2(2,6\text{-}Br_2C_6H_3)$ | $CH_2CH_3$ |
| $CH_2(2\text{-}Cl\text{-}6\text{-}FC_6H_3)$ | $CH_2CH_3$ |
| $CH_2(2\text{-}(OCH_3)C_6H_4)$ | $CH_2CH_3$ |
| $CH_2(2\text{-}(CN)C_6H_4)$ | $CH_2CH_3$ |
| $CH_2(2\text{-}(CF_3)C_6H_4)$ | $CH_2CH_3$ |
| $CH_2(2\text{-}(OCF_3)C_6H_4)$ | $CH_2CH_3$ |
| $CH_2(2\text{-}(SCH_3)C_6H_4)$ | $CH_2CH_3$ |
| $CH_2(2\text{-}(CH=CH_2)C_6H_4)$ | $CH_2CH_3$ |
| $CH_2(2\text{-}(C\equiv CH)C_6H_4)$ | $CH_2CH_3$ |
| General Structure 12, m is 5, $R^3=R^4$ is H | |
| $CH_2(C_6H_5)$ | $CH_3$ |
| $CH_2(2\text{-}FC_6H_4)$ | $CH_3$ |
| $CH_2(3\text{-}FC_6H_4)$ | $CH_3$ |
| $CH_2(4\text{-}FC_6H_4)$ | $CH_3$ |
| $CH_2(2,3\text{-}F_2C_6H_3)$ | $CH_3$ |
| $CH_2(2,4\text{-}F_2C_6H_3)$ | $CH_3$ |
| $CH_2(2,5\text{-}F_2C_6H_3)$ | $CH_3$ |
| $CH_2(2,6\text{-}F_2C_6H_3)$ | $CH_3$ |
| $CH_2(2,4,6\text{-}F_3C_6H_2)$ | $CH_3$ |
| $CH_2(2\text{-}ClC_6H_4)$ | $CH_3$ |
| $CH_2(3\text{-}ClC_6H_4)$ | $CH_3$ |
| $CH_2(4\text{-}ClC_6H_4)$ | $CH_3$ |
| $CH_2(2,6\text{-}Cl_2C_6H_3)$ | $CH_3$ |
| $CH_2(2\text{-}(CH_3)C_6H_4)$ | $CH_3$ |
| $CH_2(3\text{-}(CH_3)C_6H_4)$ | $CH_3$ |
| $CH_2(4\text{-}(CH_3)C_6H_4)$ | $CH_3$ |
| $CH_2(2\text{-pyridyl})$ | $CH_3$ |
| $CH_2(2\text{-thienyl})$ | $CH_3$ |
| $CH_2(2\text{-tetrahydrofuranyl})$ | $CH_3$ |
| $CH_2(2\text{-tetrahydropyranyl})$ | $CH_3$ |
| Q-1 | $CH_3$ |
| Q-3 | $CH_3$ |
| Q-4 | $CH_3$ |
| Q-6 | $CH_3$ |
| Q-7 | $CH_3$ |
| Q-8 | $CH_3$ |
| Q-15 | $CH_3$ |
| $CH_2(2\text{-}BrC_6H_4)$ | $CH_3$ |
| $CH_2(2,6\text{-}Br_2C_6H_3)$ | $CH_3$ |
| $CH_2(2\text{-}Cl\text{-}6\text{-}FC_6H_3)$ | $CH_3$ |
| $CH_2(2\text{-}(OCH_3)C_6H_4)$ | $CH_3$ |
| $CH_2(2\text{-}(CN)C_6H_4)$ | $CH_3$ |
| $CH_2(2\text{-}(CF_3)C_6H_4)$ | $CH_3$ |
| $CH_2(2\text{-}(OCF_3)C_6H_4)$ | $CH_3$ |
| $CH_2(2\text{-}(SCH_3)C_6H_4)$ | $CH_3$ |
| $CH_2(2\text{-}(CH=CH_2)C_6H_4)$ | $CH_3$ |
| $CH_2(2\text{-}(C\equiv CH)C_6H_4)$ | $CH_3$ |

TABLE 13

General Structure 13, p is 2

| W | $R^2$ | W | $R^2$ |
|---|---|---|---|
| $C_6H_5$ | $CH_3$ | $C_6H_5$ | $CH_2CH_3$ |
| $2\text{-}FC_6H_4$ | $CH_3$ | $2\text{-}FC_6H_4$ | $CH_2CH_3$ |
| $3\text{-}FC_6H_4$ | $CH_3$ | $2\text{-}FC_6H_4$ | $CH_2CH_3$ |
| $4\text{-}FC_6H_4$ | $CH_3$ | $4\text{-}FC_6H_4$ | $CH_2CH_3$ |
| $2,3\text{-}F_2C_6H_3$ | $CH_3$ | $2,3\text{-}F_2C_6H_3$ | $CH_2CH_3$ |
| $2,4\text{-}F_2C_6H_3$ | $CH_3$ | $2,4\text{-}F_2C_6H_3$ | $CH_2CH_3$ |
| $2,5\text{-}F_2C_6H_3$ | $CH_3$ | $2,5\text{-}F_2C_6H_3$ | $CH_2CH_3$ |
| $2,4,6\text{-}F_3C_6H_2$ | $CH_3$ | $2,4,6\text{-}F_3C_6H_2$ | $CH_2CH_3$ |
| $2\text{-}ClC_6H_4$ | $CH_3$ | $2\text{-}ClC_6H_4$ | $CH_2CH_3$ |
| $2\text{-}Cl\text{-}6\text{-}FC_6H_3$ | $CH_3$ | $2\text{-}Cl\text{-}6\text{-}FC_6H_3$ | $CH_2CH_3$ |
| $2\text{-}(CH_3)C_6H_4$ | $CH_3$ | $2\text{-}(CH_3)C_6H_4$ | $CH_2CH_3$ |
| 2-pyridyl | $CH_3$ | 2-pyridyl | $CH_2CH_3$ |
| 2-thienyl | $CH_3$ | 2-thienyl | $CH_2CH_3$ |
| 2-tetrahydrofuranyl | $CH_3$ | 2-tetrahydrofuranyl | $CH_2CH_3$ |
| $2\text{-}(OCH_3)C_6H_4$ | $CH_3$ | $2\text{-}(OCH_3)C_6H_4$ | $CH_2CH_3$ |
| $2\text{-}(CN)C_6H_4$ | $CH_3$ | $2\text{-}(CN)C_6H_4$ | $CH_2CH_3$ |
| $2\text{-}(CF_3)C_6H_4$ | $CH_3$ | $2\text{-}(CF_3)C_6H_4$ | $CH_2CH_3$ |
| $2\text{-}(OCF_3)C_6H_4$ | $CH_3$ | $2\text{-}(OCF_3)C_6H_4$ | $CH_2CH_3$ |
| $2\text{-}(SCH_3)C_6H_4$ | $CH_3$ | $2\text{-}(SCH_3)C_6H_4$ | $CH_2CH_3$ |
| $2\text{-}(CH=CH_2)C_6H_4$ | $CH_3$ | $2\text{-}(CH=CH_2)C_6H_4$ | $CH_2CH_3$ |
| $2\text{-}(C\equiv CH)C_6H_4$ | $CH_3$ | $2\text{-}(C\equiv CH)C_6H_4$ | $CH_2CH_3$ |

General Structure 13, p is 3

| W | $R^2$ | W | $R^2$ |
|---|---|---|---|
| $C_6H_5$ | $CH_3$ | $C_6H_5$ | $CH_2CH_3$ |
| $2\text{-}FC_6H_4$ | $CH_3$ | $2\text{-}FC_6H_4$ | $CH_2CH_3$ |
| $3\text{-}FC_6H_4$ | $CH_3$ | $3\text{-}FC_6H_4$ | $CH_2CH_3$ |
| $4\text{-}FC_6H_4$ | $CH_3$ | $4\text{-}FC_6H_4$ | $CH_2CH_3$ |
| $2,3\text{-}F_2C_6H_3$ | $CH_3$ | $2,3\text{-}F_2C_6H_3$ | $CH_2CH_3$ |
| $2,4\text{-}F_2C_6H_3$ | $CH_3$ | $2,4\text{-}F_2C_6H_3$ | $CH_2CH_3$ |
| $2,5\text{-}F_2C_6H_3$ | $CH_3$ | $2,5\text{-}F_2C_6H_3$ | $CH_2CH_3$ |
| $2,4,6\text{-}F_3C_6H_2$ | $CH_3$ | $2,4,6\text{-}F_3C_6H_2$ | $CH_2CH_3$ |
| $2\text{-}ClC_6H_4$ | $CH_3$ | $2\text{-}ClC_6H_4$ | $CH_2CH_3$ |
| $2\text{-}Cl\text{-}6\text{-}FC_6H_3$ | $CH_3$ | $2\text{-}Cl\text{-}6\text{-}FC_6H_3$ | $CH_2CH_3$ |
| $2\text{-}(CH_3)C_6H_4$ | $CH_3$ | $2\text{-}(CH_3)C_6H_4$ | $CH_2CH_3$ |
| 2-pyridyl | $CH_3$ | 2-pyridyl | $CH_2CH_3$ |
| 2-thienyl | $CH_3$ | 2-thienyl | $CH_2CH_3$ |
| 2-tetrahydrofuranyl | $CH_3$ | 2-tetrahydrofuranyl | $CH_2CH_3$ |

TABLE 13-continued

| W | | W | |
|---|---|---|---|
| 2-(OCH$_3$)C$_6$H$_4$ | CH$_3$ | 2-(OCH$_3$)C$_6$H$_4$ | CH$_2$CH$_3$ |
| 2-(CN)C$_6$H$_4$ | CH$_3$ | 2-(CN)C$_6$H$_4$ | CH$_2$CH$_3$ |
| 2-(CF$_3$)C$_6$H$_4$ | CH$_3$ | 2-(CF$_3$)C$_6$H$_4$ | CH$_2$CH$_3$ |
| 2-(OCF$_3$)C$_6$H$_4$ | CH$_3$ | 2-(OCF$_3$)C$_6$H$_4$ | CH$_2$CH$_3$ |
| 2-(SCH$_3$)C$_6$H$_4$ | CH$_3$ | 2-(SCH$_3$)C$_6$H$_4$ | CH$_2$CH$_3$ |
| 2-(CH=CH$_2$)C$_6$H$_4$ | CH$_3$ | 2-(CH=CH$_2$)C$_6$H$_4$ | CH$_2$CH$_3$ |
| 2-(C≡CH)C$_6$H$_4$ | CH$_3$ | 2-(C≡CH)C$_6$H$_4$ | CH$_2$CH$_3$ |

TABLE 14

General Structure 14, R$^3$=R$^4$ is H, p is 2

| W | R$^2$ | W | R$^2$ |
|---|---|---|---|
| C$_6$H$_5$ | H | C$_6$H$_5$ | CH$_3$ |
| 2-FC$_6$H$_4$ | H | 2-FC$_6$H$_4$ | CH$_3$ |
| 3-FC$_6$H$_4$ | H | 3-FC$_6$H$_4$ | CH$_3$ |
| 4-FC$_6$H$_4$ | H | 4-FC$_6$H$_4$ | CH$_3$ |
| 2,3-F$_2$C$_6$H$_3$ | H | 2,3-F$_2$C$_6$H$_3$ | CH$_3$ |
| 2,4-F$_2$C$_6$H$_3$ | H | 2,4-F$_2$C$_6$H$_3$ | CH$_3$ |
| 2,5-F$_2$C$_6$H$_3$ | H | 2,5-F$_2$C$_6$H$_3$ | CH$_3$ |
| 2,4,6-F$_3$C$_6$H$_2$ | H | 2,4,6-F$_3$C$_6$H$_2$ | CH$_3$ |
| 2-ClC$_6$H$_4$ | H | 2-ClC$_6$H$_4$ | CH$_3$ |
| 2-Cl-6-FC$_6$H$_3$ | H | 2-Cl-6-FC$_6$H$_3$ | CH$_3$ |
| 2-(CH$_3$)C$_6$H$_4$ | H | 2-(CH$_3$)C$_6$H$_4$ | CH$_3$ |
| 2-pyridyl | H | 2-pyridyl | CH$_3$ |
| 2-thienyl | H | 2-thienyl | CH$_3$ |
| 2-tetrahydrofuranyl | H | 2-tetrahydrofuranyl | CH$_3$ |
| 2-(OCH$_3$)C$_6$H$_4$ | H | 2-(OCH$_3$)C$_6$H$_4$ | CH$_3$ |
| 2-(CN)C$_6$H$_4$ | H | 2-(CN)C$_6$H$_4$ | CH$_3$ |
| 2-(CF$_3$)C$_6$H$_4$ | H | 2-(CF$_3$)C$_6$H$_4$ | CH$_3$ |
| 2-(OCF$_3$)C$_6$H$_4$ | H | 2-(OCF$_3$)C$_6$H$_4$ | CH$_3$ |
| 2-(SCH$_3$)C$_6$H$_4$ | H | 2-(SCH$_3$)C$_6$H$_4$ | CH$_3$ |
| 2-(CH=CH$_2$)C$_6$H$_4$ | H | 2-(CH=CH$_2$)C$_6$H$_4$ | CH$_3$ |
| 2-(C≡CH)C$_6$H$_4$ | H | 2-(C≡CH)C$_6$H$_4$ | CH$_3$ |

General Structure 14, R$^3$=R$^4$ is CH$_3$, p is 2

| W | R$^2$ | W | R$^2$ |
|---|---|---|---|
| C$_6$H$_5$ | H | C$_6$H$_5$ | CH$_3$ |
| 2-FC$_6$H$_4$ | H | 2-FC$_6$H$_4$ | CH$_3$ |
| 3-FC$_6$H$_4$ | H | 3-FC$_6$H$_4$ | CH$_3$ |
| 4-FC$_6$H$_4$ | H | 4-FC$_6$H$_4$ | CH$_3$ |
| 2,3-F$_2$C$_6$H$_3$ | H | 2,3-F$_2$C$_6$H$_3$ | CH$_3$ |
| 2,4-F$_2$C$_6$H$_3$ | H | 2,4-F$_2$C$_6$H$_3$ | CH$_3$ |
| 2,5-F$_2$C$_6$H$_3$ | H | 2,5-F$_2$C$_6$H$_3$ | CH$_3$ |
| 2,4,6-F$_3$C$_6$H$_2$ | H | 2,4,6-F$_3$C$_6$H$_2$ | CH$_3$ |
| 2-ClC$_6$H$_4$ | H | 2-ClC$_6$H$_4$ | CH$_3$ |
| 2-Cl-6-FC$_6$H$_3$ | H | 2-Cl-6-FC$_6$H$_3$ | CH$_3$ |
| 2-(CH$_3$)C$_6$H$_4$ | H | 2-(CH$_3$)C$_6$H$_4$ | CH$_3$ |
| 2-pyridyl | H | 2-pyridyl | CH$_3$ |
| 2-thienyl | H | 2-thienyl | CH$_3$ |
| 2-tetrahydrofuranyl | H | 2-tetrahydrofuranyl | CH$_3$ |
| 2-(OCH$_3$)C$_6$H$_4$ | H | 2-(OCH$_3$)C$_6$H$_4$ | CH$_3$ |
| 2-(CN)C$_6$H$_4$ | H | 2-(CN)C$_6$H$_4$ | CH$_3$ |
| 2-(CF$_3$)C$_6$H$_4$ | H | 2-(CF$_3$)C$_6$H$_4$ | CH$_3$ |
| 2-(OCF$_3$)C$_6$H$_4$ | H | 2-(OCF$_3$)C$_6$H$_4$ | CH$_3$ |
| 2-(SCH$_3$)C$_6$H$_4$ | H | 2-(SCH$_3$)C$_6$H$_4$ | CH$_3$ |
| 2-(CH=CH$_2$)C$_6$H$_4$ | H | 2-(CH=CH$_2$)C$_6$H$_4$ | CH$_3$ |
| 2-(C≡CH)C$_6$H$_4$ | H | 2-(C≡CH)C$_6$H$_4$ | CH$_3$ |

General Structure 14, R$^3$=R$^4$ is H, p is 3

| W | R$^2$ | W | R$^2$ |
|---|---|---|---|
| C$_6$H$_5$ | H | C$_6$H$_5$ | CH$_3$ |
| 2-FC$_6$H$_4$ | H | 2-FC$_6$H$_4$ | CH$_3$ |
| 3-FC$_6$H$_4$ | H | 3-FC$_6$H$_4$ | CH$_3$ |
| 4-FC$_6$H$_4$ | H | 4-FC$_6$H$_4$ | CH$_3$ |
| 2,3-F$_2$C$_6$H$_3$ | H | 2,3-F$_2$C$_6$H$_3$ | CH$_3$ |
| 2,4-F$_2$C$_6$H$_3$ | H | 2,4-F$_2$C$_6$H$_3$ | CH$_3$ |
| 2,5-F$_2$C$_6$H$_3$ | H | 2,5-F$_2$C$_6$H$_3$ | CH$_3$ |
| 2,4,6-F$_3$C$_6$H$_2$ | H | 2,4,6-F$_3$C$_6$H$_2$ | CH$_3$ |
| 2-ClC$_6$H$_4$ | H | 2-ClC$_6$H$_4$ | CH$_3$ |
| 2-Cl-6-FC$_6$H$_3$ | H | 2-Cl-6-FC$_6$H$_3$ | CH$_3$ |
| 2-(CH$_3$)C$_6$H$_4$ | H | 2-(CH$_3$)C$_6$H$_4$ | CH$_3$ |
| 2-pyridyl | H | 2-pyridyl | CH$_3$ |
| 2-thienyl | H | 2-thienyl | CH$_3$ |
| 2-tetrahydrofuranyl | H | 2-tetrahydrofuranyl | CH$_3$ |
| 2-(OCH$_3$)C$_6$H$_4$ | H | 2-(OCH$_3$)C$_6$H$_4$ | CH$_3$ |
| 2-(CN)C$_6$H$_4$ | H | 2-(CN)C$_6$H$_4$ | CH$_3$ |
| 2-(CF$_3$)C$_6$H$_4$ | H | 2-(CF$_3$)C$_6$H$_4$ | CH$_3$ |
| 2-(OCF$_3$)C$_6$H$_4$ | H | 2-(OCF$_3$)C$_6$H$_4$ | CH$_3$ |
| 2-(SCH$_3$)C$_6$H$_4$ | H | 2-(SCH$_3$)C$_6$H$_4$ | CH$_3$ |
| 2-(CH=CH$_2$)C$_6$H$_4$ | H | 2-(CH=CH$_2$)C$_6$H$_4$ | CH$_3$ |
| 2-(C≡CH)C$_6$H$_4$ | H | 2-(C≡CH)C$_6$H$_4$ | CH$_3$ |

General Structure 14, R$^3$=R$^4$ is CH$_3$, p is 3

| W | R$^2$ | W | R$^2$ |
|---|---|---|---|
| C$_6$H$_5$ | H | C$_6$H$_5$ | CH$_3$ |
| 2-FC$_6$H$_4$ | H | 2-FC$_6$H$_4$ | CH$_3$ |
| 3-FC$_6$H$_4$ | H | 3-FC$_6$H$_4$ | CH$_3$ |
| 4-FC$_6$H$_4$ | H | 4-FC$_6$H$_4$ | CH$_3$ |
| 2,3-F$_2$C$_6$H$_3$ | H | 2,3-F$_2$C$_6$H$_3$ | CH$_3$ |
| 2,4-F$_2$C$_6$H$_3$ | H | 2,4-F$_2$C$_6$H$_3$ | CH$_3$ |
| 2,5-F$_2$C$_6$H$_3$ | H | 2,5-F$_2$C$_6$H$_3$ | CH$_3$ |
| 2,4,6-F$_3$C$_6$H$_2$ | H | 2,4,6-F$_3$C$_6$H$_2$ | CH$_3$ |
| 2-ClC$_6$H$_4$ | H | 2-ClC$_6$H$_4$ | CH$_3$ |
| 2-Cl-6-FC$_6$H$_3$ | H | 2-Cl-6-FC$_6$H$_3$ | CH$_3$ |
| 2-(CH$_3$)C$_6$H$_4$ | H | 2-(CH$_3$)C$_6$H$_4$ | CH$_3$ |
| 2-pyridyl | H | 2-pyridyl | CH$_3$ |
| 2-thienyl | H | 2-thienyl | CH$_3$ |
| 2-tetrahydrofuranyl | H | 2-tetrahydrofuranyl | CH$_3$ |
| 2-(OCH$_3$)C$_6$H$_4$ | H | 2-(OCH$_3$)C$_6$H$_4$ | CH$_3$ |
| 2-(CN)C$_6$H$_4$ | H | 2-(CN)C$_6$H$_4$ | CH$_3$ |
| 2-(CF$_3$)C$_6$H$_4$ | H | 2-(CF$_3$)C$_6$H$_4$ | CH$_3$ |
| 2-(OCF$_3$)C$_6$H$_4$ | H | 2-(OCF$_3$)C$_6$H$_4$ | CH$_3$ |
| 2-(SCH$_3$)C$_6$H$_4$ | H | 2-(SCH$_3$)C$_6$H$_4$ | CH$_3$ |
| 2-(CH=CH$_2$)C$_6$H$_4$ | H | 2-(CH=CH$_2$)C$_6$H$_4$ | CH$_3$ |
| 2-(C≡CH)C$_6$H$_4$ | H | 2-(C≡CH)C$_6$H$_4$ | CH$_3$ |

TABLE 15

General Structure 15, R$^3$=R$^4$ is H, p is 2

| W | R$^2$ | W | R$^2$ |
|---|---|---|---|
| C$_6$H$_5$ | H | C$_6$H$_5$ | CH$_3$ |
| 2-FC$_6$H$_4$ | H | 2-FC$_6$H$_4$ | CH$_3$ |
| 3-FC$_6$H$_4$ | H | 3-FC$_6$H$_4$ | CH$_3$ |
| 4-FC$_6$H$_4$ | H | 4-FC$_6$H$_4$ | CH$_3$ |
| 2,3-F$_2$C$_6$H$_3$ | H | 2,3-F$_2$C$_6$H$_3$ | CH$_3$ |
| 2,4-F$_2$C$_6$H$_3$ | H | 2,4-F$_2$C$_6$H$_3$ | CH$_3$ |
| 2,5-F$_2$C$_6$H$_3$ | H | 2,5-F$_2$C$_6$H$_3$ | CH$_3$ |
| 2,4,6-F$_3$C$_6$H$_2$ | H | 2,4,6-F$_3$C$_6$H$_2$ | CH$_3$ |
| 2-ClC$_6$H$_4$ | H | 2-ClC$_6$H$_4$ | CH$_3$ |
| 2-Cl-6-FC$_6$H$_3$ | H | 2-Cl-6-FC$_6$H$_3$ | CH$_3$ |
| 2-(CH$_3$)C$_6$H$_4$ | H | 2-(CH$_3$)C$_6$H$_4$ | CH$_3$ |
| 2-pyridyl | H | 2-pyridyl | CH$_3$ |
| 2-thienyl | H | 2-thienyl | CH$_3$ |
| 2-tetrahydrofuranyl | H | 2-tetrahydrofuranyl | CH$_3$ |
| 2-(OCH$_3$)C$_6$H$_4$ | H | 2-(OCH$_3$)C$_6$H$_4$ | CH$_3$ |
| 2-(CN)C$_6$H$_4$ | H | 2-(CN)C$_6$H$_4$ | CH$_3$ |
| 2-(CF$_3$)C$_6$H$_4$ | H | 2-(CF$_3$)C$_6$H$_4$ | CH$_3$ |
| 2-(OCF$_3$)C$_6$H$_4$ | H | 2-(OCF$_3$)C$_6$H$_4$ | CH$_3$ |
| 2-(SCH$_3$)C$_6$H$_4$ | H | 2-(SCH$_3$)C$_6$H$_4$ | CH$_3$ |
| 2-(CH=CH$_2$)C$_6$H$_4$ | H | 2-(CH=CH$_2$)C$_6$H$_4$ | CH$_3$ |
| 2-(C≡CH)C$_6$H$_4$ | H | 2-(C≡CH)C$_6$H$_4$ | CH$_3$ |

General Structure 15, R$^3$=R$^4$ is CH$_3$, p is 2

| W | R$^2$ | W | R$^2$ |
|---|---|---|---|
| C$_6$H$_5$ | H | C$_6$H$_5$ | CH$_3$ |
| 2-FC$_6$H$_4$ | H | 2-FC$_6$H$_4$ | CH$_3$ |
| 3-FC$_6$H$_4$ | H | 3-FC$_6$H$_4$ | CH$_3$ |
| 4-FC$_6$H$_4$ | H | 4-FC$_6$H$_4$ | CH$_3$ |
| 2,3-F$_2$C$_6$H$_3$ | H | 2,3-F$_2$C$_6$H$_3$ | CH$_3$ |
| 2,4-F$_2$C$_6$H$_3$ | H | 2,4-F$_2$C$_6$H$_3$ | CH$_3$ |
| 2,5-F$_2$C$_6$H$_3$ | H | 2,5-F$_2$C$_6$H$_3$ | CH$_3$ |
| 2,4,6-F$_3$C$_6$H$_2$ | H | 2,4,6-F$_3$C$_6$H$_2$ | CH$_3$ |
| 2-ClC$_6$H$_4$ | H | 2-ClC$_6$H$_4$ | CH$_3$ |
| 2-Cl-6-FC$_6$H$_3$ | H | 2-Cl-6-FC$_6$H$_3$ | CH$_3$ |
| 2-(CH$_3$)C$_6$H$_4$ | H | 2-(CH$_3$)C$_6$H$_4$ | CH$_3$ |
| 2-pyridyl | H | 2-pyridyl | CH$_3$ |
| 2-thienyl | H | 2-thienyl | CH$_3$ |
| 2-tetrahydrofuranyl | H | 2-tetrahydrofuranyl | CH$_3$ |
| 2-(OCH$_3$)C$_6$H$_4$ | H | 2-(OCH$_3$)C$_6$H$_4$ | CH$_3$ |
| 2-(CN)C$_6$H$_4$ | H | 2-(CN)C$_6$H$_4$ | CH$_3$ |
| 2-(CF$_3$)C$_6$H$_4$ | H | 2-(CF$_3$)C$_6$H$_4$ | CH$_3$ |
| 2-(OCF$_3$)C$_6$H$_4$ | H | 2-(OCF$_3$)C$_6$H$_4$ | CH$_3$ |
| 2-(SCH$_3$)C$_6$H$_4$ | H | 2-(SCH$_3$)C$_6$H$_4$ | CH$_3$ |
| 2-(CH=CH$_2$)C$_6$H$_4$ | H | 2-(CH=CH$_2$)C$_6$H$_4$ | CH$_3$ |
| 2-(C≡CH)C$_6$H$_4$ | H | 2-(C≡CH)C$_6$H$_4$ | CH$_3$ |

General Structure 15, R$^3$=R$^4$ is H, p is 3

| W | R$^2$ | W | R$^2$ |
|---|---|---|---|
| C$_6$H$_5$ | H | C$_6$H$_5$ | CH$_3$ |
| 2-FC$_6$H$_4$ | H | 2-FC$_6$H$_4$ | CH$_3$ |

TABLE 15-continued

| W | R² | W | R² |
|---|---|---|---|
| 3-FC₆H₄ | H | 3-FC₆H₄ | CH₃ |
| 4-FC₆H₄ | H | 4-FC₆H₄ | CH₃ |
| 2,3-F₂C₆H₃ | H | 2,3-F₂C₆H₃ | CH₃ |
| 2,4-F₂C₆H₃ | H | 2,4-F₂C₆H₃ | CH₃ |
| 2,5-F₂C₆H₃ | H | 2,5-F₂C₆H₃ | CH₃ |
| 2,4,6-F₃C₆H₂ | H | 2,4,6-F₃C₆H₂ | CH₃ |
| 2-ClC₆H₄ | H | 2-ClC₆H₄ | CH₃ |
| 2-Cl-6-FC₆H₃ | H | 2-Cl-6-FC₆H₃ | CH₃ |
| 2-(CH₃)C₆H₄ | H | 2-(CH₃)C₆H₄ | CH₃ |
| 2-pyridyl | H | 2-pyridyl | CH₃ |
| 2-thienyl | H | 2-thienyl | CH₃ |
| 2-tetrahydrofuranyl | H | 2-tetrahydrofuranyl | CH₃ |
| 2-(OCH₃)C₆H₄ | H | 2-(OCH₃)C₆H₄ | CH₃ |
| 2-(CN)C₆H₄ | H | 2-(CN)C₆H₄ | CH₃ |
| 2-(CF₃)C₆H₄ | H | 2-(CF₃)C₆H₄ | CH₃ |
| 2-(OCF₃)C₆H₄ | H | 2-(OCF₃)C₆H₄ | CH₃ |
| 2-(SCH₃)C₆H₄ | H | 2-(SCH₃)C₆H₄ | CH₃ |
| 2-(CH=CH₂)C₆H₄ | H | 2-(CH=CH₂)C₆H₄ | CH₃ |
| 2-(C≡CH)C₆H₄ | H | 2-(C≡CH)C₆H₄ | CH₃ |

General Structure 15, R³=R⁴ is CH₃, p is 3

| W | R² | W | R² |
|---|---|---|---|
| C₆H₅ | H | C₆H₅ | CH₃ |
| 2-FC₆H₄ | H | 2-FC₆H₄ | CH₃ |
| 3-FC₆H₄ | H | 3-FC₆H₄ | CH₃ |
| 4-FC₆H₄ | H | 4-FC₆H₄ | CH₃ |
| 2,3-F₂C₆H₃ | H | 2,3-F₂C₆H₃ | CH₃ |
| 2,4-F₂C₆H₃ | H | 2,4-F₂C₆H₃ | CH₃ |
| 2,5-F₂C₆H₃ | H | 2,5-F₂C₆H₃ | CH₃ |
| 2,4,6-F₃C₆H₂ | H | 2,4,6-F₃C₆H₂ | CH₃ |
| 2-ClC₆H₄ | H | 2-ClC₆H₄ | CH₃ |
| 2-Cl-6-FC₆H₃ | H | 2-Cl-6-FC₆H₃ | CH₃ |
| 2-(CH₃)C₆H₄ | H | 2-(CH₃)C₆H₄ | CH₃ |
| 2-pyridyl | H | 2-pyridyl | CH₃ |
| 2-thienyl | H | 2-thienyl | CH₃ |
| 2-tetrahydrofuranyl | H | 2-tetrahydrofuranyl | CH₃ |
| 2-(OCH₃)C₆H₄ | H | 2-(OCH₃)C₆H₄ | CH₃ |
| 2-(CN)C₆H₄ | H | 2-(CN)C₆H₄ | CH₃ |
| 2-(CF₃)C₆H₄ | H | 2-(CF₃)C₆H₄ | CH₃ |
| 2-(OCF₃)C₆H₄ | H | 2-(OCF₃)C₆H₄ | CH₃ |
| 2-(SCH₃)C₆H₄ | H | 2-(SCH₃)C₆H₄ | CH₃ |
| 2-(CH=CH₂)C₆H₄ | H | 2-(CH=CH₂)C₆H₄ | CH₃ |
| 2-(C≡CH)C₆H₄ | H | 2-(C≡CH)C₆H₄ | CH₃ |

Formulations

Useful formulations of the compounds of Formula I can be prepared in conventional ways. They include dusts, granules, pellets, solutions, suspensions, emulsions, wettable powders, emulsifiable concentrates and the like. Many of these my be applied directly to the locus to be protected. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

| | Weight Percent* | | |
|---|---|---|---|
| | Active Ingredient | Diluent(s) | Surfactant(s) |
| Wettable Powders | 20-90 | 0-74 | 1-10 |
| Oil Suspensions, Emulsions, Solutions, (including Emulsifiable Concentrates) | 3-50 | 40-95 | 0-15 |
| Aqueous Suspension | 10-50 | 40-84 | 1-20 |
| Dusts | 1-25 | 70-99 | 0-5 |
| Granules and Pellets | 0.1-95 | 5-99.9 | 0-15 |
| High Strength Compositions | 90-99 | 0-10 | 0-2 |

*Active ingredients plus at least one of a surfactant or a diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins et al., "Handbook of Insecticide Dust Diluents and Carriers", 2nd Ed., Dorland Books, Caldwell, N.J., but other solids, either mined or manufactured, may be use. The more absorptive diluents are preferred for wettable powders and the denser ones for dusts. Typical liquid diluents and solvents are described in Marsden, "Solvents Guide", 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff and "Perry's Chemical Engineer's Handbook", 5th Ed., McGraw-Hill, New York, 1973, pp. 8–59ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, Jun. 23, 1959, Col. 3, line 66 through Col. 5, line 17 and Examples 1–4;

G. C. Klingman, "Weed Control as a Science", John Wiley & Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE A

| Wettable Powder | |
|---|---|
| (2α,3β,4β,5α,9aβ)-3-[(2-fluorophenyl)methoxy]-decahydro-2-methyl-2,5-methanocyclohepta[b]pyran | 60% |
| sodium alkylnaphthalenesulfonate | 2% |
| sodium liginsulfonate | 2% |
| synthetic amorphous silica | 36% |

The active ingredient is first sprayed onto the amorphous silica, then the ingredients are blended, hammer-milled until all the solids are essentially under 50 microns, reblended, and packaged.

EXAMPLE B

| Wettable Powder | |
|---|---|
| (2α,3β,4β,5α,9aβ)-3-[(2-fluorophenyl)methoxy]-decahydro-2-methyl-2,5-methanocyclohepta[b]pyran | 50% |
| sodium alkylnaphthalenesulfonate | 2% |
| low viscosity methyl cellulose | 2% |
| diatomaceous earth | 46% |

The active ingredient is first sprayed onto the diatomaceous earth, then the ingredients are blended, coarsely hammer-milled and then air-milled to produce particles essentially all below 10 microns in diameter. The product is reblended before packaging.

| Granule | |
|---|---|
| Wettable Powder of Eample B | 5% |
| attapulgite granules | 95% |

A slurry of wettable powder containing 25% solids is sprayed on the surface of attapulgite granules in a double-cone blender. The granules are dried and packaged.

EXAMPLE D

| Emulsifiable Concentrate | |
|---|---|
| (2α,3β,4β,5α,9aβ)-3-[(2-fluorophenyl)methoxy]-decahydro-2-methyl-2,5-methanocyclohepta[b]pyran | 40% |
| Atlox 3404F | 3% |
| Atlox 3404F | 3% |
| xylene | 54% |

The active ingredient and Atlox emulsifiers are dissolved in the solvent, filtered and packaged. Atlox 3403F and 3404F are blends of anionic and ionic emulsifiers from ICI Americas, Inc.

EXAMPLE E

| Low Strength Granule | |
|---|---|
| (2α,3β,4β,5α,9aβ)-3-[(2-fluorophenyl)methoxy]-decahydro-2-methyl-2,5-methanocyclohepta[b]pyran | 5% |
| attapulgite granules (U.S.S. 20–40 mesh) | 95% |

The active ingredient is dissolved in a solvent and the solution is sprayed upon dedusted granules in double-cone blender. After spraying of the solution has been completed, the material is warmed to evaporate the solvent. The material is allowed to cool and then packaged.

EXAMPLE F

| Low Strength Granule | |
|---|---|
| (2α,3β,4β,5α,9aβ)-3-[(2-fluorophenyl)methoxy]-decahydro-2-methyl-2,5-methanocyclohepta[b]pyran | 50% |
| wetting agent | 1% |
| crude ligninsulfonate salt (containing 5–20% of the natural sugars) | 10% |
| attapulgite clay | 39% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. the spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE G

| Concentrated Emulsion | |
|---|---|
| (2α,3β,4β,5α,9aβ)-3-[(2-fluorophenyl)methoxy]-decahydro-2-methyl-2,5-methanocyclohepta[b]pyran | 25% |
| xylene | 25% |
| Atlox 3404F | 5% |
| G1284 | 6% |
| ethylene glycol | 8% |
| water | 32% |

The active ingredient, solvent and emulsifiers are blended together. This solution is added to a mixture of the ethylene glycol and water with stirring.

EXAMPLE H

| Solution | |
|---|---|
| (2α,3β,4β,5α,9aβ)-3-[(2-fluorophenyl)methoxy]-decahydro-2-methyl-2,5-methanocyclohepta[b]pyran | 5% |
| water | 95% |

The compound is added directly to the water with stirring to produce the solution, which may then be packaged for use.

EXAMPLE I

| Dust | |
|---|---|
| (2α,3β,4β,5α,9aβ)-3-[(2-fluorophenyl)methoxy]-decahydro-2-methyl-2,5-methanocyclohepta[b]pyran | 10% |
| attapulgite | 10% |
| Pyrophyllite | 80% |

The active ingredient is sprayed onto the attapulgite and then passed through a hammer-mill to produce particles substantially all below 200 microns. The ground concentrate is then blended with powdered pyrophyllite until homogeneous.

UTILITY

Test results indicate compounds of this invention are active postemergence and, in particular, preemergence herbicides. Many compounds in this invention are useful for the control of selected grass and broadleaf weeds with tolerance to important agronomic crops such as barley (*Hordeum vulgare*), corn (*Zea mays*), cotton (*Gossypium hirsutum*), rape (*Brassica napus*), rice (*Oryza sativa*), sorghum (*Sorghum bicolor*), soybean (*Glycine max*), sugar beet (*Beta vulgaris*), wheat (*Triticum aestivum*), and to vegetable crops. Grass and broadleaf weed species controlled include, but are not limited to, barnyardgrass (*Echinochloa crus-galli*), blackgrass (*Alopecurus myosuroides*), crabgrass (Digitaria spp.), duck salad (*Heteranthera limosa*), foxtail (Setaria spp.), velvetlead (*Afutilon theophrasti*), and umbrella sedge (*Cyperus difformis*). Several compounds in this invention are particularly useful for the control of barnyardgrass and selected broadleaf weeds such as duck salad and umbrella sedge in upland and paddy rice.

Effective rates of application for compounds of this invention are determined by a number of factors. These factors include: formulation selected, method of application, amount and type of vegetation present, growing conditions, etc. In general terms, the subject compounds should be applied at rates from 0.01 to 20 kg/ha with a preferred rate range of 0.03 to 1 kg/ha. One skilled in the art can easily determine effective application rates necessary for desired level of weed control.

Compounds of this invention may be used alone or in combination with other commercial herbicides, insecticides, or fungicides. The following list exemplifies some of the herbicides suitable for use in mixtures. A combination of a compound from this invention with one or more of the following herbicides may be particularly useful for weed control.

| Common Name | Chemical Name |
| --- | --- |
| acetochlor | 2-chloro-N-(ethoxymethyl)-N-(2-ethyl-6-methylphenyl)acetamide |
| acifluorfen | 5-[2-chloro-4-(trifluoromethyl)phenoxy]-2-nitrobenzoic acid |
| aclonifen | 2-chloro-6-nitro-3-phenoxybenzenamine |
| acrolein | 2-propenal |
| alachlor | 2-chloro-N-(2,6-diethylphenyl)-N-(methoxymethyl)acetamide |
| alloxydim | methyl 2,2-dimethyl-4,6-dioxo-5-[1-[(2-propenyloxy)amino]butylidene]cyclohexanecarboxylate |
| ametryn | N-ethyl-N'-(1-methylethyl)-6-(methylthio)-1,3,5-triazine-2,4-diamine |
| amitrole | 1H-1,2,4-triazol-3-amine |
| AMS | ammonium sulfamate |
| anilofos | S-[2-[(4-chlorophenyl)(1-methylethyl)amino]-2-oxoethyl] O,O-dimethylphosphorodithioate |
| asulam | methyl [(4-aminophenyl)sulfonylcarbamate |
| atrazine | 6-chloro-N-ethyl-N'-(1-methylethyl)-1,3,5-triazin-2,4-diamine |
| aziprotryne | 4-azido-N-(1-methylethyl)-6-methylthio-1,3,5-triazin-2-amine |
| azoluron | N-(1-ethyl-1H-pyrazol-5-yl)-N'-phenylurea |
| barban | 4-chloro-2-butynyl 3-chlorocarbamate |
| benazolin | 4-chloro-2-oxo-3(2H)-benzothiazoleacetic acid |
| benfluralin | N-butyl-N-ethyl-2,6-dinitro-4-(trifluoromethyl)-benzenamine |
| bensulfuron | 2-[[[[(4,6-dimethoxy-2-pyrimidinyl)amino]-methylcarbonyl]amino]sulfonyl]methyl]-benzoic acid, methyl ester |

-continued

| Common Name | Chemical Name |
| --- | --- |
| bensulide | O,O-bis(1-methylethyl) S-[2-[(phenylsulfonyl)-amino]ethyl]phosphorodithioate |
| bentazon | 3-(1-methylethyl)-(1H)-2,1,3-benzothiadiazin-4(3H)-one, 2,2-dioxide |
| benzofluor | N-[4-(ethylthio)-2-(trifluoromethyl)phenyl]-methanesulfonamide |
| benzoylprop | N-benzoyl-N-(3,4-dichlorophenyl)-DL-alanine |
| benzthiazuron | N-2-benzothiazolyl-N'-methylurea |
| bialaphos | 4-(hydroxymethylphosphinyl)-L-2-amino-butanoyl-L-alanyl-L-alanine |
| bifenox | methyl 5-(2,4-dichlorophenoxy)-2-nitrobenzoate |
| bromacil | 5-bromo-6-methyl-3-(1-methylpropyl)-2,4-(1H,3H)pyrimidinedione |
| bromobutide | (+)2-bromo-3,3-dimethyl-N-(1-methyl-1-phenyl-ethyl)butanamide |
| bromofenoxim | 3,5-dibromo-4-hydroxybenzaldhyde O-(2,4-dinitrophenyl)oxime |
| bromoxynil | 3,5-dibromo-4-hydroxybenzonitrile |
| bromuron | N'-(4-bromophenyl)-N,N-dimethylurea |
| buminafos | dibutyl [1-(butylamino)cyclohexyl]phosphonate |
| butachlor | N-(butoxymethyl)-2-chloro-N-(2,6-diethyl-phenyl)acetamide |
| butamifos | O-ethyl O-(5-methyl-2-nitrophenyl)-(1methyl-propyl)phosphoramidothioate |
| buthidazole | 3-[5-(1,1-dimethylethyl)-1,3,4-thiadiazol-2-yl]-4-hydroxy-1-methyl-2-imidazolidinone |
| butralin | 4-(1,1-dimethylethyl)-N-(1-methylpropyl)-2,6-dinitrobenzenamine |
| butylate | S-ethyl bis(2-methylpropyl)carbamothioate |
| cacodylic acid | dimethyl arsinic oxide |
| carbetamide | (R)-N-ethyl-2-[[(phenylamino)carbonyl]oxy]-propanamide |
| CDAA | 2-chloro-N,N-di-2-propenylacetamide |
| CDEC | 2-chloroallyl diethyldithiocarbamate |
| chlomethoxyfen | 4-(2,4-dichlorophenoxy)-2-methoxy-1-nitro-benzene |
| chloramben | 3-amino-2,5-dichlorobenzoic acid |
| chlorbromuron | 3-(4-bromo-3-chlorophenyl)-1-methoxy-1-methylurea |
| chlorbufam | 1-methyl-2-propynl(3-chlorophenyl)carbamate |
| chlorfenac | 2,3,6-trichlorobenzeneacetic acid |
| chlorflurecomethyl | methyl 2-chloro-9-hydroxy-9H-fluorene-9-carboxylate |
| chloridazon | 5-amino-4-chloro-2-phenyl-3(2H)-pyridazinone |
| chlorimuron | 2-[[[[(4-chloro-6-methoxy-2-pyrimidinyl)ethyl-amino]carbonyl]amino]sulfonyl]benzoic acid, ethyl ester |
| chlornitrofen | 1,3,5-trichloro-2-(4-nitrophenoxy)benzene |
| chloropicrin | trichloronitromethane |
| chloroxuron | N'-[4-(4-chlorophenoxy)phenyl]-N,N-dimethyl-urea |
| chlorpropham | 1-methylethyl 3-chlorophenylcarbamate |
| chlorsulfuron | 2-chloro-N-[[(4-methoxy-6-methyl-1,3,5-triazin-2-yl)amino]carbonyl]benzenesulfonamide |
| chlorthaldimethyl | dimethyl 2,3,5,6-tetrachloro-1,4-benzene-dicarboxylate |
| chlorthiamid | 2,6-dichlorobenzene carbothioamide |
| chlortoluron | N'-(3-chloro-4-methylphenyl)-N,N-dimethylurea |
| cinmethylin | exo-1-methyl-4-(1-methylethyl)-2-[(2-methyl-phenyl)methoxy]-7-oxabicyclo-[2.2.1]heptane |
| clethodim | (E,E)-(+)-2-[1-[[(3-chloro-2-propenyl)oxy]-imino]propyl]-5-[2-(ethylthio)propyl]-3-hydroxy-2-cyclohexen-1-one |
| clomazone | 2-[(2-chlorophenyl)methyl]-4,4-dimethyl-3-isoxazolidinone |
| cloproxydim | (E,E)-2-[1-[[(3-chloro-2-propenyl)oxy)imino]-butyl]-5-[2-(ethylthio)propyl]-3-hydroxy-2-cyclohexen-1-one |
| clopyralid | 3,6-dichloro-2-pyridinecarboxylic acid |
| CMA | calcium salt of MAA |
| cyanazine | 2-[[4-chloro-6-(ethylamino)-1,3,5-triazin-2-yl]-amino]-2-methylpropanenitrile |
| cycloate | S-ethyl cyclohexylethylcarbamothioate |
| cycloxydim | 2-[1-ethoxyimino)butyl]-3-hydroxy-5-(tetra-hydro-2H-thiopyran-3-yl)-2-cyclohexene-1-one |
| cycluron | 3-cyclooctyl-1,1-dimethylurea |
| cyperquat | 1-methyl-4-phenylpyridinium |
| cyprazine | 2-chloro-4-(cyclopropylamino)-6-(isopropyl-amino)-s-triazine |

-continued

| Common Name | Chemical Name |
|---|---|
| cyprazole | N-[5-(2-chloro-1,1-dimethylethyl)-1,3,4-thiadiazol-2-yl]cyclopropanecarboxamide |
| cypromid | 3',4'-dichlorocyclopropanecarboxanilide |
| dalapon | 2,2-dichloropropanoic acid |
| dazomet | tetrahydro-3,5-dimethyl-2H-1,3,5-thiadiazine-2-thione |
| DCPA | dimethyl 2,3,5,6-tetrachloro-1,4-benzene-dicarboxylate |
| desmedipham | ethyl [3-[[(phenylamino)carbonyl]oxy]phenyl]-carbamate |
| desmetryn | 2-(isopropylamino)-4-(methylamino)-6-(methylthio)-s-triazine |
| diallate | S-(2,3-dichloro-2-propenyl)bis(1-methylethyl)-carbamothioate |
| dicamba | 3,6-dichloro-2-methoxybenzoic acid |
| dichlobenil | 2,6-dichlorobenzonitrile |
| dichlorprop | (+)-2-(2,4-dichlorophenoxy)propanoic acid |
| diclofopmethyl | (+)-2-[4-(2,4-dichlorophenoxy)phenoxy]-propanoic acid, methyl ester |
| diethatyl | N-(chloroacetyl)-N-(2,6-diethylphenyl)glycine |
| difenoxuron | N'-[4-(4-methoxyphenyl)phenyl]-N,N-dimethyl-urea |
| difenzoquat | 1,2-dimethyl-3,5-diphenyl-1H-pyrazolium ion |
| diflufenican | N-(2,4-difluorophenyl)-2-(3-trifluoromethyl-phenoxy)pyridine-3-carboxamide |
| dimefuron | N'-[3-chloro-4-[5-(1,1-dimethylethyl)-2-oxo-1,3,4-oxadiazol-3(2H)-yl]phenyl]-N,N-dimethylurea |
| dimethachlor | 2-chloro-N-(2,6-dimethylphenyl)-N-(2-methoxy-ethyl)acetamide |
| dimethametryn | N-(1,2-dimethylpropyl)-N'-ethyl-6-(methylthio)-1,3,5-triazine-2,4-diamine |
| dimethipin | 2,3-dihydro-5,6-dimethyl-1,4-dithiin 1,1,4,4-tetraoxide |
| dimethylarsinic | dimethylarsinic acid |
| dinitramine | $N^3,N^3$-diethyl-2,4-dinitro-6-(trifluoromethyl)-1,3-benzenediamine |
| dinoseb | 2-(1-methylpropyl)-4,6-dinitrophenol |
| dinoterb | 2-(1,1-dimethylethyl)-4,6-dinitrophenol |
| diphenamid | N,N-dimethyl-α-phenylbenzeneacetamide |
| dipropetryn | 6-(ethylthio)-N,N'-bis(1-methylethyl)-1,3,5-triazine-2,4-diamine |
| diquat | 6,7-dihydrodipyrido[1,2-a:2',1'-c]pyrazinediium ion |
| diuron | N'-(3,4-dichlorophenyl)-N,N-dimethylurea |
| DNOC | 2-methyl-4,6-dinitrophenol |
| DPX-V9360 | 2-[[(4,6-dimethoxypyrimidin-2-yl)amino-carbonyl]aminosulfonyl]-N,N-dimethyl 3-pyridinecarboxamide |
| DSMA | disodium salt of MAA |
| dymron | N-(4-methylphenyl)-N'-(1-methyl-1-phenyl-ethyl)urea |
| eglinazine-ethyl | N-[4-chloro-6-(ethylamino)-1,3,5-triazin-2-yl]glycine ethyl ester |
| endothall | 7-oxabicyclo[2.2.1]heptane-2,3-dicarboxylic acid |
| EPTC | S-ethyl dipropylcarbamothioate |
| ethalfluralin | N-ethyl-N-(2-methyl-2-propenyl)-2,6-dinitro-4-(trifluoromethyl)benzenamine |
| ethidimuron | N-[5-(ethylsulfonyl)-1,3,4-thiadiazol-2-yl]-N,N'-dimethylurea |
| ethofumesate | (+)-2-ethoxy-2,3-dihydro-3,3-dimethyl-5-benzo-furanyl methanesulfonate |
| fenac | 2,3,6-trichlorobenzeneacetic acid |
| fenoprop | (+)-2-(2,4,5-trichlorophenoxy)propanoic acid |
| fenoxaprop | (+)-2-[4-[(6-chloro-2-benzoxazolyl)oxy]phenoxy]-propanoic acid |
| fenuron | N,N-dimethyl-N'-phenylurea |
| fenuron TCA | Salt of fenuron and TCA |
| flamprop-M isopropyl | 1-methylethyl N-benzoyl-N-(3-chloro-4-fluorophenyl)-D-alanine |
| flamprop-methyl | methyl N-benzoyl-N-(3-chloro-4-fluorophenyl)-DL-alaninate |
| fluazifop | (+)-2-[4-[[5-(trifluoromethyl)-2-pyridinyl]oxy]phenoxy]propanoic acid |
| fluazifop-P | (R)-2-[4-[[5-(trifluoromethyl)-2-pyridinyl]oxy]phenoxy]propanoic acid |
| fluchloralin | N-(2-chloroethyl)-2,6-dinitro-N-propyl-4-(trifluoromethyl)benzenamine |
| fluometuron | N,N-dimethyl-N'-[3-(trifluoromethyl)phenyl]-urea |
| fluralin | N-butyl-N-ethyl-2,6-dinitro-4-(trifluoromethyl)-benzenamine |

-continued

| Common Name | Chemical Name |
|---|---|
| fluorodifen | p-nitrophenyl α,α,α-trifluoro-2-nitro-p-tolyl ether |
| fluoroglycofen | carboxymethyl 5-[2-chloro-4-(trifluoromethyl)-phenoxy]-2-nitrobenzoate |
| flurecol-butyl | butyl 9-hydroxy-9H-fluorene-9-carboxylate |
| fluridone | 1-methyl-3-phenyl-5-[3-(trifluoromethyl)-phenyl]-4(1H)-pyridinone |
| flurochloridone | 3-chloro-4-(chloromethyl)-1-[3-(trifluoromethyl)-phenyl]-2-pyrrolidinone |
| fluroxypyr | [(4-amino-3,5-dichloro-6-fluoro-2-pyridinyl)oxy]-acetic acid |
| fomesafen | 5-[2-chloro-4-(trifluoromethyl)phenoxy]-N-(methylsulfonyl)-2-nitrobenzamide |
| fosamine-ammonium | ethyl hydrogen (aminocarbonyl)-phosphonate ammonium ethyl |
| glufosinate-ammonium | ammonium 2-amino-4-(hydroxymethylphos-phinyl)butanoate |
| glyphosate | N-(phosphonomethyl)glycine |
| haloxyfop | 2-[4-[[3-chloro-5-(trifluoromethyl)-2-pyridinyl]-oxy]phenoxy]propanoic acid |
| hexaflurate | potassium hexafluoroarsenate |
| hexazinone | 3-cyclohexyl-6-(dimethylamino)-1-methyl-1,3,5-triazine-2,4(1H,3H)-dione |
| imazametha-benz | 6-(4-isopropyl-4-methyl-5-oxo-2-imidazolin-2-yl)-m-toluic acid, methyl ester and 6-(4-isopropyl-4-methyl-5-oxo-2-imidazolin-2-yl)-p-toluic acid, methyl ester |
| imazapyr | (+)-2-[4,5-dihydro-4-methyl-4-(1-methylethyl)-5-oxo-1H-imidazol-2-yl]-3-pyridinecarboxylic acid |
| imazaquin | 2-[4,5-dihydro-4-methyl-4-(1-methylethyl)-5-oxo-1H-imidazol-2-yl]-3-quinolinecarboxylic acid |
| imazethapyr | (+)-2-[4,5-dihydro-4-methyl-4-(1-methylethyl)-5-oxo-1H-imidazol-2-yl]-5-ethyl-3-pyridine-carboxylic acid. |
| ioxynil | 4-hydroxy-3,5-diiodobenzonitrile |
| isocarbamid | N-(2-methylpropyl)-2-oxo-1-imidazolidine-carboxamide |
| isopropalin | 4-(1-methylethyl)-2,6-dinitro-N,N-dipropyl-benzenamine |
| isoproturon | N-(4-isopropylphenyl)-N',N'-dimethylurea |
| isouron | N'-[5-(1,1-dimethylethyl)-3-isoxazolyl]-N,N-dimethylurea |
| isoxaben | N-[3-(1-ethyl-1-methylpropyl)-5-isoxazolyl]-2,6-dimethoxybenzamide |
| karbutilate | 3-[[(dimethylamino)carbonyl]amino]phenyl-(1,1-dimethylethyl)carbamate |
| lactofen | (+)-2-ethoxy-1-methyl-2-oxoethyl 5-[2-chloro-4-(trifluoromethyl)phenoxy]-2-nitrobenzoate |
| lenacil | 3-cyclohexyl-6,7-dihydro-1H-cyclopenta-pyrimidine-2,4(3H,5H)-dione |
| linuron | N'-(3,4-dichlorophenyl)-N-methoxy-N-methyl-urea |
| MAA | methylarsonic acid |
| MAMA | monoammonium salt of MAA |
| MCPA | (4-chloro-2-methylphenoxy)acetic acid |
| MCPA-thioethyl | S-ethyl (4-chloro-2-methylphenoxy)ethane-thioate |
| MCPB | 4-(4-chloro-2-methylphenoxy)butanoic acid |
| mecoprop | (+)-2-(4-chloro-2-methylphenoxy)propanoic acid |
| mefenacet | 2-(2-benzothiazolyloxy)-N-methyl-N-phenyl acetamide |
| mefluidide | N-[2,4-dimethyl-5-[[(trifluoromethyl)sulfonyl]-amino]phenyl]acetamide |
| metamitron | 4-amino-3-methyl-6-phenyl-1,2,4-triazin-5(4H)-one |
| metazachlor | 2-chloro-N-(2,6-dimethylphenyl)-N-(1(H)-pyrazol-1-ylmethyl)acetamide |
| methabenz-thiazuron | 1,3-dimethyl-3-(2-benzothiazolyl)urea |
| methalpropalin | N-(2-methyl-2-propenyl)-2,6-dinitro-N-propyl-4-(trifluoromethyl)benzenamide |
| metham | methylcarbamodithioic acid |
| methazole | 2-(3,4-dichlorophenyl)-4-methyl-1,2,4-oxadiazolidine-3,5-dione |
| methoxuron | N'-(3-chloro-4-methoxyphenyl)-N,N-dimethyl-urea |
| methoxy-phenone | (4-methoxy-3-methylphenyl)(3-methylphenyl)-methanone |
| methyldymron | N-methyl-N'-(1-methyl-1-phenylethyl)-N-phenylurea |

-continued

| Common Name | Chemical Name |
|---|---|
| metobromuron | N'-(4-bromophenyl)-N-methoxy-N-methylurea |
| metolachlo | 2-chloro-N-(2-ethyl-6-methylphenyl)-N-(2-methoxy-1-methylethyl)acetamide |
| metoxuron | N'-(3-chloro-4-methoxyphenyl)-N,N-dimethylurea |
| metribuzin | 4-amino-6-(1,1-dimethylethyl)-3-(methylthio)-1,2,4-triazin-5(4H)-one |
| metsulfuron methy | 2-[[[[(4-methoxy-6-methyl-1,3,5-triazin-2-yl)amino]carbonyl]amino]sulfonyl]benzoic acid, methyl ester |
| MH | 1,2-dihydro-3,6-pyridazinedione |
| molinate | S-ethyl hexahydro-1H-azepine-1-carbothioate |
| monalide | N-(4-chlorophenyl)-2,2-dimethylpentanamide |
| monolinuron | 3-(p-chlorophenyl)-1-methoxy-1-methylurea |
| monuron | N'-(4-chlorophenyl)-N,N-dimethylurea |
| MSMA | monosodium salt of MAA |
| naproanilide | 2-(2-naphthalenyloxy)-N-phenylpropanamide |
| napropamide | N,N-diethyl-2-(1-naphthalenyloxy)propanamide |
| naptalam | 2-[(1-naphthalenylamino)carbonyl]benzoic acid |
| neburon | 1-butyl-3-(3,4-dichlorophenyl)-1-methylurea |
| nitralin | 4-methylsulfonyl-2,6-dinitro-N,N-dipropylaniline |
| nitrofen | 2,4-dichloro-1-(4-nitrophenoxy)benzene |
| nitrofluorfen | 2-chloro-1-(4-nitrophenoxy)-4-(trifluoromethyl)benzene |
| norea | N,N-dimethyl-N'-(octahydro-4,7-methano-1H-inden-5-yl)urea 3aα,4α,5α,7α,7aα-isomer |
| norflurazon | 4-chloro-5-(methylamino)-2-[3-(trifluoromethyl)phenyl]-3(2H)-pyridazinone |
| orbencarb | S-[2-(chlorophenyl)methyl]diethylcarbamothioate |
| oryzalin | 4-(dipropylamino)-3,5-dinitrobenzenesulfonamide |
| oxadiazon | 3-[2,4-dichloro-5-(1-methylethoxy)phenyl]-5-(1,1-dimethylethyl)-1,3;4-oxadiazol-2(3H)-one |
| oxyfluorfen | 2-chloro-1-(3-ethoxy-4-nitrophenoxy)-4-(trifluoromethyl)benzene |
| paraquat | 1,1-'dimethyl-4,4'-dipyridinium ion |
| pebulate | S-propyl butylethylcarbamothioate |
| pendimethalin | N-(1-ethylpropyl)-3,4-dimethyl-2,6-dinitrobenzenamine |
| perfluidone | 1,1,1-trifluoro-N-[2-methyl-4-(phenylsulfonyl)phenyl]methanesulfonamide |
| phenisopham | 3-[[(1-methylethoxy)carbonyl]amino]phenyl ethylphenylcarbamate |
| phenmedipham | 3-[(methoxycarbonyl)amino]phenyl-(3-methylphenyl)carbamate |
| picloram | 4-amino-3,5,6-trichloro-2-pyridinecarboxylic acid |
| piperophos | S-[2-(2-methyl-1-piperidinyl)-2-oxoethyl]-O,O-dipropyl phosphorodithioate |
| pretilachlor | 2-chloro-N-(2,6-diethylphenyl)-N-(2-propoxyethyl)acetamide |
| procyazine | 2-[[4-chloro-6-(cyclopropylamino)-1,3,5-triazine-2-yl]amino]-2-methylpropanenitrile |
| prodiamine | 2,4-dinitro-N3,N3-dipropyl-6-(trifluoromethyl)-1,3-benzenediamine |
| profluralin | N-(cyclopropylmethyl)-2,6-dinitro-N-propyl-4-(trifluoromethyl)benzenamine |
| proglinazine-ethyl | N-[4-chloro-6-[(1-methylethyl)amino]-1,3,5-triazin-2-yl]glycine ethyl ester |
| prometon | 6-methoxy-N,N'-bis(1-methylethyl)-1,3,5-triazine-2,4-diamine |
| prometryn | N,N'-bis(1-methylethyl)-6-(methylthio)-1,3,5-triazine-2,4-diamine |
| pronamide | 3,5-dichloro-N-(1,1-dimethyl-2-propynyl)-benzamide |
| propachlor | 2-chloro-N-(1-methylethyl)-N-phenylacetamide |
| propanil | N-(3,4-dichlorophenyl)propanamide |
| propaquizafop | 2-[[(1-methylethylidene)amino]oxy]ethyl 2-[4-[(6-chloro-2-quinoxalinyl)oxy]phenoxy]-propanoate |
| propazine | 6-chloro-N,N'-bis(1-methylethyl)-1,3,5-triazine-2,4-diamine |
| propham | 1-methylethyl phenylcarbamate |
| propyzamide | 3,5-dichloro-N-(1,1-dimethyl-2-propynl)-benzamide |
| prosulfalin | N-[[4-(dipropylamino)-3,5-dinitrophenyl]-sulfonyl]-S,S-dimethylsulfilimine |
| prosulfocarb | S-benzyldipropylthiocarbamate |
| prynachlor | 2-chloro-N-(1-methyl-2-propynyl)acetanilide |
| pyrazon | 5-amino-4-chloro-2-phenyl-3(2H)-pyridazinone |
| pyrazosulfuron-ethyl | ethyl 5-[[[[(4,6-dimethoxy-2-pyrimidinyl)amino]carbonyl]amino]sulfonyl]-1-methyl-1H-pyrazole-4-carboxylate |
| pyrazoxyfen | 2-[[4-(2,4-dichlorobenzoyl)-1,3-dimethyl-1H-pyrazol-5-yl]oxy]-1-phenylethanone |
| pyridate | O-(6-chloro-3-phenyl-4-pyridazinyl) S-octyl carbonothioate |
| quizalofop ethyl | (+)-2-[4-[(6-chloro-2-quinoxalinyl)oxy]phenoxy]-propanoic acid, ethyl ester |
| secbumeton | N-ethyl-6-methoxy-N'-(1-methylpropyl)-1,3,5-triazine-2,4-diamine |
| sethoxydim | 2-[1-(ethoxyimino)butyl]-5-[2-(ethylthio)propyl]-3-hydroxy-2-cyclohexen-1-one |
| siduron | N-(2-methylcyclohexyl)-N'-phenylurea |
| simazine | 6-chloro-N,N'-diethyl-1,3,5-triazine-2,4-diamine |
| simetryn | N,N'-diethyl-6-(methylthio)-1,3,5-triazine-2,4-diamine |
| sodium chlorate | sodium chlorate |
| sodium monochloroacetate | chloroacetic acid, sodium salt |
| sulfometuron methyl | 2-[[[[(4,6-dimethyl-2-pyrimidinyl)amino]-carbonyl]amino]sulfonyl]benzoic acid, methyl ester |
| 2,4,5-T | (2,4,5-trichlorophenoxy)acetic acid |
| 2,3,6-TBA | 2,3,6-trichlorobenzoic acid |
| TCA | trichloroacetic acid |
| tebutam | 2,2-dimethyl-N-(1-methylethyl)-N-(phenylmethyl)propanamide |
| tebuthiuron | N-[5-(1,1-dimethylethyl)-1,3,4-thiadiazol-2-yl]-N,N'-dimethylurea |
| terbacil | 5-chloro-3-(1,1-dimethylethyl)-6-methyl-2,4-(1H,3H)-pyrimidinedione |
| terbuchlor | N-(butoxymethyl)-2-chloro-N-[2-(1,1-dimethylethyl)-6-methylphenyl]acetamide |
| terbumeton | N-(1,1-dimethylethyl)-N'-ethyl-6-methoxy-1,3,5-triazine-2,4-diamine |
| terbuthylazine | 2-(tert-butylamino)-4-chloro-6-(ethylamino)-s-triazine |
| terbutol | 2,6-di-tert-butyl-p-tolyl methylcarbamate |
| terbutryn | N-(1,1-dimethylethyl)-N'-ethyl-6-(methylthio)-1,3,5-triazine-2,4-diamine |
| thifensulfuron | 3-[[[[(4-methoxy-6-methyl-1,3,5-triazin-2-yl)amino]carbonyl]amino]sulfonyl]2-thiophene-carboxylic acid, methyl ester |
| thiameturon-methyl | methyl 3-[[[[(4-methoxy-6-methyl-1,3,5-triazin-2-yl)amino]carbonyl]amino]sulfonyl]2-thiophenecarboxylate |
| thiazafluron | N,N'-dimethyl-N-[5-(trifluoromethyl)-1,3,4-thiadiazol-2-yl]urea |
| thiobencarb | S-[(4-chlorophenyl)methyl] diethylcarbamothioate |
| tiocarbazil | S-(phenylmethyl) bis(1-methylpropyl)-carbamothioate |
| tralkoxydim | 2-[1-(ethoxyimino)propyl]-3-hydroxy-5-(2,4,6-trimethylphenyl)-2-cyclohexen-1-one |
| triallate | S-(2,3,3-trichloro-2-propenyl) bis(1-methylethyl)-carbamothioate |
| triasulfuron | 2-(2-chloroethoxy)-N-[[(4-methoxy-6-methyl-1,3,5-triazin-2-yl)amino]carbonyl]benzenesulfonamide |
| tribenuron methyl | 2-[[[[N-(4-methoxy-6-methyl-1,3,5-triazine-2-yl)-N-methylamino]-carbonyl]amino]sulfonyl]-benzoic acid, methyl ester |
| triclopyr | [(3,5,6-trichloro-2-pyridinyl)oxy]acetic acid |
| tridiphane | (+)2-(3,5-dichlorophenyl)-2-(2,2,2-trichloroethyl)oxirane |
| trietazine | 6-chloro-N,N,N'-triethyl-1,3,5-triazine-2,4-diamine |
| trifluralin | 2,6-dinitro-N,N-dipropyl-4-(trifluoromethyl)-benzenamine |
| trimeturon | 1-p-chlorophenyl-2,3,3-trimethylpseudourea |
| 2,4-D | (2,4-dichlorophenoxy)acetic acid |
| 2,4-DB | 4-(2,4-dichlorophenoxy)butanoic acid |
| vernolate | S-propyl dipropylcarbamothioate |
| xylachlor | 2-chloro-N-(2,3-dimethylphenyl)-N-(1-methylethyl)acetamide |

Selective herbicidal properties of the subject compounds were discovered in greenhouse tests as described below.

TABLE 16

General Structure I, m is 3, $R^1$ is $CH_3$; $R^6$ is anti, $R^5$ and OQ are syn to the oxygen-containing bridge, Q is $CH_2W$

| Compound | $R^5$ | $R^6$ | W | Physical/Spectral data ($\delta$ in $CDCl_3$) |
|---|---|---|---|---|
| 1 | $OCH_3$ | H | (2-$CH_3$)$C_6H_4$ | oil, NMR: 1.2–2.1(m, 11H), 1.51(s, 3H), 2.31(s,3H), 3.25 (m, 1H), 3.25(s, 3H), 3.45(m, 1H), 4.28(d, 1H), 4.54(d, 1H), 7.17(m, 3H), 7.30(m, 1H). |
| 3 | H | $OCH_3$ | (2-$CH_3$)$C_6H_4$ | oil, NMR: 1.2–2.2(m, 11H), 1.51(s, 3H), 2.30(s, 3H), 2.92 (m, 1H), 3.33(s, 3H), 3.50(m, 1H), 4.28(m, 1H), 4.50(m, 1H), 7.16(m, 3H), 7.29(m, 1H). |
| 5 | H | $OCH_3$ | (2-$CH_3$)$C_6H_4$ (OQ is anti) | m.p. 62–68° C. |
| 6 | $OCH_3$ | H | (2-$CH_3$)$C_6H_4$ | oil, NMR: 0.97(s, 3H), 1.4–2.1 (m, 11H), 1.50(s, 3H), 2.31(s, 3H), 3.10(s, 3H), 3.41(m, 1H), 4.26(d, 1H), 4.54(d, 1H), 7.15(m, 3H), 7.29(m, 1H). |

General Structure II, m is 3, $R^2$ is $CH_3$; $R^6$ is anti, $R^5$ and OQ are syn to the oxygen-containing bridge, Q is $CH_2W$

| Compound | $R^5$ | $R^6$ | W | Physical/Spectral data ($\delta$ in $CDCl_3$) |
|---|---|---|---|---|
| 2 | $OCH_3$ | H | (2-$CH_3$)$C_6H_4$ | oil, NMR: 1.1–2.2(m, 11H), 1.50(s, 3H), 2.30(s, 3H), 3.2 (m, 1H), 3.26(s, 3H), 3.48(m, 1H), 4.33(d, 1H), 4.55(d, 1H), 7.16(m, 3H), 7.30(m, 1H). |
| 4 | H | $OCH_3$ | (2-$CH_3$)$C_6H_4$ | m.p. 102–103° C. |
| 7 | $OCH_3$ | $CH_3$ | (2-$CH_3$)$C_6H_4$ | m.p. 65–71° C. |

General Structure III, $R^1$ is $CH_3$; OQ is syn to the oxygen-containing bridge, Q is $CH_2W$

| Compound | n | $R^2$ | $R^3$ | W | Physical/Spectral data ($\delta$ in $CDCl_3$) |
|---|---|---|---|---|---|
| 8 | 4 | H | $CH_3$ | (2-$CH_3$)$C_6H_4$ | oil, NMR: 1.17(s, 3H), 1.29(s, 3H), 1.5–2.1(m, 14H), 2.34(s, 3H), 3.29(dd, 1H), 4.44(d, 1H), 4.67(d, 1H), 7.15(m, 3H), 7.36(m, 1H). |
| 9 | 4 | H | $CH_3$ | $C_6H_4$ | oil, NMR: 1.18(s, 3H), 1.30(s, 3H), 1.4–2.1(m, 14H), 3.30(dd, 1H), 4.48(d, 1H), 4.69(d, 1H), 7.3(m, 5H). |
| 10 | 4 | H | $CH_3$ | 2-$FC_6H_4$ | m.p. 67–69° C. |
| 11 | 4 | H | $CH_3$ | 2-$ClC_6H_4$ | m.p. 41–43° C. |
| 12 | 4 | H | $CH_3$ | 2-Cl-6-$FC_6H_3$ | m.p. 74–75° C. |
| 13 | 4 | H | $CH_3$ | 2,6-$F_2C_6H_3$ | m.p. 100–101° C. |
| 14 | 4 | H | $CH_3$ | 2,6-$Cl_2C_6H_3$ | m.p. 58–60° C. |
| 15 | 4 | H | Et | 2-($CH_3$)$C_6H_4$ | oil, NMR: 0.80(t, 3H), 1.16(s, 3H), 1.3–2.1(m, 16H), 2.33(s, 3H), 3.32(dd, 1H), 4.43(d, 1H), 4.67(d, 1H), 7.16(m, 3H), 7.36(m, 1H). |
| 16 | 4 | H | Et | 2-$FC_6H_5$ | oil, NMR: 0.80(t, 3H), 1.17(s, 3H), 1.2–2.1(m, 16H), 3.35(dd, 1H), 4.54(d, 1H), 4.70(d, 1H), 6.9–7.3(m, 3H), 7.49(dt, 1H). |
| 17 | 2 | $CH_3$ | $CH_3$ | (2-$CH_3$)$C_6H_4$ | oil, NMR: 0.78(s, 3H), 1.12(s, 3H), 1.22(s, 3H), 1.4(m, 2H), 1.6–2.0(m, 7H), 2.34(s, 3H), 3.15(dd, 1H), 4.46(d, 1H), 4.68(d, 1H), 7.18(m, 3H), 7.39(m, 1H). |
| 18 | 2 | $CH_3$ | $CH_3$ | $C_6H_5$ | oil, NMR: 0.77(s, 3H), 1.11(s, 3H), 1.24(s, 3H), 1.4(m, 2H), 1.6–2.0(m, 7H), 3.14(dd, 1H), 4.47(d, 1H), 4.74(d, 1H), 7.2–7.4(m, 5H). |
| 19 | 2 | $CH_3$ | $CH_3$ | 2-$ClC_6H_4$ | oil, NMR: 0.78(s, 3H), 1.15(s, 3H), 1.23(s, 3H), 1.4(m, 2H), 1.6–2.0(m, 7H), 3.24(dd, 1H), 4.55(d, 1H), |

TABLE 16-continued

| | | | | | |
|---|---|---|---|---|---|
| | | | | | 4.75(d, 1H), 7.25(m, 3H), 7.61(m, 1H). |
| 20 | 2 | CH₃ | CH₃ | 2-FC₆H₄ | oil, NMR: 0.78(s, 3H), 1.11(s, 3H), 1.22(s, 3H), 1.4(m, 2H), 1.6–2.0(m, 7H), 3.18(dd, 1H), 4.55(d, 1H), 4.73(d, 1H), 6.9–7.3(m, 3H), 7.50(dt, 1H). |
| 21 | 2 | CH₃ | CH₃ | 2,6-F₂C₆H₃ | m.p. 76–78° C. |
| 22 | 2 | CH₃ | CH₃ | 2-Cl-6-FC₆H₃ | m.p. 82–85° C. |
| 23 | 2 | CH₃ | CH₃ | 2,6-Cl₂C₆H₃ | m.p. 97–100° C. |
| 24 | 4 | H | H | 2-(CH₃)C₆H₄ | oil, NMR: 1.15(s, 3H), 1.4–2.0(m, 14H), 2.36(s, 3H), 3.38(dd, 1H), 4.24(m, 1H), 4.46(d, 1H), 4.72(d, 1H), 7.17(m, 3H), 7.34(m, 1H). |
| 25 | 4 | H | H | 2-FC₆H₄ | oil, NMR: 1.15(s, 3H), 1.4–2.0(m, 14H), 3.42(dd, 1H), 4.23(m, 1H), 4.55(d, 1H), 4.73(d, 1H), 6.9–7.3(m, 3H), 7.48(dt, 1H). |
| 26 | 2 | CH₃ | H | 2-(CH₃)C₆H₄ | oil, NMR: 0.79(s, 3H), 1.10(s, 3H), 1.4(m, 2H), 1.6–2.1(m, 7H), 2.36(s, 3H), 3.18(dd, 1H), 3.87(m, 1H), 4.46(d, 1H), 4.69(d, 1H), 7.18(m, 3H), 7.35(m, 1H). |
| 27 | 2 | CH₃ | H | C₆H₅ | oil, NMR: 0.78(s, 3H), 1.12(s, 3H), 1.4(m, 2H), 1.6–2.1(m, 7H), 3.20(dd, 1H), 3.87(m, 1H), 4.48(d, 1H), 4.73(d, 1H), 7.2–7.4(m, 5H). |
| 28 | 2 | CH₃ | H | 2-FC₆H₄ | oil, NMR: 0.79(s, 3H), 1.10(s, 3H), 1.4(m, 2H), 1.6–2.1(m, 7H), 3.23(dd, 1H), 3.87(m, 1H), 4.56(d, 1H), 4.74(d, 1H), 6.9–7.3(m, 3H), 7.48(dt, 1H). |
| 29 | 2 | CH₃ | H | 2-ClC₆H₄ | oil, NMR: 0.80(s, 3H), 1.15(s, 3H), 1.4(m, 2H), 1.6–2.2(m, 7H), 3.28(dd, 1H), 3.88(m, 1H), 4.58(d, 1H), 4.76(d, 1H), 7.25(m, 3H), 7.58(m, 1H). |
| 34 | 4 | H | H | 2-ClC₆H₄ | oil, NMR: 1.20(s, 3H), 1.4–2.0(m, 14H), 3.48(dd, 1H), 4.25(m, 1H), 4.58(d, 1H), 4.77(d, 1H), 7.1–7.4(m, 3H), 7.56(m, 1H). |
| 35 | 4 | H | H | 2-Cl-6-FC₆H₃ | m.p. 68–70° C. |
| 36 | 4 | H | H | 2,6-F₂C₆H₃ | oil, NMR: 1.08(s, 3H), 1.4–2.0(m, 14H), 3.39(dd, 1H), 4.20(m, 1H), 4.54(d, 1H), 4.76(d, 1H), 6.87(m, 2H), 7.25(m, 1H). |
| 37 | 4 | H | H | 2,3-F₂C₆H₃ | oil, NMR: 1.15(s, 3H), 1.4–2.0(m, 14H), 3.43(dd, 1H), 4.23(m, 1H), 4.58(d, 1H), 4.74(d, 1H), 7.06(m, 2H), 7.27(m, 1H). |
| 41 | 2 | H | H | 2-FC₆H₄ | oil, NMR: 1.10(s, 3H), 1.3–2.3(m, 9H), 3.23(dd, 1H), 4.19(m, 1H), 4.56(d, 1H), 4.73(d, 1H), 6.9–7.3(m, 3H), 7.48(dt, 1H). |
| 43 | 2 | CH₃ | H | 2,6-F₂C₆H₃ | oil, NMR: 0.79(s, 3H), 1.03(s, 3H), 1.3–2.2(m, 9H), 3.20(dd, 1H), 3.83(m, 1H), 4.55(d, 1H), 4.75(d, 1H), 6.8–6.9(m, 2H), 7.26(m, 1H). |
| 44 | 2 | CH₃ | H | 2-Cl, 6-FC₆H₃ | oil, NMR: 0.79(s, 3H), 1.05(s, 3H), 1.2–2.2(m, 9H), 3.19(dd, 1H), 3.83(m, 1H), 4.62(dd, 1H), 4.81(dd, 1H), 6.96(m, 1H), 7.1–7.3(m, 2H). |

General Structure V, m is 4, R¹=R³=R⁴ is CH₃;
OQ is syn to the oxygen-containing bridge, Q is CH₂W.

| Compound | W | Physical/Spectral Data (δ in CDCl₃) |
|---|---|---|
| 30 | 2-(CH₃)C₆H₄ | m.p. 68–75° C. |
| 31 | C₆H₅ | m.p. 78–79° C. |
| 32 | 2-FC₆H₄ | m.p. 82–84° C. |

TABLE 16-continued

| 33 | 2-ClC₆H₄ | | m.p. 79–80° C. |

General Structure XIII, R² is Et; oxygen atoms are syn

| Compound | p | W | Diastereomer | Physical/Spectral Data (δ in CDCl₃) |
|---|---|---|---|---|
| 38 | 3 | 2-(CH₃)C₆H₄ | less polar | oil, NMR: 1.03(t, 3H), 1.5–1.8(m, 7H), 1.8–2.0(m, 5H), 2.12(m, 2H), 2.31(s, 3H), 4.12(m, 1H), 5.07(d, 1H), 7.10(m, 2H), 7.18(t, 1H), 7.42(d, 1H). |
| 39 | 3 | 2-(CH₃)C₆H₄ | more polar | oil, NMR: 0.98(t, 3H), 1.4–1.6(m, 5H), 1.7–1.9(m, 4H), 1.9–2.1(m, 2H), 2.1–2.2(m, 2H), 2.24(m, 1H), 2.31(s, 3H), 3.89(m, 1H), 4.52(d, 1H), 7.1–7.2(m, 3H), 7.51(d, 1H). |
| 40 | 3 | C₆H₅ | more polar | oil, NMR: 0.98(t, 3H), 1.4–2.3(m, 14H), 3.86(dd, 1H), 4.41(dd, 1H), 7.33(m, 5H). |
| 42 | 3 | C₆H₅ | less polar | oil, NMR: 1.04(t, 3H), 1.4–2.2(m, 14H), 4.11(dd, 1H), 4.88(d, 1H), 7.30(m, 5H). |
| 45 | 2 | C₆H₅ | W is β | oil, NMR: 1.01(t, 3H), 1.4–2.3(m, 12H), 3.87(dd, 1H), 4.31(m, 1H), 7.2–7.4(m, 5H). |

| Compound | P | W | Diastereomer | Physical/Spectral Data (δ CDCl₃) |
|---|---|---|---|---|
| 46 | 2 | C₆H₅ | W is α | oil, NMR: 1.00(t, 3H), 1.2–2.4(m, 12H), 3.83(dd, 1H), 5.05(m, 1H), 7.2–7.4(m, 5H). |
| 47 | 2 | 2-FC₆H₄ | W is β | oil, NMR. 1.02(t, 3H), 1.4–1.7(m, 5H), 1.7–2.1(m, 6H), 2.24(dd, 1H), 3.88(d, 1H), 4.67(d, 1H), 6.98(dd, 1H), 7.13(t, 1H), 7.2(m, 1H), 7.54(5, 1H). |

TEST A

Seeds of barley (*Hordeum vulgare*), barnyardgrass (*Echinochloa crus-galli*), bedstraw (*Galium aparine*), blackgrass (*Alopecurus myosuroides*), cheatgrass (*Bromus secalinus*), chickweed (*Stellaria media*), cocklebur (*Xanthium pensylvanicum*), corn (*Zea mays*), cotton (*Gossypium hirsutum*), crabgrass (*Digitaria* spp.), giant foxtail (*Setaria faberii*), lambsquarters (*Chenopodium album*), morningglory (*Ipomoea hederacea*), rape (*Brassica napus*), rice (*Oryza sativa*), sorghum (*Sorghum bicolor*), soybean (*Glycine max*), sugar beet (*Beta vulgaris*), velvetlead (*Abutilon theophrasti*), wheat (*Triticum aestivum*), wild buckwheat (*Polygonum convolvulus*), and wild oat (*Avena fatua*) and purple nutsedge (*Cyperus rotundus*) tubers were planted and treated preemergence with test chemicals dissolved in a non-phytotoxic solvent. At the same time, these crop and weed species were also treated with postemergence applications of test compounds. Plants ranged in height from two to eighteen cm (one to four leaf stage) for postemergence treatments. Treated plants and controls were maintained in a greenhouse for twelve to sixteen days after which all species were compared to controls and visually evaluated. Plant response ratings, summarized in Table A, are based on a scale of 0 to 10 where 0 is no effect and 10 is complete control. A dash (-) response means no test result.

TABLE A

Rate (200 g/ha) COMPOUND

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|---|
| POSTEMERGENCE | | | | | | | | | | | | | | | | | | | | | | | | |
| Barley | 0 | 0 | 0 | 0 | 0 | 0 | 0 | 0 | 0 | 0 | 2 | 0 | 3 | 0 | 0 | 3 | 0 | 2 | 3 | 0 | 0 | 0 | 0 | 0 |
| Barnyardgrass | 0 | 0 | 0 | 0 | 0 | 0 | 0 | 0 | 2 | 7 | 1 | 0 | 3 | 0 | — | — | 0 | 0 | 0 | 2 | 2 | 0 | 0 | 7 |
| Bedstraw | — | — | — | — | — | — | — | 0 | 0 | 0 | 0 | 0 | 0 | 0 | 0 | 0 | 0 | 0 | 3 | 0 | 3 | 0 | 0 | 2 |
| Blackgrass | — | — | — | — | — | — | — | 2 | 2 | 0 | 2 | 0 | 2 | 2 | 0 | 3 | 7 | — | 6 | 4 | 7 | 7 | 2 | 3 |
| Cheatgrass | 0 | 0 | 0 | 0 | 0 | 0 | 0 | 1 | 0 | 0 | 0 | 0 | 0 | 0 | 0 | 2 | 0 | 3 | 3 | 3 | 0 | 2 | 0 | 0 |
| Chickweed | — | — | — | — | — | — | — | 4 | — | 2 | 0 | 0 | 2 | 0 | 0 | 0 | 0 | 0 | 0 | 0 | 0 | 0 | 0 | 0 |
| Cocklebur | 1 | 0 | 1 | 0 | 0 | 0 | 1 | — | — | — | — | — | — | — | — | — | — | — | — | — | — | — | — | 2 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Cotton | 0 | 0 | 0 | 0 | 0 | 2 | 0 | 0 | 0 | 0 | 0 | 0 | 0 | 0 | 0 | 0 | 0 | 0 | 0 | 0 | 0 | 0 | 0 | 0 |
| Crabgrass | 0 | 0 | 0 | 0 | 0 | 0 | 0 | 0 | 0 | 0 | 0 | 0 | 0 | 0 | 0 | 0 | 2 | 3 | 0 | 0 | 0 | 0 | 0 | 2 |
| Giant foxtail | 0 | 5 | 0 | 0 | 0 | 2 | 0 | 0 | 0 | 0 | 2 | 2 | 0 | 0 | 0 | 0 | 0 | 0 | 0 | 0 | 2 | 0 | 0 | 0 |
| Lambsquarters | — | — | — | — | — | — | — | 3 | 0 | 2 | 0 | 0 | 0 | — | 0 | 0 | — | 4 | 4 | 3 | 0 | 4 | — | 0 |
| Morningglory | 0 | 0 | 0 | 0 | 1 | 0 | 0 | 0 | 0 | 0 | 0 | 0 | 0 | 0 | 1 | 0 | 0 | 0 | 0 | 0 | 1 | 0 | 0 | 0 |
| Nutsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rape | — | — | — | — | — | — | — | 0 | 0 | 2 | 0 | 3 | 4 | 0 | 3 | 3 | 0 | 0 | 2 | 0 | 2 | 2 | 2 | 2 |
| Rice | 0 | 0 | 0 | 0 | 0 | 0 | 0 | 0 | 0 | 0 | 0 | 0 | 2 | 0 | 0 | 0 | 0 | 0 | 0 | 0 | 0 | 0 | 0 | 0 |

TABLE A-continued

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|---|
| Sorghum | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Soybean | 0 | 0 | 0 | 0 | 0 | 0 | 0 | 0 | 0 | 0 | 0 | 1 | 0 | 0 | 0 | 0 | 0 | 0 | 0 | 0 | 0 | 0 | 0 | 0 |
| Sugar beet | 0 | 0 | 0 | 0 | 0 | 0 | 0 | 1 | 1 | 3 | 5 | 2 | 6 | 3 | 7 | 5 | 0 | 2 | 2 | 0 | 3 | 2 | 2 | 4 |
| Velvetleaf | 4 | 0 | 0 | 0 | 0 | 0 | 0 | 0 | 0 | 0 | 0 | 1 | 2 | 0 | 0 | 0 | — | — | — | 0 | — | 0 | 0 | 5 |
| Wheat | 0 | 0 | 0 | 0 | 0 | 0 | 0 | 0 | 0 | 0 | 2 | 0 | 2 | 3 | 0 | 2 | 0 | 0 | 0 | 0 | 2 | 0 | 0 | 2 |
| Wild buckwheat | — | — | — | — | — | — | — | 2 | 3 | 0 | 2 | 0 | 2 | 0 | 0 | 0 | 0 | 0 | 0 | 0 | 0 | 0 | 0 | 2 |
| Wild oat | 0 | 0 | 0 | 0 | 0 | 0 | 0 | 0 | 0 | 0 | 0 | 0 | 0 | 2 | 0 | 0 | 0 | 3 | 2 | 0 | 3 | 0 | 0 | 2 |

Rate (200 g/ha) COMPOUND

| | 25 | 26 | 27 | 28 | 29 | 30 | 31 | 32 | 33 | 34 | 35 | 36 | 37 | 38 | 39 | 40 | 41 | 43 | 44 | 45 | 46 | 47 |
|---|---|---|---|---|---|---|---|---|---|---|---|---|---|---|---|---|---|---|---|---|---|---|
| POSTEMERGENCE | | | | | | | | | | | | | | | | | | | | | | |
| Barley | 0 | 0 | 0 | 2 | 2 | 0 | 0 | 0 | 0 | 0 | 0 | 0 | 2 | 0 | 0 | 0 | 3 | 0 | 0 | 0 | 0 | 0 |
| Barnyardgrass | 9 | 9 | 9 | 9 | 9 | 0 | 0 | 0 | 0 | 9 | 8 | 9 | 9 | 0 | 0 | 8 | 9 | 9 | 6 | 0 | 0 | 0 |
| Bedstraw | 2 | 2 | 0 | 0 | 2 | 0 | 0 | 0 | 0 | 0 | 0 | 0 | 0 | 0 | 0 | 0 | 2 | 0 | 0 | 0 | 0 | 2 |
| Blackgrass | 3 | 2 | 4 | 0 | 0 | 0 | 0 | 0 | 0 | 3 | 0 | 9 | 5 | 0 | 0 | 8 | 9 | 2 | 3 | 0 | 0 | 0 |
| Cheatgrass | 0 | 3 | 2 | 0 | 0 | 0 | 0 | 0 | 0 | 0 | 0 | 0 | 0 | 0 | 0 | 2 | 2 | 3 | 0 | 0 | 0 | 0 |
| Chickweed | 0 | 0 | 0 | 0 | 0 | 0 | 0 | 0 | 0 | 0 | 3 | 0 | 0 | 0 | 0 | 2 | 2 | 3 | 0 | 0 | 0 | 0 |
| Cocklebur | 2 | 1 | — | 2 | 1 | 2 | 2 | 2 | 2 | — | — | — | — | — | — | — | — | 0 | 0 | 3 | 0 | 0 |
| Corn | 0 | 1 | 1 | 2 | 1 | 0 | 0 | 0 | 0 | 0 | 0 | 0 | 0 | 0 | 0 | 0 | 9 | 1 | 0 | 0 | 0 | 0 |
| Cotton | 0 | 0 | 0 | 2 | 2 | 0 | 0 | 0 | 0 | 0 | 0 | 0 | 0 | 0 | 0 | 0 | 0 | 0 | 0 | 0 | 0 | 0 |
| Crabgrass | 8 | 0 | 0 | 0 | 0 | 0 | 0 | 0 | 0 | 0 | 0 | 3 | — | 0 | 0 | 3 | 9 | 0 | 0 | 0 | 0 | 0 |
| Giant foxtail | 1 | 0 | 2 | 3 | 0 | 2 | 0 | 0 | 0 | 0 | 0 | 0 | 0 | 0 | 0 | 0 | 5 | 0 | 0 | 0 | 0 | 0 |
| Lambsquarters | 0 | 0 | 0 | 0 | 0 | 0 | 2 | 0 | 0 | 3 | 0 | 0 | 0 | 0 | 0 | 5 | — | 5 | 9 | 0 | 0 | 2 |
| Morningglory | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Nutsedge | 0 | 0 | 0 | — | 0 | 0 | 0 | 0 | — | 0 | — | 0 | — | — | 0 | — | 0 | — | — | 0 | 0 | 0 |
| Rape | 2 | 2 | 2 | 0 | 0 | 0 | 0 | 0 | 0 | 2 | 0 | 0 | 0 | 0 | 0 | 0 | 0 | 0 | 0 | 0 | 0 | 0 |
| Rice | 0 | 0 | 0 | 0 | 0 | 0 | 0 | 0 | 0 | 0 | 0 | 0 | 0 | 0 | 0 | 0 | 2 | 0 | 0 | 0 | 0 | 0 |
| Sorghum | 0 | 1 | 1 | 4 | 1 | 0 | 0 | 0 | 0 | 0 | 0 | 0 | 0 | 0 | 0 | 0 | 2 | 0 | 0 | 0 | 0 | 0 |
| Soybean | 0 | 0 | 1 | 1 | 0 | 0 | 0 | 0 | 0 | 0 | 1 | 1 | 0 | 0 | 0 | 0 | 3 | 0 | 0 | 0 | 0 | 0 |
| Sugar beet | 4 | 5 | 3 | 4 | 3 | 0 | 0 | 0 | 0 | 2 | 0 | 0 | 0 | 0 | 2 | 3 | 0 | 0 | 0 | 0 | 0 | 0 |
| Velvetleaf | 5 | 4 | 1 | 5 | 2 | 0 | 0 | 0 | 0 | 0 | 3 | 3 | 0 | 0 | 0 | 0 | 7 | — | 3 | 0 | 0 | 0 |
| Wheat | 0 | 0 | 2 | 2 | 0 | 0 | 0 | 0 | 0 | 0 | 0 | 0 | 0 | 0 | 0 | 2 | 2 | 0 | 0 | 0 | 0 | 0 |
| Wild buckwheat | 2 | 0 | 0 | 0 | 0 | 2 | 2 | 0 | 0 | 3 | 9 | — | 3 | 0 | 3 | 4 | 2 | 0 | 0 | 0 | 0 | 0 |
| Wild oat | 2 | 0 | 2 | 2 | 0 | 0 | 0 | 0 | 0 | 0 | 0 | 0 | 2 | 0 | 0 | 0 | 0 | 0 | 0 | 0 | 0 | 0 |

Rate (50 g/ha) COMPOUND

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 |
|---|---|---|---|---|---|---|---|---|---|---|---|---|---|---|---|---|---|---|---|---|---|---|---|---|---|
| POSTEMERGENCE | | | | | | | | | | | | | | | | | | | | | | | | | |
| Barley | 0 | 0 | 0 | 0 | 0 | 0 | 0 | 0 | 0 | 0 | 0 | 0 | 0 | 0 | 0 | 0 | 0 | 2 | 0 | 0 | 0 | 0 | 0 | 0 |
| Barnyardgrass | 0 | 0 | 0 | 0 | 0 | 0 | 0 | 0 | 0 | 0 | 0 | 0 | 1 | 0 | — | — | 0 | 0 | 0 | 0 | 0 | 0 | 0 | 0 | 2 |
| Bedstraw | — | — | — | — | — | — | — | 0 | 0 | 0 | 0 | 0 | 0 | 0 | 0 | 0 | 0 | 0 | 0 | 0 | 0 | 0 | 0 | 0 | 0 |
| Blackgrass | — | — | — | — | — | — | — | 0 | 0 | 0 | 0 | 2 | 0 | 0 | 0 | 6 | 8 | — | — | 2 | 7 | 2 | 2 | 2 |
| Cheatgrass | 0 | 0 | 0 | 0 | 0 | 0 | 0 | 0 | 0 | 0 | 0 | 0 | 0 | — | 0 | 0 | 0 | 3 | 3 | 0 | 0 | 0 | 0 | 0 | 0 |
| Chickweed | — | — | — | — | — | — | — | 0 | 0 | 0 | 0 | 0 | 0 | 0 | 0 | 0 | 0 | 0 | 0 | 0 | 0 | 0 | 0 | 0 | 0 |
| Cocklebur | 1 | 0 | 1 | 0 | 0 | 0 | 0 | — | — | — | — | — | — | — | — | — | — | — | — | — | — | — | — | — | — |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Cotton | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 0 | 0 | 0 | 0 | 0 | 0 | 0 | 0 | 0 | 0 | 0 | 0 | 0 | 0 | 0 | 0 | 0 | 0 | 0 | 2 | 0 | 0 | 0 | 0 | 0 |
| Giant foxtail | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Lambsquarters | — | — | — | — | — | — | — | 0 | 0 | — | 0 | 0 | 0 | 0 | 0 | 0 | 0 | — | 0 | 2 | 0 | 0 | 0 | 0 | 0 |
| Morningglory | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Nutsedge | — | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rape | — | — | — | — | — | — | — | 0 | 0 | 3 | 0 | 0 | 0 | 0 | 3 | 2 | 0 | 0 | 0 | 0 | 0 | 0 | 0 | 0 | 0 |
| Rice | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sorghum | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Soybean | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sugar beet | 0 | 0 | 0 | 0 | 0 | 0 | 0 | 0 | 0 | 3 | 4 | 4 | 5 | 3 | 4 | 4 | 0 | 0 | 0 | 0 | 4 | 1 | 0 | 2 | 3 |
| Velvetleaf | 0 | 0 | 0 | 0 | 0 | 0 | 0 | 0 | 0 | 0 | 0 | 0 | 0 | 0 | 0 | 0 | 0 | 0 | 0 | 0 | — | — | — | 2 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild buckwheat | — | — | — | — | — | — | — | 0 | 2 | 0 | 0 | 0 | 0 | 0 | 0 | 0 | 0 | 0 | 0 | 0 | 0 | 0 | 0 | 0 | 0 |
| Wild oat | 0 | 0 | 0 | 0 | 0 | 0 | 0 | 0 | 0 | 0 | 0 | 0 | 0 | 0 | 0 | 0 | 0 | 0 | 0 | 2 | 0 | 2 | 0 | 0 | 0 |

Rate (50 g/ha) COMPOUND / Rate (10 g/ha) COMPOUND

| | 26 | 27 | 28 | 29 | 30 | 31 | 32 | 33 | 34 | 35 | 36 | 37 | 38 | 39 | 40 | 41 | 42 | 43 | 44 | 45 | 46 | 47 | 42 |
|---|---|---|---|---|---|---|---|---|---|---|---|---|---|---|---|---|---|---|---|---|---|---|---|
| POSTEMERGENCE | | | | | | | | | | | | | | | | | | | | | | | |
| Barley | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Barnyardgrass | 4 | 3 | 5 | 1 | 0 | 0 | 0 | 0 | 2 | 2 | 5 | 4 | 0 | 0 | 2 | 0 | 0 | 0 | 0 | 0 | 0 | 0 | 0 |
| Bedstraw | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Blackgrass | 0 | 2 | 2 | 0 | 0 | 0 | 0 | 0 | 0 | 7 | 0 | 0 | 0 | 4 | 0 | 0 | 0 | 0 | 0 | 0 | 0 | 0 | 0 |
| Cheatgrass | 0 | 0 | 0 | 0 | 0 | 0 | 0 | 0 | 0 | 0 | 0 | 0 | 0 | 4 | 0 | 0 | 0 | 0 | 0 | 0 | 0 | 0 | 0 |
| Chickweed | 0 | 0 | 0 | 0 | 0 | 0 | 0 | 0 | 0 | — | 0 | 0 | 0 | 0 | 0 | 0 | 0 | 0 | 0 | 0 | 0 | 0 | 0 |
| Cocklebur | 0 | 1 | — | 0 | 0 | 0 | — | — | — | — | — | — | — | — | — | — | 0 | — | 0 | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Cotton | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 0 | 0 | 0 | 0 | 0 | 0 | 0 | 0 | 0 | 0 | — | 0 | 0 | 0 | 3 | 0 | 0 | 0 | 0 | 0 | 0 | 0 | 0 |
| Giant foxtail | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Lambsquarters | 0 | 0 | 0 | 0 | 0 | 0 | 0 | 0 | 0 | 0 | 0 | — | — | 2 | 2 | 0 | 0 | 0 | 0 | 0 | 0 | 0 | 0 |
| Morningglory | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

TABLE A-continued

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|---|
| Nutsedge | 0 | 0 | 0 | 0 | 0 | 0 | 0 | 0 | 0 | 0 | 0 | 0 | 0 | 0 | — | — | 0 | 0 | 0 | 0 | 0 | 0 | | 0 |
| Rape | 0 | 0 | 0 | 0 | 0 | 0 | 0 | 0 | 0 | 0 | 0 | 0 | 0 | 0 | 0 | 0 | 0 | 0 | 0 | 0 | 0 | 0 | | 0 |
| Rice | 0 | 0 | 0 | 0 | 0 | 0 | 0 | 0 | 0 | 0 | 0 | 0 | 0 | 0 | 0 | 0 | 0 | 0 | 0 | 0 | 0 | 0 | | 0 |
| Sorghum | 0 | 0 | 0 | 0 | 0 | 0 | 0 | 0 | 0 | 0 | 0 | 0 | 0 | 0 | 2 | 0 | 0 | 0 | 0 | 0 | 0 | 0 | | 0 |
| Soybean | 0 | 0 | 0 | 0 | 0 | 0 | 0 | 0 | 0 | 0 | 1 | 0 | 0 | 0 | 0 | 0 | 0 | 0 | 0 | 0 | 0 | 0 | | 0 |
| Sugar beet | 4 | 3 | 3 | 2 | 0 | 0 | 0 | 0 | 0 | 0 | 0 | 0 | 0 | 0 | 0 | 0 | 0 | 0 | 0 | 0 | 0 | 0 | | 0 |
| Velvetleaf | 1 | 0 | 1 | 0 | 0 | 0 | 0 | 0 | 0 | 1 | 0 | 0 | 0 | 0 | 0 | 0 | 0 | 0 | 0 | 0 | 0 | 0 | | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | | 0 |
| Wild buckwheat | 0 | 0 | 0 | 0 | 0 | 0 | 0 | 0 | 0 | 0 | 3 | 0 | 0 | 2 | 2 | 0 | 0 | — | — | 0 | 0 | 0 | | 0 |
| Wild oat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | | 0 |

Rate (200 g/ha) COMPOUND

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|---|
| PREEMERGENCE | | | | | | | | | | | | | | | | | | | | | | | | |
| Barley | 0 | 0 | 0 | 0 | 0 | 0 | 0 | 0 | 0 | 0 | 0 | 0 | 0 | 0 | 2 | 0 | 0 | 0 | 0 | 0 | 0 | 0 | 0 | 2 |
| Barnyardgrass | 9 | 1 | 8 | 0 | 0 | 9 | 0 | 7 | 8 | 10 | 2 | 9 | 10 | 0 | 0 | 0 | 0 | 7 | 2 | 4 | 8 | 1 | 0 | 10 |
| Bedstraw | — | — | — | — | — | — | — | 0 | — | 0 | 0 | 0 | 0 | 0 | 3 | 0 | 0 | 0 | 0 | 0 | 0 | 0 | 0 | 0 |
| Blackgrass | — | — | — | — | — | — | — | 2 | 0 | 3 | 0 | 2 | 4 | 0 | 3 | 2 | 0 | 2 | 0 | 2 | 0 | 0 | 0 | 4 |
| Cheatgrass | 0 | 0 | 0 | 0 | 0 | 0 | 0 | 0 | 2 | 2 | 0 | 0 | 6 | 0 | 4 | 2 | 0 | 0 | 0 | 0 | 0 | 0 | 0 | 5 |
| Chickweed | — | — | — | — | — | — | — | 0 | 0 | 0 | 0 | 0 | 4 | 0 | 0 | 6 | 0 | 4 | 0 | 0 | 0 | 0 | 0 | 2 |
| Cocklebur | — | 0 | 0 | 0 | — | — | 0 | — | — | — | — | — | — | — | — | — | — | — | — | — | — | — | — | — |
| Corn | 0 | 0 | 0 | 0 | 0 | 0 | 0 | 0 | 0 | 0 | 0 | 0 | 1 | 0 | 0 | 0 | 0 | 0 | 0 | 0 | 0 | 0 | 0 | 1 |
| Cotton | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 8 | 4 | 9 | 0 | 0 | 3 | 0 | 2 | 7 | 8 | 0 | 3 | 9 | 0 | 0 | 0 | 0 | 0 | 0 | 2 | 0 | 0 | 0 | 9 |
| Giant foxtail | 9 | 6 | 9 | 0 | 0 | 8 | 0 | 3 | 5 | 6 | 3 | 6 | 8 | 0 | 0 | 0 | 0 | 3 | 5 | 2 | 0 | 2 | 0 | 8 |
| Lambsquarters | — | — | — | — | — | — | — | 0 | — | 3 | 0 | 0 | 0 | 0 | 0 | 0 | 0 | 3 | 0 | 6 | 0 | 0 | 0 | 0 |
| Morningglory | 0 | 0 | 0 | 0 | 0 | 0 | 0 | 0 | 0 | 0 | 0 | 0 | 0 | 0 | 0 | 0 | 0 | — | — | 0 | 0 | 0 | 0 | 0 |
| Nutsedge | 0 | 0 | — | 0 | 0 | 9 | 0 | 0 | 0 | 3 | 0 | 0 | 0 | 0 | 0 | 0 | 0 | 0 | 0 | 0 | 0 | 0 | 0 | 4 |
| Rape | — | — | — | — | — | — | — | 0 | 0 | 0 | 2 | 0 | 0 | 0 | 2 | 2 | 0 | 0 | 0 | 0 | 0 | 0 | 0 | 3 |
| Rice | 0 | 0 | 0 | 0 | 0 | 0 | 0 | 0 | 0 | 0 | 0 | 2 | 0 | 0 | 0 | 0 | 0 | 0 | 0 | 0 | 0 | 0 | 0 | 3 |
| Sorghum | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 2 |
| Soybean | 0 | 0 | 0 | 0 | 0 | 0 | 0 | 0 | 0 | 0 | 0 | 0 | 2 | 0 | 0 | 0 | 0 | 0 | 0 | 0 | 0 | 0 | 0 | 1 |
| Sugar beet | 0 | 0 | 0 | 0 | 0 | 0 | 0 | 0 | 4 | 1 | 2 | 2 | 2 | 2 | 4 | 3 | 0 | 0 | 0 | 0 | 0 | 0 | 0 | 3 |
| Velvetleaf | 1 | 0 | 0 | 0 | 0 | 0 | 0 | 0 | 0 | 0 | 0 | 0 | 1 | 0 | 0 | 0 | 0 | 0 | 0 | 0 | 0 | 2 | 0 | 0 |
| Wheat | 0 | 0 | 0 | 0 | 0 | 0 | 0 | 0 | 0 | 0 | 0 | 0 | 0 | 0 | 2 | 0 | 0 | 0 | 0 | 0 | 0 | 0 | 0 | 2 |
| Wild buckwheat | — | — | — | — | — | — | — | 0 | 6 | 2 | 0 | 0 | 0 | 0 | 2 | 3 | 0 | 0 | 0 | 0 | 0 | 0 | 0 | 0 |
| Wild oat | 0 | 0 | 0 | 0 | 0 | 0 | 0 | 0 | 0 | 0 | 0 | 0 | 2 | 0 | 0 | 0 | 0 | 0 | 0 | 0 | 3 | 0 | 0 | 2 |

Rate (200 g/ha) COMPOUND

| | 25 | 26 | 27 | 28 | 29 | 30 | 31 | 32 | 33 | 34 | 35 | 36 | 37 | 38 | 39 | 40 | 41 | 43 | 44 | 45 | 46 | 47 |
|---|---|---|---|---|---|---|---|---|---|---|---|---|---|---|---|---|---|---|---|---|---|---|
| PREEMERGENCE | | | | | | | | | | | | | | | | | | | | | | |
| Barley | 2 | 2 | 2 | 2 | 0 | 0 | 0 | 0 | 0 | 0 | 0 | 0 | 0 | 0 | 0 | 0 | 3 | 0 | 0 | 0 | 0 | 0 |
| Barnyardgrass | 10 | 10 | 10 | 10 | 10 | 0 | 7 | 2 | 0 | 10 | 9 | 10 | 10 | 0 | 4 | 10 | 10 | 10 | 10 | 7 | 0 | 1 |
| Bedstraw | 0 | 0 | 0 | 0 | 0 | 0 | 0 | 2 | 0 | 0 | 0 | 2 | 0 | 0 | 0 | 0 | 7 | — | — | 0 | 0 | 0 |
| Blackgrass | 9 | 6 | 6 | 2 | 6 | 4 | 6 | 7 | 3 | 3 | 5 | 9 | 3 | 0 | 2 | 9 | — | 7 | 6 | 7 | 0 | 4 |
| Cheatgrass | 2 | 4 | 3 | 4 | 3 | 1 | 3 | 2 | — | 0 | 0 | 4 | 2 | 0 | 0 | 3 | 4 | 5 | 0 | 7 | 0 | 3 |
| Chickweed | 0 | 2 | 3 | 0 | 4 | 0 | 0 | 0 | — | 0 | 0 | 0 | 2 | 0 | 0 | 0 | 2 | 5 | 2 | 0 | 0 | 0 |
| Cocklebur | 1 | 0 | 0 | 1 | 0 | — | — | — | 0 | — | — | — | — | — | — | — | — | 0 | 0 | 0 | 0 | 0 |
| Corn | 2 | 1 | 3 | 5 | 3 | 0 | 0 | 0 | 0 | 0 | 0 | 2 | 0 | 0 | 0 | 3 | 10 | 1 | 0 | 0 | 3 | 6 |
| Cotton | 0 | 0 | 0 | 0 | 0 | 0 | 0 | 0 | 0 | 0 | 0 | 0 | 0 | 0 | 0 | 0 | 3 | 0 | 0 | 0 | 0 | 0 |
| Crabgrass | 9 | 9 | 10 | 10 | 9 | 2 | 2 | 0 | 0 | 9 | 9 | 9 | 9 | 0 | 7 | 10 | 10 | 10 | 8 | 9 | 0 | — |
| Giant foxtail | 9 | 10 | 10 | 10 | 10 | 8 | 9 | 8 | 5 | 8 | 8 | 9 | 9 | 0 | 8 | 9 | 10 | 7 | 7 | 5 | 1 | 8 |
| Lambsquarters | 0 | 0 | 3 | 0 | 0 | 0 | 0 | 0 | 3 | 0 | 2 | 3 | 0 | 0 | 5 | 0 | 5 | 2 | 2 | 0 | 0 | 0 |
| Morningglory | 0 | 0 | — | 0 | 0 | 0 | 0 | 0 | 0 | 0 | 0 | 0 | 0 | 0 | 0 | 0 | 0 | 0 | 0 | 0 | 0 | 0 |
| Nutsedge | 0 | — | 0 | — | 0 | 0 | — | — | 0 | 0 | 0 | 0 | 0 | 0 | 0 | 0 | 2 | 0 | 0 | 0 | 0 | 0 |
| Rape | 2 | 2 | 2 | 2 | 0 | 0 | 0 | 0 | 0 | 0 | 0 | 0 | 0 | 0 | 0 | 0 | 3 | 0 | 0 | 0 | 0 | 0 |
| Rice | 0 | 0 | 2 | 2 | 0 | 0 | 0 | 0 | 0 | 0 | 0 | 0 | 0 | 0 | 0 | 0 | 0 | 0 | 0 | 0 | 0 | 0 |
| Sorghum | 2 | 2 | 1 | 1 | 0 | 0 | 0 | 0 | 0 | 0 | 0 | 3 | 2 | 0 | 0 | 5 | 3 | 1 | 0 | 0 | 0 | 0 |
| Soybean | 0 | 0 | 0 | 2 | 0 | 0 | 0 | 0 | 0 | 0 | 0 | 0 | 0 | 0 | 0 | 0 | 4 | 0 | 0 | 0 | 0 | 1 |
| Sugar beet | 3 | 2 | 4 | 3 | 2 | 0 | 0 | 0 | 0 | 0 | 0 | 0 | 0 | 0 | 0 | 0 | 4 | 0 | 0 | 0 | 0 | 0 |
| Velvetleaf | 2 | 2 | 1 | 4 | 2 | 0 | 0 | 0 | 0 | 0 | 5 | 6 | 3 | 0 | 0 | 2 | 8 | 5 | 2 | 0 | 0 | 0 |
| Wheat | 0 | 0 | 3 | 2 | 2 | 0 | 0 | 0 | 0 | 0 | 0 | 0 | 0 | 0 | 0 | 0 | 2 | 2 | 2 | 0 | 0 | 0 |
| Wild buckwheat | 0 | 0 | 0 | 0 | 0 | 0 | 0 | 0 | 0 | — | — | — | 0 | 0 | 2 | 2 | — | — | 0 | 0 | 0 | 0 |
| Wild oat | 2 | 2 | 4 | 5 | 4 | 0 | 2 | 2 | 0 | 0 | 0 | 8 | 0 | 0 | 0 | 4 | 7 | 8 | 2 | 0 | 0 | 0 |

Rate (50 g/ha) COMPOUND

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 |
|---|---|---|---|---|---|---|---|---|---|---|---|---|---|---|---|---|---|---|---|---|---|---|---|---|---|
| PREEMERGENCE | | | | | | | | | | | | | | | | | | | | | | | | | |
| Barley | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Barnyardgrass | 0 | 0 | 0 | 0 | 0 | 0 | 0 | 1 | 2 | 3 | 0 | 0 | 0 | 0 | 0 | 0 | 0 | 0 | 0 | 0 | 0 | 0 | 0 | 8 | 10 |
| Bedstraw | — | — | — | — | — | — | — | 0 | 0 | 0 | 0 | 0 | 0 | 0 | 0 | 0 | 0 | 0 | 0 | 0 | 0 | 0 | 0 | 0 | 0 |
| Blackgrass | — | — | — | — | — | — | — | 0 | 0 | 0 | 0 | 0 | 0 | 0 | 0 | 0 | 0 | 0 | 0 | 0 | 0 | 0 | 0 | 0 | 2 |
| Cheatgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 2 | 0 |
| Chickweed | — | — | — | — | — | — | — | 0 | 0 | 0 | 0 | 0 | 0 | 0 | 0 | 0 | 0 | 0 | 0 | 0 | 0 | 0 | 0 | 0 | 0 |
| Cocklebur | — | 0 | 0 | 0 | 0 | 0 | 0 | — | — | — | — | — | — | — | — | — | — | — | — | — | — | — | — | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Cotton | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 6 | 0 | 0 | 0 | 0 | 2 | 0 | 0 | 2 | 2 | 0 | 0 | 0 | 0 | 0 | 0 | 0 | 0 | 0 | 2 | 0 | 0 | 0 | 5 | 8 |

TABLE A-continued

| | | | | | | | | | | | | | | | | | | | | | | | | | |
|---|---|---|---|---|---|---|---|---|---|---|---|---|---|---|---|---|---|---|---|---|---|---|---|---|---|
| Giant foxtail | 0 | 0 | 5 | 0 | 0 | 4 | 0 | 0 | 0 | 2 | 0 | 0 | 0 | 0 | 0 | 0 | 0 | 0 | 3 | 2 | 0 | 0 | 0 | 6 | 7 |
| Lambsquarters | — | — | — | — | — | — | — | 0 | 2 | 2 | 0 | 0 | 0 | 0 | 0 | 0 | 0 | 3 | 0 | 3 | 0 | 0 | 0 | 0 | 0 |
| Morningglory | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Nutsedge | 0 | 0 | — | 0 | 0 | 0 | 0 | 0 | 0 | 0 | 0 | 0 | 0 | 0 | 0 | 0 | — | 0 | — | 0 | 0 | 0 | 0 | — | 0 |
| Rape | — | — | — | — | — | — | — | 0 | 0 | 0 | 0 | 0 | 0 | 0 | 0 | 0 | 0 | 0 | 0 | 0 | 0 | 0 | 0 | 2 | 0 |
| Rice | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sorghum | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Soybean | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sugar beet | 0 | 0 | 0 | 0 | 0 | 0 | 0 | 0 | 0 | 0 | 0 | 0 | 0 | 0 | 2 | 2 | 0 | 0 | 0 | 0 | 0 | 0 | 0 | 2 | 2 |
| Velvetleaf | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild buckwheat | — | — | — | — | — | — | — | 0 | 0 | 0 | 0 | 0 | 0 | 0 | 0 | 0 | 0 | 0 | 0 | 0 | 0 | 0 | 0 | 0 | 0 |
| Wild oat | 0 | 0 | 0 | 0 | 0 | 0 | 0 | 0 | 0 | 0 | 0 | 0 | 0 | 0 | 0 | 0 | 0 | 0 | 0 | 0 | 2 | 0 | 0 | 0 | 0 |

| | Rate (50 g/ha) COMPOUND | | | | | | | | | | | | | | | | | | | | | | Rate (10 g/ha) COMPOUND |
|---|---|---|---|---|---|---|---|---|---|---|---|---|---|---|---|---|---|---|---|---|---|---|---|
| | 26 | 27 | 28 | 29 | 30 | 31 | 32 | 33 | 34 | 35 | 36 | 37 | 38 | 39 | 40 | 41 | 42 | 43 | 44 | 45 | 46 | 47 | 42 |
| PREEMERGENCE | | | | | | | | | | | | | | | | | | | | | | | |
| Barley | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Barnyardgrass | 10 | 10 | 10 | 10 | 0 | 0 | 0 | 0 | 6 | 8 | 10 | 6 | 0 | 0 | 5 | 10 | 0 | 10 | 8 | 1 | 0 | 2 | 0 |
| Bedstraw | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Blackgrass | 0 | 0 | 0 | 2 | 4 | 4 | 2 | 3 | 0 | 5 | 7 | 2 | 0 | 0 | 4 | 5 | 0 | 2 | 2 | 0 | 0 | 0 | 0 |
| Cheatgrass | 0 | 0 | 0 | — | 0 | 0 | 0 | 3 | 0 | 0 | 0 | 0 | 0 | 0 | 2 | 0 | 0 | 0 | 0 | 2 | 0 | 0 | 0 |
| Chickweed | 0 | 0 | 0 | 0 | 0 | 0 | 0 | 0 | 0 | 0 | 0 | 0 | 0 | 0 | 2 | — | — | 0 | 0 | 0 | 0 | 0 | 0 |
| Cocklebur | — | 0 | — | 0 | — | — | 0 | — | — | — | — | — | — | — | — | — | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 0 | 3 | 0 | 0 | 0 | 0 | 0 | 0 | 0 |
| Cotton | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 2 | 5 | 8 | 5 | 0 | 0 | 0 | 0 | 2 | 0 | 9 | 5 | 0 | 2 | 9 | 9 | 0 | 9 | 7 | 8 | 0 | 3 | 0 |
| Giant foxtail | 8 | 9 | 10 | 9 | 0 | 3 | 2 | 0 | 4 | 6 | 8 | 5 | 0 | 0 | 7 | 8 | 0 | 3 | 3 | 1 | 0 | 0 | 0 |
| Lambsquarters | 0 | 0 | 0 | 0 | 0 | 0 | 0 | 0 | 0 | 0 | 3 | 0 | 0 | 3 | — | 3 | 0 | 0 | 0 | 0 | 0 | 0 | 0 |
| Morningglory | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Nutsedge | 0 | 0 | 0 | 0 | 0 | 0 | 0 | 0 | 0 | 0 | 0 | 0 | 0 | 0 | 0 | 0 | 0 | 0 | — | 0 | 0 | 0 | 0 |
| Rape | 0 | 2 | 0 | 0 | 0 | 0 | 0 | 0 | 0 | 0 | 0 | 0 | 0 | 0 | 0 | 1 | 0 | 0 | 0 | 0 | 0 | 0 | 0 |
| Rice | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sorghum | 0 | 0 | 0 | 0 | 0 | 0 | 0 | 0 | 0 | 0 | 0 | 0 | 0 | 0 | 0 | 1 | 0 | 0 | 0 | 0 | 0 | 0 | 0 |
| Soybean | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sugar beet | 0 | 2 | 2 | 2 | 0 | 0 | 0 | 0 | 0 | 0 | 0 | 0 | 0 | 0 | 0 | 2 | 0 | 0 | 0 | 0 | 0 | 0 | 0 |
| Velvetleaf | 1 | 0 | 2 | 0 | 0 | 0 | 0 | 0 | 0 | 0 | 2 | 0 | 0 | 0 | 0 | 0 | 0 | 0 | 0 | 0 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild buckwheat | 0 | 0 | 0 | 0 | 0 | 0 | 0 | 0 | — | — | — | — | 0 | 0 | 0 | 0 | — | — | — | 0 | 0 | 0 | — |
| Wild oat | 0 | 2 | 3 | 2 | 0 | 0 | 0 | 0 | 0 | 0 | 0 | 0 | 0 | 0 | 2 | 0 | 0 | 3 | 0 | 0 | 0 | 0 | 0 |

TEST B

The compounds evaluated in this test were formulated in a non-phytoxic solvent and applied to the soil surface before plant seedlings emerged (preemergence application), to water that covered the soil surface (paddy application), and to plants that were in the one-to-four leaf stage (postemergence application). A sandy loam soil was used for the preemergence and postemergence tests, while a silt loam soil was used in the paddy test. Water depth was approximately 2.5 cm for the paddy test and was maintained at this level for the duration of the test.

Plant species in the preemergence and postemergence tests consisted of barley (*Hordeum vulgare*), bedstraw (*Galium aparine*), blackgrass (*Alopecurus myosuroides*), chickweed (*Stellaria media*), corn (*Zea mays*), cotton (*Gossypium hirsutum*), crabgrass (*Digitaria sanguinalis*), downy brome (*Bromus tectorum*), giant foxtail (*Setaria faberii*), lambsquarters (*Chenopodium album*), morningglory (*Ipomoea hederacea*), pigweed (*Amaranthus retroflexus*), rape (*Brassica napus*), ryegrass (*Lolium multiflorum*), sorghum (*Sorghum bicolor*), soybean (*Glycine max*), speedwell (*Veronica persica*), sugar beet (*Beta vulgaris*), velvetlead (*Abutilon theophrasti*), wheat (*Triticum aestivum*), wild buckwheat (*Polygonum convolvulus*), and wild oat (*Avena fatua*). All plant species were planted one day before application of the compound for the preemergence portion of this test. Plantings of these species were adjusted to produce plants of appropriate size for the postemergence portion of the test. Plant species in the paddy test consisted of barnyardgrass (*Echinochloa crus-galli*), rice (*Oryza sativa*), umbrella sedge (*Cyperus difformis*) and duck salad (*Heteranthera limosa*).

All plant species were grown using normal greenhouse practices. Visual evaluations of injury expressed on treated plants, when compared to untreated controls, were recorded approximately fourteen to twenty one days after application of the test compound. Plant response ratings, summarized in Table B, were recorded on a 0 to 10 scale where 0 is no effect and 10 is complete control. A dash (-) response means no test result.

TABLE B

| | Rate | | | | | | | | | | | | | | | | | | | |
|---|---|---|---|---|---|---|---|---|---|---|---|---|---|---|---|---|---|---|---|---|
| | (500 g/ha) | | (250 g/ha) | | | | | | | | (125 g/ha) | | | | | | | | (62 g/ha) | |
| | COMPOUND | | | | | | | | | | | | | | | | | | | |
| | 40 | 41 | 25 | 26 | 27 | 28 | 29 | 36 | 40 | 41 | 43 | 25 | 26 | 27 | 28 | 29 | 36 | 40 | 41 | 25 | 26 |
| POSTEMERGENCE | | | | | | | | | | | | | | | | | | | | | |
| Barley Igri | 4 | 1 | 1 | 2 | 0 | 2 | 0 | 0 | 4 | 0 | — | 0 | 0 | 0 | 0 | 0 | 0 | 2 | 0 | 0 | 0 |

5,407,901

TABLE B-continued

|  | | | | | | | | | | | | | | | | | | | | |
|---|---|---|---|---|---|---|---|---|---|---|---|---|---|---|---|---|---|---|---|---|
| Bedstraw | 0 | 8 | 2 | 0 | 0 | 2 | 2 | 5 | 0 | 6 | — | 2 | 0 | 0 | 0 | 0 | 0 | 3 | 1 | 0 |
| Blackgrass | 10 | 9 | 9 | 5 | 7 | 5 | 4 | 9 | 9 | 9 | — | 8 | 2 | 7 | 4 | 1 | 9 | 4 | 9 | 4 | 0 |
| Chickweed | 0 | 5 | 2 | 4 | 6 | 4 | 0 | 4 | 0 | 4 | — | 0 | 2 | 3 | 0 | 0 | 2 | 0 | 4 | 0 | 0 |
| Corn | 0 | — | 0 | 0 | 0 | 0 | 0 | 3 | 0 | 2 | — | 0 | 0 | 0 | 0 | 0 | 0 | 0 | 0 | 0 | 0 |
| Cotton | 0 | — | 0 | 0 | 0 | 0 | 0 | 4 | 0 | 0 | — | 0 | 0 | 0 | 0 | 0 | 0 | 0 | 0 | 0 | 0 |
| Crabgrass | 4 | 9 | 4 | 4 | 4 | 5 | 0 | 6 | 0 | 8 | — | 3 | 2 | 0 | 3 | 0 | 4 | 0 | 5 | 2 | 0 |
| Downy brome | 3 | 3 | 2 | 1 | 3 | 0 | 4 | 0 | 0 | 0 | — | 0 | 0 | 2 | 0 | 1 | 0 | 0 | 0 | 0 | 0 |
| Duck salad | 7 | 6 | 0 | 0 | 9 | 9 | 0 | 0 | 3 | 5 | 6 | 0 | 0 | 1 | 6 | 0 | 0 | 3 | 2 | 0 | 0 |
| Giant foxtail | 8 | 9 | 5 | 6 | 7 | 7 | 4 | 9 | 7 | 5 | — | 3 | 4 | 6 | 6 | 3 | 6 | 3 | 3 | 0 | 0 |
| Lambsquarters | 5 | 9 | 4 | 3 | 3 | 2 | 3 | 6 | 4 | 9 | — | 1 | 0 | 2 | 2 | 0 | 6 | 0 | 8 | 0 | 0 |
| Morningglory | 0 | — | 5 | 0 | 0 | 0 | 4 | 0 | 0 | 2 | — | 3 | 0 | 0 | 0 | 0 | 0 | 0 | 0 | 0 | 0 |
| Pigweed | 0 | 4 | 4 | 0 | 0 | 0 | 0 | 5 | 0 | 2 | — | 3 | 0 | 0 | 0 | 0 | 2 | 0 | 0 | 0 | 0 |
| Rape | 0 | 0 | 0 | 0 | 0 | 0 | 0 | 0 | 0 | 0 | — | 0 | 0 | 0 | 0 | 0 | 0 | 0 | 0 | 0 | 0 |
| Ryegrass | 9 | 9 | 7 | 2 | 3 | 4 | 2 | 2 | 7 | 7 | — | 4 | 2 | 1 | 2 | 0 | 0 | 4 | 6 | 2 | 0 |
| Sorghum | 7 | 4 | 0 | 0 | 0 | 0 | 0 | 3 | 3 | 3 | — | 0 | 0 | 0 | 0 | 0 | 2 | 2 | 2 | 0 | 0 |
| Soybean | 0 | — | 0 | 0 | 0 | 3 | 0 | 0 | 0 | 2 | — | 0 | 0 | 0 | 2 | 0 | 0 | 0 | 0 | 0 | 0 |
| Speedwell | 0 | 5 | 6 | 5 | 0 | 2 | 0 | 8 | 0 | 5 | — | 2 | 2 | 0 | 0 | 0 | 5 | 0 | 3 | 0 | 0 |
| Sugar beet | 7 | 8 | 3 | 0 | 0 | 0 | 0 | 2 | 0 | 0 | — | 2 | 0 | 0 | 0 | 0 | 0 | 0 | 0 | 0 | 0 |
| Velvetleaf | 0 | 6 | 4 | 6 | 0 | 0 | 4 | 6 | 0 | 4 | — | 3 | 3 | 0 | 0 | 0 | 4 | 0 | 2 | 0 | 2 |
| Wheat | 4 | 3 | 0 | 1 | 0 | 1 | 3 | 0 | 4 | 3 | — | 2 | 0 | 0 | 0 | 0 | 0 | 2 | 3 | 0 | 0 |
| Wild buckwheat | — | 9 | 3 | 0 | 0 | 0 | 3 | 7 | — | 8 | — | 2 | 0 | 0 | 0 | 0 | 7 | — | 7 | 0 | |
| Wild oat | 3 | 2 | 2 | 2 | 1 | 0 | 0 | 0 | 0 | 2 | — | 0 | 0 | 0 | 0 | 0 | 0 | 0 | 0 | 0 | 0 |
| Barnyardgrass | 10 | 10 | 9 | 9 | 9 | 9 | 10 | 10 | 10 | 10 | 9 | 9 | 9 | 9 | 9 | 9 | 10 | 9 | 10 | 9 | 9 |
| Rice Japonica | 8 | 9 | 0 | 6 | 6 | 2 | 0 | 2 | 8 | 8 | 9 | 0 | 0 | 2 | 0 | 0 | 1 | 7 | 7 | 0 | 0 |
| Umbrella sedge | 9 | 9 | 8 | 9 | 9 | 9 | 9 | 6 | 9 | 9 | 9 | 7 | 9 | 9 | 9 | 9 | 2 | 9 | 8 | 5 | 9 |

| | Rate | | | | | | | | | | | | | | | | | | | | |
|---|---|---|---|---|---|---|---|---|---|---|---|---|---|---|---|---|---|---|---|---|---|
| | (62 g/ha) | | | | | | | (31 g/ha) | | | | | | | | (16 g/ha) | | | | | | (4 g/ha) |
| | COMPOUND | | | | | | | | | | | | | | | | | | | | | |
| | 27 | 28 | 29 | 36 | 40 | 41 | 43 | 25 | 26 | 27 | 28 | 29 | 36 | 40 | 41 | 25 | 26 | 27 | 28 | 29 | 36 | 43 | 43 |
| | POSTEMERGENCE | | | | | | | | | | | | | | | | | | | | | |
| Barley Igri | 0 | 0 | 0 | 0 | 0 | 0 | — | 0 | 0 | 0 | 0 | 0 | 0 | 0 | 0 | 0 | 0 | 0 | 0 | 0 | 0 | — | — |
| Bedstraw | 0 | 0 | 0 | 0 | 0 | 0 | — | 0 | 0 | 0 | 0 | 0 | 0 | 0 | 0 | 0 | 0 | 0 | 0 | 0 | 0 | — | — |
| Blackgrass | 2 | 1 | 0 | 3 | 0 | 9 | — | 2 | 0 | 2 | 0 | 0 | 0 | 0 | 4 | 0 | 0 | 0 | 0 | 0 | 0 | — | — |
| Chickweed | 0 | 0 | 0 | 0 | 0 | 2 | — | 0 | 0 | 0 | 0 | 0 | 0 | 0 | 0 | 0 | 0 | 0 | 0 | 0 | 0 | — | — |
| Corn | 0 | 0 | 0 | 0 | 0 | 0 | — | 0 | 0 | 0 | 0 | 0 | 0 | 0 | 0 | 0 | 0 | 0 | 0 | 0 | 0 | — | — |
| Cotton | 0 | 0 | 0 | 0 | 0 | 0 | — | 0 | 0 | 0 | 0 | 0 | 0 | 0 | 0 | 0 | 0 | 0 | 0 | 0 | 0 | — | — |
| Crabgrass | 0 | 3 | 0 | 2 | 0 | 4 | — | 0 | 0 | 0 | 0 | 0 | 0 | 0 | 0 | 0 | 0 | 0 | 0 | 0 | 0 | — | — |
| Downy brome | 0 | 0 | 0 | 0 | 0 | 0 | — | 0 | 0 | 0 | 0 | 0 | 0 | 0 | 0 | 0 | 0 | 0 | 0 | 0 | 0 | — | — |
| Duck salad | 0 | 2 | 0 | 0 | 0 | 0 | 0 | 0 | 0 | 0 | 0 | 0 | 0 | 0 | 0 | 0 | 0 | 0 | 0 | 0 | 0 | 0 | 0 |
| Giant foxtail | 0 | 3 | 0 | 2 | 0 | 3 | — | 0 | 0 | 0 | 3 | 0 | 0 | 0 | 0 | 0 | 0 | 0 | 0 | 0 | 0 | — | — |
| Lambsquarters | 0 | 0 | 0 | 2 | 0 | 8 | — | 0 | 0 | 0 | 0 | 0 | 2 | 0 | 8 | 0 | 0 | 0 | 0 | 0 | 0 | — | — |
| Morningglory | 0 | 0 | 0 | 0 | 0 | 0 | — | 0 | 0 | 0 | 0 | 0 | 0 | 0 | 0 | 0 | 0 | 0 | 0 | 0 | 0 | — | — |
| Pigweed | 0 | 0 | 0 | 0 | 0 | 0 | — | 0 | 0 | 0 | 0 | 0 | 0 | 0 | 0 | 0 | 0 | 0 | 0 | 0 | 0 | — | — |
| Rape | 0 | 0 | 0 | 0 | 0 | 0 | — | 0 | 0 | 0 | 0 | 0 | 0 | 0 | 0 | 0 | 0 | 0 | 0 | 0 | 0 | — | — |
| Ryegrass | 0 | 0 | 0 | 0 | 2 | 4 | — | 0 | 0 | 0 | 0 | 0 | 0 | 0 | 0 | 0 | 0 | 0 | 0 | 0 | 0 | — | — |
| Sorghum | 0 | 0 | 0 | 2 | 0 | 0 | — | 0 | 0 | 0 | 0 | 0 | 0 | 0 | 0 | 0 | 0 | 0 | 0 | 0 | 0 | — | — |
| Soybean | 0 | 0 | 0 | 0 | 0 | 0 | — | 0 | 0 | 0 | 0 | 0 | 0 | 0 | 0 | 0 | 0 | 0 | 0 | 0 | 0 | — | — |
| Speedwell | 0 | 0 | 0 | 5 | 0 | 3 | — | 0 | 0 | 0 | 0 | 0 | 3 | 0 | 0 | 0 | 0 | 0 | 0 | 0 | 3 | — | — |
| Sugar beet | 0 | 0 | 0 | 0 | 0 | 0 | — | 0 | 0 | 0 | 0 | 0 | 0 | 0 | 0 | 0 | 0 | 0 | 0 | 0 | 0 | — | — |
| Velvetleaf | 0 | 0 | 0 | 0 | 0 | 0 | — | 0 | 0 | 0 | 0 | 0 | 0 | 0 | 0 | 0 | 0 | 0 | 0 | 0 | 0 | — | — |
| Wheat | 0 | 0 | 0 | 0 | 0 | 0 | — | 0 | 0 | 0 | 0 | 0 | 0 | 0 | 0 | 0 | 0 | 0 | 0 | 0 | 0 | — | — |
| Wild buckwheat | 0 | 0 | 0 | 3 | 0 | 7 | — | 0 | 0 | 0 | 0 | 0 | 3 | 0 | 5 | 0 | 0 | 0 | 0 | 0 | 0 | — | — |
| Wild oat | 0 | 0 | 0 | 0 | 0 | 0 | — | 0 | 0 | 0 | 0 | 0 | 0 | 0 | 0 | 0 | 0 | 0 | 0 | 0 | 0 | — | — |
| Barnyardgrass | 9 | 9 | 9 | 10 | 8 | 9 | 9 | 9 | 9 | 9 | 9 | 7 | 9 | 6 | 9 | 9 | 7 | 7 | 9 | 0 | 9 | 8 | 8 |
| Rice Japonica | 0 | 0 | 0 | 0 | 3 | 5 | 6 | 0 | 0 | 0 | 0 | 0 | 0 | 1 | 3 | 0 | 0 | 0 | 0 | 0 | 0 | 1 | 0 |
| Umbrella sedge | 9 | 9 | 9 | 0 | 9 | 8 | 8 | 0 | 0 | 8 | 8 | 0 | 0 | 6 | 7 | 0 | 0 | 0 | 7 | 0 | 0 | 0 | 0 |

| | Rate | | | | | | | | | | | | | | | | | | |
|---|---|---|---|---|---|---|---|---|---|---|---|---|---|---|---|---|---|---|---|
| | (500 g/ha) | | (250 g/ha) | | | | | | | | | (125 g/ha) | | | | | | | |
| | COMPOUND | | | | | | | | | | | | | | | | | | |
| | 40 | 41 | 25 | 26 | 27 | 28 | 29 | 36 | 40 | 41 | 43 | 25 | 26 | 27 | 28 | 29 | 36 | 40 | 41 |
| | PREEMERGENCE | | | | | | | | | | | | | | | | | | |
| Barley Igri | 5 | 3 | 0 | 0 | 0 | 0 | 0 | 0 | 2 | 1 | 2 | 0 | 0 | 0 | 0 | 0 | 0 | 0 | 0 |
| Bedstraw | — | — | 0 | 4 | 3 | 0 | 3 | 7 | 2 | 0 | 9 | 0 | 0 | 0 | 0 | 0 | 5 | 0 | 0 |
| Blackgrass | 10 | 10 | 10 | 8 | 8 | 10 | 7 | 10 | 10 | 10 | 10 | 10 | 7 | 7 | 10 | 5 | 10 | 10 | 10 |
| Chickweed | 9 | 7 | 6 | 8 | 8 | 7 | 5 | 9 | 9 | 7 | 9 | 4 | 7 | 7 | 6 | 3 | 0 | 4 | 5 |
| Corn | 2 | 9 | 2 | 0 | 2 | 2 | 0 | 2 | 0 | 6 | 6 | 0 | 0 | 0 | 0 | 0 | 0 | 0 | 2 |
| Cotton | 0 | 2 | 0 | 3 | 0 | 0 | 0 | 0 | 0 | 2 | 7 | 0 | 2 | 0 | 0 | 0 | 0 | 0 | 0 |
| Crabgrass | 10 | 10 | 10 | 9 | 10 | 10 | 10 | 10 | 10 | 10 | 10 | 9 | 8 | 10 | 10 | 8 | 8 | 8 | 10 |
| Downy brome | 9 | 7 | 3 | 0 | 3 | 6 | 0 | 4 | 9 | 6 | 6 | 0 | 0 | 2 | 5 | 0 | 0 | 4 | 4 |
| Duck salad | — | — | — | — | — | — | — | — | — | — | — | — | — | — | — | — | — | — | — |
| Giant foxtail | 9 | 10 | 10 | 9 | 9 | 10 | 9 | 10 | 7 | 10 | 10 | 9 | 9 | 8 | 10 | 9 | 8 | 6 | 10 |
| Lambsquarters | 9 | 9 | 7 | 8 | 6 | 7 | 0 | 8 | 9 | 9 | 9 | 5 | 3 | 5 | 6 | 0 | 4 | — | 8 |
| Morningglory | 0 | 0 | 3 | 0 | 2 | 2 | 0 | 6 | 0 | 0 | 0 | 2 | 0 | 0 | 2 | 0 | 4 | 0 | 0 |
| Pigweed | 7 | 9 | 0 | 0 | 7 | 6 | 7 | 4 | 4 | 8 | 7 | 0 | 0 | 2 | 3 | 5 | 1 | 4 | 8 |
| Rape | 0 | 6 | 0 | 0 | 0 | 0 | 0 | 3 | 0 | 5 | 0 | 0 | 0 | 0 | 0 | 0 | 0 | 0 | 4 |
| Ryegrass | 10 | 10 | 10 | 10 | 6 | 10 | 6 | 9 | 10 | 9 | 10 | 7 | 7 | 5 | 10 | 4 | 9 | 8 | 7 |
| Sorghum | 5 | 4 | 4 | 2 | 5 | 4 | 0 | 6 | 4 | 2 | 3 | 2 | 0 | 3 | 2 | 0 | 4 | 1 | 2 |
| Soybean | 0 | 4 | 2 | — | 0 | 0 | — | 0 | 0 | 0 | 4 | 0 | — | 0 | 0 | 0 | 0 | 0 | 0 |

TABLE B-continued

|  | \multicolumn{17}{c}{} |
|---|---|---|---|---|---|---|---|---|---|---|---|---|---|---|---|---|---|
| Speedwell | 9 | 8 | 5 | 7 | 6 | 7 | 3 | 6 | 9 | 8 | 6 | 3 | 3 | 2 | 5 | 0 | 5 | 4 | 5 |
| Sugar beet | 9 | 7 | 0 | 0 | 4 | 4 | 3 | 6 | 6 | 7 | 4 | 0 | 0 | 3 | 3 | 2 | 3 | 0 | 3 |
| Velvetleaf | 5 | 8 | 5 | 8 | 3 | 7 | 4 | 5 | 2 | 8 | 8 | 2 | 3 | 2 | 5 | 2 | 3 | 2 | 7 |
| Wheat | 5 | 2 | 3 | 0 | 3 | 0 | 3 | 0 | 0 | 2 | 5 | 3 | 0 | 0 | 0 | 0 | 0 | 0 | 0 |
| Wild buckwheat | — | 9 | 0 | 5 | 6 | 5 | 3 | 9 | 0 | 9 | 8 | 0 | 3 | 4 | 3 | 0 | 5 | 0 | 5 |
| Wild oat | 4 | 5 | 0 | 3 | 3 | 6 | 3 | 5 | 4 | 5 | 5 | 0 | 0 | 0 | 4 | 0 | 3 | 4 | 3 |
| Barnyardgrass | — | — | — | — | — | — | — | — | — | — | — | — | — | — | — | — | — | — | — |
| Rice Japonica | — | — | — | — | — | — | — | — | — | — | — | — | — | — | — | — | — | — | — |
| Umbrella sedge | — | — | — | — | — | — | — | — | — | — | — | — | — | — | — | — | — | — | — |

| | Rate | | | |
|---|---|---|---|---|
| | (62 g/ha) | (31 g/ha) | (16 g/ha) | (4 g/ha) |
| | COMPOUND | | | |
| | 25 26 27 28 29 36 40 41 43 | 25 26 27 28 29 36 40 41 | 25 26 27 28 29 36 43 | 43 |
| | PREEMERGENCE | | | |
| Barley Igri | 0 0 0 0 0 0 0 0 | 0 0 0 0 0 0 0 0 | 0 0 0 0 0 0 0 | 0 |
| Bedstraw | 0 0 0 0 0 2 0 0 | 2 0 0 0 0 0 0 0 | 0 0 0 0 0 . 0 0 | 0 |
| Blackgrass | 8 4 6 8 4 10 8 10 | 6 6 3 4 5 3 5 1 | 9 3 0 3 4 3 4 0 | 0 |
| Chickweed | 3 4 6 5 2 0 0 5 | 2 0 0 4 4 0 0 0 | 2 0 0 0 3 0 0 0 | 0 |
| Corn | 0 0 0 0 0 0 0 0 | 3 0 0 0 0 0 0 0 | 0 0 0 0 0 0 0 0 | 0 |
| Cotton | 0 0 0 0 0 0 0 0 | 4 0 0 0 0 0 0 0 | 0 0 0 0 0 0 0 0 | 0 |
| Crabgrass | 9 5 9 10 8 8 6 10 | 9 8 — 8 9 5 7 2 | 9 6 2 5 7 5 5 5 | 0 |
| Downy brome | 0 0 0 3 0 0 4 0 | 4 0 0 0 0 0 0 0 | 0 0 0 0 0 0 0 0 | 0 |
| Duck salad | — — — — — — — — | — — — — — — — — | — — — — — — — | — |
| Giant foxtail | 8 6 7 10 8 7 3 10 | 8 6 4 7 8 6 7 0 | 8 4 2 5 5 5 3 4 | 0 |
| Lambsquarters | 4 3 4 2 0 4 — 8 | 8 3 3 3 0 0 2 8 | 7 0 3 0 0 0 0 7 | 0 |
| Morningglory | 0 0 0 0 0 0 0 0 | 0 0 0 0 0 0 0 0 | 0 0 0 0 0 0 0 0 | 0 |
| Pigweed | 0 0 2 0 2 0 2 6 | 3 0 0 0 0 0 0 2 | 4 0 0 0 0 0 0 0 | 0 |
| Rape | 0 0 0 0 0 0 0 4 | 0 0 0 0 0 0 0 0 | 0 0 0 0 0 0 0 0 | 0 |
| Ryegrass | 6 4 4 . 6 3 2 8 3 | 4 4 3 4 4 0 0 3 | 3 0 3 3 0 0 3 0 | 0 |
| Sorghum | 0 0 2 0 0 2 0 0 | 0 0 0 0 0 0 2 0 | 0 0 0 0 0 0 0 0 | 0 |
| Soybean | 0 0 0 0 0 0 0 0 | 0 0 0 0 0 0 0 0 | 0 0 0 0 0 0 0 0 | 0 |
| Speedwell | 0 0 0 3 0 2 0 3 | 6 0 0 0 0 0 3 0 | 0 0 0 0 0 0 0 2 | 0 |
| Sugar beet | 0 0 0 0 0 3 0 2 | 4 0 0 0 0 0 3 0 | 0 0 0 0 0 0 0 2 | 0 |
| Velvetleaf | 0 2 0 2 2 3 0 5 | 6 0 0 0 0 0 3 0 | 3 0 0 0 0 0 0 3 | 0 |
| Wheat | 0 0 0 0 0 0 0 0 | 2 0 0 0 0 0 0 0 | 0 0 0 0 0 0 0 0 | 0 |
| Wild buckwheat | 0 0 4 0 0 4 0 3 | 0 0 0 3 0 0 — 0 | 0 0 0 0 3 0 0 — | 0 |
| Wild oat | 0 0 0 0 0 0 0 2 | 0 0 0 0 0 0 0 0 | 0 . 0 0 0 0 0 0 | 0 |
| Barnyardgrass | — — — — — — — — | — — — — — — — — | — — — — — — — | — |
| Rice Japonica | — — — — — — — — | — — — — — — — — | — — — — — — — | — |
| Umbrella sedge | — — — — — — — — | — — — — — — — — | — — — — — — — | — |

TEST C scale where 0 is no effect and 10 is complete control. A dash (-) response means no test result.

TABLE C

| | Rate (500 g/ha) | | | Rate (250 g/ha) | | | Rate (125 g/ha) | | | Rate (64 g/ha) | | | Rate (32 g/ha) | | |
|---|---|---|---|---|---|---|---|---|---|---|---|---|---|---|---|
| | COMPOUND | | | | | | | | | | | | | | |
| | 25 | 27 | 28 | 25 | 27 | 28 | 25 | 27 | 28 | 25 | 27 | 28 | 25 | 27 | 28 |
| PADDY | | | | | | | | | | | | | | | |
| Arrowhead | — | 8 | 8 | — | 6 | 5 | — | 3 | 2 | — | 0 | 1 | — | 0 | 0 |
| Barnyardgrass | 10 | 10 | 10 | 8 | 10 | 10 | 7 | 10 | 10 | 7 | 7 | 9 | 5 | 6 | 8 |
| Duck salad | 10 | — | 10 | 10 | — | 10 | 6 | — | 10 | 4 | — | 10 | 0 | — | 9 |
| Japonica rice | 1 | 4 | 2 | 1 | 3 | 4 | 0 | 1 | 1 | 0 | 0 | 0 | 0 | 0 | 0 |
| Umbrella sedge | 8 | 9 | 9 | 9 | 9 | 9 | 8 | 9 | 9 | 7 | 8 | 9 | 0 | 7 | 8 |
| Waterchestnut | 3 | 3 | 7 | 3 | 3 | 7 | 0 | 2 | 4 | 0 | 0 | 1 | 0 | 0 | 0 |

Plastic pots were partially filled with silt loam soil. The soil was then saturated with water. Japonica rice (*Oryza sativa*) seedlings at the 2.0 to 2.5 leaf stage, seeds selected from barnyardgrass (*Echinochloa crus-galli*), duck salad (*Heteranthera limosa*), umbrella sedge (*Cyperus difformis*), and tubers selected from arrowhead (*Sagittaria* spp.), and waterchestnut (*Eleocharis* spp.), were planted into this soil. After planting, water levels were raised to 3 cm above the soil surface and maintained at this level throughout the test. The compounds indicated were formulated in a non-phytotoxic solvent and applied directly to the paddy water. Treated plants and controls were maintained in a greenhouse for approximately 21 days, after which all species were compared to controls and visually evaluated. Plant response ratings, summarized in Table C, are reported on a 0 to 10

TEST D

Plastic pots were partially filled with silt loam soil. The soil was then flooded with water, Japonica rice (*Oryza sativa*) sprouted seeds and 1.5 leaf transplants were planted in the soil. Seeds of barnyardgrass (*Echinochloa crus-galli*) were planted in saturated soil and plants grown to the 1 leaf, 2 leaf and 3 leaf stages for testing. At testing, the water level for all plantings was raised to 2 cm above the soil surface. The compounds indicated were formulated in a non-phytotoxic solvent and applied directly to the paddy water. Treated plants and controls were maintained in a greenhouse for approximately 21 days, after which all species were compared to controls and visually evaluated. Plant response ratings, summarized in Table D are reported on a 0 to 10 scale where 0 is no effect and 10 is complete control. A dash (-) response means no test result.

TABLE D

| | COMPOUND | | | | |
|---|---|---|---|---|---|
| Rate (1000 g/ha) | 26 | 27 | 28 | 29 | 36 |
| PADDY | | | | | |
| 1-LF B.Y.Grass | 10 | 10 | 10 | 10 | 10 |
| 2-LF B.Y.Grass | 10 | 10 | 10 | 10 | 10 |
| 3-lf B.Y.Grass | 10 | 10 | 10 | 10 | 9 |
| Jap Direct Seed | 9 | 9 | 9 | 7 | 9 |
| Jap Rice Eff | 6 | 8 | 5 | 3 | 0 |

| | COMPOUND | | | | | | |
|---|---|---|---|---|---|---|---|
| Rate (500 g/ha) | 25 | 26 | 27 | 28 | 29 | 36 | 43 |
| PADDY | | | | | | | |
| 1-LF B.Y.Grass | 10 | 10 | 10 | 10 | 10 | 10 | — |
| 2-LF B.Y.Grass | 10 | 10 | 10 | 10 | 9 | 9 | 10 |
| 3-lf B.Y.Grass | 9 | 9 | 10 | 10 | 10 | 8 | 10 |
| Jap Direct Seed | 6 | 7 | 8 | 8 | 6 | 6 | 10 |
| Jap Rice Eff | 4 | 2 | 5 | 5 | 0 | 0 | 4 |

| | COMPOUND | | | | | | |
|---|---|---|---|---|---|---|---|
| Rate (250 g/ha) | 25 | 26 | 27 | 28 | 29 | 36 | 43 |
| PADDY | | | | | | | |
| 1-LF B.Y.Grass | 10 | 10 | 10 | 10 | 10 | 10 | — |
| 2-LF B.Y.Grass | 9 | 10 | 10 | 10 | 10 | 9 | 10 |
| 3-lf B.Y.Grass | 8 | 9 | 10 | 10 | 10 | 7 | 10 |
| Jap Direct Seed | 4 | 7 | 5 | 5 | 4 | 5 | 10 |
| Jap Rice Eff | 5 | 2 | 0 | 3 | 0 | 0 | 2 |

| | COMPOUND | | | | | | | |
|---|---|---|---|---|---|---|---|---|
| Rate (125 g/ha) | 25 | 26 | 27 | 28 | 29 | 36 | 41 | 43 |
| PADDY | | | | | | | | |
| 1-LF B.Y.Grass | 9 | 10 | 10 | 10 | 10 | 10 | — | — |
| 2-LF B.Y.Grass | 6 | 6 | 10 | 10 | 9 | 9 | 8 | 10 |
| 3-lf B.Y.Grass | 6 | 6 | 9 | 10 | 7 | 7 | 9 | 9 |
| Jap Direct Seed | 2 | 2 | 1 | 2 | 2 | 1 | 8 | 8 |
| Jap Rice Eff | 0 | 0 | 1 | 0 | 0 | 0 | 1 | 2 |

| | COMPOUND | | | | | | | |
|---|---|---|---|---|---|---|---|---|
| Rate (64 g/ha) | 25 | 26 | 27 | 28 | 29 | 36 | 41 | 43 |
| PADDY | | | | | | | | |
| 1-LF B.Y.Grass | 9 | 9 | 10 | 10 | 9 | 10 | — | — |
| 2-LF B.Y.Grass | 8 | 5 | 9 | 8 | 9 | 8 | 8 | 9 |
| 3-lf B.Y.Grass | 4 | 4 | 7 | 8 | 7 | 5 | 7 | 7 |
| Jap Direct Seed | 5 | 0 | 1 | 1 | 1 | 0 | 7 | 7 |
| Jap Rice Eff | 0 | 0 | 0 | 0 | 0 | 0 | 0 | 0 |

| | COMPOUND | | |
|---|---|---|---|
| Rate (32 g/ha) | 25 | 41 | 43 |
| PADDY | | | |
| 1-LF B.Y.Grass | 9 | — | — |
| 2-LF B.Y.Grass | 3 | 4 | 8 |
| 3-lf B.Y.Grass | 2 | 3 | 6 |
| Jap Direct Seed | 0 | 0 | 5 |
| Jap Rice Eff | 0 | 0 | 1 |

| | COMPOUND |
|---|---|
| Rate (16 g/ha) | 41 |
| PADDY | |
| 2-LF B.Y.Grass | 3 |
| 3-lf B.Y.Grass | 0 |
| Jap Direct Seed | 0 |
| Jap Rice Eff | 1 |

| | COMPOUND |
|---|---|
| Rate (8 g/ha) | 41 |
| PADDY | |
| 2-LF B.Y.Grass | 0 |
| 3-lf B.Y.Grass | 0 |
| Jap Direct Seed | 0 |
| Jap Rice Eff | 0 |

TEST E

Seeds of barnyardgrass (*Echinochloa crus-galli*), corn (*Zea mays*), cotton (*Gossypium hirsutam*), crabgrass (Digitaria spp.), fall panicum (*Panicum dicholomiflorum*), giant foxtail (*Setaria faberii*), green foxtail (*Setaria vividis*), johnson grass (*Sorghum halepense*), signalgrass (*Brachiaria platyphylla*), soybean (*Glycine max*) and wild proso (*Pancium miliaceum*) were planted into a silt loam soil. The compounds indicated were dissolved in a non-phytotoxic solvent, and then applied to the soil surface within one day after the seeds were planted.

Treated plants and untreated controls were maintained in the greenhouse approximately 21 days, then treated plants were compared to untreated controls and visually evaluated. Plant response ratings, summarized in Table E, are reported on a 0 to 10 scale where 0 is no effect and 10 is complete control.

TABLE E

| | COMPOUND | | COMPOUND |
|---|---|---|---|
| Rate (500 g/ha) | 28 | Rate (250 g/ha) | 28 |
| PRE-EMERGENCE | | PRE-EMERGENCE | |
| Barnyardgrass | 10 | Green Foxtail | 10 |
| Corn | 6 | Johnson Grass | 8 |
| Cotton | 0 | Signalgrass | 10 |
| Crabgrass | 10 | Soybean | 0 |
| Fall Panicum | 10 | Wild Proso | 10 |
| Giant Foxtail | 10 | Rate (125 g/ha) | 28 |
| Green Foxtail | 10 | PRE-EMERGENCE | |
| Johnson Grass | 9 | | |
| Signalgrass | 10 | Barnyardgrass | 10 |
| Soybean | 1 | Corn | 2 |
| Wild Proso | 10 | Cotton | 0 |
| Rate (250 g/ha) | 28 | Crabgrass | 8 |
| PRE-EMERGENCE | | Fall Panicum | 10 |
| | | Giant Foxtail | 10 |
| Barnyardgrass | 10 | Green Foxtail | 8 |
| Corn | 5 | Johnson Grass | 7 |
| Cotton | 0 | Signalgrass | 10 |
| Crabgrass | 10 | Soybean | 0 |
| Fall Panicum | 10 | Wild Proso | 9 |
| Giant Foxtail | 10 | | |
| Rate (62 g/ha) | 28 | Rate (31 g/ha) | 28 |
| PRE-EMERGENCE | | PRE-EMERGENCE | |
| Barnyardgrass | 10 | Barnyardgrass | 10 |
| Corn | 1 | Corn | 0 |
| Cotton | 0 | Cotton | 0 |
| Crabgrass | 7 | Crabgrass | 6 |
| Fall Panicum | 10 | Fall Panicum | 8 |
| Giant Foxtail | 8 | Giant Foxtail | 8 |
| Green Foxtail | 6 | Green Foxtail | 4 |
| Johnson Grass | 2 | Johnson Grass | 0 |
| Signalgrass | 9 | Signalgrass | 9 |
| Soybean | 0 | Soybean | 0 |
| Wild Proso | 9 | Wild Proso | 9 |

TEST F

Compounds evaluated in this test were formulated in a non-phytotoxic solvent and applied to the soil surface before plant seedlings emerged (preemergence application) and to plants that were in the one-to-four leaf stage (postemergence application). A sandy loam soil was used for the preemergence test while a mixture of sandy loam soil and greenhouse potting mix in a 60:40 ratio was used for the postemergence test. Test compounds were applied within approximately one day after planting seeds for the preemergence test. Plantings of these crops and weed species were adjusted to produce plants of appropriate size for the postemergence test. All plant species were grown using normal greenhouse practices. Crop and weed species include winter barley (*Hordeum vulgare* cv. 'Igri'), blackgrass (*Alopecurus myosuroides*), chickweed (*Stellaria media*), downy brome (*Bromus tectorum*), field violet (*Viola aryensis*), galium (*Galium aparine*), green foxtail (*Setaria viridis*), kochia (*Kochia scoparia*), lambsquarters (*Chenopodium album*), Persian speedwell (*Veronica persica*), rape (*Brassica napus* cv. 'Jet Neuf'), ryegrass (*Lolium multiflorum*), sugar beet (*Beta vulgaris* cv. 'US1'), sunflower (*Helianthus annuus* cv. 'Russian Giant'), spring wheat (*Triticum aestivum* cv. 'ERA'), winter wheat (*Triticum aestivum* cv. 'Talent'), wild buckwheat (*Polygonum convolvulus*), wild mustard (*Sinapis arvensis*), wild oat (*Avena fatua*), and wild radish (*Raphanus raphanistrum*). Blackgrass and wild oat were treated postemergence at two growth stages. The first stage (1) was when the plants had two to three leaves. The second stage (2) was when the plants had approximately four leaves or in the initial stages of tillering. Treated plants and untreated controls were maintained in a greenhouse for approximately 21 to 28 days, after which all treated plants were compared to untreated controls and visually evaluated. Plant response ratings, summarized in Table F, are based upon a 0 to 10 scale where 0 is no effect and 10 is complete control. A dash response (-) means no test result.

TABLE F

| | COMPOUND | | COMPOUND |
|---|---|---|---|
| Rate (500 g/ha) POST-EMERGENCE | 41 | Rate (500 g/ha) PRE-EMERGENCE | 41 |
| Blackgrass (1) | 5 | Blackgrass (1) | 9 |
| Blackgrass (2) | 5 | Blackgrass (2) | 8 |
| Chickweed | 3 | Chickweed | 9 |
| Downy brome | 0 | Downy brome | 4 |
| Field violet | 4 | Field violet | 9 |
| Galium (1) | 3 | Galium (1) | 8 |
| Galium (2) | 3 | Galium (2) | 8 |
| Green foxtail | 0 | Green foxtail | 10 |
| Kochia | 4 | Kochia | 10 |
| Lambsquarters | 5 | Lambsquarters | — |
| Persn Speedwell | 2 | Persn Speedwell | 7 |
| Rape | 0 | Rape | 6 |
| Ryegrass | 2 | Ryegrass | 10 |
| Sugar beet | 4 | Sugar beet | 8 |
| Sunflower | 2 | Sunflower | 2 |
| Wheat (Spring) | 3 | Wheat (Spring) | 3 |
| Wheat (Winter) | 2 | Wheat (Winter) | 2 |
| Wild buckwheat | 5 | Wild buckwheat | 8 |
| Wild mustard | 3 | Wild mustard | 5 |
| Wild oat (1) | 2 | Wild oat (1) | 5 |
| Wild oat (2) | 2 | Wild oat (2) | 6 |
| Wild radish | 0 | Wild radish | 2 |
| Winter Barley | 2 | Winter Barley | 3 |
| | COMPOUND | | COMPOUND |
| Rate (250 g/ha) POST-EMERGENCE | 41 | Rate (250 g/ha) PRE-EMERGENCE | 41 |
| Blackgrass (1) | 3 | Blackgrass (1) | 7 |
| Blackgrass (2) | 3 | Blackgrass (2) | 6 |
| Chickweed | 2 | Chickweed | 7 |
| Downy brome | 0 | Downy brome | 0 |
| Field violet | 2 | Field violet | 7 |
| Galium (1) | 0 | Galium (1) | 6 |
| Galium (2) | 0 | Galium (2) | 5 |
| Green foxtail | 0 | Green foxtail | 10 |
| Kochia | 2 | Kochia | 7 |
| Lambsquarters | 3 | Lambsquarters | — |
| Persn Speedwell | 0 | Persn Speedwell | 5 |
| Rape | 0 | Rape | 4 |
| Ryegrass | 0 | Ryegrass | 8 |
| Sugar beet | 2 | Sugar beet | 6 |
| Sunflower | 0 | Sunflower | 0 |
| Wheat (Spring) | 0 | Wheat (Spring) | 0 |
| Wheat (Winter) | 0 | Wheat (Winter) | 0 |
| Wild buckwheat | 4 | Wild buckwheat | 6 |
| Wild mustard | 0 | Wild mustard | 4 |
| Wild oat (1) | 0 | Wild oat (1) | 2 |
| Wild oat (2) | 0 | Wild oat (2) | 3 |
| Wild radish | 0 | Wild radish | 0 |
| Winter Barley | 0 | Winter Barley | 0 |
| | COMPOUND | | COMPOUND |
| Rate (125 g/ha) POST-EMERGENCE | 41 | Rate (64 g/ha) POST-EMERGENCE | 41 |
| Blackgrass (1) | 0 | Blackgrass (1) | 0 |
| Blackgrass (2) | 0 | Blackgrass (2) | 0 |
| Chickweed | 0 | Chickweed | 0 |
| Downy brome | 0 | Downy brome | 0 |
| Field violet | 0 | Field violet | 0 |
| Galium (1) | 0 | Galium (1) | 0 |
| Galium (2) | 0 | Galium (2) | 0 |
| Green foxtail | 0 | Green foxtail | 0 |
| Kochia | 0 | Kochia | 0 |
| Lambsquarters | 2 | Lambsquarters | 0 |
| Persn Speedwell | 0 | Persn Speedwell | 0 |
| Rape | 0 | Rape | 0 |
| Ryegrass | 0 | Ryegrass | 0 |
| Sugar beet | 0 | Sugar beet | 0 |
| Sunflower | 0 | Sunflower | 0 |
| Wheat (Spring) | 0 | Wheat (Spring) | 0 |
| Wheat (Winter) | 0 | Wheat (Winter) | 0 |
| Wild buckwheat | 2 | Wild buckwheat | 0 |
| Wild mustard | 0 | Wild mustard | 0 |
| Wild oat (1) | 0 | Wild oat (1) | 0 |
| Wild oat (2) | 0 | Wild oat (2) | 0 |
| Wild radish | 0 | Wild radish | 0 |
| Winter Barley | 0 | Winter Barley | 0 |
| | COMPOUND | | COMPOUND |
| Rate (64 g/ha) PRE-EMERGENCE | 41 | Rate (32 g/ha) POST-EMERGENCE | 41 |
| Blackgrass (1) | 2 | Blackgrass (1) | 0 |
| Blackgrass (2) | 3 | Blackgrass (2) | 0 |
| Chickweed | 3 | Chickweed | 0 |
| Downy brome | 0 | Downy brome | 0 |
| Field violet | 3 | Field violet | 0 |
| Galium (1) | 2 | Galium (1) | 0 |
| Galium (2) | 2 | Galium (2) | 0 |
| Green foxtail | 7 | Green foxtail | 0 |
| Kochia | 2 | Kochia | 0 |
| Lambsquarters | — | Lambsquarters | 0 |
| Persn Speedwell | 3 | Persn Speedwell | 0 |
| Rape | 2 | Rape | 0 |
| Ryegrass | 4 | Ryegrass | 0 |
| Sugar beet | 3 | Sugar beet | 0 |
| Sunflower | 0 | Sunflower | 0 |
| Wheat (Spring) | 0 | Wheat (Spring) | 0 |
| Wheat (Winter) | 0 | Wheat (Winter) | 0 |
| Wild buckwheat | 2 | Wild buckwheat | 0 |
| Wild mustard | 0 | Wild mustard | 0 |
| Wild oat (1) | 0 | Wild oat (1) | 0 |
| Wild oat (2) | 0 | Wild oat (2) | 0 |
| Wild radish | 0 | Wild radish | 0 |
| Winter Barley | 0 | Winter Barley | 0 |
| | COMPOUND | | COMPOUND |
| Rate (32 g/ha) PRE-EMERGENCE | 41 | Rate (16 g/ha) POST-EMERGENCE | 41 |
| Blackgrass (1) | 0 | Blackgrass (1) | 0 |
| Blackgrass (2) | 0 | Blackgrass (2) | 0 |
| Chickweed | 0 | Chickweed | 0 |
| Downy brome | 0 | Downy brome | 0 |

TABLE F-continued

| | | | |
|---|---|---|---|
| Field violet | 0 | Field violet | 0 |
| Galium (1) | 0 | Galium (1) | 0 |
| Galium (2) | 0 | Galium (2) | 0 |
| Green foxtail | 3 | Green foxtail | 0 |
| Kochia | 0 | Kochia | 0 |
| Lambsquarters | — | Lambsquarters | 0 |
| Persn Speedwell | 0 | Persn Speedwell | 0 |
| Rape | 0 | Rape | 0 |
| Ryegrass | 0 | Ryegrass | 0 |
| Sugar beet | 0 | Sugar beet | 0 |
| Sunflower | 0 | Sunflower | 0 |
| Wheat (Spring) | 0 | Wheat (Spring) | 0 |
| Wheat (Winter) | 0 | Wheat (Winter) | 0 |
| Wild buckwheat | 0 | Wild buckwheat | 0 |
| Wild mustard | 0 | Wild mustard | 0 |
| Wild oat (1) | 0 | Wild oat (1) | 0 |
| Wild oat (2) | 0 | Wild oat (2) | 0 |
| Wild radish | 0 | Wild radish | 0 |
| Winter Barley | 0 | Winter Barley | 0 |

| | COMPOUND |
|---|---|
| Rate (16 g/ha) PRE-EMERGENCE | 41 |
| Blackgrass (1) | 0 |
| Blackgrass (2) | 0 |
| Chickweed | 0 |
| Downy brome | 0 |
| Field violet | 0 |
| Galium (1) | 0 |
| Galium (2) | 0 |
| Green foxtail | 0 |
| Kochia | 0 |
| Lambsquarters | - |
| Persn Speedwell | 0 |
| Rape | 0 |
| Ryegrass | 0 |
| Sugar beet | 0 |
| Sunflower | 0 |
| Wheat (Spring) | 0 |
| Wheat (Winter) | 0 |
| Wild buckwheat | 0 |
| Wild mustard | 0 |
| Wild oat (1) | 0 |
| Wild oat (2) | 0 |
| Wild radish | 0 |
| Winter Barley | 0 |

What is claimed is:

1. A compound of Formulae III through VI and stereoisomers thereof

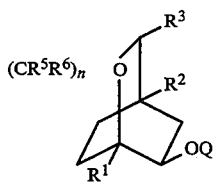

III:

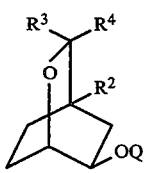

IV:

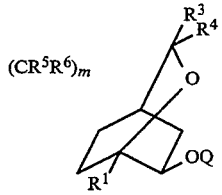

V:

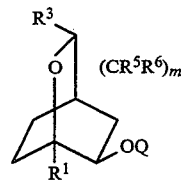

VI:

wherein n is 2, 3 or 4;

m is 3, 4 or 5;

$R^1$ is straight chain $C_1$–$C_3$ alkyl;

$R^2$ is H, $C_1$–$C_4$ alkyl, $C_2$–$C_4$ alkenyl or $C_2$–$C_4$ alkynyl;

$R^3$ is $R^4$ are independently H, $C_1$–$C_4$ alkyl, $C_2$–$C_4$ alkenyl, $C_2$–$C_4$ alkynyl or $C_1$–$C_3$ alkyl substituted with $OCH_3$ or $OCH_2CH_3$;

$R^5$ and $R^6$ are independently H, $OCH_3$ or $C_1$–$C_2$ alkyl;

Q is $CH_2W$ or

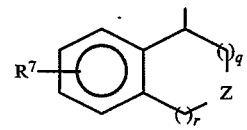

q and r are independently 0–2;

$R^7$ is H, halogen, $C_1$–$C_3$ alkyl, $OR^8$, $SR^8$ or CN;

$R^8$ is $C_1$–$C_3$ alkyl or $C_1$–$C_3$ haloalkyl;

Z is $CH_2$, $NR^9$, O, S or may be CH and taken to form a double bond with an adjacent carbon;

$R^9$ is H or $C_1$–$C_3$ alkyl;

W is phenyl optionally substituted with 1–3 substituents selected from halogen, $C_1$–$C_3$ alkyl, $C_1$–$C_3$ alkoxy, OH, CN, $C_1$–$C_3$ haloalkyl, $C_1$–$C_3$ haloalkoxy, $C_1$–$C_3$ alkylthio, $C_2$–$C_4$ alkenyl and $C_2$–$C_4$ alkynyl; or W is 5-, 6- or 7-membered heterocyclic ring containing 0–2 nitrogens, 0–2 oxygens or 0–2 sulfurs, each ring optionally substituted with 1–2 substituents selected from halogen, $CH_3$ and $OCH_3$;

provided that 1) the sum of q and r is 0–2;

2) if the sum of q and r is 0 then Z is $CH_2$; and 3) if W is a heterocycle then the total number of heteroatoms contained within the heterocyclic rings is 3 or less.

2. Compounds of claim 1 wherein the formulas are selected from III and V and

W is phenyl optionally substituted by 1–2 substituents selected from F, Cl, Br, $CH_3$ and $OCH_3$; or W is tetrahydropyran, tetrahydrofuran, thiophene, isoxazole, pyridine or pyrazine, each ring optionally substituted with 1–2 substituents selected from F, Cl, Br, $CH_3$ and $OCH_3$;

Q is $CH_2W$ or

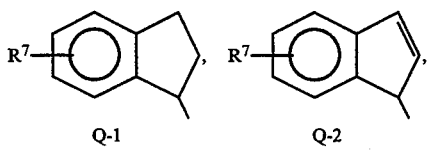

Q-1       Q-2

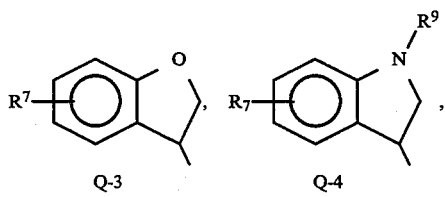

Q-3       Q-4

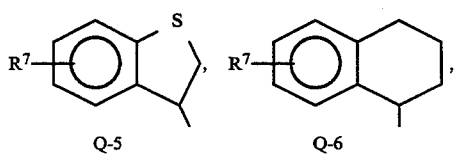

Q-5       Q-6

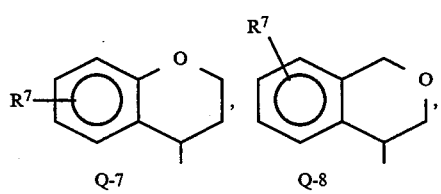

Q-7       Q-8

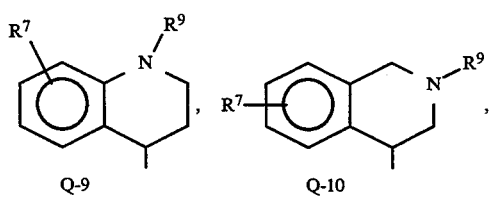

Q-9       Q-10

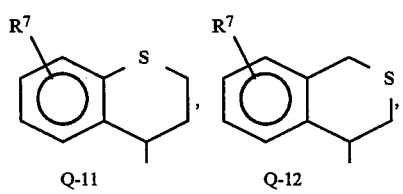

Q-11       Q-12

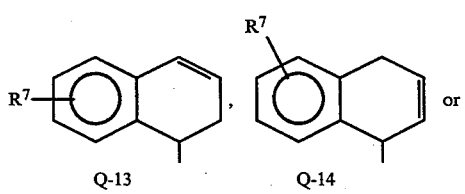

Q-13       Q-14   or

-continued

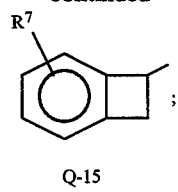

Q-15

$R^5$ and $R^6$ are independently H or $C_1$–$C_2$ alkyl.

3. Compounds of claim 2 selected from formulas III and V wherein:
  $R^2$ is H, $C_1$–$C_3$ alkyl, $C_2$–$C_3$ alkenyl or $C_2$–$C_3$ alkynyl.

4. Compounds of claim 3 selected from formula III and V wherein:
  $R^3$ is H, $C_1$–$C_3$ alkyl, $C_3$–$C_4$ alkenyl or $C_3$–$C_4$ alkynyl;
  $R^4$ is H, $C_1$–$C_3$ alkyl, $C_3$–$C_4$ alkenyl or $C_3$–$C_4$ alkynyl.

5. Compounds of claim 4 selected from formula III and V wherein:
  Q is $CH_2W$ or Q-1, Q-3, Q-4, Q-6, Q-7, Q-8 or Q-15;
  $R^5$ and $R^6$ are independently H;
  W is phenyl optionally substituted with 1-2 substituents selected from F, Cl, Br and $CH_3$; tetrahydrofuran; thiophene optionally substituted with Cl or Br; or pyridine.

6. Compounds of claim 5 selected from formula III and V wherein:
  $R^1$ is $CH_3$ or $CH_2CH_3$;
  $R^2$ is H, $CH_3$, $CH_2CH_3$ or allyl; and
  $R^3$ and $R^4$ are H.

7. Compounds of claim 6 wherein the Formula is Formula V.

8. A compound of claim 1 selected from the group consisting of:
  ($2\alpha,3\beta,4a\beta,5\alpha,7a\beta$)-3-[(2-fluorophenyl)methoxy]-octahydro-2,4a-dimethyl-2,5-methanocyclopenta[b]pyran, ($2\alpha,3\beta,4a\beta,5\alpha,9a\beta$)-3-[(2,6-difluorophenyl)-methoxy]decahydro-2-methyl-2,5-methanocyclohepta-[b]pyran, ($2\alpha,3\beta,4a\beta,5\alpha,7a\beta$)-3-[(2-fluorophenyl)-methoxy]octahydro-2-methyl-2,5-methanocyclopenta-[b]pyran, ($2\alpha,3\beta,4a\beta,5\alpha,9a\beta$)-3-[(2-fluorophenyl)-methoxy]decahydro-2-methyl-2,5-methanocyclohepta-[b]pyran, ($2\alpha,3\beta,4a\beta,5\alpha,7a\beta$)-octahydro-2,4a-dimethyl-3-(phenylmethoxy)-2,5-methanocyclopenta[b]-pyran, ($2\alpha,3\beta,4a\beta,5\alpha,7a\beta$)-3-[(2-chlorophenyl)methoxy]octahydro-2,4a-dimethyl-2,5-methanocyclopenta[b]pyran and ($2\alpha,3\beta,4a\beta,5\alpha,7a\beta$)-octahydro-2,4a-dimethyl-3-[(2-methylphenyl)methoxy]-2,5-methanocyclopenta[b]pyran.

9. An agriculturally suitable composition for controlling the growth of undesired vegetation comprising an effective amount of the compound of claim 1 and at least one of the following: surfactant, solid diluent or liquid diluent.

10. A method for controlling the growth of undesired vegetation which comprises applying to the locus to be protected an effective amount of a compound of claim 1.

* * * * *